US011311520B2

(12) United States Patent
Klar et al.

(10) Patent No.: US 11,311,520 B2
(45) Date of Patent: Apr. 26, 2022

(54) SUBSTITUTED DIHYDROIMIDAZOPYRIDINEDIONES AS MKNK1 AND MKNK2 INHIBITORS

(71) Applicants: Bayer Pharma Aktiengesellschaft, Berlin (DE); Bayer Aktiengesellschaft, Leverkusen (DE)

(72) Inventors: Ulrich Klar, Berlin (DE); Rolf Bohlmann, Berlin (DE); Heike Schäcke, Berlin (DE); Detlev Sülzle, Berlin (DE); Stephan Menz, Berlin (DE); Olaf Panknin, Berlin (DE)

(73) Assignees: Bayer Pharma Aktiengesellschaft, Berlin (DE); Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 16/983,768

(22) Filed: Aug. 3, 2020

(65) Prior Publication Data

US 2021/0085656 A1    Mar. 25, 2021

Related U.S. Application Data

(63) Continuation of application No. 16/479,461, filed as application No. PCT/EP2018/050840 on Jan. 15, 2018, now abandoned.

(30) Foreign Application Priority Data

Jan. 20, 2017 (EP) .................................. 17152508
Jun. 30, 2017 (EP) .................................. 17179210

(51) Int. Cl.
| | | |
|---|---|---|
| C07D 471/04 | (2006.01) |
| A61K 31/437 | (2006.01) |
| A61K 31/5386 | (2006.01) |
| C07D 473/34 | (2006.01) |
| C07D 495/04 | (2006.01) |
| C07D 495/14 | (2006.01) |
| C07D 498/08 | (2006.01) |
| C07D 513/04 | (2006.01) |
| C07D 519/00 | (2006.01) |

(52) U.S. Cl.
CPC ........ *A61K 31/437* (2013.01); *A61K 31/5386* (2013.01); *C07D 471/04* (2013.01); *C07D 473/34* (2013.01); *C07D 495/04* (2013.01); *C07D 495/14* (2013.01); *C07D 498/08* (2013.01); *C07D 513/04* (2013.01); *C07D 519/00* (2013.01)

(58) Field of Classification Search
CPC .. C07D 471/04; C07D 473/04; C07D 495/04; C07D 498/08; C07D 513/04; C07D 519/00; A61K 31/437; A61K 31/5386
See application file for complete search history.

(56) References Cited

FOREIGN PATENT DOCUMENTS

WO    WO 2015/200481 A1 * 12/2015

OTHER PUBLICATIONS

Hou et al., Targeting Mnks for Cancer Therapy, Oncotarget, vol. 3, No. 2, pp. 118-131 (2012).*
Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Acute Leukemia, Merck Manual (Online Edition) 6 pages, pp. 1-6 (2013).*
Damasio, Alzheimer's Disease and related dementias, Cecil Textbook of Medicine, 20th Edition, vol. 2, pp. 1992-1996, 1996.*
Layzer, Degenerative diseases of the nervous system, Cecil Textbook of Medicine, 20th Edition, vol. 2, pp. 2050-2057, 1996.*

* cited by examiner

*Primary Examiner* — Deepak R Rao
(74) *Attorney, Agent, or Firm* — Morrison & Foerster LLP

(57) ABSTRACT

The present invention relates to substituted dihydroimidazopyridinedione compounds of general formula (I) as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyperproliferative, angiogenesis disorders, inflammatory diseases or diseases associated with inflammatory pain, as a sole agent or in combination with other active ingredients.

7 Claims, No Drawings

Specification includes a Sequence Listing.

SEQUENCE LISTING

<160> NUMBER OF SEQ ID NOS: 1

<210> SEQ ID NO 1
<211> LENGTH: 14
<212> TYPE: PRT
<213> ORGANISM: Unknown
<220> FEATURE:
<223> OTHER INFORMATION: biotin-Ahx-IKKRKLTRRKSLKG

<400> SEQUENCE: 1

Ile Lys Lys Arg Lys Leu Thr Arg Arg Lys Ser Leu Lys Gly
1               5                   10

SUBSTITUTED DIHYDROIMIDAZOPYRIDINEDIONES AS MKNK1 AND MKNK2 INHIBITORS

CROSS REFERENCE TO RELATED APPLICATIONS

This application is a continuation of U.S. application Ser. No. 16/479,461, which adopts the international filing date of Jan. 15, 2018, which is the national stage application under 35 U.S.C. § 371 of International Application No. PCT/EP2018/050840, filed internationally on Jan. 15, 2018, which claims the benefit of European Application Nos. 17152508.2, filed Jan. 20, 2017 and 17179210.4, filed Jun. 30, 2017.

SUBMISSION OF SEQUENCE LISTING ON ASCII TEXT FILE

The content of the following submission on ASCII text file is incorporated herein by reference in its entirety: a computer readable form (CRF) of the Sequence Listing (file name 777052036001SEQLIST.TXT, date recorded: Jul. 31, 2020, size: 1 KB).

The present invention relates to substituted dihydroimidazopyridinedione compounds of general formula (I) as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyperproliferative, angiogenesis disorders, inflammatory diseases or diseases associated with inflammatory pain, as a sole agent or in combination with other active ingredients.

BACKGROUND OF THE INVENTION

The present invention relates to chemical compounds that inhibit MKNK1 kinase (also known as MAP Kinase interacting Kinase, Mnk1) and/or MKNK2 kinase (also known as MAP Kinase interacting Kinase, Mnk2). Human MKNKs comprise a group of four proteins encoded by two genes (Gene symbols: MKNK1 and MKNK2) by alternative splicing. The b-forms lack a MAP kinase-binding domain situated at the C-terminus. The catalytic domains of the MKNK1 and MKNK2 are very similar and contain a unique DFD (Asp-Phe-Asp) motif in subdomain VII, which usually is DFG (Asp-Phe-Gly) in other protein kinases and suggested to alter ATP binding [Jauch et al., Structure 13, 1559-1568, 2005 and Jauch et al., EMBO J25, 4020-4032, 2006]. MKNK1a binds to and is activated by ERK and p38 MAP Kinases, but not by JNK1. MKNK1a binds to and is activated only by ERK. MKNK1b has low activity under all conditions and MKNK2b has a basal activity independent of ERK or p38 MAP Kinase. [Buxade M et al., Frontiers in Bioscience 5359-5374, May 1, 2008]

KNKs have been shown to phosphorylate eukaryotic initiation factor 4E (eIF4E), heterogeneous nuclear RNA-binding protein A1 (hnRNP A1), polypyrimidine-tract binding protein-associated splicing factor (PSF), cytoplasmic phospholipase A2 (cPLA2) and Sprouty 2 (hSPRY2) [Buxade M et al., Frontiers in Bioscience 5359-5374, May 1, 2008].

eIF4E is an oncogene that is amplified in many cancers and is phosphorylated exclusively by MKNKs proteins as shown by KO-mouse studies [Konicek et al., Cell Cycle 7:16, 2466-2471, 2008; Ueda et al., Mol Cell Biol 24, 6539-6549, 2004]. eIF4E has a pivotal role in enabling the translation of cellular mRNAs. eIF4E binds the 7-methyl-guanosine cap at the 5' end of cellular mRNAs and delivers them to the ribosome as part of the eIF4F complex, also containing eIF4G and eIF4A. Though all capped mRNAs require eIF4E for translation, a pool of mRNAs is exceptionally dependent on elevated eIF4E activity for translation. These so-called "weak mRNAs" are usually less efficiently translated due to their long and complex 5'UTR region and they encode proteins that play significant roles in all aspects of malignancy including VEGF, FGF-2, c-Myc, cyclin D1, survivin, BCL-2, MCL-1, MMP-9, heparanase, etc. Expression and function of eIF4E is elevated in multiple human cancers and directly related to disease progression [Konicek et al., Cell Cycle 7:16, 2466-2471, 2008].

MKNK1 and MKNK2 are the only kinases known to phosphorylate eIF4E at Ser209. Overall translation rates are not affected by eIF4E phosphorylation, but it has been suggested that eIF4E phosphorylation contributes to polysome formation (i.e. multiple ribosome on a single mRNA) that ultimately enables more efficient translation of "weak mRNAs" [Buxade M et al., Frontiers in Bioscience 5359-5374, May 1, 2008]. Alternatively, phosphorylation of eIF4E by MKNK proteins might facilitate eIF4E release from the 5' cap so that the 48S complex can move along the "weak mRNA" in order to locate the start codon [Blagden S P and Willis A E, Nat Rev Clin Oncol. 8(5):280-91, 2011]. Accordingly, increased eIF4E phosphorylation predicts poor prognosis in non-small cell lung cancer patients [Yoshizawa et al., Clin Cancer Res. 16(1):240-8, 2010]. Further data point to a functional role of MKNK1 in carcinogenesis, as overexpression of constitutively active MKNK1, but not of kinase-dead MKNK1, in mouse embryo fibroblasts accelerates tumor formation [Chrestensen C. A. et al., Genes Cells 12, 1133-1140, 2007]. Moreover, increased phosphorylation and activity of MKNK proteins correlate with overexpression of HER2 in breast cancer [Chrestensen, C. A. et al., J. Biol. Chem. 282, 4243-4252, 2007]. Constitutively active, but not kinase-dead, MKNK1 also accelerated tumor growth in a model using Eμ-Myc transgenic hematopoietic stem cells to produce tumors in mice. Comparable results were achieved when an eIF4E carrying a S209D mutation was analyzed. The S209D mutation mimicks a phosphorylation at the MKNK1 phosphorylation site. In contrast, a non-phosphorylatable form of eIF4E attenuated tumor growth [Wendel H G, et al., Genes Dev. 21(24):3232-7, 2007]. A selective MKNK inhibitor that blocks eIF4E phosphorylation induces apoptosis and suppresses proliferation and soft agar growth of cancer cells in vitro. This inhibitor also suppresses outgrowth of experimental B16 melanoma pulmonary metastases and growth of subcutaneous HCT116 colon carcinoma xenograft tumors without affecting body weight [Konicek et al., Cancer Res. 71(5):1849-57, 2011]. In summary, eIF4E phosphorylation through MKNK protein activity can promote cellular proliferation and survival and is critical for malignant transformation. Inhibition of MKNK activity may provide a tractable cancer therapeutic approach.

Furthermore it has been found that MKNK1 is an acinar cell-specific kinase required for exocrine pancreatic secretion [Cendrowski J, Sanchez-Arévalo Lobo V J, Sendler M, et al. Gut Published Online First: Jul. 18, 2014; doi:10.1136/gutinl-2013-306068].

The kinases MKNK1 and MKNK2 are important downstream targets of the Erk and p38 mitogen-activated protein kinase (MAPK) pathways and their activity can also be modulated by MAPK independent signals. The MKNKs are directly involved in regulating mRNA translation and, therefore, are key mediators of oncogenic progression and cytokine signaling. In particular, MAPK pathways such as Erk and p38 have been shown to play important roles in modulating immune responses by mediating the production of cytokines that control the initiation of innate immunity; the activation of adaptive immunity; and by regulating cellular responses to cytokines involved in immune responses. In addition, Erk and p38 contribute to pain sensitivity and p38 kinase inhibitors have shown pre-clinical and clinical efficacy regarding pain [Brown, Heitmeyer, et al., J Inflamm (Lond), 2008; Hill, Dabbagh, et al., J Pharmacol Exp TherJi, 2008; Gereau, et al., Brain Res Rev, 2009; Cheng, Dauch, et al., Mol Pain, 2010; Anand, Shenoy, et al., European Journal of Pain, 2011; Daves, Aitchison, et al., American College of Rheumatology Annual Meeting, 2012; Lin, Wang, et al., Curr Med Chem, 2014]. As MKNK kinases are effectors of MAPK pathways, these observations suggest that they may play important roles in mediating cytokine production and inflammatory pain. Recent studies support the involvement of MKNK kinases in different inflammatory processes [Rowlett, Chrestensen, et al., Am J Physiol Gastrointest Liver Physiol, 2008; Kjellerup, Kragballe, et al., Experimental Dermatology, 2008; Melemedjian, Asiedu, et al., J Neurosci, 2010; Fortin, Mayer, et al., Journal of Leukocyte Biolog, 2013]. Due to the induction of MKNK kinases by different inflammatory stimuli (sterile inflammation and pathogens) and their ability to regulate the expression of different cytokines which mediate the pathogenesis of multiple disorders such as auto-immune diseases, allergies, neurological disorders, sepsis, cardiovascular diseases, metabolic diseases, obesity and cancer. MKNKs represent a central node in regulating inflammation. [Joshi et al.; *World J Biol Chem* 2014 Aug. 26; 5(3): 321-333; Joschi et al., *Biomol Concepts*. 2012 April; 3(2): 127-139]

Imbalance in cytokines from Interleukin-1 family and their role in the pathogenesis of Endometriosis has been reported in the literature [*American Journal of Reproductive Immunology* 68 (2012) 138-145] as well as the possible pathophysiological roles of Mitogen-Activated Protein Kinases (MAPKs) in Endometriosis [Yoshino et al.; *AJRI* 2004; 52: 306-311]. More recently, the role of pro-inflammatory cytokines for evaluation of inflammatory status and their pathogenetic mechanisms in endometriosis has been illustrated [Tosti et al.; *Reproductive Sciences* 2015, 1-7; Malutan et al., *Centr Eur J Immunol* 2015; 40 (1): 96-102; Soo Hyun Ahn et al., *BioMed Research International, Vol.* 2015, Article ID 795976, 12 pages]. Women with endometriosis have elevated levels of key pro-inflammatory cytokines, i.e. IL-1β, IL-6, and TNF-α. At the same time, IL-1β and IL-6 could be used as predictors for endometriosis.

WO2015200481 describes 2,3-dihydroimidazo[1,5-a]pyridine-1,5-dione derivatives as inhibitors of MAP kinase interacting kinase (Mnk), as well as related compositions and methods containing or utilizing the same, in particular the use of said derivative as a medicine in the oncological field.

WO2017087808 relates to compounds having activity as inhibitors of MAP kinase interacting kinase (Mnk), for example Mnk1 and Mnk2, as well as to related compositions and methods for utilizing the inventive compounds as therapeutic agents for treatment of Mnk dependent diseases, including the treatment of cancer.

Substituted dihydroimidazopyridinedione compounds of general formula (I) have not been disclosed in prior art for the treatment or prophylaxis of different diseases.

So, the state of the art described above does not describe the specific substituted dihydroimidazopyridinedione compounds of general formula (I) of the present invention as defined herein or a stereoisomer, a tautomer, an N-oxide, a hydrate, a solvate, or a salt thereof, or a mixture of same, as described and defined herein, and as hereinafter referred to as "compounds of the present invention", or their pharmacological activity.

It has now been found, and this constitutes the basis of the present invention, that said compounds of the present invention have surprising and advantageous properties.

In particular, said compounds of the present invention have been found to effectively inhibit MKNK1 kinase.

Furthermore, the compounds according to the present invention have been found to effectively inhibit MKNK2 kinase.

In contrast to other MKNK1 and/or MKNK2 kinase inhibitors, the dihydroimidazopyridinediones according to the invention are mainly active on sterile and pathogenic inflammatory responses and do not interfere directly with cell viability.

The dihydroimidazopyridinediones according to the present invention may be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK1 and/or MKNK2 kinase, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The dihydroimidazopyridinediones according to the present invention may be used for the treatment or prophylaxis of inflammatory and/or immunological diseases as described in the summary of the invention.

Furthermore, the compounds according to the invention may be used for the treatment or prophylaxis of a gynecological disease, preferably dysmenorrhea, dyspareunia or endometriosis, adenomyosis, endometriosis-associated pain, or other endometriosis-associated symptoms, wherein said symptoms are in particular endometriosis-associated proliferation, dysmenorrhea, dyspareunia, dysuria, or dyschezia.

SUMMARY OF THE INVENTION

The present invention covers compounds of general formula (A)

(A)

in which:
$R^1$ represents a group selected from:

in which
X represents $NR^7$, O or S,
Y represent N or C, and * indicates the connection to the rest of the molecule;
$R^2$ represents a hydrogen atom or a group $C_1$-$C_3$-alkyl, halo-$C_1$-$C_6$-alkyl-, —(C=O)—$C_1$-$C_6$-alkyl, —(C=O)—$C_3$-$C_6$-cycloalkyl, —N(H)$R^4$, —(C=O)OH, —(C=O)—N($R^{5a}$)$R^5$, —(C=O)—$NR^5$—$C_1$-$C_6$-alkyl, —(C=O)—$NR^5$—$C_3$-$C_6$-cycloalkyl, —(C=O)—O—$C_1$-$C_6$-alkyl, —(C=O)—O—$C_3$-$C_6$-cycloalkyl, —($SO_2$)—$C_1$-$C_6$-alkyl, —($SO_2$)—$C_1$-$C_6$-aryl, -aryl;
$R^3$ represents a hydrogen atom, a halogen atom, cyano, hydroxy, —$C_1$-$C_6$-alkoxy or a group $C_1$-$C_3$-alkyl;
$R^4$ represents a hydrogen atom, $C_1$-$C_6$-alkyl-, halo-$C_1$-$C_6$-alkyl-, —(C=O)—$C_1$-$C_6$-alkyl, —(C=O)—$C_3$-$C_6$-cycloalkyl, $C_1$-$C_6$-alkoxy $C_1$-$C_6$-alkyl-, hydroxy-$C_1$-$C_6$-alkyl-, halo-$C_1$-$C_6$-alkoxy-$C_1$-$C_6$-alkyl-, —(C=O)—N($R^{5a}$)$R^5$;

$R^5$, $R^{5a}$ are the same or different and independently selected from each other representing a hydrogen atom or a group selected from:
$C_1$-$C_6$-alkyl-, $C_1$-$C_6$-alkyl-($C_1$-$C_6$-alkyl-)N $C_1$-$C_6$-alkyl-, $C_1$-$C_6$-alkylloxy-$C_1$-$C_6$-alkyl-,
$C_3$-$C_6$-cycloalkyl-, 3- to 10-membered heterocycloalkyl-, aryl-, and heteroaryl-; wherein said $C_1$-$C_6$-alkyl-, $C_3$-$C_6$-cycloalkyl-, 3- to 10-membered heterocycloalkyl-, aryl- and heteroaryl- group is optionally substituted, identically or differently, with 1, 2, 3, 4 or 5 $R^8$ groups;
or
N($R^{5a}$)$R^5$ together represent a 3- to 10-membered heterocycloalkyl- group, said group being optionally substituted, identically or differently, with 1, 2, 3, 4 or 5 $R^8$ groups;
$R^6$, $R^{6a}$ are the same or different and independently selected from one another, represent hydrogen, fluoro, hydroxy or a group halo-$C_1$-$C_3$-alkyl;
$R^7$ represents hydrogen, 3- to 10-membered heterocyloalkyl, —(C=O)—O—$C_1$-$C_6$-alkyl, —(C=O)—N(H)—$C_1$-$C_6$-alkyl, —(C=O)—N(—$C_1$-$C_6$-alkyl)-$C_1$-$C_6$-alkyl, —S(=O)$_2$—$C_1$-$C_6$-alkyl, —S(=O)$_2$—$C_1$-$C_6$-aryl, —$C_1$-$C_6$-alkyl-(C=O)—N(H)—$C_1$-$C_6$-alkyl, said group being optionally substituted, identically or differently, with 1, 2, 3 or 4 $R^8$-groups
$R^8$ represents hydrogen, halogen, cyano, hydroxy, a group —$C_1$-$C_3$-alkyl, —$C_1$-$C_3$-alkyl-OH, —$C_1$-$C_6$-alkoxy, —(C=O)—$C_1$-$C_6$-alkyl, —(C=O)—$C_3$-$C_6$-cycloalkyl, —C(C=O)—OH, —C(C=O)—O—$C_1$-$C_6$-alkyl, —$NH_2$, —N(H)—$C_1$-$C_3$-alkyl, —N(—$C_1$-$C_3$-alkyl)-$C_1$-$C_3$-alkyl, —(C=O)—N(H)—$C_1$-$C_6$-alkyl, —(C=O)—N(—$C_1$-$C_6$-alkyl)-$C_1$-$C_6$-alkyl, —NH(C=O)—O—$C_1$-$C_6$-alkyl;
$R^9$, $R^{9a}$ are the same or different and independently selected from each other, and represents a hydrogen or a group —$C_1$-$C_3$-alkyl, or
together represent —($CH_2$—$CH_2$—)—, —($CH_2$—$CR^6$($R^{6a}$)—$CH_2$—)—, —($CH_2$—Z—$CH_2$—)—, —($CH_2$—$CH_2$—Z—$CH_2$—$CH_2$)—, —($CH_2$—$CH_2$—$CR^6$($R^{6a}$)—$CH_2$—)—, —($CH_2$—$CH_2$—$CR^6$($R^{6a}$)—$CH_2$—$CH_2$—)—;
Z represents $NR^7$, O, S, S(=O) or $SO_2$;
or a tautomer, an N oxide, a hydrate, a solvate, a salt thereof, or a mixture of same.

The present invention further relates to methods of preparing compounds of general formula (I), to pharmaceutical compositions and combinations comprising said compounds, to the use of said compounds for manufacturing a pharmaceutical composition for the treatment or prophylaxis of a disease, as well as to intermediate compounds useful in the preparation of said compounds.

DETAILED DESCRIPTION OF THE INVENTION

The terms as mentioned in the present text have preferably the following meanings:

The term "halogen atom", "halo-" or "Hal-" is to be understood as meaning a fluorine, chlorine, bromine or iodine atom, preferably a fluorine, chlorine or bromine atom.

The term "$C_1$-$C_{10}$-alkyl" is to be understood as preferably meaning a linear or branched, saturated, monovalent hydrocarbon group having 1, 2, 3, 4, 5, 6, 7, 8, 9 or 10 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3, 4, 5 or 6 carbon atoms ("$C_1$-$C_6$-alkyl"), more particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group; even more particularly 1, 2 or 3 carbon atoms ("$C_1$-$C_3$-alkyl"), e.g. a methyl, ethyl, n-propyl- or iso-propyl group.

The term "$C_1$-$C_{10}$-alkylene" is to be understood as preferably meaning a linear or branched, saturated, bivalent hydrocarbon group having 1, 2, 3, 4, 5, 6, 7, 8, 9 or 10 carbon atoms, e.g. a methylene, ethylene, n-propylene, n-butylene, n-pentylene, 2-methylbutylene, n-hexylene, 3-methylpentylene group, or an isomer thereof. Particularly, said group is linear and has 2, 3, 4 or 5 carbon atoms ("$C_2$-$C_5$-alkylene"), e.g. an ethylene, n-propylene, n-butylene, n-pentylene group, more particularly 3 or 4 carbon atoms ("$C_3$-$C_4$-alkylene"), e.g. an n-propylene or n-butylene group.

The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said halo-$C_1$-$C_6$-alkyl group is, for example, —$CF_3$, —$CHF_2$, —$CH_2F$, —$CF_2CF_3$ or —$CH_2CF_3$.

The term "$C_1$-$C_6$-alkoxy" is to be understood as preferably meaning a linear or branched, saturated, monovalent, hydrocarbon group of formula —O—($C_1$-$C_6$-alkyl), in which the term "$C_1$-$C_6$-alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said halo-$C_1$-$C_6$-alkoxy group is, for example, —$OCF_3$, —$OCHF_2$, —$OCH_2F$, —$OCF_2CF_3$ or —$OCH_2CF_3$.

The term "$C_1$-$C_6$-alkoxy-$C_1$-$C_6$-alkyl" is to be understood as preferably meaning a linear or branched, saturated, monovalent $C_1$-$C_6$-alkyl group, as defined supra, in which one or more of the hydrogen atoms is replaced, in identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, or an isomer thereof.

The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is replaced, in identically or differently, by a halogen atom. Particularly, said halogen atom is F. Said halo-$C_1$-$C_6$-alkoxy-$C_1$-$C_6$-alkyl group is, for example, —$CH_2CH_2OCF_3$, —$CH_2CH_2OCHF_2$, —$CH_2CH_2OCH_2F$, —$CH_2CH_2OCF_2CF_3$ or —$CH_2CH_2OCH_2CF_3$.

The term "$C_2$-$C_{10}$-alkenyl" is to be understood as preferably meaning a linear or branched, monovalent hydrocarbon group, which contains one or more double bonds, and which has 2, 3, 4, 5, 6, 7, 8, 9 or 10 carbon atoms, particularly 2, 3, 4, 5 or 6 carbon atoms ("$C_2$-$C_6$-alkenyl"), more particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, iso-propenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl)ethenyl, buta-1,3-dienyl, penta-1,4-dienyl, hexa-1,5-dienyl, or methylhexadienyl group. Particularly, said group is vinyl or allyl.

The term "$C_2$-$C_{10}$-alkynyl" is to be understood as preferably meaning a linear or branched, monovalent hydrocarbon group which contains one or more triple bonds, and which contains 2, 3, 4, 5, 6, 7, 8, 9 or 10 carbon atoms, particularly 2, 3, 4, 5 or 6 carbon atoms ("$C_2$-$C_6$-alkynyl"), more particularly 2 or 3 carbon atoms ("$C_2$-$C_3$-alkynyl"). Said $C_2$-$C_{10}$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3- ynyl, 1,1-dimethylbut-2-ynyl, or 3,3-dimethylbut-1-ynyl group. Particularly, said alkynyl group is ethynyl, prop-1-ynyl, or prop-2-ynyl.

The term "$C_3$-$C_{10}$-cycloalkyl" is to be understood as meaning a saturated, monovalent, mono-, or bicyclic hydrocarbon ring which contains 3, 4, 5, 6, 7, 8, 9 or 10 carbon atoms ("$C_3$-$C_{10}$-cycloalkyl"). Said $C_3$-$C_{10}$-cycloalkyl group is for example, a monocyclic hydrocarbon ring, e.g. a cyclopropyl, cyclobutyl, cyclopentyl, cyclohexyl, cycloheptyl, cyclooctyl, cyclononyl or cyclodecyl, or a bicyclic hydrocarbon ring, e.g. a perhydropentalenylene or decalin ring. Particularly, said ring contains 3, 4, 5 or 6 carbon atoms ("$C_3$-$C_6$-cycloalkyl").

The term "$C_3$-$C_6$-cycloalkyloxy" refers to a ($C_3$-$C_6$-cycloalkyl)-O— group in which "$C_3$-$C_6$-cycloalkyl" is as defined herein. Examples include, but are not limited to, cyclopropanoxy and cyclobutanoxy.

The term "$C_4$-$C_{10}$-cycloalkenyl" is to be understood as preferably meaning a non-aromatic, monovalent, mono- or bicyclic hydrocarbon ring which contains 4, 5, 6, 7, 8, 9 or 10 carbon atoms and one, two, three or four double bonds, in conjugation or not, as the size of said cycloalkenyl ring allows. Said $C_4$-$C_{10}$-cycloalkenyl group is for example, a monocyclic hydrocarbon ring, e.g. a cyclobutenyl, cyclopentenyl, or cyclohexenyl or a bicyclic hydrocarbon, e.g.:

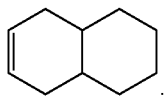

The term "$C_5$-$C_8$-cycloalkenyloxy" refers to a ($C_5$-$C_8$-cycloalkenyl)-O— group in which "$C_5$-$C_8$-cycloalkenyl" is as defined herein.

The term "3- to 10-membered heterocycloalkyl", is to be understood as meaning a saturated, monovalent, mono- or bicyclic hydrocarbon ring which contains 2, 3, 4, 5, 6, 7, 8 or 9 carbon atoms, and one or more heteroatom-containing groups selected from —C(=O)—, —O—, —S—, —S(=O)—, —S(=O)$_2$—, —N($R^a$)—, in which $R^a$ represents a hydrogen atom or a $C_1$-$C_6$-alkyl group; it being possible for said heterocycloalkyl group to be attached to the rest of the molecule via any one of the carbon atoms or, if present, the nitrogen atom. Heterospirocycloalkyl, heterobicycloalkyl and bridged heterocycloalkyl, as defined infra, are also included within the scope of this definition.

The term "heterospirocycloalkyl" is to be understood as meaning a saturated, monovalent bicyclic hydrocarbon radical in which the two rings share one common ring carbon atom, and wherein said bicyclic hydrocarbon radical contains 2, 3, 4, 5, 6, 7, 8 or 9 carbon atoms, and one or more heteroatom-containing groups selected from C(=O), O, S, S(=O), S(=O)$_2$, $NR^a$, in which $R^a$ represents a hydrogen atom or a $C_1$-$C_6$-alkyl- or $C_3$-$C_7$-cycloalkyl- group; it being possible for said heterospirocycloalkyl- group to be attached to the rest of the molecule via any one of the carbon atoms or, if present, the nitrogen atom. Said heterospirocycloalkyl-group is, for example, azaspiro[2.3]hexyl-, azaspiro[3.3]heptyl-, oxaazaspiro[3.3]heptyl-, thiaazaspiro[3.3]heptyl-, oxaspiro[3.3]heptyl-, oxazaspiro[5.3]nonyl-, oxazaspiro[4.3]octyl-, oxazaspiro[5.5]undecyl-, diazaspiro[3.3]heptyl-, thiazaspiro[3.3]heptyl-, thiazaspiro[4.3]octyl-, or azaspiro[5.5]decyl-.

The term "heterobicycloalkyl" is to be understood as meaning a saturated, monovalent bicyclic hydrocarbon radical in which the two rings share two immediately adjacent ring atoms, and wherein said bicyclic hydrocarbon radical contains 2, 3, 4, 5, 6, 7, 8 or 9 carbon atoms, and one or more heteroatom-containing groups selected from C(=O), O, S, S(=O), S(=O)$_2$, $NR^a$, in which $R^a$ represents a hydrogen atom or a $C_1$-$C_6$-alkyl- or $C_3$-$C_7$-cycloalkyl- group; it being possible for said heterobicycloalkyl- group to be attached to the rest of the molecule via any one of the carbon atoms or, if present, the nitrogen atom. Said heterobicyoalkyl- group is, for example, azabicyclo[3.3.0]octyl-, azabicyclo[4.3.0]nonyl-, diazabicyclo[4.3.0]nonyl-, oxazabicyclo[4.3.0]nonyl-, thiazabicyclo[4.3.0]nonyl-, or azabicyclo[4.4.0]decyl-.

The term "bridged heterocycloalkyl" is to be understood as meaning a saturated, monovalent bicyclic hydrocarbon radical in which the two rings share two common ring atoms which are not immediately adjacent, and wherein said bicyclic hydrocarbon radical contains 2, 3, 4, 5, 6, 7, 8 or 9 carbon atoms, and one or more heteroatom-containing groups selected from C(=O), O, S, S(=O), S(=O)$_2$, $NR^a$, in which $R^a$ represents a hydrogen atom, or a $C_1$-$C_6$-alkyl- or $C_3$-$C_7$-cycloalkyl- group; it being possible for said bridged heterocycloalkyl- group to be attached to the rest of the molecule via any one of the carbon atoms or, if present, the nitrogen atom. Said bridged heterocycloalkyl- group is, for example, azabicyclo[2.2.1]heptyl-, oxazabicyclo[2.2.1]heptyl-, thiazabicyclo[2.2.1]heptyl-, diazabicyclo[2.2.1]heptyl-, azabicyclo[2.2.2]octyl-, diazabicyclo[2.2.2]octyl-, oxazabicyclo[2.2.2]octyl-, thiazabicyclo[2.2.2]octyl-, azabicyclo[3.2.1]octyl-, diazabicyclo[3.2.1]octyl-, oxazabicyclo[3.2.1]octyl-, thiazabicyclo[3.2.1]octyl-, azabicyclo[3.3.1]nonyl-, diazabicyclo[3.3.1]nonyl-, oxazabicyclo[3.3.1]nonyl-, thiazabicyclo[3.3.1]nonyl-, azabicyclo[4.2.1]nonyl-, diazabicyclo[4.2.1]nonyl-, oxazabicyclo[4.2.1]nonyl, thiazabicyclo[4.2.1]nonyl-, azabicyclo[3.3.2]decyl-, diazabicyclo[3.3.2]decyl-, oxazabicyclo[3.3.2]decyl-, thiazabicyclo[3.3.2]decyl-, or azabicyclo[4.2.2]decyl-.

Particularly, said 3- to 10-membered heterocycloalkyl can contain 2, 3, 4, or 5 carbon atoms, and one or more of the above-mentioned heteroatom-containing groups (a "3- to 6-membered heterocycloalkyl"), more particularly said 3- to 10-membered heterocycloalkyl can contain 4 or 5 carbon atoms, and one or more of the above-mentioned heteroatom-containing groups (a "5- to 6-membered heterocycloalkyl").

Particularly, without being limited thereto, said 3- to 10-membered heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example.

Said 3- to 10-membered heterocycloalkyl can be bicyclic, such as, without being limited thereto, a 5,5-membered ring, e.g. a hexahydrocyclopenta[c]pyrrol-2(1H)-yl ring, or a 5,6-membered bicyclic ring, e.g. a hexahydropyrrolo[1,2-a]pyrazin-2(1H)-yl ring.

The term "4- to 10-membered heterocycloalkenyl", is to be understood as meaning an non-aromatic, unsaturated, monovalent, mono- or bicyclic hydrocarbon ring which contains 3, 4, 5, 6, 7, 8 or 9 carbon atoms, and one or more heteroatom-containing groups selected from —C(=O)—, —O—, —S—, —S(=O)—, —S(=O)$_2$—, —N($R^a$)—, in which $R^a$ represents a hydrogen atom or a $C_1$-$C_6$-alkyl group; it being possible for said heterocycloalkenyl group to be attached to the rest of the molecule via any one of the carbon atoms or, if present, the nitrogen atom. Examples of said heterocycloalkenyl are e.g. 4H-pyranyl, 2H-pyranyl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl, or 4H-[1,4]thiazinyl group.

The term "aryl" is to be understood as preferably meaning a monovalent, aromatic or partially aromatic, mono-, bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group; or a biphenyl group, or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a ring having 13 carbon atoms, (a "$C_{13}$-aryl" group), e.g. a fluorenyl group, or a ring having 14 carbon atoms, (a "$C_{14}$-aryl" group), e.g. an anthranyl group. Preferably, the aryl group is a phenyl group.

The term "heteroaryl" is understood as preferably meaning a monovalent, monocyclic, bicyclic or tricyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$, particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitrobenzene)-sulfonyloxy, (4-isopropyl-benzene)sulfonyloxy, (2,4,6-tri-isopropyl-benzene)-sulfonyloxy, (2,4,6-trimethylbenzene)sulfonyloxy, (4-tertbutyl-benzene)sulfonyloxy, benzenesulfonyloxy, and (4-methoxy-benzene)sulfonyloxy.

As used herein, the term "protective group" is a protective group attached to a nitrogen in intermediates used for the preparation of compounds of the general formula (I). Such groups are introduced e.g. by chemical modification of the respective amino group in order to obtain chemoselectivity in a subsequent chemical reaction. Protective groups for amino groups are described for example in T. W. Greene and P. G. M. Wuts in *Protective Groups in Organic Synthesis*, $3^{rd}$ edition, Wiley 1999; more specifically, said groups can be selected from substituted sulfonyl groups, such as mesyl-, tosyl- or phenylsulfonyl-, acyl groups such as benzoyl, acetyl or tetrahydropyranoyl-, or carbamate based groups, such as tert.-butoxycarbonyl (Boc), or can include silicon, as in e.g. 2-(trimethylsilyl)ethoxymethyl (SEM).

The invention includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2H$ (deuterium), $^3H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$, and $^{131}I$, respectively. Certain isotopic variations of a compound of the invention, for example, those in which one or more radioactive isotopes such as $^3H$ or $^{14}C$ are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

The compounds of the present invention may contain sulphur atoms which are asymmetric, such as an asymmetric sulphoxide or sulphoximine group, of structure:

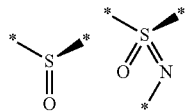

for example, in which * indicates atoms to which the rest of the molecule can be bound.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

Pure stereoisomers can be obtained by resolution of racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R) or (S) isomers, or (E) or (Z) isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

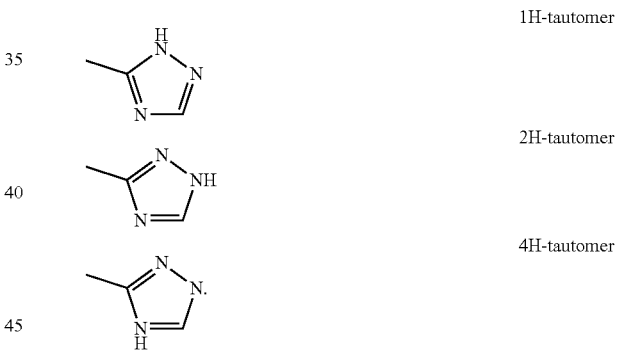

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio.

In the case of stoichiometric solvates, e.g. a hydrate, hemi-, (semi-), mono-, sesqui-, di-, tri-, tetra-, penta- etc.

solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol, or with a quarternary ammonium salt, such as tetramethylammonium, tetraethylammonium, tetra(n-propyl)ammonium, tetra (n-butyl)ammonium, or N-benzyl-N,N,N-trimethylammonium.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

Furthermore, the present invention includes all possible crystalline forms, or polymorphs, of the compounds of the present invention, either as single polymorphs, or as a mixture of more than one polymorphs, in any ratio.

In accordance with a first aspect, the present invention covers compounds of general formula (A)

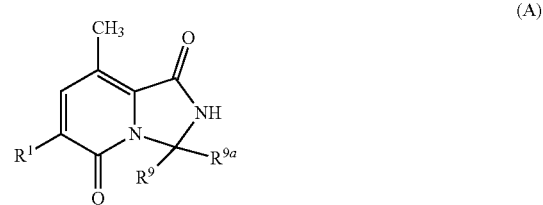

(A)

in which:
$R^1$ represents a group selected from:

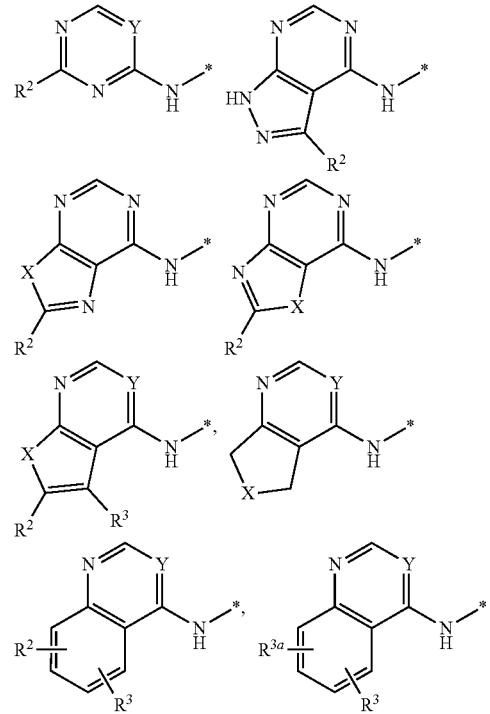

in which
X represents $NR^7$, O or S,
Y represent N or C, and * indicates the connection to the rest of the molecule;
$R^2$ represents a hydrogen atom or a group $C_1$-$C_3$-alkyl, halo-$C_1$-$C_6$-alkyl-, —(C=O)—$C_1$-$C_6$-alkyl, —(C=O)—$C_3$-$C_6$-cycloalkyl, —N(H)$R^4$, —(C=O)OH, —(C=O)—N($R^{5a}$)$R^5$, —(C=O)—$NR^5$—$C_1$-$C_6$-alkyl, —(C=O)—$NR^5$—$C_3$-$C_6$-cycloalkyl, —(C=O)—O—$C_1$-$C_6$-alkyl, —(C=O)—O—$C_3$-$C_6$-cycloalkyl, —(SO$_2$)—$C_1$-$C_6$-alkyl, —(SO$_2$)—$C_1$-$C_6$-aryl, -aryl;
$R^3$ and $R^{3a}$ are the same or different and independently selected from one another represents hydrogen atom, a halogen atom, cyano, hydroxy, —$C_1$-$C_6$-alkoxy, $C_1$-$C_3$-alky-1, halo-$C_1$-$C_3$-alkyl-,
$R^4$ represents a hydrogen atom, $C_1$-$C_6$-alkyl-, halo-$C_1$-$C_6$-alkyl-, —(C=O)—$C_1$-$C_6$-alkyl, —(C=O)—$C_3$-$C_6$-cycloalkyl, $C_1$-$C_6$-alkoxy $C_1$-$C_6$-alkyl-, hydroxy-$C_1$-$C_6$-alkyl-, halo-$C_1$-$C_6$-alkoxy-$C_1$-$C_6$-alkyl-, —(C=O)—N($R^{5a}$)$R^5$;

$R^5$, $R^{5a}$ are the same or different and independently selected from each other representing a hydrogen atom or a group selected from:

- $C_1$-$C_6$-alkyl-, $C_1$-$C_6$-alkyl-($C_1$-$C_6$-alkyl-)N $C_1$-$C_6$-alkyl-, $C_1$-$C_6$-alkyloxy-$C_1$-$C_6$-alkyl-, $C_3$-$C_6$-cycloalkyl-, 3- to 10-membered heterocycloalkyl-, aryl-, and heteroaryl-; wherein said $C_1$-$C_6$-alkyl-, $C_3$-$C_6$-cycloalkyl-, 3- to 10-membered heterocycloalkyl-, aryl- and heteroaryl- group is optionally substituted, identically or differently, with 1, 2, 3, 4 or 5 $R^8$ groups;

or

N($R^{5a}$)$R^5$ together represent a 3- to 10-membered heterocycloalkyl- group, said group being optionally substituted, identically or differently, with 1, 2, 3, 4 or 5 $R^8$-groups;

$R^6$, $R^{6a}$ are the same or different and independently selected from one another, represent a hydrogen, fluoro, hydroxy or a group halo-$C_1$-$C_3$-alkyl;

$R^7$ represents hydrogen, 3- to 10-membered heterocycloalkyl-, —(C=O)—O—$C_1$-$C_6$-alkyl, —(C=O)—N(H)—$C_1$-$C_6$-alkyl, —(C=O)—N(—$C_1$-$C_6$-alkyl)-$C_1$-$C_6$-alkyl, —S(=O)$_2$—$C_1$-$C_6$-alkyl, —S(=O)$_2$—$C_1$-$C_6$-aryl, —$C_1$-$C_6$-alkyl-(C=O)—N(H)—$C_1$-$C_6$-alkyl, said group being optionally substituted, identically or differently, with 1, 2, 3 or 4 $R^8$-groups $R^8$ represents hydrogen, halogen, cyano, hydroxy, a group —$C_1$-$C_3$-alkyl, —$C_1$-$C_3$-alkyl-OH, —$C_1$-$C_6$-alkoxy, —(C=O)—$C_1$-$C_6$-alkyl, —(C=O)—$C_3$-$C_6$-cycloalkyl, —C(C=O)—OH, —C(C=O)—O—$C_1$-$C_6$-alkyl, —NH$_2$, —N(H)—$C_1$-$C_3$-alkyl, —N(—$C_1$-$C_3$-alkyl)-$C_1$-$C_3$-alkyl, —(C=O)—N(H)—$C_1$-$C_6$-alkyl, —(C=O)—N(—$C_1$-$C_6$-alkyl)-$C_1$-$C_6$-alkyl, —NH(C=O)—O—$C_1$-$C_6$-alkyl;

$R^9$, $R^{9a}$ are the same or different and independently selected from each other, and represents a hydrogen or a group —$C_1$-$C_3$-alkyl, or together represent —(CH$_2$—CH$_2$—)—, —(CH$_2$—CR$^6$(R$^{6a}$)—CH$_2$—)—, —(CH$_2$—Z—CH$_2$—)—, —(CH$_2$—CH$_2$—Z—CH$_2$—CH$_2$)—, —(CH$_2$—CH$_2$—CR$^6$(R$^{6a}$)—CH$_2$-)—, —(CH$_2$—CH$_2$—CR$^6$(R$^{6a}$)—CH$_2$—CH$_2$-)—;

Z represents NR$^7$, O, S, S(=O) or SO$_2$;

or a tautomer, an N oxide, a hydrate, a solvate, a salt thereof, or a mixture of same.

In accordance with a second aspect, the present invention covers compounds of general formula (Ia):

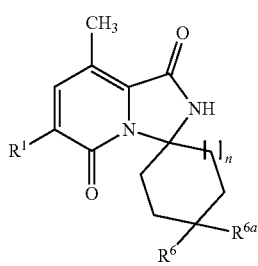

(Ia)

in which:
$R^1$ represents a group selected from:

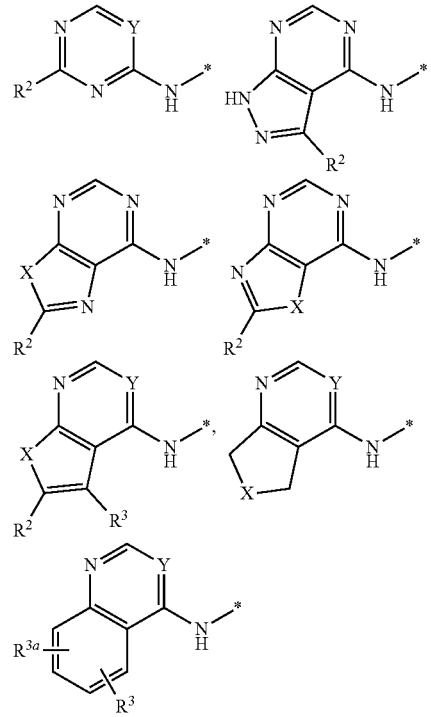

in which
X represents NR$^7$, O or S,
Y represent N or C, and * indicates the connection to the rest of the molecule;
n 0 or 1
$R^2$ represents a hydrogen atom or a group $C_1$-$C_3$-alkyl, halo-$C_1$-$C_6$-alkyl-, —(C=O)—$C_1$-$C_6$-alkyl, —(C=O)—$C_3$-$C_6$-cycloalkyl, —N(H)R$^4$, —(C=O)OH, (C=O)—N(R$^{5a}$)R$^5$, —(C=O)—NR$^5$—$C_1$-$C_6$-alkyl, —(C=O)—NR$^5$—$C_3$-$C_6$-cycloalkyl, —(C=O)—O—$C_1$-$C_6$-alkyl, —(C=O)—O—$C_3$-$C_6$-cycloalkyl, —(SO$_2$)—$C_1$-$C_6$-alkyl, —(SO$_2$)—$C_1$-$C_6$-aryl, -aryl;

$R^3$ and $R^{3a}$ are the same or different and independently selected from one another represent a hydrogen atom, a halogen atom, cyano, hydroxy, —$C_1$-$C_6$-alkoxy, $C_1$-$C_3$-alkyl, halo-$C_1$-$C_3$-alkyl;

$R^4$ represents a hydrogen atom $C_1$-$C_6$-alkyl-, halo-$C_1$-$C_6$-alkyl-, —(C=O)—$C_1$-$C_6$-alkyl, —(C=O)—$C_3$-$C_6$-cycloalkyl, $C_1$-$C_6$-alkoxy $C_1$-$C_6$-alkyl-, hydroxy-$C_1$-$C_6$-alkyl-, halo-$C_1$-$C_6$-alkoxy-$C_1$-$C_6$-alkyl-, —(C=O)—N(R$^{5a}$)R$^5$;

$R^5$, $R^{5a}$ are the same or different and independently selected from each other representing a hydrogen atom or a group selected from:

- $C_1$-$C_6$-alkyl-, $C_1$-$C_6$-alkyl-($C_1$-$C_6$-alkyl-)N $C_1$-$C_6$-alkyl-, $C_1$-$C_6$-alkyloxy-$C_1$-$C_6$-alkyl-, $C_3$-$C_6$-cycloalkyl-, 3- to 10-membered heterocycloalkyl-, aryl-, and heteroaryl-; wherein said $C_1$-$C_6$-alkyl-, $C_3$-$C_6$-cycloalkyl-, 3- to 10-membered heterocycloalkyl-, aryl- and heteroaryl- group is optionally substituted, identically or differently, with 1, 2, 3, 4 or 5 $R^8$ groups;

or

N($R^{5a}$)$R^5$ together represent a 3- to 10-membered heterocycloalkyl- group, said group being optionally substituted, identically or differently, with 1, 2, 3, 4 or 5 $R^8$ groups;

$R^6$, $R^{6a}$ are the same or different and independently selected from one another represent a hydrogen, fluoro, hydroxy or a group halo-$C_1$-$C_3$-alkyl;

$R^7$ represents hydrogen, a group —$C_1$-$C_6$-alkyl, 3- to 10-membered heterocycloalkyl-, —(C=O)—O—$C_1$-$C_6$-alkyl, —(C=O)—N(H)—$C_1$-$C_6$-alkyl, —(C=O)—N(—$C_1$-$C_6$-alkyl)-$C_1$-$C_6$-alkyl,
—S(=O)$_2$—$C_1$-$C_6$-alkyl, —S(=O)$_2$—$C_1$-$C_6$-aryl, —$C_1$-$C_6$-alkyl-(C=O)—N(H)—$C_1$-$C_6$-alkyl; said group being optionally substituted, identically or differently, with 1, 2, 3 or 4 $R^8$ groups $R^8$ represents hydrogen, halogen, cyano, hydroxy, a group —$C_1$-$C_3$-alkyl, —$C_1$-$C_3$-alkyl-OH, —$C_1$-$C_6$-alkoxy, —(C=O)—$C_1$-$C_6$-alkyl, —(C=O)—$C_3$-$C_6$-cycloalkyl, —C(C=O)—OH, —C(C=O)—O—$C_1$-$C_6$-alkyl, —NH$_2$, —N(H)—$C_1$-$C_3$-alkyl, —N(—$C_1$-$C_3$-alkyl)-$C_1$-$C_3$-alkyl, —(C=O)—N(H)—$C_1$-$C_6$-alkyl, —(C=O)—N(—$C_1$-$C_6$-alkyl)-$C_1$-$C_6$-alkyl, —NH(C=O)—O—$C_1$-$C_6$-alkyl;

or a tautomer, an N oxide, a hydrate, a solvate, a salt thereof, or a mixture of same The present invention refers as well to compounds of general formula (Ia):

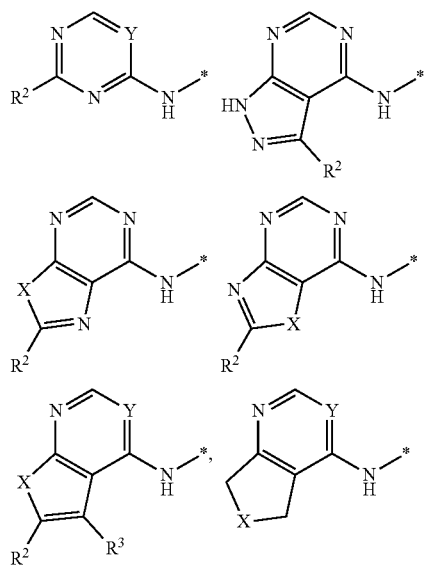

(Ia)

in which:

$R^1$ represents a group selected from:

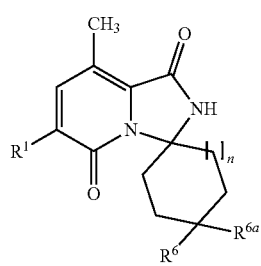

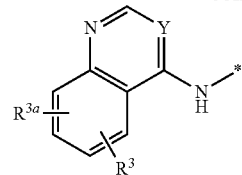

in which

X represents $NR^7$, O or S,

Y represent N or C, and * indicates the connection to the rest of the molecule;

n 0 or 1

$R^2$ represents a hydrogen atom or a group $C_1$-$C_3$-alkyl, halo-$C_1$-$C_6$-alkyl-, —(C=O)—$C_1$-$C_6$-alkyl, —(C=O)—$C_3$-$C_6$-cycloalkyl, —N(H)$R^4$, —(C=O)OH, (C=O)—N($R^{5a}$)$R^5$, —(C=O)—N$R^5$—$C_1$-$C_6$-alkyl, —(C=O)—N$R^5$—$C_3$-$C_6$-cycloalkyl, —(C=O)—O—$C_1$-$C_6$-alkyl, —(C=O)—O—$C_3$-$C_6$-cycloalkyl, —(SO$_2$)—$C_1$-$C_6$-alkyl, —(SO$_2$)—$C_1$-$C_6$-aryl, -aryl;

$R^3$ represents a hydrogen atom, a halogen atom, cyano, hydroxy, —$C_1$-$C_6$-alkoxy or a group $C_1$-$C_3$-alkyl;

$R^4$ represents a hydrogen atom $C_1$-$C_6$-alkyl-, halo-$C_1$-$C_6$-alkyl-, —(C=O)—$C_1$-$C_6$-alkyl, —(C=O)—$C_3$-$C_6$-cycloalkyl, $C_1$-$C_6$-alkoxy $C_1$-$C_6$-alkyl-, hydroxy-$C_1$-$C_6$-alkyl-, halo-$C_1$-$C_6$-alkoxy-$C_1$-$C_6$-alkyl-, —(C=O)—N($R^{5a}$)$R^5$;

$R^5$, $R^{5a}$ are the same or different and independently selected from each other representing a hydrogen atom or a group selected from:

$C_1$-$C_6$-alkyl-, $C_1$-$C_6$-alkyl-($C_1$-$C_6$-alkyl-)N $C_1$-$C_6$-alkyl-, $C_1$-$C_6$-alkyloxy-$C_1$-$C_6$-alkyl-, $C_3$-$C_6$-cycloalkyl-, 3- to 10-membered heterocycloalkyl-, aryl-, and heteroaryl-;

wherein said $C_1$-$C_6$-alkyl-, $C_3$-$C_6$-cycloalkyl-, 3- to 10-membered heterocycloalkyl-, aryl- and heteroaryl-group is optionally substituted, identically or differently, with 1, 2, 3, 4 or 5 $R^8$ groups;

or

N($R^{5a}$)$R^5$ together represent a 3- to 10-membered heterocycloalkyl- group, said group being optionally substituted, identically or differently, with 1, 2, 3, 4 or 5 $R^8$ groups;

$R^6$, $R^{6a}$ are the same or different and independently selected from each other, and represents a hydrogen or fluoro;

$R^7$ represents hydrogen, a group —$C_1$-$C_6$-alkyl, 3- to 10-membered heterocycloalkyl-, —(C=O)—O—$C_1$-$C_6$-alkyl, —(C=O)—N(H)—$C_1$-$C_6$-alkyl, —(C=O)—N(—$C_1$-$C_6$-alkyl)-$C_1$-$C_6$-alkyl, —S(=O)$_2$—$C_1$-$C_6$-alkyl, —S(=O)$_2$—$C_1$-$C_6$-aryl, —$C_1$-$C_6$-alkyl-(C=O)—N(H)—$C_1$-$C_6$-alkyl; said group being optionally substituted, identically or differently, with 1, 2, 3 or 4 $R^8$ groups $R^8$ represents hydrogen, halogen, cyano, hydroxy, a group —$C_1$-$C_3$-alkyl, —$C_1$-$C_3$-alkyl-OH, —$C_1$-$C_6$-alkoxy, —(C=O)—$C_1$-$C_6$-alkyl, —(C=O)—$C_3$-$C_6$-cycloalkyl, —C(C=O)—OH, —C(C=O)—O—$C_1$-$C_6$-alkyl, —NH$_2$, —N(H)—$C_1$-$C_3$-alkyl, —N(—$C_1$-$C_3$-alkyl)-$C_1$-$C_3$-alkyl, —(C=O)—N(H)—$C_1$-$C_6$-alkyl, —(C=O)—N(—$C_1$-$C_6$-alkyl)-$C_1$-$C_6$-alkyl, —NH(C=O)—O—$C_1$-$C_6$-alkyl;

or a tautomer, an N oxide, a hydrate, a solvate, a salt thereof, or a mixture of same.

In accordance with a second aspect, the present invention covers compounds of general formula (Ia):

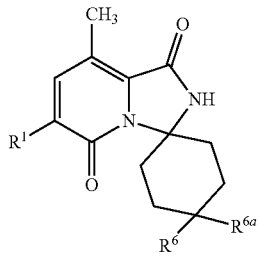

in which:
R¹ represents a group selected from:

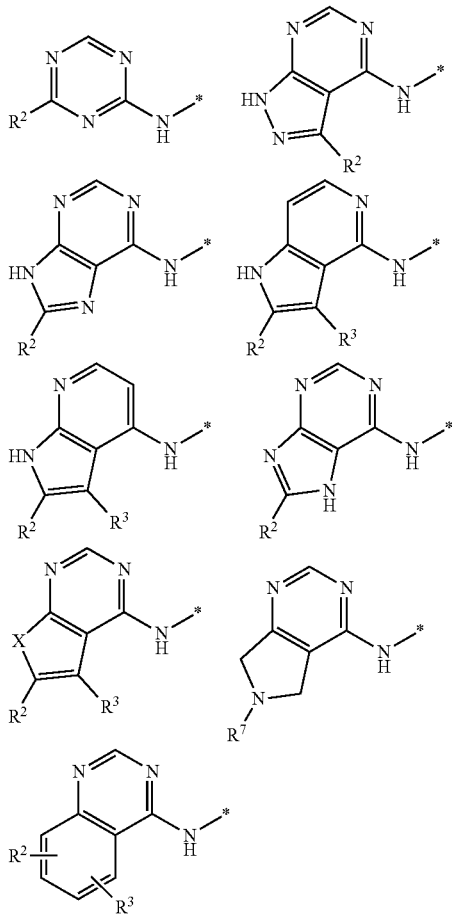

in which
X represents NR⁷, O or S and * indicates the connection to the rest of the molecule;
R² represents a hydrogen atom or a group $C_1$-$C_3$-alkyl, halo-$C_1$-$C_6$-alkyl-, —(C═O)—$C_1$-$C_6$-alkyl, —(C═O)—$C_3$-$C_6$-cycloalkyl, —N(H)R⁴, —(C═O)OH, (C═O)—N(R^{5a})R⁵, —(C═O)—NR⁵—$C_1$-$C_6$-alkyl, —(C═O)—NR⁵—$C_3$-$C_6$-cycloalkyl, —(C═O)—O—$C_1$-$C_6$-alkyl, —(C═O)—O—$C_3$-$C_6$-cycloalkyl, —(SO₂)—$C_1$-$C_6$-alkyl, —(SO₂)—$C_1$-$C_6$-aryl, -aryl;
R³ represents a hydrogen atom, a halogen atom, cyano, hydroxy, —$C_1$-$C_6$-alkoxy or a group $C_1$-$C_3$-alkyl;

R⁴ represents a hydrogen atom, $C_1$-$C_6$-alkyl-, halo-$C_1$-$C_6$-alkyl-, —(C═O)—$C_1$-$C_6$-alkyl, —(C═O)—$C_3$-$C_6$-cycloalkyl, $C_1$-$C_6$-alkoxy $C_1$-$C_6$-alkyl-, hydroxy-$C_1$-$C_6$-alkyl-, halo-$C_1$-$C_6$-alkoxy-$C_1$-$C_6$-alkyl-, —(C═O)—N(R^{5a})R⁵;
R⁵, R^{5a} are the same or different and independently selected from each other representing a hydrogen atom or a group selected from:
$C_1$-$C_6$-alkyl-, $C_1$-$C_6$-alkyl-($C_1$-$C_6$-alkyl-)N $C_1$-$C_6$-alkyl-, $C_1$-$C_6$-alkyloxy-$C_1$-$C_6$-alkyl-, $C_3$-$C_6$-cycloalkyl-, 3- to 10-membered heterocycloalkyl-, aryl-, and heteroaryl-; wherein said $C_1$-$C_6$-alkyl-, $C_3$-$C_6$-cycloalkyl-, 3- to 10-membered heterocycloalkyl-, aryl- and heteroaryl-group is optionally substituted, identically or differently, with 1, 2, 3, 4 or 5 R⁸ groups;
or
N(R^{5a})R⁵ together represent a 3- to 10-membered heterocycloalkyl- group, said group being optionally substituted, identically or differently, with 1, 2, 3, 4 or 5 R⁸ groups;
R⁶, R^{6a} are the same or different and independently selected from each other, and represents a hydrogen or fluoro;
R⁷ represents hydrogen, a group —$C_1$-$C_6$-alkyl, 3- to 10-membered heterocycloalkyl-, —(C═O)—O—$C_1$-$C_6$-alkyl, —(C═O)—N(H)—$C_1$-$C_6$-alkyl, —(C═O)—N(—$C_1$-$C_6$-alkyl)-$C_1$-$C_6$-alkyl, —S(═O)₂—$C_1$-$C_6$-alkyl, —S(═O)₂—$C_1$-$C_6$-aryl-$C_1$-$C_6$-alkyl-(C═O)—N(H)—$C_1$-$C_6$-alkyl, said group being optionally substituted, identically or differently, with 1, 2, 3 or 4 R⁸ groups
R⁸ represents hydrogen, halogen, cyano, hydroxy, a group —$C_1$-$C_3$-alkyl, —$C_1$-$C_3$-alkyl-OH, —$C_1$-$C_6$-alkoxy, —(C═O)—$C_1$-$C_6$-alkyl, —(C═O)—$C_3$-$C_6$-cycloalkyl, —C(C═O)—OH, —C(C═O)—O—$C_1$-$C_6$-alkyl, —NH₂, —N(H)—$C_1$-$C_3$-alkyl, —N(—$C_1$-$C_3$-alkyl)-$C_1$-$C_3$-alkyl, —(C═O)—N(H)—$C_1$-$C_6$-alkyl, —(C═O)—N(—$C_1$-$C_6$-alkyl)-$C_1$-$C_6$-alkyl, —NH(C═O)—O—$C_1$-$C_6$-alkyl;
or a tautomer, an N oxide, a hydrate, a solvate, a salt thereof, or a mixture of same.

In accordance with a third aspect, the present invention covers compounds of general formula (Ia):

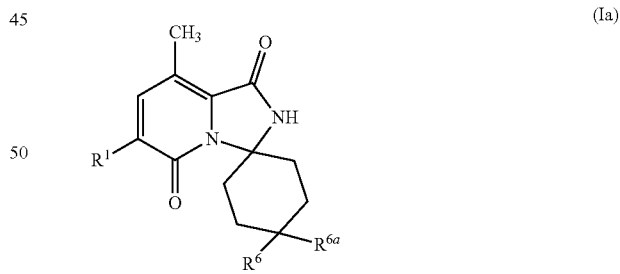

in which:
R¹ represents a group selected from:

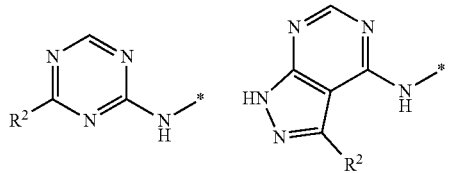

-continued

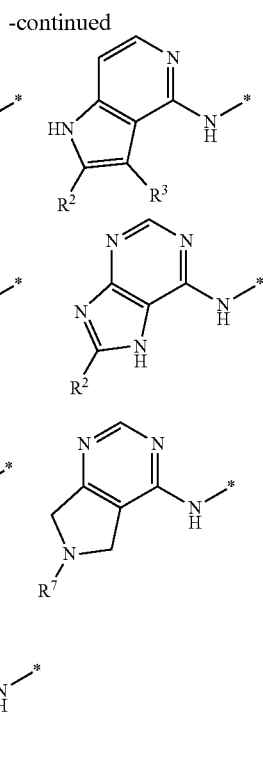

in which
X represents NR⁷, O or S and * indicates the connection to the rest of the molecule;

R² represents a hydrogen atom or a group $C_1$-$C_3$-alkyl, halo-$C_1$-$C_6$-alkyl-, —(C=O)—$C_1$-$C_6$-alkyl, —(C=O)—$C_3$-$C_6$-cycloalkyl, —N(H)R⁴, —(C=O)OH, (C=O)—N(R⁵ᵃ)R⁵, —(C=O)—NR⁵—$C_1$-$C_6$-alkyl, —(C=O)—NR⁵—$C_3$-$C_6$-cycloalkyl, —(C=O)—O—$C_1$-$C_6$-alkyl, —(C=O)—O—$C_3$-$C_6$-cycloalkyl, —(SO₂)—$C_1$-$C_6$-alkyl, —(SO₂)—$C_1$-$C_6$-aryl, -aryl;

R³ and R³ᵃ are the same or different and independently selected from one another represent a hydrogen atom, a halogen atom, cyano, hydroxy, —$C_1$-$C_6$-alkoxy, $C_1$-$C_3$-alkyl, halo-$C_1$-$C_3$-alkyl;

R⁴ represents a hydrogen atom, $C_1$-$C_6$-alkyl-, halo-$C_1$-$C_6$-alkyl-, —(C=O)—$C_1$-$C_6$-alkyl, —(C=O)—$C_3$-$C_6$-cycloalkyl, $C_1$-$C_6$-alkoxy $C_1$-$C_6$-alkyl-, hydroxy-$C_1$-$C_6$-alkyl-, halo-$C_1$-$C_6$-alkoxy-$C_1$-$C_6$-alkyl-, —(C=O)—N(R⁵ᵃ)R⁵;

R⁵, R⁵ᵃ are the same or different and independently selected from each other representing a hydrogen atom or a group selected from:
$C_1$-$C_6$-alkyl-, $C_1$-$C_6$-alkyl-($C_1$-$C_6$-alkyl-)N $C_1$-$C_6$-alkyl-, $C_1$-$C_6$-alkyloxy-$C_1$-$C_6$-alkyl-, $C_3$-$C_6$-cycloalkyl-, 3- to 10-membered heterocycloalkyl-, aryl-, and heteroaryl-; wherein said $C_1$-$C_6$-alkyl-, $C_3$-$C_6$-cycloalkyl-, 3- to 10-membered heterocycloalkyl-, aryl- and heteroaryl- group is optionally substituted, identically or differently, with 1, 2, 3, 4 or 5 R⁸ groups;
or
N(R⁵ᵃ)R⁵ together represent a 3- to 10-membered heterocycloalkyl- group, said group being optionally substituted, identically or differently, with 1, 2, 3, 4 or 5 R⁸ groups;

R⁶, R⁶ᵃ are the same or different and independently selected from one another represent a hydrogen, fluoro, hydroxy or a group halo-$C_1$-$C_3$-alkyl;

R⁷ represents hydrogen, a group —$C_1$-$C_6$-alkyl, 3- to 10-membered heterocycloalkyl-, —(C=O)—O—$C_1$-$C_6$-alkyl, —(C=O)—N(H)—$C_1$-$C_6$-alkyl, —(C=O)—N(—$C_1$-$C_6$-alkyl)-$C_1$-$C_6$-alkyl, —S(=O)₂—$C_1$-$C_6$-alkyl, —S(=O)₂—$C_1$-$C_6$-aryl, —$C_1$-$C_6$-alkyl-(C=O)—N(H)—$C_1$-$C_6$-alkyl, said group being optionally substituted, identically or differently, with 1, 2, 3 or 4 R⁸ groups R⁸ represents hydrogen, halogen, cyano, hydroxy, a group —$C_1$-$C_3$-alkyl, —$C_1$-$C_3$-alkyl-OH, —$C_1$-$C_6$-alkoxy, —(C=O)—$C_1$-$C_6$-alkyl, —(C=O)—$C_3$-$C_6$-cycloalkyl, —C(C=O)—OH, —C(C=O)—O—$C_1$-$C_6$-alkyl, —NH₂, —N(H)—$C_1$-$C_3$-alkyl, —N(—$C_1$-$C_3$-alkyl)-$C_1$-$C_3$-alkyl, —(C=O)—N(H)—$C_1$-$C_6$-alkyl, —(C=O)—N(—$C_1$-$C_6$-alkyl)-$C_1$-$C_6$-alkyl, —NH(C=O)—O—$C_1$-$C_6$-alkyl;

or a tautomer, an N oxide, a hydrate, a solvate, a salt thereof, or a mixture of same.

According to a further aspect of the present invention R² represents a —(C=O)—$C_1$-$C_6$-alkyl, —(C=O)—$C_3$-$C_6$-cycloalkyl, —N(H)R⁴, —(C=O)OH, (C=O)—N(R⁵ᵃ)R⁵, —(C=O)—NR⁵—$C_1$-$C_6$-alkyl, —(C=O)—NR⁵—$C_3$-$C_6$-cyclo alkyl, —N(R⁴)—(C=O)—N(R⁵ᵃ)R⁵, —(C=O)—O—$C_1$-$C_6$-alkyl, —(C=O)—O—$C_3$-$C_6$-cycloalkyl.

According to a further aspect of the present invention R³ and R³ᵃ are the same or different and independently selected from one another represent a hydrogen atom, a halogen atom, —$C_1$-$C_6$-alkoxy, $C_1$-$C_3$-alkyl-, halo-$C_1$-$C_3$-alkyl-, particularly hydrogen, fluor, chlor, methyl, or methoxy.

According to a further aspect of the present invention R⁴ represents a hydrogen atom $C_1$-$C_6$-alkyl-, halo-$C_1$-$C_6$-alkyl-, —(C=O)—$C_1$-$C_6$-alkyl, —(C=O)—$C_3$-$C_6$-cycloalkyl, $C_1$-$C_6$-alkoxy-$C_1$-$C_6$-alkyl-, hydroxy-$C_1$-$C_6$-alkyl-, halo-$C_1$-$C_6$-alkoxy-$C_1$-$C_6$-alkyl-.

In accordance to a further aspect of the present invention R⁵, R⁵ᵃ are the same or different and independently selected from each other representing a hydrogen atom or a group selected from: $C_1$-$C_6$-alkyl-, $C_1$-$C_6$-alkyl-($C_1$-$C_6$-alkyl-)N $C_1$-$C_6$-alkyl-, $C_1$-$C_6$-alkyloxy-$C_1$-$C_6$-alkyl-, $C_3$-$C_6$-cycloalkyl-, 3- to 10-membered heterocycloalkyl-, aryl-, and heteroaryl-; wherein said $C_1$-$C_6$-alkyl-, $C_3$-$C_6$-cycloalkyl-, 3- to 10-membered heterocycloalkyl-, aryl- and heteroaryl- group is optionally substituted, identically or differently, with 1, 2 or 3 R⁸ groups; furthermore according to the invention N(R⁵ᵃ)R⁵ together represent in particular a 3- to 6-membered mono-heterocycloalkyl- group, said group being optionally substituted, identically or differently, with 1, 2 or 3 R⁸-groups.

In accordance to a further aspect of the present invention N(R⁵ᵃ)R⁵ is defined by R⁵ᵃ representing a hydrogen and R⁵ a group selected from: $C_1$-$C_6$-alkyl-, $C_1$-$C_6$-alkyl-($C_1$-$C_6$-alkyl-)N $C_1$-$C_6$-alkyl-, $C_1$-$C_6$-alkyloxy-$C_1$-$C_6$-alkyl-, $C_3$-$C_6$-cycloalky or R⁵ᵃ representing a $C_1$-$C_6$-alkyl-, and R⁵ a group selected from: $C_1$-$C_6$-alkyl-, $C_1$-$C_6$-alkyl-($C_1$-$C_6$-alkyl-)N $C_1$-$C_6$-alkyl-, $C_1$-$C_6$-alkyloxy-$C_1$-$C_6$-alkyl-, $C_3$-$C_6$-cycloalky-.

In accordance to a further aspect of the present invention N(R⁵ᵃ)R⁵ together represent:

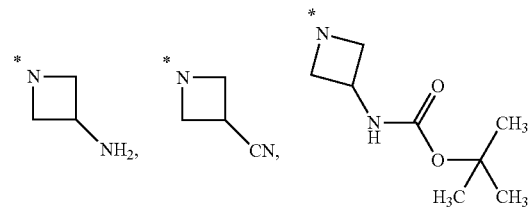

-continued

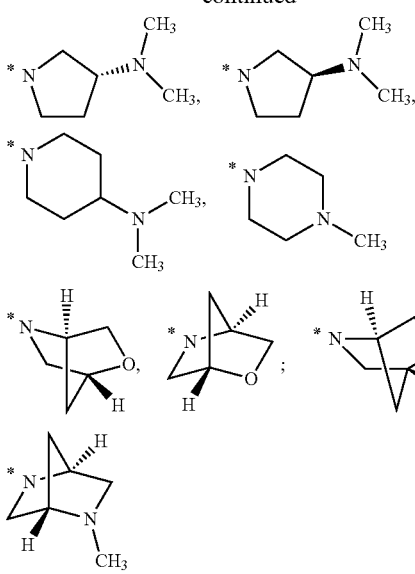

According to a further aspect of the present invention $R^7$ represents hydrogen, a group —$C_1$-$C_6$-alkyl, —(C=O)—O—$C_1$-$C_6$-alkyl, —(C=O)—N(H)—$C_1$-$C_6$-alkyl, —(C=O)—N(—$C_1$-$C_6$-alkyl)-$C_1$-$C_6$-alkyl, —$C_1$-$C_6$-alkyl-(C=O)—N(H)—$C_1$-$C_6$-alkyl, said group being optionally substituted, identically or differently, with 1, 2, 3 or 4 $R^8$-groups.

According to a further aspect of the present invention $R^8$ represents hydrogen, halogen, cyano, hydroxy, a group —$C_1$-$C_3$-alkyl, —$C_1$-$C_3$-alkyl-OH, —$C_1$-$C_6$-alkoxy.

According to a further aspect of the present invention $R^9$, $R^{9a}$ are the same or different and independently selected from each other represent hydrogen or a group —$C_1$-$C_3$-alkyl, in particular a methyl.

According to a further aspect of the present invention $R^9$ and $R^{9a}$ together represent —(CH$_2$—CH$_2$—CH$_2$—)—, —(CH$_2$—Z—CH$_2$—)—, —(CH$_2$—CH$_2$—CH$_2$—CH$_2$—)— and Z represents S(=O) or SO$_2$; particularly —(CH$_2$—CH$_2$—CH$_2$—CH$_2$—CH$_2$—)—, —(CH$_2$—CH$_2$—CF$_2$—CH$_2$—CH$_2$—)—, —(CH$_2$—CH$_2$—C(OH)CF$_3$—CH$_2$—CH$_2$—)—.

According to a further aspect of the present invention $R^9$ and $R^{9a}$ together represent —(CH$_2$—CH$_2$—Z—CH$_2$—CH$_2$—)— in which Z represents S, S(=O) or SO$_2$; particularly —(CH$_2$—CH$_2$—S—CH$_2$—CH$_2$—)—, —(CH$_2$—CH$_2$—SO$_2$—CH$_2$—CH$_2$—)—.

A further aspect of the present invention refers to the compounds of general formula (B):

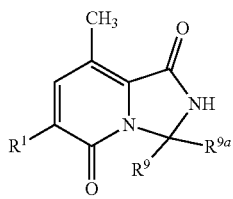

(B)

in which
$R^1$ represents a group selected from:

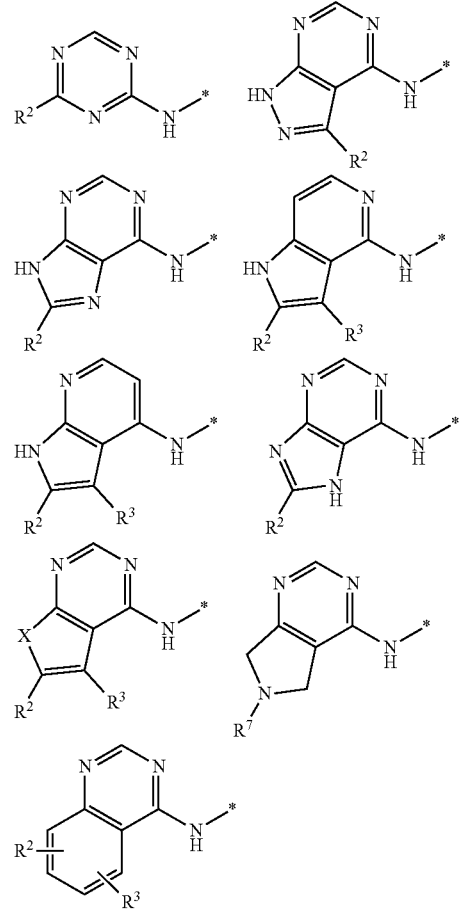

X represents $NR^7$, O or S and * indicates the connection to the rest of the molecule;
$R^2$ represents a hydrogen atom or a group $C_1$-$C_3$-alkyl, halo-$C_1$-$C_6$-alkyl-, —(C=O)—$C_1$-$C_6$-alkyl, —(C=O)—$C_3$-$C_6$-cycloalkyl, —N(H)$R^4$, —(C=O)OH, (C=O)—N($R^{5a}$)$R^5$, —(C=O)—$NR^5$—$C_1$-$C_6$-alkyl, —(C=O)—$NR^5$—$C_3$-$C_6$-cycloalkyl, —(C=O)—O—$C_1$-$C_6$-alkyl, —(C=O)—O—$C_3$-$C_6$-cycloalkyl, —(SO$_2$)—$C_1$-$C_6$-alkyl, —(SO$_2$)—$C_1$-$C_6$-aryl, -aryl;
$R^3$ represents a hydrogen atom, a halogen atom, cyano, hydroxy, —$C_1$-$C_6$-alkoxy or a group $C_1$-$C_3$-alkyl-;
$R^4$ represents a hydrogen atom, $C_1$-$C_6$-alkyl-, halo-$C_1$-$C_6$-alkyl-, —(C=O)—$C_1$-$C_6$-alkyl, —(C=O)—$C_3$-$C_6$-cycloalkyl, $C_1$-$C_6$-alkoxy $C_1$-$C_6$-alkyl-, hydroxy-$C_1$-$C_6$-alkyl-, halo-$C_1$-$C_6$-alkoxy-$C_1$-$C_6$-alkyl-, —(C=O)—N($R^{5a}$)$R^5$;
$R^5$, $R^{5a}$ are the same or different and independently selected from each other representing a hydrogen atom or a group selected from:
$C_1$-$C_6$-alkyl-, $C_1$-$C_6$-alkyl-($C_1$-$C_6$-alkyl-)N $C_1$-$C_6$-alkyl-, $C_1$-$C_6$-alkyloxy-$C_1$-$C_6$-alkyl-, $C_3$-$C_6$-cycloalkyl-, 3- to 10-membered heterocycloalkyl-, aryl-, and heteroaryl-; wherein said $C_1$-$C_6$-alkyl-, $C_3$-$C_6$-cycloalkyl-, 3- to 10-membered heterocycloalkyl-, aryl- and heteroaryl-group is optionally substituted, identically or differently, with 1, 2, 3, 4 or 5 $R^8$ groups;

or
N($R^{5a}$)$R^5$ together represent a 3- to 10-membered heterocycloalkyl- group, said group being optionally substituted, identically or differently, with 1, 2, 3, 4 or 5 $R^8$ groups;

$R^6$, $R^{6a}$ are the same or different and independently selected from one another represent a hydrogen, or fluoro;

$R^8$ represents hydrogen, halogen, cyano, hydroxy, a group —$C_1$-$C_3$-alkyl, —$C_1$-$C_3$-alkyl-OH, —$C_1$-$C_6$-alkoxy, —(C=O)—$C_1$-$C_6$-alkyl, —(C=O)—$C_3$-$C_6$-cycloalkyl, —C(C=O)—OH, —C(C=O)—O—$C_1$-$C_6$-alkyl, —$NH_2$, —N(H)—$C_1$-$C_3$-alkyl, —N(—$C_1$-$C_3$-alkyl)-$C_1$-$C_3$-alkyl, —(C=O)—N(H)—$C_1$-$C_6$-alkyl, —(C=O)—N(—$C_1$-$C_6$-alkyl)-$C_1$-$C_6$-alkyl, —NH(C=O)—O—$C_1$-$C_6$-alkyl;

$R^9$, $R^{9a}$ are the same or different and independently selected from each other, and represents a hydrogen or a group —$C_1$-$C_3$-alkyl, or together represent —($CH_2$—$CH_2$—)—, —($CH_2$—$CR^6(R^{6a})$—$CH_2$-)—, —($CH_2$—Z—$CH_2$-)—, —($CH_2$—$CH_2$—Z—$CH_2$—$CH_2$)—, —($CH_2$—$CH_2$—$CR^6(R^{6a})$—$CH_2$-)—, —($CH_2$—$CH_2$—$CR^6(R^{6a})$—$CH_2$—$CH_2$—)—;

Z represents $NR^7$, O, S, S(=O) or $SO_2$;

or a tautomer, an N oxide, a hydrate, a solvate, a salt thereof, or a mixture of same.

A further aspect of the present invention refers to the compounds of general formula (B):

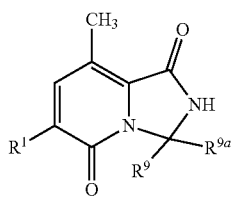

(B)

in which
$R^1$ represents a group selected from:

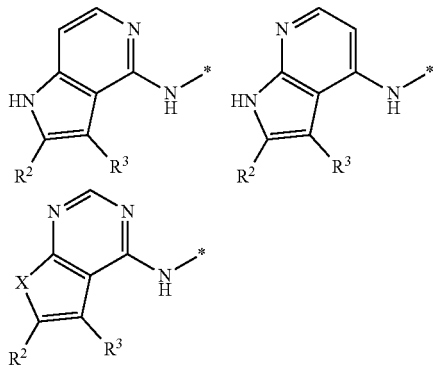

X represents $NR^7$, O or S and * indicates the connection to the rest of the molecule;

$R^2$ represents a hydrogen atom or a group $C_1$-$C_3$-alkyl, halo-$C_1$-$C_6$-alkyl-, —(C=O)—$C_1$-$C_6$-alkyl, —(C=O)—$C_3$-$C_6$-cycloalkyl, —N(H)$R^4$, —(C=O)OH, (C=O)—N($R^{5a}$)$R^5$, —(C=O)—$NR^5$—$C_1$-$C_6$-alkyl, —(C=O)—$NR^5$—$C_3$-$C_6$-cycloalkyl, —(C=O)—O—$C_1$-$C_6$-alkyl, —(C=O)—O—$C_3$-$C_6$-cycloalkyl, —($SO_2$)—$C_1$-$C_6$-alkyl, —($SO_2$)—$C_1$-$C_6$-aryl, -aryl;

$R^3$ represents a hydrogen atom, a halogen atom, cyano, hydroxy, —$C_1$-$C_6$-alkoxy or a group $C_1$-$C_3$-alkyl-;

$R^4$ represents a hydrogen atom, $C_1$-$C_6$-alkyl-, halo-$C_1$-$C_6$-alkyl-, —(C=O)—$C_1$-$C_6$-alkyl, —(C=O)—$C_3$-$C_6$-cycloalkyl, $C_1$-$C_6$-alkoxy $C_1$-$C_6$-alkyl-, hydroxy-$C_1$-$C_6$-alkyl-, halo-$C_1$-$C_6$-alkoxy-$C_1$-$C_6$-alkyl-, —(C=O)—N($R^{5a}$)$R^5$;

$R^5$, $R^{5a}$ are the same or different and independently selected from each other representing a hydrogen atom or a group selected from:

$C_1$-$C_6$-alkyl-, $C_1$-$C_6$-alkyl-($C_1$-$C_6$-alkyl-)N $C_1$-$C_6$-alkyl-, $C_1$-$C_6$-alkyloxy-$C_1$-$C_6$-alkyl-, $C_3$-$C_6$-cycloalkyl-, 3- to 10-membered heterocycloalkyl-, aryl-, and heteroaryl-; wherein said $C_1$-$C_6$-alkyl-, $C_3$-$C_6$-cycloalkyl-, 3- to 10-membered heterocycloalkyl-, aryl- and heteroaryl-group is optionally substituted, identically or differently, with 1, 2, 3, 4 or 5 $R^8$ groups;

or
N($R^{5a}$)$R^5$ together represent a 3- to 10-membered heterocycloalkyl- group,
said group being optionally substituted, identically or differently, with 1, 2, 3, 4 or 5 $R^8$ groups;

$R^6$, $R^{6a}$ are the same or different and independently selected from one another represent a hydrogen, or fluoro;

$R^8$ represents hydrogen, halogen, cyano, hydroxy, a group —$C_1$-$C_3$-alkyl, —$C_1$-$C_3$-alkyl-OH, —$C_1$-$C_6$-alkoxy, —(C=O)—$C_1$-$C_6$-alkyl, —(C=O)—$C_3$-$C_6$-cycloalkyl, —C(C=O)—OH, —C(C=O)—O—$C_1$-$C_6$-alkyl, —$NH_2$, —N(H)—$C_1$-$C_3$-alkyl, —N(—$C_1$-$C_3$-alkyl)-$C_1$-$C_3$-alkyl, —(C=O)—N(H)—$C_1$-$C_6$-alkyl, —(C=O)—N(—$C_1$-$C_6$-alkyl)-$C_1$-$C_6$-alkyl, —NH(C=O)—O—$C_1$-$C_6$-alkyl;

$R^9$, $R^{9a}$ are the same or different and independently selected from each other, and represents a hydrogen or a group —$C_1$-$C_3$-alkyl, or
together represent —($CH_2$—$CH_2$—)—, —($CH_2$—$CR_6(R_{6a})$—$CH_2$-)—, —($CH_2$—Z—$CH_2$-)—, —($CH_2$—$CH_2$—Z—$CH_2$—$CH_2$)—, —($CH_2$—$CH_2$—$CR_6(R^{6a})$—$CH_2$-)—, —($CH_2$—$CH_2$—$CR_6(R^{6a})$—$CH_2$—$CH_2$-)—;

Z represents $NR^7$, O, S, S(=O) or $SO_2$;

or a tautomer, an N oxide, a hydrate, a solvate, a salt thereof, or a mixture of same.

A further aspect of the present invention refers to the compounds of general formula (B):

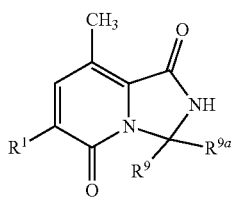

(B)

in which
$R^1$ represents

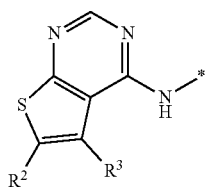

$R^2$ represents a hydrogen, —(C=O)OH, (C=O)—N($R^{5a}$)$R^5$, in which N($R^{5a}$)$R^5$ is defined by $R^{5a}$ representing a hydrogen and $R^5$ a group selected from: $C_1$-$C_6$-alkyl-, $C_1$-$C_6$-alkyl-($C_1$-$C_6$-alkyl-)N $C_1$-$C_6$-alkyl-, $C_1$-$C_6$-alkyloxy-$C_1$-$C_6$-alkyl-, $C_3$-$C_6$-cycloalky; or $R^{5a}$ representing a $C_1$-$C_6$-alkyl-, and $R^5$ a group selected from: $C_1$-$C_6$-alkyl-, $C_1$-$C_6$-alkyl-($C_1$-$C_6$-alkyl-)N $C_1$-$C_6$-alkyl-, $C_1$-$C_6$-alkyloxy-$C_1$-$C_6$-alkyl-, $C_3$-$C_6$-cycloalky; or N($R^{5a}$)$R^5$ together represent:

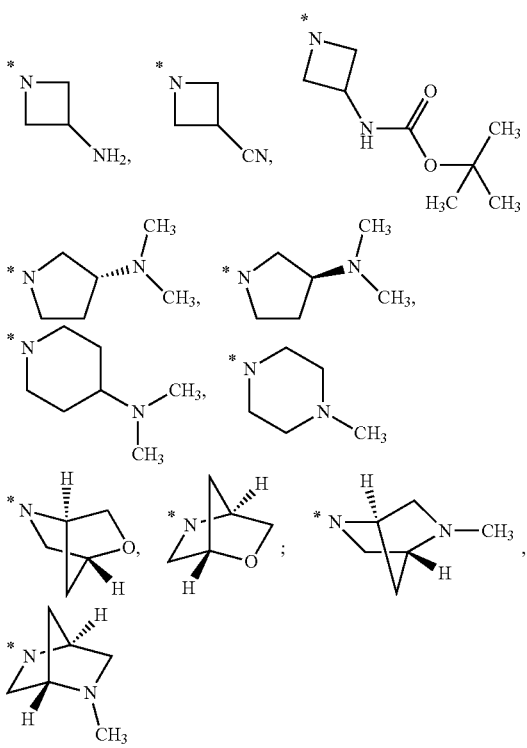

$R^3$ represents a hydrogen atom or methyl;
$R^9$, $R^{9a}$ are the same or different and independently selected from each other, and represents a hydrogen or a methyl, or together represent —($CH_2$—$CH_2$—$CH_2$_)—, —($CH_2$—$CH_2$—$CH_2$—$CH_2$_)—, —($CH_2$—$CH_2$—$CH_2$—$CH_2$—$CH_2$_)—, —($CH_2$—$CH_2$—$CF_2$—$CH_2$—$CH_2$_)—, —($CH_2$—$CH_2$—C(OH)$CF_3$—$CH_2$—$CH_2$_)—;

or a tautomer, an N oxide, a hydrate, a solvate, a salt thereof, or a mixture of same.

A further aspect of the present invention refers to the compounds of general formula (B):

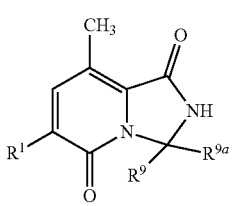

(B)

in which
$R^1$ represents

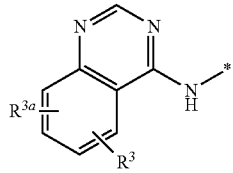

$R^3$ and $R^{3a}$ are the same or different and independently selected from one another represent a hydrogen atom, a halogen atom, cyano, hydroxy, —$C_1$-$C_6$-alkoxy, $C_1$-$C_3$-alkyl-, halo-$C_1$-$C_3$-alkyl-;

$R^9$, $R^{9a}$ are the same or different and independently selected from each other, and represents a hydrogen or a methyl, or together represent —($CH_2$—$CH_2$—$CH_2$_)—, —($CH_2$—$CH_2$—$CH_2$—$CH_2$_)—, —($CH_2$—$CH_2$—S—$CH_2$—$CH_2$)—, —($CH_2$—$CH_2$—$SO_2$—$CH_2$—$CH_2$)—, —($CH_2$—$CH_2$—$CH_2$—$CH_2$—$CH_2$_)—, —($CH_2$—$CH_2$—$CF_2$—$CH_2$—$CH_2$_)—, —($CH_2$—$CH_2$—C(OH)$CF_3$—$CH_2$—$CH_2$_)—;

or a tautomer, an N oxide, a hydrate, a solvate, a salt thereof, or a mixture of same.

A further aspect of the present invention refers to the compounds of general formula (Ib):

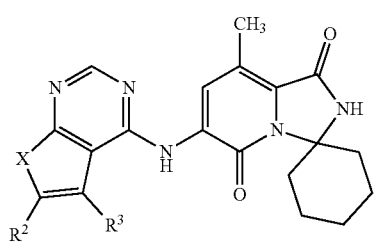

(Ib)

in which
X represents NH, O or S;
$R^2$ represents a hydrogen atom or a group $C_1$-$C_3$-alkyl, halo-$C_1$-$C_6$-alkyl-, —(C=O)—$C_1$-$C_6$-alkyl, —(C=O)—$C_3$-$C_6$-cycloalkyl, —N(H)$R^4$, —(C=O)OH, (C=O)—N($R^{5a}$)$R^5$, —(C=O)—$NR^5$—$C_1$-$C_6$-alkyl, —(C=O)—$NR^5$—$C_3$-$C_6$-cycloalkyl, —(C=O)—O—$C_1$-$C_6$-alkyl, —(C=O)—O—$C_3$-$C_6$-cycloalkyl, —($SO_2$)—$C_1$-$C_6$-alkyl, —($SO_2$)—$C_1$-$C_6$-aryl, -aryl;

$R^3$ represents a hydrogen atom, a halogen atom, cyano, hydroxy, —$C_1$-$C_6$-alkoxy or a group $C_1$-$C_3$-alkyl;

$R^4$ represents a hydrogen atom, $C_1$-$C_6$-alkyl-, halo-$C_1$-$C_6$-alkyl-, —(C=O)—$C_1$-$C_6$-alkyl, —(C=O)—$C_3$-$C_6$-cycloalkyl, $C_1$-$C_6$-alkoxy $C_1$-$C_6$-alkyl-, hydroxy-$C_1$-$C_6$-alkyl-, halo-$C_1$-$C_6$-alkoxy-$C_1$-$C_6$-alkyl-, —(C=O)—N($R^{5a}$)$R^5$;

$R^5$, $R^{5a}$ are the same or different and independently selected from each other representing a hydrogen atom or a group selected from:
$C_1$-$C_6$-alkyl-, $C_1$-$C_6$-alkyl-($C_1$-$C_6$-alkyl-)N $C_1$-$C_6$-alkyl-, $C_1$-$C_6$-alkyloxy-$C_1$-$C_6$-alkyl-, $C_3$-$C_6$-cycloalkyl-, 3- to 10-membered heterocycloalkyl-, aryl-, and heteroaryl-; wherein said $C_1$-$C_6$-alkyl-, $C_3$-$C_6$-cycloalkyl-, 3- to 10-membered heterocycloalkyl-, aryl- and heteroaryl-group is optionally substituted, identically or differently, with 1, 2, 3, 4 or 5 $R^8$ groups;

or N($R^{5a}$)$R^5$ together represent a 3- to 10-membered heterocycloalkyl- group,
said group being optionally substituted, identically or differently, with 1, 2, 3, 4 or 5 $R^8$-groups;
$R^8$ represents hydrogen, halogen, cyano, hydroxy, a group —$C_1$-$C_3$-alkyl, —$C_1$-$C_3$-alkyl-OH, —$C_1$-$C_6$-alkoxy, —(C=O)—$C_1$-$C_6$-alkyl, —(C=O)—$C_3$-$C_6$-cycloalkyl, —C(C=O)—OH, —C(C=O)—O—$C_1$-$C_6$-alkyl, —$NH_2$, —N(H)—$C_1$-$C_3$-alkyl, —N(—$C_1$-$C_3$-alkyl)-$C_1$-$C_3$-alkyl, —(C=O)—N(H)—$C_1$-$C_6$-alkyl, —(C=O)—N(—$C_1$-$C_6$-alkyl)-$C_1$-$C_6$-alkyl, —NH(C=O)—O—$C_1$-$C_6$-alkyl;
or a tautomer, an N oxide, a hydrate, a solvate, a salt thereof, or a mixture of same.

It is to be understood that the present invention relates to any sub combination within any embodiment or aspect of the present invention of compounds of general formula I, Ia and Ib, supra.

More particularly still, the present invention covers compounds of general formula I which are disclosed in the Examples section of this text, infra.

In accordance with another aspect, the present invention covers methods of preparing compounds of the present invention, said methods comprising the steps as described in the Experimental Section herein Synthesis of Compounds of General Formula (I) of the Present Invention Compounds of general formula (I) can be synthesized according to the general procedure depicted in Scheme 1, wherein LG stands for a leaving group such as a chlorine, bromine or iodine atom and PG stands for an optionally applied protective group.

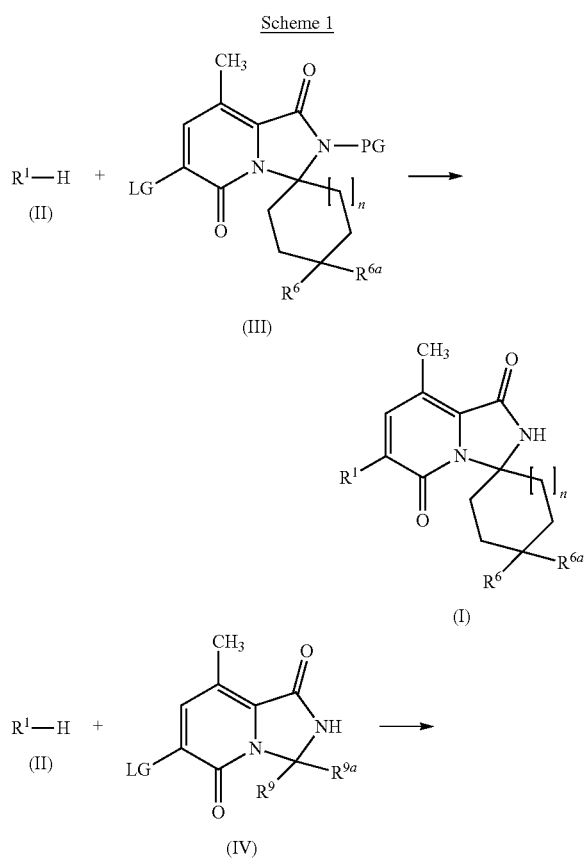

Scheme 1

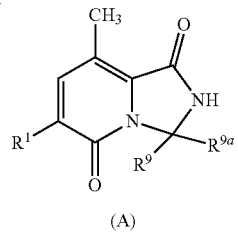

(A)

Scheme 1 exemplifies the main route that allows variations in n, $R^1$, $R^6$, $R^{6a}$, $R^9$ and $R^{9a}$. The coupling of compounds of formula (II) in which the reacting hydrogen atom is attached to a basic nitrogen atom with dihydroimidazopyridinediones such as (III) or (IV) can be achieved by nucleophilic aromatic substitution, Ullmann-type coupling conditions (see e.g. Honghua Rao et al., Chem. Eur. J. 2006, 12, 3636, and literature cited therein) or Buchwald-Hartwig type coupling conditions (see e.g. J. Y. Yoon et al., Synthesis 2009, (5), 815, and literature cited therein) to give, after removal of an optionally applied protective group PG, compounds of formulae (I) or (A).

Compounds of formula (II) are commercially available or can be synthesised by adapting procedures known to the person skilled in the art. The compounds of formula (II) can be used either as free base or as corresponding salt with organic or inorganic acids.

Compounds of formulae (III) or (IV) can be synthesised according to procedures described in WO 2015/200481.

Modification of any of the substituents, $R^1$, $R^6$, $R^{6a}$, $R^9$ and $R^{9a}$ can be achieved before and/or after the exemplified transformation. However, also other routes may be used to synthesise the target compounds, in accordance with common general knowledge of a person skilled in the art of organic synthesis.

Said modifications can be such as the introduction of protecting groups, cleavage of protecting groups, reduction or oxidation of functional groups, formation or cleavage of esters or carboxamides, halogenation, metallation, substitution or other reactions known to a person skilled in the art. These transformations include those which introduce a functionality which allows for further interconversion of substituents.

For example, the transformation of acids present in formulae (I), (II), (III), (IV) or (A) into amides can be achieved with a suitable coupling agent, such as HATU, TBTU, or 2,4,6-tripropyl-1,3,5,2,4,6-trioxatriphosphinane 2,4,6-trioxide (also known as T3P).

Interconversion of any of the substituents as defined herein for $R^1$, $R^6$, $R^{6a}$, $R^9$, $R^{9a}$ and PG can be achieved before and/or after the exemplified transformations as described supra.

Appropriate protecting groups and their introduction and cleavage are well-known to a person skilled in the art (see for example T. W. Greene and P. G. M. Wuts in Protective Groups in Organic Synthesis, $3^{rd}$ edition, Wiley 1999). Further, it is possible that two or more successive steps may be performed without work-up being performed between said steps, e.g. a "one-pot" reaction, as it is well-known to a person skilled in the art.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x CF$_3$COOH", "x Na$^+$", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

The IUPAC names of the examples and intermediates were generated using the program 'ACD/Name batch version 12.01' from ACD LABS, and were adapted if needed.

The various aspects of the invention described in this application are illustrated by the following examples which are not meant to limit the invention in any way.

Example 1

N-{4-[(8'-Methyl-1',5'-dioxo-1',5'-dihydro-2'H-spiro[cyclohexane-1,3'-imidazo[1,5-a]pyridin]-6'-yl)amino]-1,3,5-triazin-2-yl}cyclopropanecarboxamide

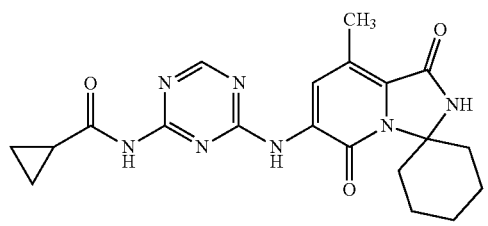 [SMILES: Cc1cc(Nc2ncnc(NC(=O)C3CC3)n2)c(=O)n2c1C(=O)NC21CCCCC1]

To a solution of 420 mg (1.35 mmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 266 mg (1.49 mmol) N-(4-amino-1,3,5-triazin-2-yl)cyclopropanecarboxamide (prepared according to example 1a) in 50 mL 1,4-dioxane was added 1.3 g cesium carbonate and the mixture was degassed and purged with argon several times. 84 mg 4,5-bis(diphenylphosphino)-9,9-dimethylxanthene, 69 mg 2-(dicyclohexyl-phosphino)-2',4',6'-triisopropylbiphenyl, 32 mg palladium(II)acetate and 132 mg tris(dibenzylideneacetone)dipalladium(0) were added and the mixture was stirred at 100° C. for 2.5 hours. Dichloromethane and methanol were added, the precipitate filtered off and the filtrate concentrated. The residue was purified by repeated flash chromatography (Biotage SNAP cartridge silica 25 g, methanol:dichloromethane) to give 193 mg (35%) of the title compound.

LC-MS: m/z=410.2 [M+H]$^+$.

$^1$H-NMR (400 MHz, DMSO-d6), δ [ppm]=0.84-0.94 (4H), 1.23 (1H), 1.45 (2H), 1.56-1.80 (5H), 2.19 (1H), 2.48 (3H), 2.96 (2H), 8.52 (1H), 8.65 (1H), 8.91 (1H), 10.18 (1H), 11.24 (1H).

Example 1a

N-(4-Amino-1,3,5-triazin-2-yl)cyclopropanecarboxamide

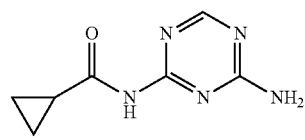

A mixture of 20 g (136 mmol) 1,3,5-triazine-2,4-diamine hydrochloride (CAS-No of free base: 504-08-5), 500 mL water and 20 g (130 mmol) cyclopropanecarbonyl cyclopropanecarboxylate was stirred for 1 day at RT. 20 g (130 mmol) cyclopropanecarbonyl cyclopropanecarboxylate was added into the reaction and stirring was continued for 1 day at room temperature. Another batch of 20 g (130 mmol) cyclopropanecarbonyl cyclopropanecarboxylate was added and stirring was continued for 3 days at room temperature. The above procedure was repeated once and the solutions of two batch reaction were combined. The solids were filtered off and the crude product purified by Flash-Prep-HPLC (column C18 silica gel; mobile phase, ACN/water (0.05% NH4OH)=5% increasing to ACN/water (0.05% NH4OH)=20% within 12 min; Detector, UV 254 nm) to give 10.5 g (22%) of the title compound.

LC-MS: m/z=180 [M+H]$^+$.

Example 2

6'-[(4-Amino-1,3,5-triazin-2-yl)amino]-8'-methyl-2'H-spiro[cyclohexane-1,3'-imidazo[1,5-a]pyridine]-1',5'-dione

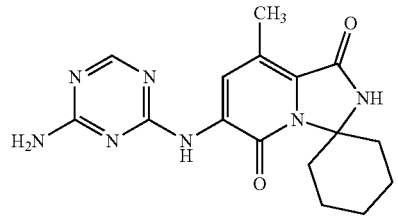 [SMILES: Cc1cc(Nc2ncnc(N)n2)c(=O)n2c1C(=O)NC21CCCCC1]

A mixture of 190 mg (464 µmol) N-{4-[(8'-methyl-1',5'-dioxo-1',5'-dihydro-2'H-spiro[cyclohexane-1,3'-imidazo[1,5-a]pyridin]-6'-yl)amino]-1,3,5-triazin-2-yl}cyclopropanecarboxamide (prepared according to example 1) 4.4 mL tetrahydrofuran, 8.8 mL ethanol and 4.4 mL potassium hydroxide solution (50% in water) was stirred at RT overnight. The mixture was extracted with ethyl acetate, washed with water and dried over sodium sulfate. After filtration and removal of the solvents 129 mg (81%) of the title compound was isolated.

LC-MS: m/z=342.2 [M+H]$^+$.

$^1$H-NMR (400 MHz, DMSO-d6), δ [ppm]=1.23 (1H), 1.44 (2H), 1.56-1.78 (5H), 2.47 (3H), 2.95 (2H), 7.46 (2H), 8.06 (1H), 8.27 (1H), 8.46 (1H), 10.13 (1H).

Example 3

1-{4-[(8'-Methyl-1',5'-dioxo-1',5'-dihydro-2'H-spiro[cyclohexane-1,3'-imidazo[1,5-a]pyridin]-6'-yl)amino]-1,3,5-triazin-2-yl}-3-propylurea

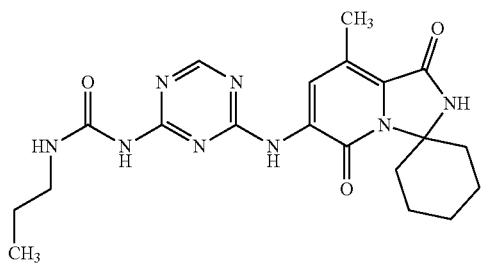 [SMILES: CCCNC(=O)Nc1ncnc(Nc2cc(C)c3n(c2=O)C2(CCCCC2)NC3=O)n1]

To a solution of 6'-[(4-amino-1,3,5-triazin-2-yl)amino]-8'-methyl-2'H-spiro[cyclohexane-1,3'-imidazo[1,5-a]pyridine]-1',5'-dione (prepared according to example 2) in 0.5 mL DMA was added 5.6 mg sodium hydride (60% oil dispersion) and the mixture was stirred at RT for 15 minutes. 13 µL 1-isocyanatopropane were added and stirring continued for 3 hours. The mixture was concentrated, water was added, the precipitate filtered off and dried to give 16 mg (29%) of the title compound.

LC-MS: m/z=427.2 [M+H]+.

$^1$H-NMR (400 MHz, DMSO-d6), δ [ppm]=0.89 (3H), 1.23 (1H), 1.46 (2H), 1.51 (2H), 1.58-1.79 (5H), 2.48 (3H), 2.97 (2H), 3.18 (2H), 8.52 (1H), 8.57 (1H), 8.94 (1H), 10.15 (1H), 10.19 (1H).

Example 4

8'-Methyl-6'-(quinolin-4-ylamino)-2'H-spiro[cyclohexane-1,3'-imidazo[1,5-a]pyridine]-1',5'-dione

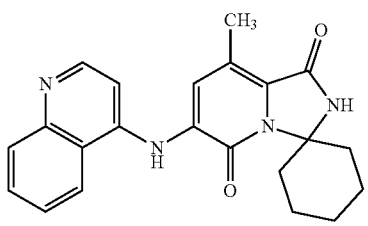 [SMILES: Cc1cc(Nc2ccnc3ccccc23)c(=O)n2c1C(=O)NC21CCCCC1]

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 51 mg (353 µmol) quinolin-4-amine (CAS-No: 578-68-7) in 12 mL 1,4-dioxane was added 314 mg cesium carbonate and the mixture was degassed and purged with argon several times. 20 mg 4,5-bis(diphenylphosphino)-9,9-dimethylxanthene, 16 mg 2-(dicyclohexyl-phosphino)-2',4',6'-triisopropylbiphenyl, 7.7 mg palladium(II)acetate and 31 mg tris(dibenzylideneacetone)dipalladium(0) were added and the mixture was stirred at 100° C. for 2 hours. Dichloromethane and methanol were added, the precipitate filtered off and the filtrate concentrated. The residue was purified by flash chromatography (Biotage SNAP cartridge silica 25 g, methanol:dichloromethane) to give 70 mg (55%) of the title compound.

LC-MS: m/z=375.4 [M+H]+.

$^1$H-NMR (400 MHz, DMSO-d6), δ [ppm]=1.24 (1H), 1.50 (2H), 1.59-1.82 (5H), 2.45 (3H), 3.03 (2H), 7.35 (1H), 7.37 (1H), 7.60 (1H), 7.76 (1H), 7.98 (1H), 8.17 (1H), 8.60 (1H), 8.70 (1H), 10.13 (1H).

Example 5

8'-Methyl-6'-(thieno[2,3-d]pyrimidin-4-ylamino)-2'H-spiro[cyclohexane-1,3'-imidazo[1,5-a]pyridine]-1',5'-dione

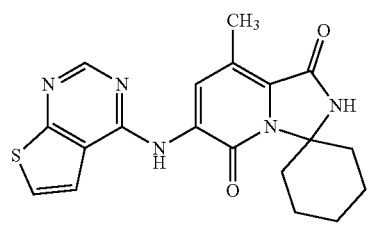 [SMILES: Cc1cc(Nc2ncnc3sccc23)c(=O)n2c1C(=O)NC21CCCCC1]

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 53 mg (353 µmol) thieno[2,3-d]pyrimidin-4-amine (CAS-No: 14080-56-9) in 12 mL 1,4-dioxane was added 314 mg cesium carbonate and the mixture was degassed and purged with argon several times. 20 mg 4,5-bis(diphenylphosphino)-9,9-dimethylxanthene, 16 mg 2-(dicyclohexyl-phosphino)-2',4',6'-triisopropylbiphenyl, 7.7 mg palladium(II)acetate and 31 mg tris(dibenzylideneacetone)dipalladium(0) were added and the mixture was stirred at 100° C. for 2 hours. Dichloromethane and methanol were added, the precipitate filtered off and the filtrate concentrated. The residue was purified by flash chromatography (Biotage SNAP cartridge silica 25 g, methanol:dichloromethane) to give 68 mg (53%) of the title compound.

LC-MS: m/z=382.4 [M+H]+.

$^1$H-NMR (400 MHz, DMSO-d6), δ [ppm]=1.24 (1H), 1.49 (2H), 1.57-1.81 (5H), 2.50 (3H*), 3.01 (2H), 7.83 (2H), 8.62 (1H), 8.69 (1H), 9.05 (1H), 10.21 (1H);

*: hidden by solvent peak.

Example 6

8'-Methyl-6'-(7H-pyrrolo[2,3-d]pyrimidin-4-ylamino)-2'H-spiro[cyclohexane-1,3'-imidazo[1,5-a]pyridine]-1',5'-dione

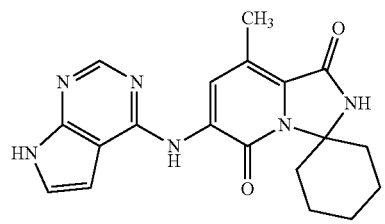 [SMILES: Cc1cc(Nc2ncnc3[nH]ccc23)c(=O)n2c1C(=O)NC21CCCCC1]

To a solution of 100 mg (321 µmol) 6'-bromo-8'-methyl-2'H-spiro[cyclohexane-1,3'-imidazo[1,5-a]pyridine]-1',5'- dione (CAS-No: 1849592-70-6; PCT Int. Appl. (2015), WO 2015200481) and 47 mg (353 µmol) 7H-pyrrolo[2,3-d]pyrimidin-4-amine (CAS-No: 1500-85-2) in 12 mL 1,4-dioxane was added 314 mg cesium carbonate and the mixture was degassed and purged with argon several times. 20 mg 4,5-bis(diphenylphosphino)-9,9-dimethylxanthene, 16 mg 2-(dicyclohexyl-phosphino)-2',4',6'-triisopropylbiphenyl, 7.7 mg palladium(II)acetate and 31 mg tris(dibenzylideneacetone)dipalladium(0) were added and the mixture was stirred at 100° C. for 2 hours. Dichloromethane and methanol were added, the precipitate filtered off and the filtrate concentrated. The residue was purified by flash chromatography (Biotage SNAP cartridge silica 25 g, methanol:dichloromethane) to give 26 mg (21%) of the title compound.

LC-MS: m/z=365.4 [M+H]+.

1H-NMR (400 MHz, DMSO-d6), δ [ppm]=1.24 (1H), 1.48 (2H), 1.57-1.80 (5H), 2.47 (3H), 3.02 (2H), 6.77 (1H), 7.37 (1H), 8.46 (1H), 8.61 (1H), 8.72 (1H), 10.13 (1H), 12.02 (1H).

Example 7

8'-Methyl-6'-(1H-pyrazolo[3,4-d]pyrimidin-4-ylamino)-2'H-spiro[cyclohexane-1,3'-imidazo[1,5-a]pyridine]-1',5'-dione

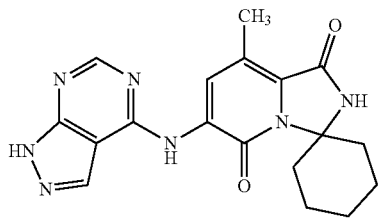

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 47 mg (353 µmol) 1H-pyrazolo[3,4-d]pyrimidin-4-amine (CAS-No: 2380-63-4) in 12 mL 1,4-dioxane was added 314 mg cesium carbonate and the mixture was degassed and purged with argon several times. 20 mg 4,5-bis(diphenylphosphino)-9,9-dimethylxanthene, 16 mg 2-(dicyclohexyl-phosphino)-2',4',6'-triisopropylbiphenyl, 7.7 mg palladium(II)acetate and 31 mg tris(dibenzylideneacetone)dipalladium(0) were added and the mixture was stirred at 100° C. for 2.5 hours. Dichloromethane and methanol were added, the precipitate filtered off and the filtrate concentrated. The residue was purified by flash chromatography (Biotage SNAP cartridge silica 25 g, methanol:dichloromethane) to give 14 mg (11%) of the title compound.

LC-MS: m/z=366.3 [M+H]+.

1H-NMR (400 MHz, DMSO-d6), δ [ppm]=1.23 (1H), 1.49 (2H), 1.59-1.80 (5H), 2.51 (3H*), 3.02 (2H), 8.55 (2H), 8.68 (1H), 9.38 (1H), 10.20 (1H), 13.79 (1H);

*: hidden by solvent peak.

Example 8

8'-Methyl-6'-(quinazolin-4-ylamino)-2'H-spiro[cyclohexane-1,3'-imidazo[1,5-a]pyridine]-1',5'-dione

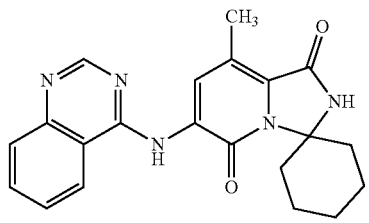 [SMILES: Cc1cc(Nc2ncnc3ccccc23)c(=O)n2c1C(=O)NC21CCCCC1]

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 51 mg (353 µmol) quinazolin-4-amine (CAS-No: 15018-66-3) in 12 mL 1,4-dioxane was added 314 mg cesium carbonate and the mixture was degassed and purged with argon several times. 20 mg 4,5-bis(diphenylphosphino)-9,9-dimethylxanthene, 16 mg 2-(dicyclohexyl-phosphino)-2',4',6'-triisopropylbiphenyl, 7.7 mg palladium(II)acetate and 31 mg tris(dibenzylideneacetone)dipalladium(0) were added and the mixture was stirred at 100° C. for 2.5 hours. Dichloromethane and methanol were added, the precipitate filtered off and the filtrate concentrated. The residue was purified by flash chromatography (Biotage SNAP cartridge silica 25 g, methanol:dichloromethane) to give 68 mg (54%) of the title compound.

LC-MS: m/z=376.4 [M+H]+.

1H-NMR (400 MHz, DMSO-d6), δ [ppm]=1.25 (1H), 1.51 (2H), 1.60-1.81 (5H), 2.51 (3H*), 3.03 (2H), 7.72 (1H), 7.88 (1H), 7.94 (1H), 8.24 (1H), 8.73 (1H), 8.83 (1H), 9.41 (1H), 10.24 (1H);

*: hidden by solvent peak.

Example 9

4-[(8'-Methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid

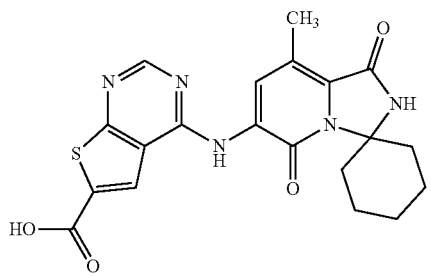 [SMILES: Cc1cc(Nc2ncnc3sc(C(=O)O)cc23)c(=O)n2c1C(=O)NC21CCCCC1]

A mixture of 293 mg (646 µmol) ethyl 4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylate (prepared according to example 9a) 10 mL tetrahydrofuran, 10 mL ethanol and 12.9 mL lithium hydroxide solution (1M in water) was stirred at RT overnight. Water was added and the mixture was acidified with hydrochloric acid. The precipitate was filtered off, washed with water and dried to give 250 mg (86%) of the title compound.

LC-MS: m/z=426.4 [M+H]+.

1H-NMR (400 MHz, DMSO-d6), δ [ppm]=1.24 (1H), 1.49 (2H), 1.58-1.81 (5H), 2.50 (3H*), 3.01 (2H), 8.49 (1H), 8.54 (1H), 8.71 (1H), 9.46 (1H), 10.24 (1H), 13.76 (1H);

*: hidden by solvent peak.

Example 9a

Ethyl 4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylate

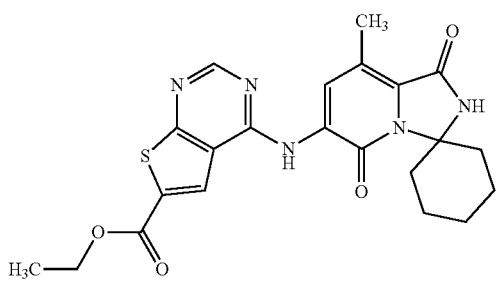 [SMILES: CCOC(=O)c1cc2c(Nc3cc(C)c4n(c3=O)C3(CCCCC3)NC4=O)ncnc2s1]

To a solution of 700 mg (2.25 mmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 518 mg (2.45 mmol) methyl 4-aminothieno[2,3-d]pyrimidine-6-carboxylate (CAS-No: 155087-15-3) in 84 mL 1,4-dioxane were added 2.2 g cesium carbonate and the mixture was degassed and purged with argon several times. 139 mg 4,5-bis(diphenylphosphino)-9,9-dimethylxanthene, 115 mg 2-(dicyclohexyl-phosphino)-2',4',6'-triisopropylbiphenyl, 54 mg palladium(II)acetate and 220 mg tris(dibenzylideneacetone)dipalladium(0) were added and the mixture was stirred at 100° C. for 2 hours. Dichloromethane and ethanol were added and the mixture concentrated. The residue was purified by repeated flash chromatography (Biotage SNAP cartridge silica 100 g, ethanol:dichloromethane) to product digested with dichloromethane and methanol to give 293 mg (29%) of the title compound.

LC-MS: m/z=454.4 [M+H]+.

Example 10

N,N-Dimethyl-4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxamide

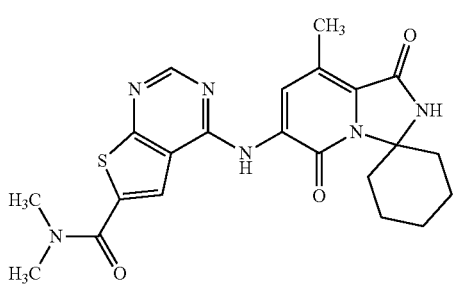 [SMILES: Cc1cc(Nc2ncnc3sc(C(=O)N(C)C)cc23)c(=O)n2c1C(=O)NC21CCCCC1]

A mixture of 50 mg (118 μmol) 4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 9), 1.9 mL N,N-dimethylacetamide, 164 μL N-ethyl-N-isopropylpropan-2-amine, 235 μL N-methylmethanamine (2M in tetrahydrofuran) and 210 μL 2,4,6-tripropyl-1,3,5,2,4,6-trioxatriphosphinane 2,4,6-trioxide solution (50% in N,N-dimethylformamide) was stirred at RT for 3 hours. The mixture was concentrated, water was added and the precipitate digested with ethanol and diethyl ether to give after drying 39.0 mg (70%) of the title compound.

LC-MS: m/z=453.4 [M+H]+.

1H-NMR (400 MHz, DMSO-d6), δ [ppm]=1.23 (1H), 1.49 (2H), 1.59-1.80 (5H), 2.50 (3H*), 2.97-3.19 (5H), 3.23-3.45 (3H), 8.28 (1H), 8.56 (1H), 8.70 (1H), 9.35 (1H), 10.23 (1H);

*: hidden by solvent peak.

Example 11

N-(2-Methoxyethy)-N-methyl-4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxamide

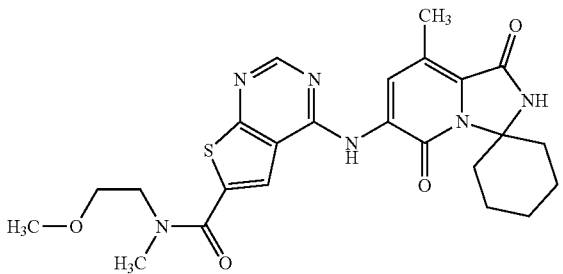 [SMILES: COCCN(C)C(=O)c1cc2c(Nc3cc(C)c4n(c3=O)C3(CCCCC3)NC4=O)ncnc2s1]

A mixture of 50 mg (118 μmol) 4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 9), 1.9 mL N,N-dimethylacetamide, 164 μL N-ethyl-N-isopropylpropan-2-amine, 50 μL N-(methoxyethyl)methylamine and 210 μL 2,4,6-tripropyl-1,3,5,2,4,6-trioxatriphosphinane 2,4,6-trioxide solution (50% in N,N-dimethylformamide) was stirred at RT overnight. The mixture was concentrated, water was added and the precipitate digested with ethanol and diethyl ether to give after drying 41.0 mg (67%) of the title compound.

LC-MS: m/z=497.2 [M+H]+.

1H-NMR (400 MHz, CHLOROFORM-d), δ [ppm]=1.46 (3H), 1.64 (2H), 1.84 (1H), 2.03 (2H), 2.63 (3H), 3.15 (2H), 3.21-3.40 (3H), 3.42 (3H), 3.65 (2H), 3.76 (2H), 7.33 (1H), 7.71 (1H), 8.76 (1H), 8.78 (1H), 8.85 (1H).

Example 12

8'-Methyl-6'-({6-[(4-methylpiperazin-1-yl)carbonyl]thieno[2,3-d]pyrimidin-4-yl}amino)-2'H-spiro[cyclohexane-1,3'-imidazo[1,5-a]pyridine]-1',5'-dione

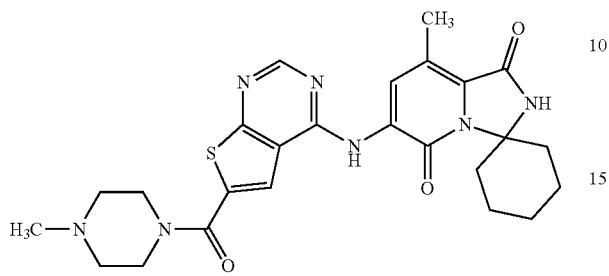

A mixture of 50 mg (118 μmol) 4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 9), 1.9 mL N,N-dimethylacetamide, 164 μL N-ethyl-N-isopropylpropan-2-amine, 47 mg 1-methylpiperazine and 210 μL 2,4,6-tripropyl-1,3,5,2,4,6-trioxatriphosphinane 2,4,6-trioxide solution (50% in N,N-dimethylformamide) was stirred at RT overnight. The mixture was concentrated, water was added and the precipitate digested with ethanol and diethyl ether to give after drying 42.0 mg (67%) of the title compound.

LC-MS: m/z=508.2 [M+H]$^+$.

$^1$H-NMR (400 MHz, CHLOROFORM-d), δ [ppm]=1.46 (2H), 1.60 (1H), 1.64 (2H), 1.84 (1H), 2.03 (2H), 2.35 (3H), 2.48 (4H), 2.63 (3H), 3.15 (2H), 3.79 (4H), 7.41 (1H), 7.55 (1H), 8.75 (1H), 8.78 (1H), 8.85 (1H).

Example 13

N-[2-(Dimethylamino)ethyl]-N-methyl-4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxamide

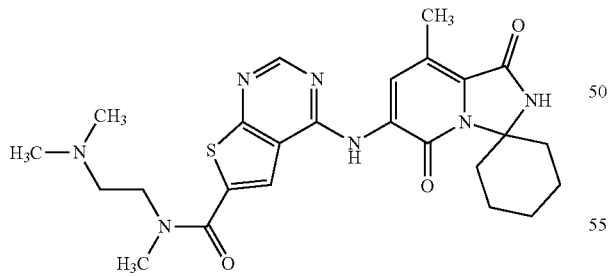

A mixture of 50 mg (118 μmol) 4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 9), 1.9 mL N,N-dimethylacetamide, 164 μL N-ethyl-N-isopropylpropan-2-amine, 61 μL N,N,N-trimethylethylendiamin and 210 μL 2,4,6-tripropyl-1,3,5,2,4,6-trioxatriphosphinane 2,4,6-trioxide solution (50% in N,N-dimethylformamide) was stirred at RT overnight. The mixture was concentrated, and the residue purified by flash chromatography (Biotage SNAP cartridge NH 11 g, methanol:dichloromethane) to give 33.0 mg (52%) of the title compound.

LC-MS: m/z=510.6 [M+H]$^+$.

$^1$H-NMR (400 MHz, CHLOROFORM-d), δ [ppm]=1.47 (2H), 1.57 (1H), 1.64 (2H), 1.85 (1H), 2.01 (2H), 2.28 (6H), 2.58 (2H), 2.63 (3H), 3.15 (2H), 3.26 (3H), 3.68 (2H), 7.55 (1H), 7.69 (1H), 8.76 (1H), 8.78 (1H), 8.85 (1H).

Example 14

6'-[(6-{[4-(Dimethylamino)piperidin-1-yl]carbonyl}thieno[2,3-d]pyrimidin-4-yl)amino]-8'-methyl-2'H-spiro[cyclohexane-1,3'-imidazo[1,5-a]pyridine]-1',5'-dione

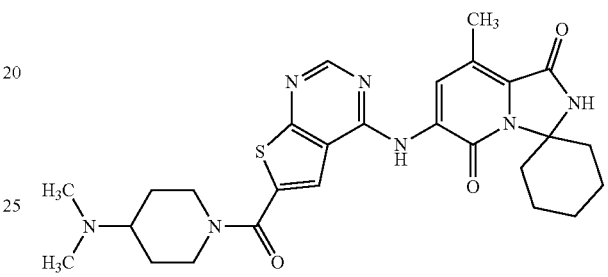

A mixture of 50 mg (118 μmol) 4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 9), 1.9 mL N,N-dimethylacetamide, 164 μL N-ethyl-N-isopropylpropan-2-amine, 60 mg 4-(dimethylamino)piperidine and 210 μL 2,4,6-tripropyl-1,3,5,2,4,6-trioxatriphosphinane 2,4,6-trioxide solution (50% in N,N-dimethylformamide) was stirred at RT overnight. The mixture was concentrated, and the residue purified by flash chromatography (Biotage SNAP cartridge NH 11 g, methanol:dichloromethane) to give 25.0 mg (63%) of the title compound.

LC-MS: m/z=536.6 [M+H]$^+$.

$^1$H-NMR (400 MHz, CHLOROFORM-d), δ [ppm]=1.21-1.35 (2H), 1.40-1.60 (7H), 1.64 (2H), 1.82-2.07 (5H), 2.32 (6H), 2.47 (1H), 2.63 (3H), 3.15 (2H), 7.22 (1H), 7.56 (1H), 8.75 (1H), 8.78 (1H), 8.84 (1H).

Example 15

5-Methyl-4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid

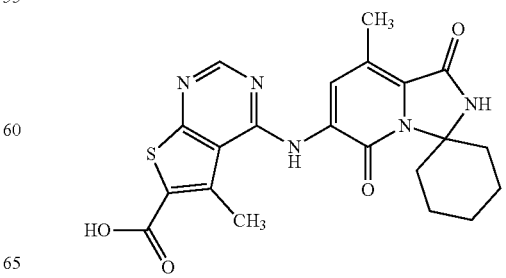

A mixture of 357 mg (764 μmol) ethyl 5-methyl-4-[(8'-methyl-1',5'-dioxo-01',5'-dihydro-2'H-spiro[cyclohexane-1,3'-imidazo[1,5-a]pyridin]-6'-yl)amino]thieno[2,3-d]pyrimidine-6-carboxylate (prepared according to example 15a) 11.8 mL tetrahydrofuran, 11.8 mL ethanol and 15.3 mL lithium hydroxide solution (1M in water) was stirred at RT overnight. Water was added and the mixture was acidified with hydrochloric acid. The precipitate was filtered off, washed with water and dried to give 273 mg (77%) of the title compound.

LC-MS: m/z=440.4 [M+H]$^+$.

$^1$H-NMR (400 MHz, DMSO-d6), δ [ppm]=1.28 (1H), 1.50 (2H), 1.59-1.73 (3H), 1.77 (2H), 2.50 (3H*), 2.99 (2H), 3.10 (3H), 8.75 (2H), 9.35 (1H), 10.23 (1H), 13.80 (1H);

*: hidden by solvent peak.

Example 15a

Ethyl 5-methyl-4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylate

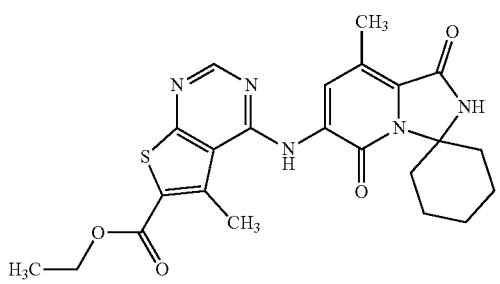 [SMILES: CCOC(=O)c1sc2ncnc(Nc3cc(C)c4n(c3=O)C3(CCCCC3)NC4=O)c2c1C]

To a solution of 700 mg (2.25 mmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 587 mg (2.45 mmol) ethyl 4-amino-5-methyl-5,6-dihydrothieno[2,3-d]pyrimidine-6-carboxylate (purchased from Santai Labs Inc.; can also be prepared according to Indian Journal of Chemistry, Section B: 1976, 14, 357-360) in 84 mL 1,4-dioxane was added 2.2 g cesium carbonate and the mixture was degassed and purged with argon several times. 139 mg 4,5-bis(diphenylphosphino)-9,9-dimethylxanthene, 115 mg 2-(dicyclohexyl-phosphino)-2',4',6'-triisopropylbiphenyl, 54 mg palladium(II)acetate and 220 mg tris(dibenzylideneacetone)dipalladium(0) were added and the mixture was stirred at 100° C. for 2 hours. Water was added, the precipitate filtered off and washed with methanol/dichloromethane. The aqueous layer was extracted with methanol/dichloromethane and the combined organic layers concentrated. The residue was purified by flash chromatography (Biotage SNAP cartridge silica 50 g, methanol:dichloromethane) to give 357 mg (34%) of the title compound.

LC-MS: m/z=468.5 [M+H]$^+$.

Example 16

N,N,5-trimethyl-4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxamide

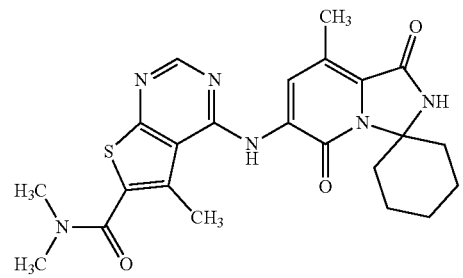 [SMILES: Cc1cc(Nc2ncnc3sc(C(=O)N(C)C)c(C)c23)c(=O)n2c1C(=O)NC21CCCCC1]

A mixture of 53 mg (121 μmol) 5-methyl-4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 15), 1.9 mL N,N-dimethylacetamide, 168 μL N-ethyl-N-isopropylpropan-2-amine, 241 μL N-methylmethanamine (2M in tetrahydrofuran) and 215 μL 2,4,6-tripropyl-1,3,5,2,4,6-trioxatriphosphinane 2,4,6-trioxide solution (50% in N,N-dimethylformamide) was stirred at RT overnight. Another portion N-methylmethanamine (2M in tetrahydrofuran) was added and stirring continued at 50° C. for 3 hours. Water was added, the precipitate filtered off and dried to give 50 mg (80%) of the title compound.

LC-MS: m/z=467.5 [M+H]$^+$.

$^1$H-NMR (400 MHz, DMSO-d6), δ [ppm]=1.27 (1H), 1.49 (2H), 1.59-1.72 (3H), 1.76 (2H), 2.52 (3H*), 2.70 (3H), 2.91-3.10 (8H), 8.73 (1H), 8.77 (1H), 9.25 (1H), 10.22 (1H);

*: hidden by solvent peak.

Example 17

N-[2-(dimethylamino)ethyl]-N,5-dimethyl-4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxamide

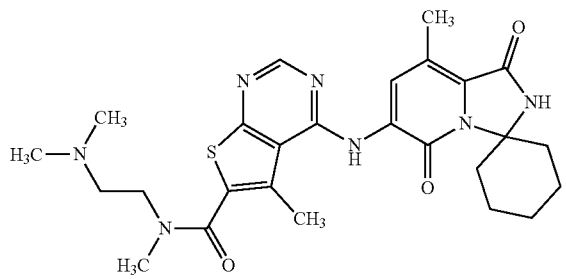 [SMILES: Cc1cc(Nc2ncnc3sc(C(=O)N(C)CCN(C)C)c(C)c23)c(=O)n2c1C(=O)NC21CCCCC1]

A mixture of 53 mg (121 µmol) 5-methyl-4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 15), 1.9 mL N,N-dimethylacetamide, 168 µL N-ethyl-N-isopropylpropan-2-amine, 63 µL N,N,N-trimethylethylendiamin and 215 µL 2,4,6-tripropyl-1,3,5,2,4,6-trioxatriphosphinane 2,4,6-trioxide solution (50% in N,N-dimethylformamide) was stirred at RT overnight. Water was added, the precipitate filtered off and dried to give 52 mg (78%) of the title compound.

LC-MS: m/z=524.6 [M+H]$^+$.

$^1$H-NMR (400 MHz, DMSO-d6), δ [ppm]=1.28 (1H), 1.49 (2H), 1.59-1.72 (3H), 1.76 (2H), 1.99 (2H), 2.23 (3H), 2.52 (6H*), 2.72 (3H), 2.92-3.07 (5H), 3.43 (1H), 3.61 (1H), 8.73 (1H), 8.77 (1H), 9.25 (1H), 10.22 (1H);

*: hidden by solvent peak.

Example 18

N-(2-methoxyethyl)-N,5-dimethyl-4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxamide

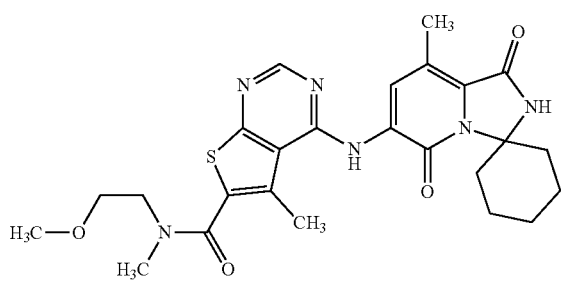 [SMILES: COCCN(C)C(=O)c1sc2ncnc(Nc3cc(C)c4n(c3=O)C3(CCCCC3)NC4=O)c2c1C]

A mixture of 53 mg (121 µmol) 5-methyl-4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 15), 1.9 mL N,N-dimethylacetamide, 168 µL N-ethyl-N-isopropylpropan-2-amine, 52 µL N-(methoxyethyl)methylamine and 215 µL 2,4,6-tripropyl-1,3,5,2,4,6-trioxatriphosphinane 2,4,6-trioxide solution (50% in N,N-dimethylformamide) was stirred at RT overnight. Water was added, the precipitate filtered off and dried to give 49 mg (76%) of the title compound.

LC-MS: m/z=511.5 [M+H]$^+$.

$^1$H-NMR (400 MHz, DMSO-d6), δ [ppm]=1.28 (1H), 1.49 (2H), 1.59-1.72 (3H), 1.76 (2H), 2.52 (3H*), 2.69 (3H), 2.94-3.06 (5H), 3.18-3.73 (7H), 8.73 (1H), 8.77 (1H), 9.24 (1H), 10.22 (1H);

*: hidden by solvent peak.

Example 19

8'-methyl-6'-({5-methyl-6-[(4-methylpiperazin-1-yl)carbonyl]thieno[2,3-d]pyrimidin-4-yl}amino)-2'H-spiro[cyclohexane-1,3'-imidazo[1,5-a]pyridine]-1',5'-dione

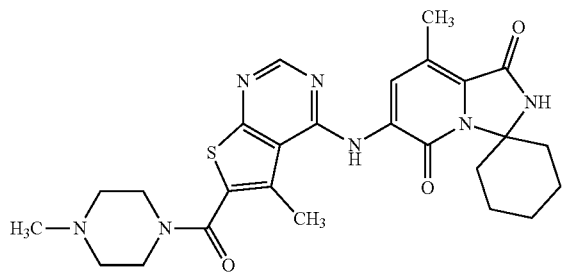 [SMILES: Cc1cc(Nc2ncnc3sc(C(=O)N4CCN(C)CC4)c(C)c23)c(=O)n2c1C(=O)NC21CCCCC1]

A mixture of 53 mg (121 µmol) 5-methyl-4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 15), 1.9 mL N,N-dimethylacetamide, 168 µL N-ethyl-N-isopropylpropan-2-amine, 48 mg 1-methylpiperazine and 215 µL 2,4,6-tripropyl-1,3,5,2,4,6-trioxatriphosphinane 2,4,6-trioxide solution (50% in N,N-dimethylformamide) was stirred at RT overnight. Another 36 mg 1-methylpiperazine and 143 µL 2,4,6-tripropyl-1,3,5,2,4,6-trioxatriphosphinane 2,4,6-trioxide solution (50% in N,N-dimethylformamide) were added and stirring continued at 50° C. for 3 hours. Water was added, the precipitate filtered off and dried to give 51 mg (77%) of the title compound.

LC-MS: m/z=522.5 [M+H]$^+$.

$^1$H-NMR (400 MHz, DMSO-d6), δ [ppm]=1.28 (1H), 1.49 (2H), 1.59-1.72 (3H), 1.77 (2H), 2.21 (3H), 2.29-2.43 (4H), 2.52 (3H*), 2.72 (3H), 2.99 (2H), 3.36-3.74 (4H), 8.73 (1H), 8.76 (1H), 9.25 (1H), 10.22 (1H).

Example 20

6'-[(6-{[4-(Dimethylamino)piperidin-1-yl]carbonyl}-5-methylthieno[2,3-d]pyrimidin-4-yl)amino]-8'-methyl-2'H-spiro[cyclohexane-1,3'-imidazo[1,5-a]pyridine]-1',5'-dione

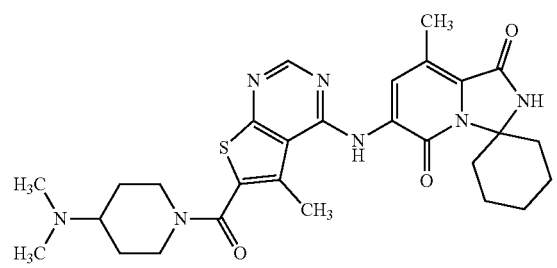 [SMILES: Cc1cc(Nc2ncnc3sc(C(=O)N4CCC(N(C)C)CC4)c(C)c23)c(=O)n2c1C(=O)NC21CCCCC1]

A mixture of 53 mg (121 µmol) 5-methyl-4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 15), 1.9 mL N,N-dimethylacetamide, 168 µL N-ethyl-N-isopropylpropan-2-amine, 62 mg N,N-dimethylpiperidin-4-amine and 215 μL 2,4,6-tripropyl-1,3,5,2,4,6-trioxatriphosphinane 2,4,6-trioxide solution (50% in N,N-dimethylformamide) was stirred at RT overnight. Another 46 mg N,N-dimethylpiperidin-4-amine and 144 μL 2,4,6-tripropyl-1,3,5,2,4,6-trioxatriphosphinane 2,4,6-trioxide solution (50% in N,N-dimethylformamide) were added and stirring continued at 50° C. overnight. Water was added, the precipitate filtered off washed with DMSO and dried to give 25 mg (34%) of the title compound.

LC-MS: m/z=550.6 [M+H]$^+$.

$^1$H-NMR (400 MHz, DMSO-d6), δ [ppm]=1.27 (1H), 1.32-1.44 (2H), 1.49 (2H), 1.60-1.91 (8H), 2.25 (6H), 2.54 (3H), 2.71 (3H), 2.80-3.20 (4H), 3.73 (1H), 4.45 (1H), 8.73 (1H), 8.77 (1H), 9.25 (1H), 10.22 (1H).

Example 21

6'-[(2-Aminopyrimidin-4-yl)amino]-8'-methyl-2'H-spiro[cyclohexane-1,3'-imidazo[1,5-a]pyridine]-1',5'-dione

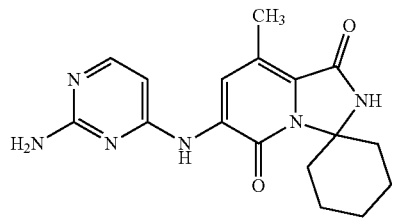 [SMILES: Cc1cc(Nc2ccnc(N)n2)c(=O)n2c1C(=O)NC21CCCCC1]

To a solution of 700 mg (2.25 mmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 520 mg (2.47 mmol) tert-butyl (4-aminopyrimidin-2-yl)carbamate (CAS-No: 262295-93-2) in 20 mL dimethyl acetamide was added 2.20 g cesium carbonate and the mixture was degassed and purged with argon several times. 139 mg 4,5-bis(diphenylphosphino)-9,9-dimethylxanthene, 115 mg 2-(dicyclohexyl-phosphino)-2',4',6'-triisopropylbiphenyl, 54 mg palladium(II)acetate and 220 mg tris(dibenzylideneacetone) dipalladium(0) were added and the mixture was stirred at 100° C. for 2 hours. The mixture was concentrated and the residue purified by flash chromatography (Biotage SNAP cartridge NH 55 g, methanol: dichloromethane) followed by preparative TLC (methanol: dichloromethane) to give 45 mg (6%) of the title compound.

LC-MS: m/z=341.3 [M+H]$^+$.

$^1$H-NMR (400 MHz, DMSO-d6), δ [ppm]=1.21 (1H), 1.44 (2H), 1.58-1.78 (5H), 2.47 (3H), 2.99 (2H), 6.44-6.51 (3H), 7.88 (1H), 8.71 (1H), 8.77 (1H), 10.03 (1H).

Example 22

8'-Methyl-6'-(1H-pyrrolo[2,3-b]pyridin-4-ylamino)-2'H-spiro[cyclohexane-1,3'-imidazo[1,5-a]pyridine]-1',5'-dione

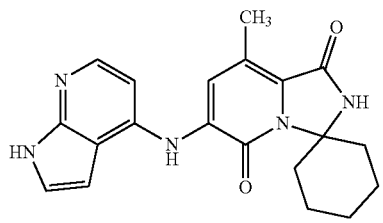 [SMILES: Cc1cc(Nc2ccnc3[nH]ccc23)c(=O)n2c1C(=O)NC21CCCCC1]

To a solution of 100 mg (321 μmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 47 mg (353 μmol) 1H-pyrrolo[2,3-b]pyridin-4-amine (CAS-No: 74420-00-1) in 12 mL 1,4-dioxane was added 314 mg cesium carbonate and the mixture was degassed and purged with argon several times. 20 mg 4,5-bis(diphenylphosphino)-9,9-dimethylxanthene, 16 mg 2-(dicyclohexyl-phosphino)-2',4',6'-triisopropylbiphenyl, 7.7 mg palladium(II)acetate and 31 mg tris(dibenzylideneacetone)dipalladium(0) were added and the mixture was stirred at 100° C. for 2 hours. The mixture was concentrated and the residue purified by flash chromatography (Biotage SNAP cartridge NH 28 g, methanol:dichloromethane) followed by preparative TLC (methanol:dichloromethane) to give 8 mg (7%) of the title compound.

LC-MS: m/z=364.5 [M+H]$^+$.

$^1$H-NMR (400 MHz, DMSO-d6), δ [ppm]=1.24 (1H), 1.48 (2H), 1.57-1.80 (5H), 2.43 (3H), 3.03 (2H), 6.48 (1H), 7.06 (1H), 7.21 (1H), 7.35 (1H), 8.09 (1H), 8.20 (1H), 10.04 (1H), 11.62 (1H).

Example 23

1-{4-[(8'-Methyl-1',5'-dioxo-1',5'-dihydro-2'H-spiro[cyclohexane-1,3'-imidazo[1,5-a]pyridin]-6'-yl)amino]pyrimidin-2-yl}-3-propylurea

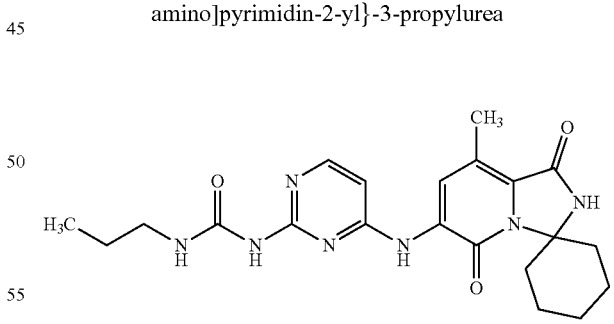

To a solution of 6'-[(2-aminopyrimidin-4-yl)amino]-8'-methyl-2'H-spiro[cyclohexane-1,3'-imidazo[1,5-a]pyridine]-1',5'-dione (prepared according to example 25) in 250 μL DMA was added 3.5 mg sodium hydride (60% oil dispersion) and the mixture was stirred at RT for 15 minutes. 7.2 μL 1-isocyanatopropane were added and stirring continued overnight. The mixture was concentrated and the residue purified by preparative TLC (methanol:dichloromethane) to give 9 mg (29%) of the title compound.

LC-MS: m/z=426.4 [M+H]$^+$.

¹H-NMR (400 MHz, DMSO-d6), δ [ppm]=0.89 (3H), 1.21 (1H), 1.45 (2H), 1.50 (2H), 1.61-1.78 (5H), 2.52 (3H), 2.99 (2H), 3.18 (2H), 6.92 (1H), 8.11 (1H), 8.80 (1H), 9.25-9.34 (2H), 9.84 (1H), 10.08 (1H).

Example 24

8'-methyl-6'-(9H-purin-6-ylamino)-2'H-spiro[cyclohexane-1,3'-imidazo[1,5-a]pyridine]-1',5'-dione

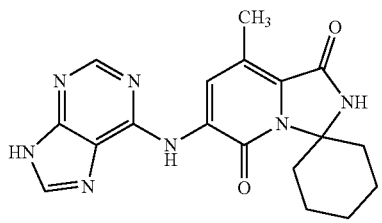 [SMILES: Cc1cc(Nc2ncnc3[nH]cnc23)c(=O)n2c1C(=O)NC21CCCCC1]

To a solution of 100 mg (321 μmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 60.7 mg (353 μmol) 9H-purin-6-amine hydrochloride (CAS-No: 2922-28-3) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. Another 60.7 mg (353 μmol) 9H-purin-6-amine hydrochloride were added and stirring continued at 100-150° C. for 8 hours. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 150° C. for 3 hours. The mixture was concentrated and the residue purified by flash chromatography (Biotage SNAP cartridge silica 10 g, methanol:dichloromethane) to give 7 mg (6%) of the title compound.

LC-MS: m/z=366.3 [M+H]⁺.

¹H-NMR (400 MHz, DMSO-d6), δ [ppm]=1.25 (1H), 1.49 (2H), 1.59-1.81 (5H), 2.52 (3H), 3.00 (2H), 8.39 (1H), 8.59 (1H), 8.74 (1H), 8.89 (1H), 10.16 (1H), 13.44 (1H).

Example 25

N-[2-(Dimethylamino)ethyl]-4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxamide

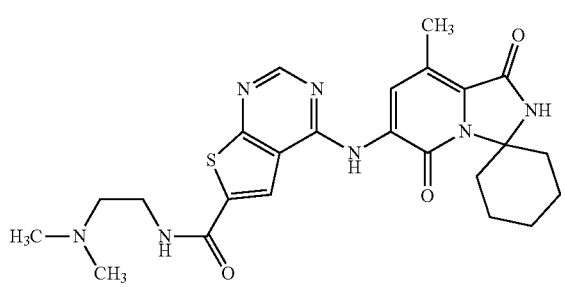 [SMILES: Cc1cc(Nc2ncnc3sc(C(=O)NCCN(C)C)cc23)c(=O)n2c1C(=O)NC21CCCCC1]

A mixture of 50 mg (118 μmol) 4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 9), 1.9 mL N,N-dimethylacetamide, 164 μL N-ethyl-N-isopropylpropan-2-amine, 51 μL N,N-dimethylethane-1,2-diamine and 210 μL 2,4,6-tripropyl-1,3,5,2,4,6-trioxatriphosphinane 2,4,6-trioxide solution (50% in N,N-dimethylformamide) was stirred at RT overnight. The mixture was concentrated, and the residue purified by flash chromatography (Biotage SNAP cartridge NH 11 g+silica 10 g, methanol:dichloromethane) to give 48.0 mg (78%) of the title compound.

LC-MS: m/z=496.6 [M+H]⁺.

¹H-NMR (400 MHz, CHLOROFORM-d), δ [ppm]=1.28 (1H), 1.40-1.57 (2H), 1.64 (2H), 1.86 (1H), 2.02 (2H), 2.39 (6H), 2.63 (3H), 2.65 (2H), 3.16 (2H), 3.60 (2H), 7.05 (1H), 7.69 (1H), 7.90 (1H), 8.78 (1H), 8.80 (1H), 8.86 (1H).

Example 26

1-({4-[(8'-Methyl-1',5'-dioxo-1',5'-dihydro-2'H-spiro[cyclohexane-1,3'-imidazo[1,5-a]pyridin]-6'-yl)amino]thieno[2,3-d]pyrimidin-6-yl}carbonyl)azetidine-3-carbonitrile

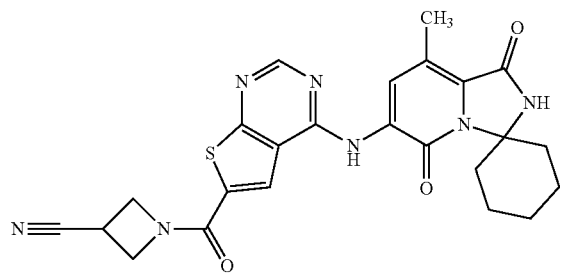 [SMILES: Cc1cc(Nc2ncnc3sc(C(=O)N4CC(C#N)C4)cc23)c(=O)n2c1C(=O)NC21CCCCC1]

A mixture of 50 mg (118 μmol) 4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 9), 1.9 mL N,N-dimethylacetamide, 164 μL N-ethyl-N-isopropylpropan-2-amine, 56 mg azetidine-3-carbonitrile hydrochloride and 210 μL 2,4,6-tripropyl-1,3,5,2,4,6-trioxatriphosphinane 2,4,6-trioxide solution (50% in N,N-dimethylformamide) was stirred at RT overnight. The mixture was concentrated, water added, the precipitate filtered off, washed with water and dried to give 26.0 mg (43%) of the title compound.

LC-MS: m/z=490.5 [M+H]⁺.

¹H-NMR (400 MHz, CHLOROFORM-d), δ [ppm]=1.23 (1H), 1.35-1.52 (2H), 1.64 (2H), 1.84 (1H), 2.03 (2H), 2.63 (3H), 3.16 (2H), 3.67 (1H), 4.71 (4H), 7.00 (1H), 7.85 (1H), 8.81 (1H), 8.84 (2H).

Example 27 tert-Butyl [1-({4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidin-6-yl}carbonyl)azetidin-3-yl]carbamate

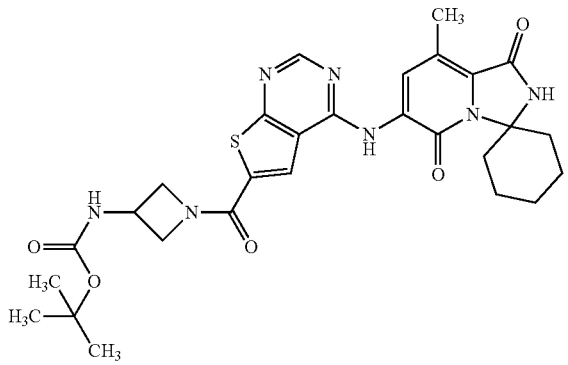 [SMILES: Cc1cc(Nc2ncnc3sc(C(=O)N4CC(NC(=O)OC(C)(C)C)C4)cc23)c(=O)n2c1C(=O)NC21CCCCC1]

A mixture of 100 mg (235 μmol) 4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 9), 3.7 mL N,N-dimethylacetamide, 328 μL N-ethyl-N-isopropylpropan-2-amine, 196 mg tert-butyl azetidin-3-ylcarbamate hydrochloride and 420 μL 2,4,6-tripropyl-1,3,5,2,4,6-trioxatriphosphinane 2,4,6-trioxide solution (50% in N,N-dimethylformamide) was stirred at RT overnight. The mixture was concentrated, water added, the precipitate filtered off, washed with water, ethanol and diethyl ether and dried to give 106.0 mg (74%) of the title compound.

LC-MS: m/z=580.6 [M+H]+.

$^1$H-NMR (400 MHz, CHLOROFORM-d), δ [ppm]=1.49-1.60 (3H), 1.47 (9H), 1.64 (2H), 1.84 (1H), 2.02 (2H), 2.63 (3H), 3.11-3.21 (2H), 3.97-4.26 (1H), 4.27-4.49 (1H), 4.64 (2H), 4.84 (1H), 5.02 (1H), 7.36 (1H), 7.82 (1H), 8.79 (1H), 8.82 (1H), 8.85 (1H).

Example 28

6'-({6-[(3-Aminoazetidin-1-yl)carbonyl]thieno[2,3-d]pyrimidin-4-yl}amino)-8'-methyl-2'H-spiro[cyclohexane-1,3'-imidazo[1,5-a]pyridine]-1',5'-dione

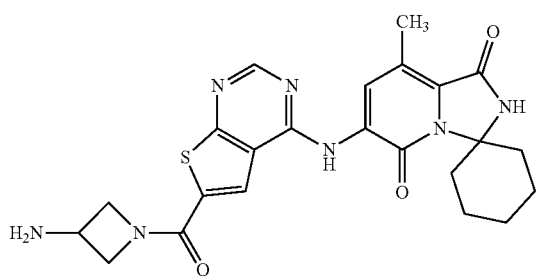 [SMILES: Cc1cc(Nc2ncnc3sc(C(=O)N4CC(N)C4)cc23)c(=O)n2c1C(=O)NC21CCCCC1]

A mixture of 74 mg (128 μM) tert-butyl [1-({4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidin-6-yl}carbonyl)azetidin-3-yl]carbamate (prepared according to example 27) and 197 μL trifluoroacetic acid in 5.0 mL dichloromethane was stirred at RT for 2.5 days. The mixture was poured into aqueous ammonia (25%) and extracted with dichloromethane/methanol. The organic layer was washed with water, dried over sodium sulfate. After filtration and concentration the residue was digested with ethanol and dried to give 45.0 mg (70%) of the title compound.

LC-MS: m/z=480.4 [M+H]+.

$^1$H-NMR (400 MHz, DMSO-d6), δ [ppm]=1.23 (1H), 1.49 (2H), 1.59-1.81 (5H), 2.30 (2H), 2.52 (3H), 3.02 (2H), 3.73 (1H), 3.84 (1H), 4.25 (2H), 4.77 (1H), 8.22 (1H), 8.48 (1H), 8.67 (1H), 9.50 (1H), 10.24 (1H).

Example 29

6'-[(6-{[(3R)-3-(Dimethylamino)pyrrolidin-1-yl]carbonyl}thieno[2,3-d]pyrimidin-4-yl)amino]-8'-methyl-2'H-spiro[cyclohexane-1,3'-imidazo[1,5-a]pyridine]-1',5'-dione

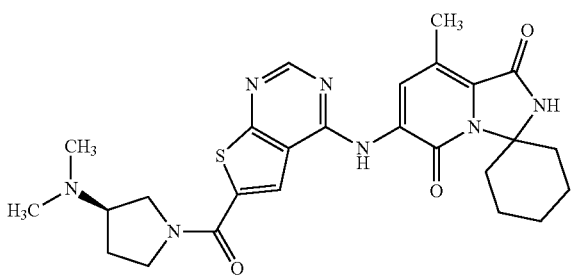 [SMILES: Cc1cc(Nc2ncnc3sc(C(=O)N4CC[C@@H](N(C)C)C4)cc23)c(=O)n2c1C(=O)NC21CCCCC1]

A mixture of 50 mg (118 μmol) 4[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 9), 1.9 mL N,N-dimethylacetamide, 164 μL N-ethyl-N-isopropylpropan-2-amine, 54 mg (3R)—N,N-dimethylpyrrolidin-3-amine and 210 μL 2,4,6-tripropyl-1,3,5,2,4,6-trioxatriphosphinane 2,4,6-trioxide solution (50% in N,N-dimethylformamide) was stirred at RT overnight. The mixture was concentrated, and the residue purified by flash chromatography (Biotage SNAP cartridge NH 11 g+silica 10 g, methanol:dichloromethane) to give 25.0 mg (39%) of the title compound.

LC-MS: m/z=522.6 [M+H]+.

$^1$H-NMR (400 MHz, CHLOROFORM-d), δ [ppm]=1.36-1.52 (3H), 1.64 (2H), 1.84 (1H), 1.92-2.48 (4H), 2.30+2.33 (6H), 2.63 (3H), 2.81 (1H), 3.16 (2H), 3.43-4.10 (4H), 7.13 (1H), 7.79+7.82 (1H), 8.74-8.81 (2H), 8.84+8.87 (1H).

Example 30

6'-[(6-{[(3S)-3-(Dimethylamino)pyrrolidin-1-yl]carbonyl}thieno[2,3-d]pyrimidin-4-yl)amino]-8'-methyl-2'H-spiro[cyclohexane-1,3'-imidazo[1,5-a]pyridin]-1',5'-dione

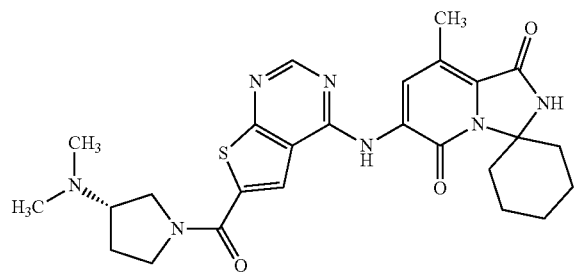 [SMILES: Cc1cc(Nc2ncnc3sc(C(=O)N4CC[C@H](N(C)C)C4)cc23)c(=O)n2c1C(=O)NC21CCCCC1]

A mixture of 50 mg (118 μmol) 4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 9), 1.9 mL N,N-dimethylacetamide, 164 μL N-ethyl-N-isopropylpropan-2-amine, 54 mg (3S)—N,N-dimethylpyrrolidin-3-amine and 210 μL 2,4,6-tripropyl-1,3,5,2,4,6-trioxatriphosphinane 2,4,6-trioxide solution (50% in N,N-dimethylformamide) was stirred at RT overnight. The mixture was concentrated, and the residue purified by flash chromatography (Biotage SNAP cartridge NH 11 g+silica 10 g, methanol:dichloromethane) to give 20.0 mg (29%) of the title compound.

LC-MS: m/z=522.6 [M+H]+.

1H-NMR (400 MHz, CHLOROFORM-d), δ [ppm]=1.39-1.53 (3H), 1.64 (2H), 1.84 (1H), 1.94-2.53 (10H), 2.63 (3H), 2.80 (1H), 3.16 (2H), 3.41-4.12 (4H), 7.37 (1H), 7.80+7.82 (1H), 8.79 (2H), 8.87 (1H).

Example 31

8'-Methyl-6'-(thieno[2,3-d]pyrimidin-4-ylamino)-2'H-spiro[cyclohexane-1,3'-imidazo[1,5-a]pyridine]-1',5'-dione hydrochloride

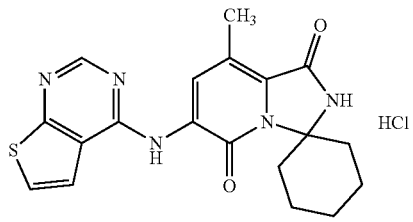 [SMILES: Cc1cc(Nc2ncnc3sccc23)c(=O)n2c1C(=O)NC21CCCCC1 ; Cl]

A mixture of 30 mg (79 μmol) 8'-methyl-6'-(thieno[2,3-d]pyrimidin-4-ylamino)-2'H-spiro[cyclohexane-1,3'-imidazo[1,5-a]pyridine]-1',5'-dione (prepared according to example 5) and 118 μL hydrochloric acid (4M in 1,4-dioxane) in 5 mL 1,4-dioxane was stirred at RT for 10 minutes, concentrated and dried to give 32 mg (93%) of the title compound.

LC-MS: m/z=382.3 [M+H]+.

1H-NMR (400 MHz, DMSO-d6), δ [ppm]=1.23 (1H), 1.51 (1H), 1.58-1.81 (5H), 2.52 (3H*), 3.01 (2H), 7.83 (2H), 8.62 (1H), 8.69 (1H), 9.05 (1H), 10.21 (1H)

*: hidden by solvent peak.

Example 32

8'-Methyl-6'-(7H-pyrrolo[2,3-d]pyrimidin-4-ylamino)-2'H-spiro[cyclohexane-1,3'-imidazo[1,5-a]pyridine]-1',5'-dione hydrochloride

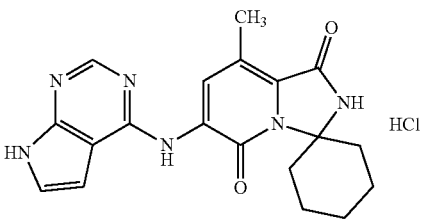 [SMILES: Cc1cc(Nc2ncnc3[nH]ccc23)c(=O)n2c1C(=O)NC21CCCCC1 ; Cl]

A mixture of 13 mg (36 μmol) 8'-methyl-6'-(7H-pyrrolo[2,3-d]pyrimidin-4-ylamino)-2'H-spiro[cyclohexane-1,3'-imidazo[1,5-a]pyridine]-1',5'-dione (prepared according to example 6) and 54 μL hydrochloric acid (4M in 1,4-dioxane) in 4.3 mL 1,4-dioxane was stirred at RT for 10 minutes, concentrated and dried to give 13.4 mg (89%) of the title compound.

LC-MS: m/z=365.4 [M+H]+.

1H-NMR (400 MHz, DMSO-d6), δ [ppm]=1.23 (1H), 1.48 (2H), 1.59-1.80 (5H), 2.50 (3H*), 3.00 (2H), 6.81 (1H), 7.40 (1H), 8.45 (1H), 8.53 (1H), 8.73-9.02 (1H), 10.18 (1H), 12.15 (1H)

*: hidden by solvent peak.

Example 33

N,N-Dimethyl-4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxamide hydrochloride

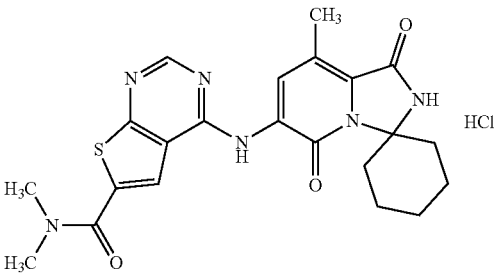 [SMILES: Cc1cc(Nc2ncnc3sc(C(=O)N(C)C)cc23)c(=O)n2c1C(=O)NC21CCCCC1 ; Cl]

A mixture of 13 mg N,N-dimethyl-4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxamide hydrochloride (prepared according to example 10) and 43 μL hydrochloric acid (4M in 1,4-dioxane) in 4.3 mL 1,4-dioxane was stirred at RT for 10 minutes, concentrated and dried to give 13.5 mg (91%) of the title compound.

LC-MS: m/z=453.4 [M+H]+.

1H-NMR (400 MHz, DMSO-d6), δ [ppm]=1.23 (1H), 1.50 (2H), 1.59-1.80 (5H), 2.50 (3H*), 3.01 (2H), 3.06 (3H), 3.35 (3H), 8.28 (1H), 8.56 (1H), 8.70 (1H), 9.36 (1H), 10.23 (1H)

*: hidden by solvent peak.

Example 34

8'-Methyl-6'-(1H-pyrazolo[3,4-d]pyrimidin-4-ylamino)-2'H-spiro[cyclohexane-1,3'-imidazo[1,5-a]pyridine]-1',5'-dione hydrochloride

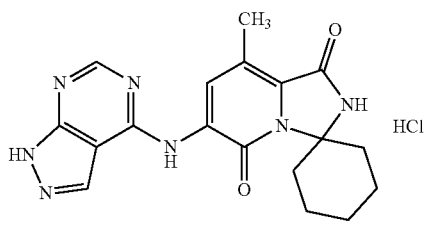 [SMILES: Cc1cc(Nc2ncnc3[nH]ncc23)c(=O)n2c1C(=O)NC21CCCCC1 ; Cl]

A mixture of 8 mg (22 µmol) 8'-methyl-6'-(1H-pyrazolo[3,4-d]pyrimidin-4-ylamino)-2'H-spiro[cyclohexane-1,3'-imidazo[1,5-a]pyridine]-1',5'-dione (prepared according to example 7) and 33 µL hydrochloric acid (4M in 1,4-dioxane) in 2.5 mL 1,4-dioxane was stirred at RT for 10 minutes, concentrated and dried to give 8 mg (82%) of the title compound.

LC-MS: m/z=366.4 [M+H]$^+$.

$^1$H-NMR (400 MHz, DMSO-d6), δ [ppm]=1.23 (1H), 1.50 (2H), 1.59-1.82 (5H), 2.52 (3H*), 3.02 (2H), 8.55 (1H), 8.57 (1H), 8.67 (1H), 9.42 (1H), 10.21 (1H), 13.80 (1H);
*: hidden by solvent peak.

Example 35 tert-Butyl 4-[(8'-methyl-1',5'-dioxo-1',5'-dihydro-2'H-spiro[cyclohexane-1,3'-imidazo[1,5-a]pyridin]-6'-yl)amino]-5,7-dihydro-6H-pyrrolo[3,4-d]pyrimidine-6-carboxylate

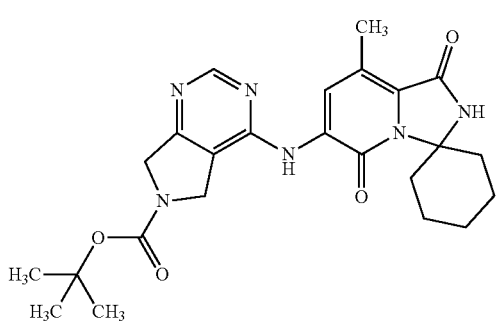 [SMILES: Cc1cc(Nc2ncnc3c2CN(C(=O)OC(C)(C)C)C3)c(=O)n2c1C(=O)NC21CCCCC1]

To a solution of 150 mg (482 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 125 mg (530 µmol) tert-butyl 4-amino-5,7-dihydro-6H-pyrrolo[3,4-d]pyrimidine-6-carboxylate (CAS-No: 1227461-25-7) in 18 mL 1,4-dioxane was added 471 mg cesium carbonate and the mixture was degassed and purged with argon several times. 30 mg 4,5-bis(diphenylphosphino)-9,9-dimethylxanthene, 24.6 mg 2-(dicyclohexyl-phosphino)-2',4',6'-triisopropylbiphenyl, 11.6 mg palladium(II)acetate and 47.2 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, methanol:dichloromethane) to give 145 mg (61%) of the title compound.

LC-MS: m/z=467.4 [M+H]$^+$.

$^1$H-NMR (400 MHz, DMSO-d6), δ [ppm]=1.21 (1H), 1.46 (2H), 1.47+1.49 (9H), 1.57-1.80 (5H), 2.48 (3H), 2.98 (2H), 4.52 (2H), 4.68 (2H), 8.24+8.28 (1H), 8.53 (1H), 8.75 (1H), 10.19 (1H).

Example 36

6'-(6,7-Dihydro-5H-pyrrolo[3,4-d]pyrimidin-4-ylamino)-8'-methyl-2'H-spiro[cyclohexane-1,3'-imidazo[1,5-a]pyridine]-1',5'-dione

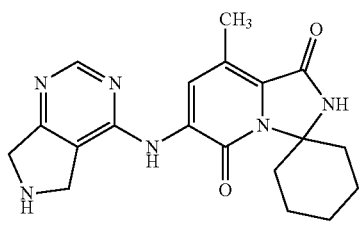 [SMILES: Cc1cc(Nc2ncnc3c2CNC3)c(=O)n2c1C(=O)NC21CCCCC1]

A mixture of 100 mg (214 µmol) tert-butyl 44(8'-methyl-1',5'-dioxo-1',5'-dihydro-2'H-spiro[cyclohexane-1,3'-imidazo[1,5-a]pyridin]-6'-yl)aminol-5,7-dihydro-6H-pyrrolo[3,4-d]pyrimidine-6-carboxylate (prepared according to example 35) and 330 µL trifluoroacetic acid in 8.4 mL dichloromethane was stirred at RT overnight. The mixture was poured into aqueous ammonia (25%) and extracted with dichloromethane/methanol. The organic layer was washed with water, dried over sodium sulfate. After filtration and concentration the residue was digested with ethanol and dried to give 37.0 mg (45%) of the title compound.

LC-MS: m/z=367.4 [M+H]$^+$.

$^1$H-NMR (400 MHz, DMSO-d6), δ [ppm]=1.22 (1H), 1.46 (2H), 1.58-1.79 (5H), 2.48 (3H), 2.88-3.08 (3H), 4.02 (2H), 4.16 (2H), 8.04 (1H), 8.55 (1H), 8.69 (1H), 10.16 (1H).

Example 37

8'-Methyl-6'-{[8-(2,2,2-trifluoroethyl)-7H-purin-6-yl]amino}-2'H-spiro[cyclohexane-1,3'-imidazo[1,5-a]pyridine]-1',5'-dione

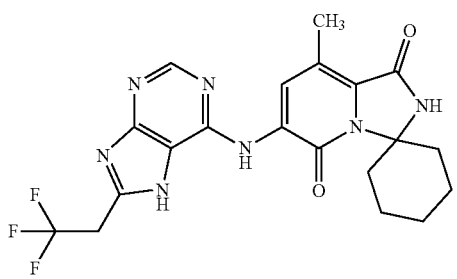 [SMILES: Cc1cc(Nc2ncnc3nc(CC(F)(F)F)[nH]c23)c(=O)n2c1C(=O)NC21CCCCC1]

To a solution of 220 mg (706 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 169 mg (777 µmol) 8-(2,2,2-trifluoroethyl)-7H-purin-6-amine (purchased from Aurora Fine Chemicals LLC) in 26.4 mL 1,4-dioxane was added 690 mg cesium carbonate and the mixture was degassed and purged with argon several times. 43.7 mg 4,5-bis(diphenylphosphino)-9,9-dimethylxanthene, 36 mg 2-(dicyclohexyl-phosphino)-2',4',6'-triisopropylbiphenyl, 17 mg palladium(II)acetate and 69.2 mg tris(dibenzylideneacetone) dipalladium(0) were added and the mixture was stirred at 100° C. for 2 hours. The mixture was concentrated and the residue purified by flash chromatography (Biotage SNAP cartridge silica 25 g, methanol:dichloromethane) to give 12 mg (4%) of the title compound.

LC-MS: m/z=448.4 [M+H]+.

1H-NMR (400 MHz, DMSO-d6), δ [ppm]=1.24 (1H), 1.49 (2H), 1.58-1.81 (5H), 2.52 (3H*), 2.99 (2H), 4.06 (2H), 8.60 (1H), 8.70 (1H), 8.85 (1H), 10.17 (1H), 13.68 (1H);

*: hidden by solvent peak.

Example 38

6'-[(5,6-Dimethylfuro[2,3-d]pyrimidin-4-yl)amino]-8'-methyl-2'H-spiro[cyclohexane-1,3'-imidazo[1,5-a]pyridine]-1',5'-dione

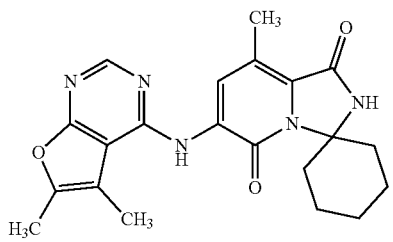 [SMILES: Cc1cc(Nc2ncnc3oc(C)c(C)c23)c(=O)n2c1C(=O)NC21CCCCC1]

To a solution of 100 mg (321 μmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 57.7 mg (353 μmol) 5,6-dimethylfuro[2,3-d]pyrimidin-4-amine (CAS-No: 5117-94-2) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, methanol:dichloromethane) to give 90 mg (68%) of the title compound.

LC-MS: m/z=394.4 [M+H]+.

1H-NMR (400 MHz, DMSO-d6), δ [ppm]=1.29 (1H), 1.48 (2H), 1.59-1.80 (5H), 2.40 (3H), 2.42 (3H), 2.52 (3H*), 2.99 (2H), 8.53 (1H), 8.65 (1H), 8.78 (1H), 10.18 (1H).

*: hidden by solvent peak.

Example 39

(RS)-6'-{[9-(2-Hydroxypropyl)-9H-purin-6-yl]amino}-8'-methyl-2'H-spiro[cyclohexane-1,3'-imidazo[1,5-a]pyridine]-1',5'-dione

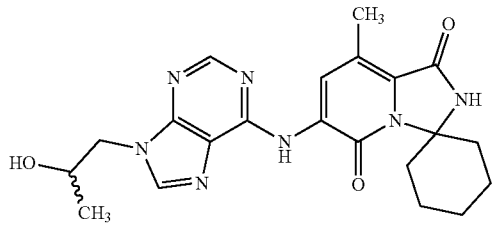 [SMILES: Cc1cc(Nc2ncnc3c2ncn3CC(C)O)c(=O)n2c1C(=O)NC21CCCCC1]

To a solution of 100 mg (321 μmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 68.3 mg (353 μmol) (RS)-1-(6-amino-9H-purin-9-yl)propan-2-ol (CAS-No: 14047-26-8) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, methanol:dichloromethane) to give 31 mg (22%) of the title compound.

LC-MS: m/z=424.2 [M+H]+.

1H-NMR (400 MHz, DMSO-d6), δ [ppm]=1.10 (3H), 1.26 (1H), 1.49 (2H), 1.59-1.82 (5H), 2.52 (3H*), 3.00 (2H), 4.03-4.13 (2H), 4.16-4.25 (1H), 5.07 (1H), 8.34 (1H), 8.62 (1H), 8.73 (1H), 8.88 (1H), 10.17 (1H);

*: hidden by solvent peak.

Example 40

N-[4-[(3,3,8-Trimethyl-1,5-dioxo-1,2,3,5-tetrahydro-imidazo[1,5-a]pyridin-6-yl)amino]-1,3,5-triazin-2-yl]cyclopropanecarboxamide

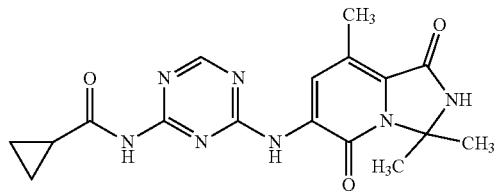 [SMILES: Cc1cc(Nc2ncnc(NC(=O)C3CC3)n2)c(=O)n2c1C(=O)NC2(C)C]

To a solution of 150 mg (553 μmol) 6-bromo-3,3,8-trimethyl-2,3-dihydroimidazo[1,5-a]pyridine-1,5-dione (prepared according to PCT Int. Appl. (2015), WO 2015200481) and 109 mg (609 μmol) N-(4-amino-1,3,5-triazin-2-yl)cyclopropanecarboxamide (prepared according to example 40a) in 21 mL 1,4-dioxane was added 541 mg cesium carbonate and the mixture was degassed and purged with argon several times. 34 mg 4,5-bis(diphenylphosphino)-9,9-dimethylxanthene, 28 mg 2-(dicyclohexyl-phosphino)-2',4',6'-triisopropylbiphenyl, 13 mg palladium(II)acetate and 54 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, methanol:dichloromethane) to give 38 mg (18%) of the title compound.

LC-MS: m/z=370.3 [M+H]$^+$.

$^1$H-NMR (400 MHz, DMSO-d6), δ [ppm]=0.85-0.94 (4H), 1.77 (6H), 2.19 (1H), 2.45 (3H), 8.53 (1H), 8.66 (1H), 8.91 (1H), 9.62 (1H), 11.24 (1H)

Example 40a

N-(4-Amino-1,3,5-triazin-2-yl)cyclopropanecarboxamide

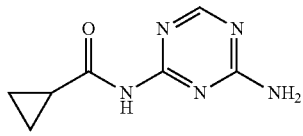 [SMILES: Nc1ncnc(NC(=O)C2CC2)n1]

A mixture of 20 g (136 mmol) 1,3,5-triazine-2,4-diamine hydrochloride (CAS-No of free base: 504-08-5), 500 mL water and 20 g (130 mmol) cyclopropanecarbonyl cyclopropanecarboxylate was stirred for 1 day at RT. 20 g (130 mmol) cyclopropanecarbonyl cyclopropanecarboxylate was added into the reaction and stirring was continued for 1 day at room temperature. Another batch of 20 g (130 mmol) cyclopropanecarbonyl cyclopropanecarboxylate was added and stirring was continued for 3 days at room temperature. The above procedure was repeated once and the solutions of two batch reaction were combined. The solids were filtered off and the crude product purified by Flash-Prep-HPLC (column: C18 silica gel; mobile phase, ACN/water (0.05% NH$_4$OH)=5% increasing to ACN/water (0.05% NH$_4$OH)=20% within 12 min; Detector, UV 254 nm) to give 10.5 g (22%) of the title compound.

LC-MS: m/z=180 [M+H]$^+$.

Example 41

6'-[(5-Fluoroquinazolin-4-yl)amino]-8'-methyl-2'H-spiro[cyclohexane-1,3'-imidazo[1,5-a]pyridine]-1',5'-dione

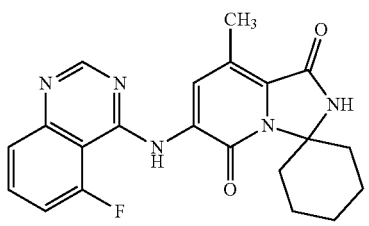 [SMILES: Cc1cc(Nc2ncnc3cccc(F)c23)c(=O)n2c1C(=O)NC21CCCCC1]

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 60.7 mg (353 µmol) 5-fluoroquinazolin-4-amine (CAS-No: 137553-48-1) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, methanol:dichloromethane) to give 103 mg (77%) of the title compound.

LC-MS: m/z=394.4 [M+H]$^+$.

$^1$H-NMR (400 MHz, DMSO-d6), δ [ppm]=1.28 (1H), 1.49 (2H), 1.59-1.81 (5H), 2.52 (3H), 3.00 (2H), 7.55 (1H), 7.73 (1H), 7.92 (1H), 8.86 (1H), 8.89 (1H), 10.05 (1H), 10.24 (1H).

Example 42

8'-Methyl-6'-[(6-{[(1R,4R)-5-methyl-2,5-diazabicyclo[2.2.1]hept-2-yl]carbonyl}thieno[2,3-d]pyrimidin-4-yl)amino]-2'H-spiro[cyclohexane-1,3'-imidazo[1,5-a]pyridine]-1',5'-dione

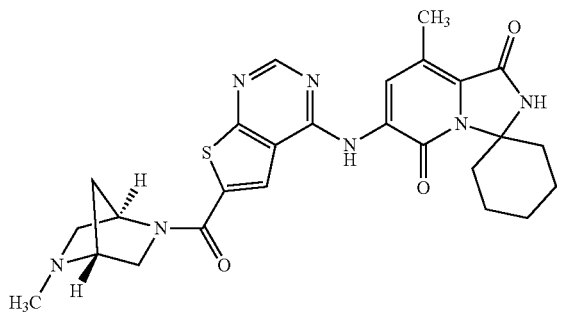 [SMILES: Cc1cc(Nc2ncnc3sc(C(=O)N4C[C@H]5C[C@@H]4CN5C)cc23)c(=O)n2c1C(=O)NC21CCCCC1]

A mixture of 60 mg (141 µmol) 4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 9), 2.2 mL N,N-dimethylacetamide, 98 µL N-ethyl-N-isopropylpropan-2-amine, 155 mg (1R,4R)-2-methyl-2,5-diazabicyclo[2.2.1]heptane dihydrobromide and 252 µL 2,4,6-tripropyl-1,3,5,2,4,6-trioxatriphosphinane 2,4,6-trioxide solution (50% in N,N-dimethylformamide) was stirred at RT for 2.5 days. Another 116 mg (1S,4S)-2-methyl-2,5-diazabicyclo[2.2.1]heptane dihydrobromide and 189 µL 2,4,6-tripropyl-1,3,5,2,4,6-trioxatriphosphinane 2,4,6-trioxide solution (50% in N,N-dimethylformamide) were added and stirring continued at 70° C. overnight. The mixture was concentrated and the residue purified by flash chromatography (Biotage SNAP cartridge NH 11 g+silica 10 g, ethanol:dichloromethane) to give 39 mg (51%) of the title compound.

LC-MS: m/z=520.4 [M+H]$^+$.

$^1$H-NMR (400 MHz, DMSO-d6), δ [ppm]=1.23 (1H), 1.50 (2H), 1.58-2.01 (7H), 2.35-2.64 (2H), 2.48-2.52 (6H*), 2.73-2.94 (1H), 3.02 (2H), 3.40-4.07 (2H), 4.72+4.99 (1H), 8.21+8.39 (1H), 8.54+8.57 (1H), 8.70 (1H), 9.44 (1H), 10.24 (1H);

*: hidden by solvent peak.

Example 43

8'-Methyl-6'-[(6-{[(1S,4S)-5-methyl-2,5-diazabicyclo[2.2.1]hept-2-yl]carbonyl}thieno[2,3-d]pyrimidin-4-yl)amino]-2'H-spiro[cyclohexane-1,3'-imidazo[1,5-a]pyridine]-1',5'-dione

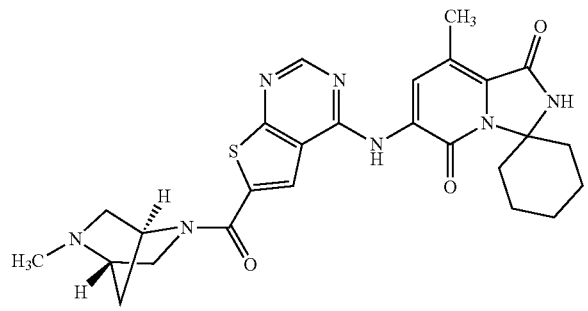 [SMILES: Cc1cc(Nc2ncnc3sc(C(=O)N4C[C@@H]5C[C@H]4CN5C)cc23)c(=O)n2c1C(=O)NC21CCCCC1]

A mixture of 60 mg (141 µmol) 4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 9), 2.2 mL N,N-dimethylacetamide, 98 µL N-ethyl-N-isopropylpropan-2-amine, 155 mg (1S,4S)-2-methyl-2,5-diazabicyclo[2.2.1]heptane dihydrobromide and 252 µL 2,4,6-tripropyl-1,3,5,2,4,6-trioxatriphosphinane 2,4,6-trioxide solution (50% in N,N-dimethylformamide) was stirred at RT for 2.5 days. Another 116 mg (1S,4S)-2-methyl-2,5-diazabicyclo[2.2.1]heptane dihydrobromide and 189 µL 2,4,6-tripropyl-1,3,5,2,4,6-trioxatriphosphinane 2,4,6-trioxide solution (50% in N,N-dimethylformamide) were added and stirring continued at 70° C. overnight. The mixture was concentrated and the residue purified by flash chromatography (Biotage SNAP cartridge NH 11 g+silica 10 g, ethanol:dichloromethane) to give 39 mg (51%) of the title compound.

LC-MS: m/z=520.4 [M+H]$^+$.

$^1$H-NMR (400 MHz, DMSO-d6), δ [ppm]=1.24 (1H), 1.49 (2H), 1.60-1.99 (7H), 2.34-2.63 (2H), 2.51-2.53 (6H*), 2.71-2.92 (1H), 3.02 (2H), 3.39-4.04 (2H), 4.70+4.97 (1H), 8.20+8.39 (1H), 8.53+8.56 (1H), 8.69 (1H), 9.44 (1H), 10.24 (1H);

*: hidden by solvent peak.

Example 44

6'-{[9-(2-Hydroxyethyl)-9H-purin-6-yl]amino}-8'-methyl-2'H-spiro[cyclohexane-1,3'-imidazo[1,5-a]pyridine]-1',5'-dione

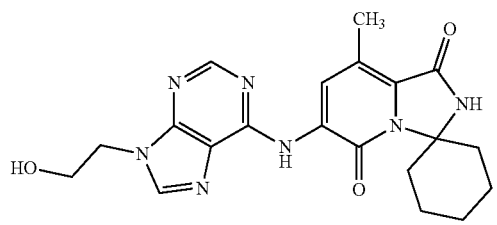 [SMILES: Cc1cc(Nc2ncnc3c2ncn3CCO)c(=O)n2c1C(=O)NC21CCCCC1]

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 63.3 mg (353 µmol) 2-(6-amino-9H-purin-9-yl)ethanol (CAS-No: 707-99-3) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, ethanol:dichloromethane) to give 92 mg (66%) of the title compound.

LC-MS: m/z=410.4 [M+H]$^+$.

$^1$H-NMR (400 MHz, DMSO-d6), δ [ppm]=1.26 (1H), 1.49 (2H), 1.59-1.81 (5H), 2.52-2.53 (3H*), 3.00 (2H), 3.79 (2H), 4.29 (2H), 5.03 (1H), 8.38 (1H), 8.62 (1H), 8.73 (1H), 8.88 (1H), 10.18 (1H);

*: hidden by solvent peak.

Example 45

Ethyl {6-[(8'-methyl-1',5'-dioxo-1',5'-dihydro-2'H-spiro[cyclohexane-1,3'-imidazo[1,5-a]pyridin]-6'-yl)amino]-9H-purin-9-yl}acetate

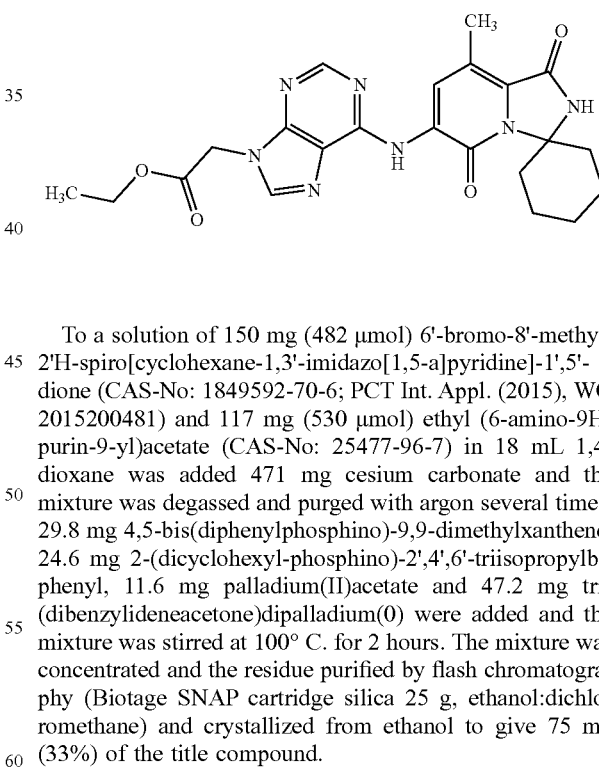

To a solution of 150 mg (482 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 117 mg (530 µmol) ethyl (6-amino-9H-purin-9-yl)acetate (CAS-No: 25477-96-7) in 18 mL 1,4-dioxane was added 471 mg cesium carbonate and the mixture was degassed and purged with argon several times. 29.8 mg 4,5-bis(diphenylphosphino)-9,9-dimethylxanthene, 24.6 mg 2-(dicyclohexyl-phosphino)-2',4',6'-triisopropylbiphenyl, 11.6 mg palladium(II)acetate and 47.2 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, ethanol:dichloromethane) and crystallized from ethanol to give 75 mg (33%) of the title compound.

LC-MS: m/z=452.4 [M+H]$^+$.

$^1$H-NMR (400 MHz, DMSO-d6), δ [ppm]=1.22 (3H), 1.25 (1H), 1.49 (2H), 1.59-1.83 (5H), 2.52 (3H*), 3.00 (2H), 4.19 (2H), 5.20 (2H), 8.41 (1H), 8.63 (1H), 8.72 (1H), 8.91 (1H), 10.19 (1H);

*: hidden by solvent peak.

Example 46

6'-[(6-Chloroquinazolin-4-yl)amino]-8'-methyl-2'H-spiro[cyclohexane-1,3'-imidazo[1,5-a]pyridine]-1',5'-dione

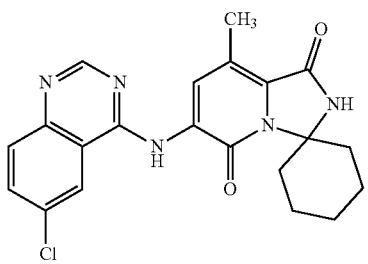 [SMILES: Cc1cc(Nc2ncnc3ccc(Cl)cc23)c(=O)n2c1C(=O)NC21CCCCC1]

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 63.5 mg (353 µmol) 6-chloroquinazolin-4-amine (CAS-No: 19808-35-6) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, ethanol:dichloromethane) to give 57 mg (41%) of the title compound.

LC-MS: m/z=410.3 [M+H]$^+$.

$^1$H-NMR (400 MHz, DMSO-d6), δ [ppm]=1.24 (1H), 1.51 (2H), 1.59-1.81 (5H), 2.52 (3H*), 3.02 (2H), 7.88 (1H), 7.95 (1H), 8.41 (1H), 8.60 (1H), 8.80 (1H), 9.46 (1H), 10.26 (1H);

*: hidden by solvent peak.

Example 47

N-[9-(beta-L-Arabinofuranosyl)-9H-purin-6-yl]-8'-methyl-1',5'-dioxo-1',5'-dihydro-2'H-spiro[cyclohexane-1,3'-imidazo[1,5-a]pyridin]-6'-amine

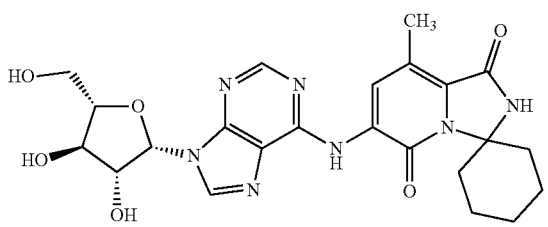 [SMILES: Cc1cc(Nc2ncnc3c2ncn3[C@H]2O[C@@H](CO)[C@H](O)[C@H]2O)c(=O)n2c1C(=O)NC21CCCCC1]

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 94.5 mg (353 µmol) 9-(beta-L-arabinofuranosyl)-9H-purin-6-amine (CAS-No: 58-61-7) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, ethanol:dichloromethane) to give 52 mg (31%) of the title compound.

LC-MS: m/z=498.4 [M+H]$^+$.

$^1$H-NMR (400 MHz, DMSO-d6), δ [ppm]=1.24 (1H), 1.49 (2H), 1.58-1.81 (5H), 2.50 (3H*), 2.99 (2H), 3.58 (1H), 3.69 (1H), 3.98 (1H), 4.18 (1H), 4.64 (1H), 5.18 (1H), 5.25 (1H), 5.54 (1H), 5.99 (1H), 8.64 (1H), 8.67 (1H), 8.72 (1H), 8.93 (1H), 10.19 (1H);

*: hidden by solvent peak.

Example 48

{6-[(8'-Methyl-1',5'-dioxo-1',5'-dihydro-2'H-spiro[cyclohexane-1,3'-imidazo[1,5-a]pyridin]-6'-yl)amino]-9H-purin-9-yl}acetic acid

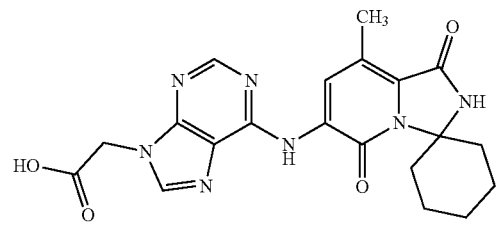 [SMILES: Cc1cc(Nc2ncnc3c2ncn3CC(=O)O)c(=O)n2c1C(=O)NC21CCCCC1]

A mixture of 69 mg (153 µmol) ethyl {6-[(8'-methyl-1',5'-dioxo-1',5'-dihydro-2'H-spiro[cyclohexane-1,3'-imidazo[1,5-a]pyridin]-6'-yl)amino]-9H-purin-9-yl}acetate (prepared according to example 45) 2.4 mL tetrahydrofuran, 2.4 mL ethanol and 3.1 mL lithium hydroxide solution (1M in water) was stirred at RT overnight. Water was added and the mixture was acidified with hydrochloric acid. The precipitate was filtered off, washed with water and dried to give 60 mg (83%) of the title compound.

LC-MS: m/z=424.2 [M+H]$^+$.

$^1$H-NMR (400 MHz, DMSO-d6), δ [ppm]=1.26 (1H), 1.49 (2H), 1.59-1.81 (5H), 2.52 (3H*), 3.00 (2H), 5.04 (2H), 8.39 (1H), 8.62 (1H), 8.73 (1H), 8.89 (1H), 10.18 (1H), 13.44 (1H);

*: hidden by solvent peak.

Example 49

N,N-Dimethyl-2-{6-[(8'-methyl-1',5'-dioxo-1',5'-dihydro-2'H-spiro[cyclohexane-1,3'-imidazo[1,5-a]pyridin]-6'-yl)amino]-9H-purin-9-yl}acetamide

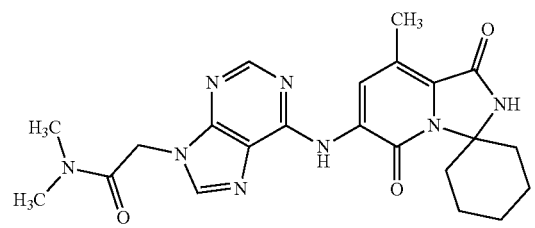 [SMILES: Cc1cc(Nc2ncnc3c2ncn3CC(=O)N(C)C)c(=O)n2c1C(=O)NC21CCCCC1]

A mixture of 28 mg (66 μmol) {6-[(8'-methyl-1',5'-dioxo-1',5'-dihydro-2'H-spiro[cyclohexane-1,3'-imidazo[1,5-a]pyridin]-6'-yl)amino]-9H-purin-9-yl}acetic acid (prepared according to example 48), 1.0 mL N,N-dimethylacetamide, 92 μL N-ethyl-N-isopropylpropan-2-amine, 132 μL N-methylmethanamine (2M in tetrahydrofuran) and 118 μL 2,4,6-tripropyl-1,3,5,2,4,6-trioxatriphosphinane 2,4,6-trioxide solution (50% in N,N-dimethylformamide) was stirred at RT overnight. The mixture was concentrated the precipitate washed with water and dried to give 24 mg (77%) of the title compound.

LC-MS: m/z=451.3 [M+H]⁺.

¹H-NMR (400 MHz, DMSO-d6), δ [ppm]=1.24 (1H), 1.49 (2H), 1.59-1.81 (5H), 2.53 (3H*), 2.87 (3H), 3.00 (2H), 3.13 (3H), 5.25 (2H), 8.30 (1H), 8.60 (1H), 8.73 (1H), 8.89 (1H), 10.18 (1H);

*: hidden by solvent peak.

Example 50

N-[2-(Dimethylamino)ethyl]-N-methyl-2-{6-[(8'-methyl-1',5'-dihydro-2'H-spiro[cyclohexane-1,3'-imidazo[1,5-a]pyridin]-6'-yl)amino]-9H-purin-9-yl}acetamide

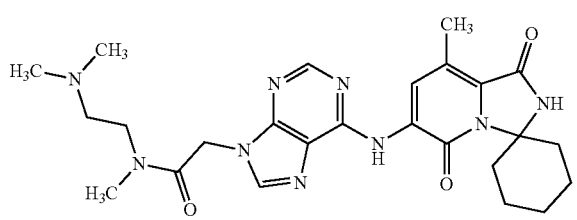 [SMILES: Cc1cc(Nc2ncnc3c2ncn3CC(=O)N(C)CCN(C)C)c(=O)n2c1C(=O)NC21CCCCC1]

A mixture of 28 mg (66 μmol) {6-[(8'-methyl-1',5'-dioxo-1',5'-dihydro-2'H-spiro[cyclohexane-1,3'-imidazo[1,5-a]pyridin]-6'-yl)amino]-9H-purin-9-yl}acetic acid (prepared according to example 48), 1.0 mL N,N-dimethylacetamide, 92 μL N-ethyl-N-isopropylpropan-2-amine, 34 μL N,N,N'-trimethylethane-1,2-diamine and 118 μL 2,4,6-tripropyl-1,3,5,2,4,6-trioxatriphosphinane 2,4,6-trioxide solution (50% in N,N-dimethylformamide) was stirred at RT overnight. The mixture was concentrated and purified by flash chromatography (Biotage SNAP cartridge NH 11 g+silica 10 g, ethanol:dichloromethane) followed by preparative TLC (methanol:dichloromethane) to give 7 mg (19%) of the title compound.

LC-MS: m/z=508.4 [M+H]⁺.

¹H-NMR (400 MHz, DMSO-d6), δ [ppm]=1.24 (1H), 1.48 (2H), 1.58-1.80 (6H), 2.14+2.26 (6H), 2.45-2.56 (5H*), 2.87+3.13 (3H), 3.00 (2H), 3.39+3.53 (2H), 5.24+5.30 (2H), 8.30+8.32 (1H), 8.60 (1H), 8.72 (1H), 8.88 (1H);

*: hidden by solvent peak.

Example 51

8'-Methyl-6'-([1,3]thiazolo[5,4-d]pyrimidin-7-ylamino)-2'H-spiro[cyclohexane-1,3'-imidazo[1,5-a]pyridine]-1',5'-dione

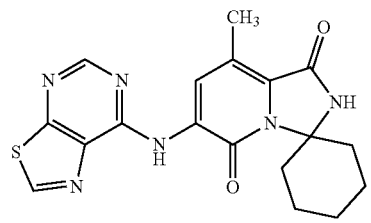 [SMILES: Cc1cc(Nc2ncnc3scnc23)c(=O)n2c1C(=O)NC21CCCCC1]

To a solution of 100 mg (321 μmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 54 mg (353 μmol) [1,3]thiazolo[5,4-d]pyrimidin-7-amine (CAS-No: 2846-90-4) in 12 mL 1,4-dioxane was added 314 mg cesium carbonate and the mixture was degassed and purged with argon several times. 20 mg 4,5-bis(diphenylphosphino)-9,9-dimethylxanthene, 16 mg 2-(dicyclohexyl-phosphino)-2',4',6'-triisopropylbiphenyl, 7.7 mg palladium(II)acetate and 31 mg tris(dibenzylideneacetone)dipalladium(0) were added and the mixture was stirred at 100° C. for 2 hours. The mixture was concentrated and the residue purified by flash chromatography (Biotage SNAP cartridge NH 28 g, ethanol:dichloromethane) to give 58 mg (45%) of the title compound.

LC-MS: m/z=383.2 [M+H]⁺.

¹H-NMR (400 MHz, DMSO-d6), δ [ppm]=1.24 (1H), 1.49 (2H), 1.59-1.80 (5H), 2.52 (3H), 2.99 (2H), 8.72 (1H), 8.83 (1H), 9.38 (1H), 9.51 (1H), 10.23 (1H).

Example 52

6'-(Furo[2,3-d]pyrimidin-4-ylamino)-8'-methyl-2'H-spiro[cyclohexane-1,3'-imidazo[1,5-a]pyridine]-1',5'-dione

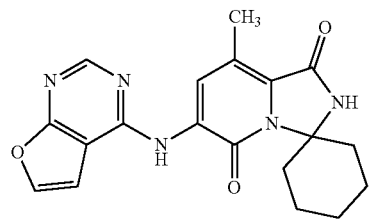 [SMILES: Cc1cc(Nc2ncnc3occc23)c(=O)n2c1C(=O)NC21CCCCC1]

To a solution of 100 mg (321 μmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 48 mg (353 μmol) furo[2,3-d]pyrimidin-4-amine (CAS-No: 186454-70-6) in 12 mL 1,4-dioxane was added 314 mg cesium carbonate and the mixture was degassed and purged with argon several times. 20 mg 4,5-bis(diphenylphosphino)-9,9-dimethylxanthene, 16 mg 2-(dicyclohexyl-phosphino)-2',4',6'-triisopropylbiphenyl, 7.7 mg palladium(II)acetate and 31 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, ethanol:dichloromethane) to give 90 mg (73%) of the title compound.

LC-MS: m/z=366.3 [M+H]+.

1H-NMR (400 MHz, DMSO-d6), δ [ppm]=1.23 (1H), 1.49 (2H), 1.59-1.80 (5H), 2.49 (3H), 3.01 (2H), 7.48 (1H), 8.01 (1H), 8.59 (1H), 8.60 (1H), 9.15 (1H), 10.19 (1H).

Example 53

N-{4-[(8'-Methyl-1',5'-dioxo-1',5'-dihydro-2'H-spiro [cyclopentane-1,3'-imidazo[1,5-a]pyridin]-6'-yl) amino]-1,3,5-triazin-2-yl}cyclopropanecarboxamide

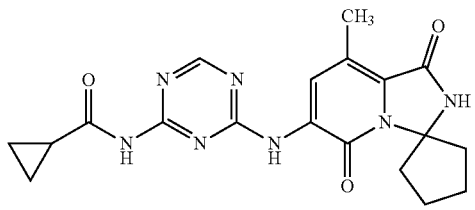 [SMILES: Cc1cc(Nc2ncnc(NC(=O)C3CC3)n2)c(=O)n2c1C(=O)NC21CCCC1]

To a solution of 150 mg (505 µmol) 6'-bromo-8'-methyl-2'H-spiro[cyclopentane-1,3'-imidazo[1,5-a]pyridine]-1',5'-dione (CAS-No: 1849592-55-7; PCT Int. Appl. (2015), WO 2015200481) and 99 mg (555 µmol) N-(4-amino-1,3,5-triazin-2-yl)cyclopropanecarboxamide (prepared according to example 1a) in 19 mL 1,4-dioxane was added 493 mg cesium carbonate and the mixture was degassed and purged with argon several times. 31 mg 4,5-bis(diphenylphosphino)-9,9-dimethylxanthene, 26 mg 2-(dicyclohexyl-phosphino)-2',4',6'-triisopropylbiphenyl, 12 mg palladium(II)acetate and 49 mg tris(dibenzylideneacetone) dipalladium(0) were added and the mixture was stirred at 100° C. for 2 hours. The mixture was concentrated and the residue purified by flash chromatography (Biotage SNAP cartridge silica 25 g, methanol:dichloromethane) to give 25 mg (12%) of the title compound.

LC-MS: m/z=396.3 [M+H]+.

1H-NMR (400 MHz, DMSO-d6), δ [ppm]=0.85-0.94 (4H), 1.68 (2H), 1.83 (2H), 1.96 (2H), 2.19 (1H), 2.45 (3H), 2.80 (2H), 8.54 (1H), 8.66 (1H), 8.92 (1H), 9.98 (1H), 11.23 (1H).

Example 54

6'-[(4-Amino-1,3,5-triazin-2-yl)amino]-8'-methyl-2'H-spiro[cyclopentane-1,3'-imidazo[1,5-a]pyridine]-1',5'-dione

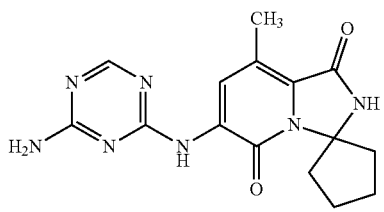 [SMILES: Cc1cc(Nc2ncnc(N)n2)c(=O)n2c1C(=O)NC21CCCC1]

To a solution of 150 mg (505 µmol) 6'-bromo-8'-methyl-2'H-spiro[cyclopentane-1,3'-imidazo[1,5-a]pyridine]-1',5'-dione (CAS-No: 1849592-55-7; PCT Int. Appl. (2015), WO 2015200481) and 99 mg (555 µmol) N-(4-amino-1,3,5-triazin-2-yl)cyclopropanecarboxamide (prepared according to example 1a) in 19 mL 1,4-dioxane was added 493 mg cesium carbonate and the mixture was degassed and purged with argon several times. 31 mg 4,5-bis(diphenylphosphino)-9,9-dimethylxanthene, 26 mg 2-(dicyclohexyl-phosphino)-2',4',6'-triisopropylbiphenyl, 12 mg palladium(II)acetate and 49 mg tris(dibenzylideneacetone) dipalladium(0) were added and the mixture was stirred at 100° C. for 2 hours. The mixture was concentrated and the residue purified by flash chromatography (Biotage SNAP cartridge silica 25 g, methanol:dichloromethane) to give 55 mg (32%) of the title compound.

LC-MS: m/z=328.2 [M+H]+.

1H-NMR (400 MHz, DMSO-d6), δ [ppm]=1.67 (2H), 1.77-1.87 (2H) 1.90-2.01 (2H), 2.46 (3H), 2.80 (2H), 7.46 (2H), 8.05 (1H), 8.27 (1H), 8.47 (1H), 9.93 (1H).

Example 55

8'-Methyl-6'-(7H-pyrrolo[2,3-d]pyrimidin-4-ylamino)-2'H-spiro[cyclopentane-1,3'-imidazo[1,5-a] pyridine]-1',5'-dione

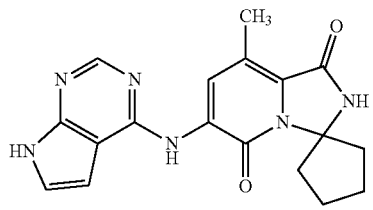 [SMILES: Cc1cc(Nc2ncnc3[nH]ccc23)c(=O)n2c1C(=O)NC21CCCC1]

To a solution of 100 mg (337 µmol) 6'-bromo-8'-methyl-2'H-spiro[cyclopentane-1,3'-imidazo[1,5-a]pyridine]-1',5'-dione (CAS-No: 1849592-55-7; PCT Int. Appl. (2015), WO 2015200481) and 50 mg (370 µmol) 7H-pyrrolo[2,3-d]pyrimidin-4-amine (CAS-No: 1500-85-2) in 12 mL 1,4-dioxane was added 329 mg cesium carbonate and the mixture was degassed and purged with argon several times. 21 mg 4,5-bis(diphenylphosphino)-9,9-dimethylxanthene, 17 mg 2-(dicyclohexyl-phosphino)-2',4',6'-triisopropylbiphenyl, 8 mg palladium(II)acetate and 33 mg tris(dibenzylideneacetone) dipalladium(0) were added and the mixture was stirred at 100° C. for 2 hours. The mixture was concentrated and the residue purified by flash chromatography (Biotage SNAP cartridge silica 25 g, methanol:dichloromethane) to give 47 mg (36%) of the title compound.

LC-MS: m/z=351.3 [M+H]+.

1H-NMR (400 MHz, DMSO-d6), δ [ppm]=1.71 (2H), 1.79-1.91 (2H), 1.91-2.03 (2H), 2.50 (3H*), 2.84 (2H), 6.80 (1H), 7.37 (1H), 8.46 (1H), 8.63 (1H), 8.73 (1H), 9.93 (1H), 12.01 (1H);

*: at least partially hidden by solvent peak.

Example 56

8'-Methyl-6'-(thieno[2,3-d]pyrimidin-4-ylamino)-2'H-spiro[cyclopentane-1,3'-imidazo[1,5-a]pyridine]-1',5'-dione

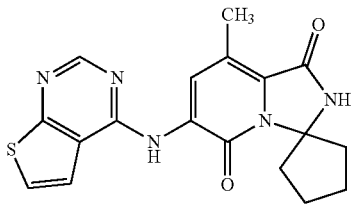 [SMILES: Cc1cc(Nc2ncnc3sccc23)c(=O)n2c1C(=O)NC21CCCC1]

To a solution of 100 mg (337 µmol) 6'-bromo-8'-methyl-2'H-spiro[cyclopentane-1,3'-imidazo[1,5-a]pyridine]-1',5'-dione (CAS-No: 1849592-55-7; PCT Int. Appl. (2015), WO 2015200481) and 56 mg (370 µmol) thieno[2,3-d]pyrimidin-4-amine (CAS-No: 14080-56-9) in 12 mL 1,4-dioxane was added 329 mg cesium carbonate and the mixture was degassed and purged with argon several times. 21 mg 4,5-bis(diphenylphosphino)-9,9-dimethylxanthene, 17 mg 2-(dicyclohexyl-phosphino)-2',4',6'-triisopropylbiphenyl, 8 mg palladium(II)acetate and 33 mg tris(dibenzylideneacetone) dipalladium(0) were added and the mixture was stirred at 100° C. for 2 hours. The mixture was concentrated and the residue purified by flash chromatography (Biotage SNAP cartridge silica 25 g, methanol:dichloromethane) to give 54 mg (41%) of the title compound.

LC-MS: m/z=368.2 [M+H]$^+$.

$^1$H-NMR (400 MHz, DMSO-d6), δ [ppm]=1.72 (2H), 1.85 (2H), 1.99 (2H), 2.50 (3H*), 2.83 (2H), 7.81 (1H), 7.86 (1H), 8.63 (1H), 8.69 (1H), 9.08 (1H), 10.01 (1H);

*: at least partially hidden by solvent peak.

Example 57

6'-(3H-Imidazo[4,5-b]pyridin-7-ylamino)-8'-methyl-2'H-spiro[cyclohexane-1,3'-imidazo[1,5-a]pyridine]-1',5'-dione

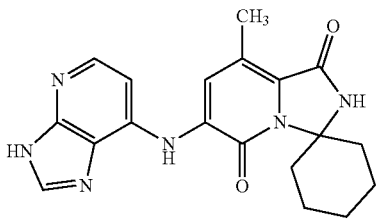 [SMILES: Cc1cc(Nc2ccnc3[nH]cnc23)c(=O)n2c1C(=O)NC21CCCCC1]

A mixture of 40 mg (86 µmol) tert-butyl 6'-(3H-imidazo[4,5-b]pyridin-7-ylamino)-8'-methyl-1',5'-dioxo-1',5'-dihydro-2'H-spiro[cyclohexane-1,3'-imidazo[1,5-a]pyridine]-2'-carboxylate (prepared according to example 57a) and 133 µL trifluoroacetic acid in 3.4 mL dichloromethane was stirred at RT overnight. The mixture was poured into aqueous ammonia (25%) and extracted with dichloromethane/methanol. The organic layer was washed with water, dried over sodium sulfate. After filtration and concentration the residue was digested with ethanol and diethyl ether and dried to give 10 mg (30%) of the title compound.

LC-MS: m/z=365.3 [M+H]$^+$.

$^1$H-NMR (400 MHz, DMSO-d6), δ [ppm]=1.25 (1H), 1.47 (2H), 1.58-1.83 (5H), 2.52 (3H*), 3.00 (2H), 7.34 (1H), 7.50 (1H), 8.21 (1H), 8.29 (1H), 8.62 (1H), 10.08 (1H), 13.06 (1H);

*: at least partially hidden by solvent peak.

Example 57a tert-Butyl 6'-(3H-imidazo[4,5-b]pyridin-7-ylamino)-8'-methyl-1',5'-dioxo-1',5'-dihydro-2'H-spiro[cyclohexane-1,3'-imidazo[1,5-a]pyridine]-2'-carboxylate

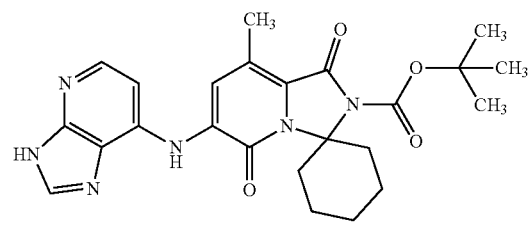 [SMILES: Cc1cc(Nc2ccnc3[nH]cnc23)c(=O)n2c1C(=O)N(C(=O)OC(C)(C)C)C21CCCCC1]

To a solution of 168 mg (408 µmol) tert-butyl 6'-bromo-8'-methyl-1',5'-dioxo-1',5'-dihydro-2'H-spiro[cyclohexane-1,3'-imidazo[1,5-a]pyridine]-2'-carboxylate (prepared according to example 57b) and 71 mg (531 µmol) 3H-imidazo[4,5-b]pyridin-7-amine (CAS-No: 6703-44-2) in 12 mL 1,4-dioxane was added 399 mg cesium carbonate and the mixture was degassed and purged with argon several times. 25 mg 4,5-bis(diphenylphosphino)-9,9-dimethylxanthene, 21 mg 2-(dicyclohexyl-phosphino)-2',4',6'-triisopropylbiphenyl, 9.8 mg palladium(II)acetate and 40 mg tris(dibenzylideneacetone) dipalladium(0) were added and the mixture was stirred at 100° C. for 2 hours. The mixture was concentrated and the residue purified by flash chromatography (Biotage SNAP cartridge silica 25 g, ethanol:dichloromethane) and chrystallization from dichloromethane to give 22 mg (11%) of the title compound.

LC-MS: m/z=465.4 [M+H]$^+$.

Example 57b tert-Butyl 6'-bromo-8'-methyl-1',5'-dioxo-1',5'-dihydro-2'H-spiro[cyclohexane-1,3'-imidazo[1,5-a]pyridine]-2'-carboxylate

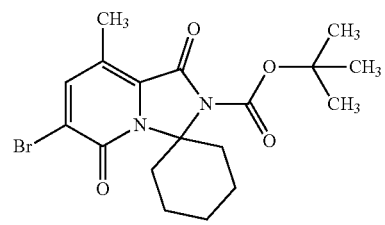 [SMILES: Cc1cc(Br)c(=O)n2c1C(=O)N(C(=O)OC(C)(C)C)C21CCCCC1]

To a solution of 425 mg (1.37 mmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) in 11.6 mL tetrahydrofurane were added 33 mg N,N-dimethylpyridin-4-amine, 628 mg di-tert-butyl carbonate and the mixture was stirred at RT for 2 days and 60° C. overnight. The mixture was concentrated and the residue purified by flash chromatography (Biotage SNAP cartridge silica 25 g, ethylacetate:n-hexane) to give 504 mg (90%) of the title compound.

LC-MS: m/z=411.2 [M+H]$^+$.

Example 58

4-[(8'-Methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxylic acid

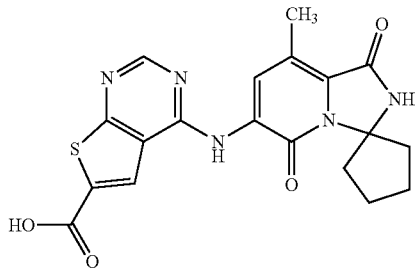 [SMILES: Cc1cc(Nc2ncnc3sc(C(=O)O)cc23)c(=O)n2c1C(=O)NC21CCCC1]

A mixture of 400 mg (940 µmol) methyl 4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxylate (prepared according to example 58a) 14.5 mL tetrahydrofuran, 14.5 mL ethanol and 18.8 mL lithium hydroxide solution (1M in water) was stirred at RT overnight. Water was added and the mixture was acidified with hydrochloric acid. The precipitate was filtered off, washed with water and dried to give 340 mg (84%) of the title compound.

LC-MS: m/z=412.2[M+H]$^+$.

$^1$H-NMR (400 MHz, DMSO-d6), δ [ppm]=1.72 (2H), 1.85 (2H), 1.99 (2H), 2.48 (3H*), 2.83 (2H), 8.47 (1H), 8.51 (1H), 8.70 (1H), 9.45 (1H), 10.03 (1H), 13.76 (1H);

*: at least partially hidden by solvent peak.

Example 58a

Methyl 4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxylate

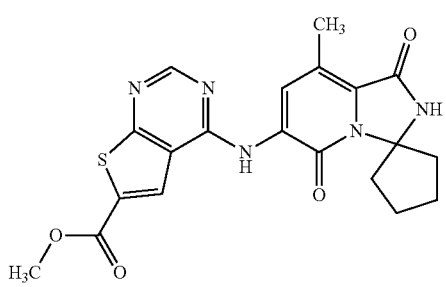 [SMILES: COC(=O)c1cc2c(Nc3cc(C)c4n(c3=O)C3(CCCC3)NC4=O)ncnc2s1]

To a solution of 500 mg (1.68 mmol) 6'-bromo-8'-methyl-2'H-spiro[cyclopentane-1,3'-imidazo[1,5-a]pyridine]-1',5'-dione (CAS-No: 1849592-55-7; PCT Int. Appl. (2015), WO 2015200481) and 387 mg (1.85 mmol) methyl 4-aminothieno[2,3-d]pyrimidine-6-carboxylate (CAS-No: 155087-15-3) in 68 mL N,N-dimethylacetamide was added 1.64 g cesium carbonate and the mixture was degassed and purged with argon several times. 104 mg 4,5-bis(diphenylphosphino)-9,9-dimethylxanthene, 86 mg 2-(dicyclohexyl-phosphino)-2',4',6'-triisopropylbiphenyl, 40 mg palladium(II)acetate and 165 mg tris(dibenzylideneacetone) dipalladium(0) were added and the mixture was stirred at 100° C. for 2 hours. The mixture was concentrated and the residue purified by flash chromatography (Biotage SNAP cartridge silica 50 g, methanol:dichloromethane) and chrystallization from dichloromethane to give 400 mg (56%) of the title compound.

LC-MS: m/z=426.3 [M+H]$^+$.

Example 59

N-[2-(Dimethylamino)ethyl]-4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxamide

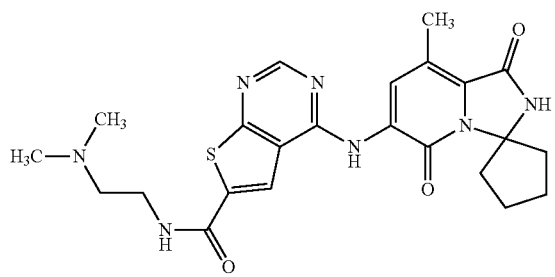 [SMILES: Cc1cc(Nc2ncnc3sc(C(=O)NCCN(C)C)cc23)c(=O)n2c1C(=O)NC21CCCC1]

A mixture of 50 mg (122 µmol) 4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxylic acid (prepared according to example 58), 1.9 mL N,N-dimethylacetamide, 169 µL N-ethyl-N-isopropylpropan-2-amine, 53 µL N,N-dimethylethane-1,2-diamine and 217 µL 2,4,6-tripropyl-1,3,5,2,4,6-trioxatriphosphinane 2,4,6-trioxide solution (50% in N,N-dimethylformamide) was stirred at RT overnight. Another portion of 53 µL N,N-dimethylethane-1,2-diamine and 217 µL 2,4,6-tripropyl-1,3,5,2,4,6-trioxatriphosphinane 2,4,6-trioxide solution (50% in N,N-dimethylformamide) was added and stirring continued at RT overnight. The mixture was concentrated, and the residue purified by flash chromatography (Biotage SNAP cartridge NH 11 g, ethanol:dichloromethane) to give 38 mg (62%) of the title compound.

LC-MS: m/z=482.3 [M+H]$^+$.

$^1$H-NMR (400 MHz, DMSO-d6), δ [ppm]=1.76 (2H), 1.86 (2H), 1.99 (2H), 2.20 (6H), 2.44 (2H), 2.51 (3H*), 2.83 (2H), 3.40 (2H), 8.48 (1H), 8.72 (1H), 8.78 (1H), 8.90 (1H), 9.02 (1H), 10.03 (1H);

*: at least partially hidden by solvent peak.

Example 60

N-[2-(Dimethylamino)ethyl]-N-methyl-4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxamide

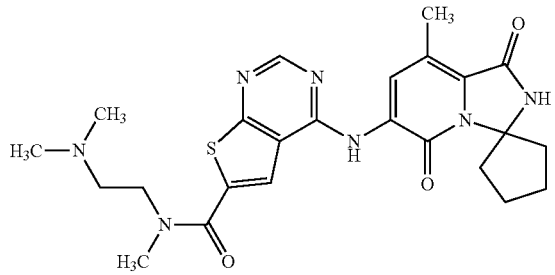 [SMILES: Cc1cc(Nc2ncnc3sc(C(=O)N(C)CCN(C)C)cc23)c(=O)n2c1C(=O)NC21CCCC1]

A mixture of 50 mg (122 µmol) 4-[(8'-methyl-1',5'-dioxo-1',5'-dihydro-2'H-spiro[cyclopentane-1,3'-imidazo[1,5-a]pyridin]-6'-ylamino]thieno[2,3-d]pyrimidine-6-carboxylic acid (prepared according to example 58), 1.9 mL N,N-dimethylacetamide, 169 µL N-ethyl-N-isopropylpropan-2-amine, 63 µL N,N,N'-trimethylethane-1,2-diamine and 217 µL 2,4,6-tripropyl-1,3,5,2,4,6-trioxatriphosphinane 2,4,6-trioxide solution (50% in N,N-dimethylformamide) was stirred at RT overnight. The mixture was concentrated, and the residue purified by flash chromatography (Biotage SNAP cartridge NH 11 g, ethanol:dichloromethane) to give 49 mg (77%) of the title compound.

LC-MS: m/z=496.3 [M+H]$^+$.

$^1$H-NMR (400 MHz, CHLOROFORM-d), δ [ppm]=1.78-1.92 (4H), 2.19 (2H), 2.28 (6H), 2.58 (2H), 2.63 (3H), 3.01-3.13 (2H), 3.26 (3H), 3.68 (2H), 6.73 (1H), 7.72 (1H), 8.72 (1H), 8.78 (1H), 8.87 (1H).

Example 61

1-({4-[(8'-Methyl-1',5'-dioxo-1',5'-dihydro-2'H-spiro[cyclopentane-1,3'-imidazo[1,5-a]pyridin]-6'-yl)amino]thieno[2,3-d]pyrimidin-6-yl}carbonyl)azetidine-3-carbonitrile

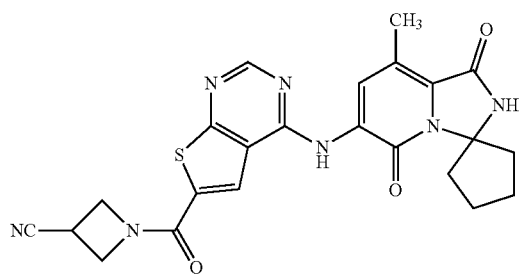 [SMILES: Cc1cc(Nc2ncnc3sc(C(=O)N4CC(C#N)C4)cc23)c(=O)n2c1C(=O)NC21CCCC1]

A mixture of 50 mg (122 µmol) 4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxylic acid (prepared according to example 58), 1.9 mL N,N-dimethylacetamide, 169 µL N-ethyl-N-isopropylpropan-2-amine, 58 mg azetidine-3-carbonitrile hydrochloride and 217 µL 2,4,6-tripropyl-1,3,5,2,4,6-trioxatriphosphinane 2,4,6-trioxide solution (50% in N,N-dimethylformamide) was stirred at RT overnight. The mixture was concentrated, and the residue purified by flash chromatography (Biotage SNAP cartridge NH 11 g, ethanol:dichloromethane) to give 52 mg (85%) of the title compound.

LC-MS: m/z=476.3 [M+H]$^+$.

$^1$H-NMR (400 MHz, DMSO-d6), δ [ppm]=1.74 (2H), 1.85 (2H), 1.99 (2H), 2.47 (3H), 2.83 (2H), 3.97 (1H), 4.27 (1H), 4.41 (1H), 4.91 (2H), 8.33 (1H), 8.52 (1H), 8.69 (1H), 9.51 (1H), 10.05 (1H).

Example 62 tert-Butyl [1-({4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidin-6-yl}carbonyl)azetidin-3-yl]carbamate

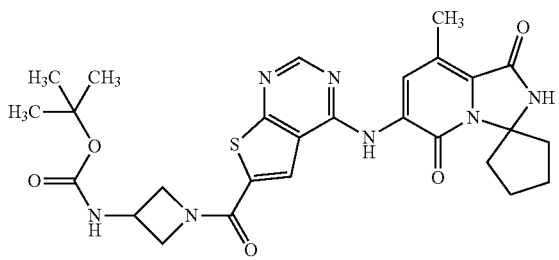 [SMILES: Cc1cc(Nc2ncnc3sc(C(=O)N4CC(NC(=O)OC(C)(C)C)C4)cc23)c(=O)n2c1C(=O)NC21CCCC1]

A mixture of 85 mg (207 µmol) 4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxylic acid (prepared according to example 58), 3.3 mL N,N-dimethylacetamide, 288 µL N-ethyl-N-isopropylpropan-2-amine, 172 mg tert-butyl azetidin-3-ylcarbamate hydrochloride and 369 µL 2,4,6-tripropyl-1,3,5,2,4,6-trioxatriphosphinane 2,4,6-trioxide solution (50% in N,N-dimethylformamide) was stirred at RT overnight. The mixture was concentrated, and the residue purified by flash chromatography (Biotage SNAP cartridge NH 11 g, ethanol:dichloromethane) to give 94 mg (76%) of the title compound.

LC-MS: m/z=566.3 [M+H]$^+$.

$^1$H-NMR (400 MHz, DMSO-d6), δ [ppm]=1.40 (9H), 1.72 (2H), 1.85 (2H), 1.99 (2H), 2.47 (3H), 2.83 (2H), 3.99 (1H), 4.32 (1H), 4.44 (2H), 4.87 (1H), 7.72 (1H), 8.26 (1H), 8.49 (1H), 8.67 (1H), 9.59 (1H), 10.04 (1H).

Example 63

6'-[(6-{[(3R)-3-(Dimethylamino)pyrrolidin-1-yl]carbonyl}thieno[2,3-d]pyrimidin-4-yl)amino]-8'-methyl-2'H-spiro[cyclopentane-1,3'-imidazo[1,5-a]pyridine]-1',5'-dione

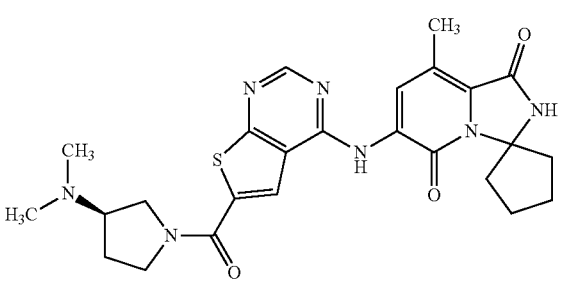 [SMILES: Cc1cc(Nc2ncnc3sc(C(=O)N4CC[C@@H](N(C)C)C4)cc23)c(=O)n2c1C(=O)NC21CCCC1]

A mixture of 50 mg (122 μmol) 4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxylic acid (prepared according to example 58), 1.9 mL N,N-dimethylacetamide, 169 μL N-ethyl-N-isopropylpropan-2-amine, 56 mg (3R)—N,N-dimethylpyrrolidin-3-amine and 217 μL 2,4,6-tripropyl-1,3,5,2,4,6-trioxatriphosphinane 2,4,6-trioxide solution (50% in N,N-dimethylformamide) was stirred at RT overnight. The mixture was concentrated, and the residue purified by flash chromatography (Biotage SNAP cartridge NH 11 g, ethanol:dichloromethane) to give 33 mg (48%) of the title compound.

LC-MS: m/z=508.3 [M+H]$^+$.

$^1$H-NMR (400 MHz, CHLOROFORM-d), δ [ppm]=1.76-2.06 (5H), 2.20 (3H), 2.30+2.33 (6H), 2.63 (3H), 2.72-2.91 (1H), 3.02-3.12 (2H), 3.45-4.07 (4H), 6.84 (1H), 7.80+7.83 (1H), 8.73+8.76 (1H), 8.79 (1H), 8.85+8.89 (1H).

Example 64

6'-[(6-{[4-(Dimethylamino)piperidin-1-yl]carbonyl}thieno[2,3-d]pyrimidin-4-yl)amino]-8'-methyl-2'H-spiro[cyclopentane-1,3'-imidazo[1,5-a]pyridine]-1',5'-dione

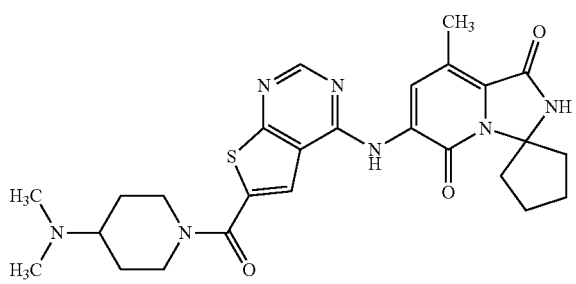 [SMILES: Cc1cc(Nc2ncnc3sc(C(=O)N4CCC(N(C)C)CC4)cc23)c(=O)n2c1C(=O)NC21CCCC1]

A mixture of 50 mg (122 μmol) 4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxylic acid (prepared according to example 58), 1.9 mL N,N-dimethylacetamide, 169 μL N-ethyl-N-isopropylpropan-2-amine, 62 MG N,N-dimethylpiperidin-4-amine and 217 μL 2,4,6-tripropyl-1,3,5,2,4,6-trioxatriphosphinane 2,4,6-trioxide solution (50% in N,N-dimethylformamide) was stirred at RT overnight. The mixture was concentrated, and the residue purified by flash chromatography (Biotage SNAP cartridge NH 11 g, ethanol:dichloromethane) to give 45 mg (67%) of the title compound.

LC-MS: m/z=522.3 [M+H]$^+$.

$^1$H-NMR (400 MHz, DMSO-d6), δ [ppm]=1.43 (2H), 1.73 (2H), 1.85 (4H), 1.99 (2H), 2.21 (6H), 2.40 (1H), 2.48 (3H), 2.83 (2H), 2.89-3.28 (2H), 4.32 (2H), 8.19 (1H), 8.57 (1H), 8.69 (1H), 9.38 (1H), 10.03 (1H).

Example 65

8'-Methyl-6'-({6-[(1R,4R)-2-oxa-5-azabicyclo[2.2.1]hept-5-ylcarbonyl]thieno[2,3-d]pyrimidin-4-yl}amino)-2'H-spiro[cyclohexane-1,3'-imidazo[1,5-a]pyridine]-1',5'-dione

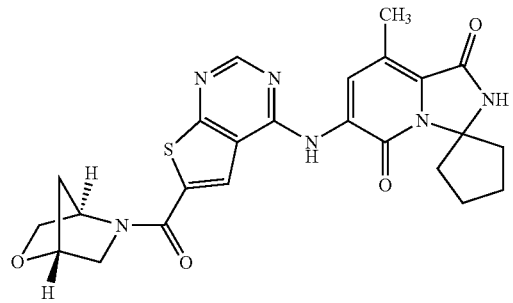 [SMILES: Cc1cc(Nc2ncnc3sc(C(=O)N4C[C@H]5C[C@@H]4CO5)cc23)c(=O)n2c1C(=O)NC21CCCC1]

A mixture of 70 mg (165 μmol) 4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 9), 2.6 mL N,N-dimethylacetamide, 115 μL N-ethyl-N-isopropylpropan-2-amine, 89 mg (1R,4R)-2-oxa-5-azabicyclo[2.2.1]heptane hydrochloride and 293 μL 2,4,6-tripropyl-1,3,5,2,4,6-trioxatriphosphinane 2,4,6-trioxide solution (50% in N,N-dimethylformamide) was stirred at RT for 2.5 days. The mixture was concentrated, water added the precipitate filtered and dried to give 69 mg (79%) of the title compound.

LC-MS: m/z=507.3 [M+H]$^+$.

$^1$H-NMR (400 MHz, DMSO-d6), δ [ppm]=1.23 (1H), 1.50 (2H), 1.59-1.80 (5H), 1.85-2.02 (2H), 2.52 (3H*), 3.02 (2H), 3.39+3.88 (1H), 3.57+3.98 (1H), 3.81+3.89+3.97 (2H), 4.71+4.79 (1H), 4.94+5.23 (1H), 8.27+8.40 (1H), 8.53+8.57 (1H), 8.69 (1H), 9.44 (1H), 10.23 (1H);

*: at least partially hidden by solvent peak.

Example 66

8'-Methyl-6'-({6-[(1S,4S)-2-oxa-5-azabicyclo[2.2.1]hept-5-ylcarbonyl]thieno[2,3-d]pyrimidin-4-yl}amino)-2'H-spiro[cyclohexane-1,3'-imidazo[1,5-a]pyridine]-1',5'-dione

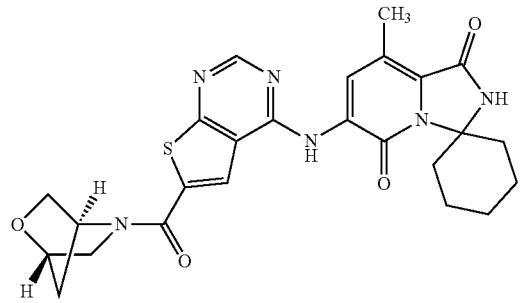 [SMILES: Cc1cc(Nc2ncnc3sc(C(=O)N4C[C@@H]5C[C@H]4CO5)cc23)c(=O)n2c1C(=O)NC21CCCCC1]

A mixture of 80 mg (188 μmol) 4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 9), 3.0 mL N,N- dimethylacetamide, 131 µL N-ethyl-N-isopropylpropan-2-amine, 102 mg (1S,4S)-2-oxa-5-azabicyclo[2.2.1]heptane hydrochloride and 336 µL 2,4,6-tripropyl-1,3,5,2,4,6-trioxatriphosphinane 2,4,6-trioxide solution (50% in N,N-dimethylformamide) was stirred at RT for 2.5 days. The mixture was concentrated, water added the precipitate filtered and dried to give 86 mg (86%) of the title compound.

LC-MS: m/z=507.3 [M+H]$^+$.

$^1$H-NMR (400 MHz, DMSO-d6), δ [ppm]=1.24 (1H), 1.49 (2H), 1.59-1.80 (5H), 1.84-2.01 (2H), 2.52 (3H*), 3.02 (2H), 3.39+3.87 (1H), 3.56+3.98 (1H), 3.81+3.89+3.97 (2H), 4.71+4.79 (1H), 4.94+5.23 (1H), 8.27+8.40 (1H), 8.53+8.57 (1H), 8.69 (1H), 9.44 (1H), 10.23 (1H)

*: at least partially hidden by solvent peak.

Example 67

8'-methyl-6'-(9H-purin-6-ylamino)-2'H-spiro[cyclopentane-1,3'-imidazo[1,5-a]pyridine]-1',5'-dione

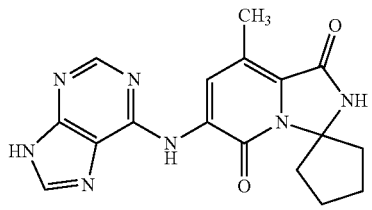 [SMILES: Cc1cc(Nc2ncnc3[nH]cnc23)c(=O)n2c1C(=O)NC21CCCC1]

To a solution of 100 mg (337 µmol) 6'-bromo-8'-methyl-2'H-spiro[cyclopentane-1,3'-imidazo[1,5-a]pyridine]-1',5'-dione (CAS-No: 1849592-55-7; PCT Int. Appl. (2015), WO 2015200481) and 64 mg (370 µmol) 9H-purin-6-amine hydrochloride (CAS-No: 2922-28-3) in 12.6 mL 1,4-dioxane was added 329 mg cesium carbonate and the mixture was degassed and purged with argon several times. 21 mg 4,5-bis(diphenylphosphino)-9,9-dimethylxanthene, 17 mg 2-(dicyclohexyl-phosphino)-2',4',6'-triisopropylbiphenyl, 8.1 mg palladium(II)acetate and 33 mg tris(dibenzylideneacetone) dipalladium(0) were added and the mixture was stirred at 100° C. for 2 hours. The mixture was concentrated and the residue purified by flash chromatography (Biotage SNAP cartridge silica 25 g, methanol:dichloromethane) and chrystallization from methanol to give 10 mg (8%) of the title compound.

LC-MS: m/z=352.3 [M+H]$^+$.

$^1$H-NMR (400 MHz, DMSO-d6), δ [ppm]=1.71 (2H), 1.85 (2H), 1.99 (2H), 2.49 (3H*), 2.84 (2H), 8.39 (1H), 8.59 (1H), 8.73 (1H), 8.86 (1H), 9.96 (1H), 13.45 (1H);

*: at least partially hidden by solvent peak.

Example 68

8'-methyl-6'-(1H-pyrazolo[3,4-d]pyrimidin-4-ylamino)-2'H-spiro[cyclopentane-1,3'-imidazo[1,5-a]pyridine]-1',5'-dione

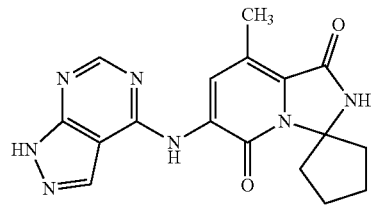 [SMILES: Cc1cc(Nc2ncnc3[nH]ncc23)c(=O)n2c1C(=O)NC21CCCC1]

To a solution of 100 mg (337 µmol) 6'-bromo-8'-methyl-2'H-spiro[cyclopentane-1,3'-imidazo[1,5-a]pyridine]-1',5'-dione (CAS-No: 1849592-55-7; PCT Int. Appl. (2015), WO 2015200481) and 50 mg (370 µmol) 1H-pyrazolo[3,4-d]pyrimidin-4-amine (CAS-No: 2380-63-4) in 12.6 mL 1,4-dioxane was added 329 mg cesium carbonate and the mixture was degassed and purged with argon several times. 21 mg 4,5-bis(diphenylphosphino)-9,9-dimethylxanthene, 17 mg 2-(dicyclohexyl-phosphino)-2',4',6'-triisopropylbiphenyl, 8.1 mg palladium(II)acetate and 33 mg tris(dibenzylideneacetone) dipalladium(0) were added and the mixture was stirred at 100° C. for 2 hours. The mixture was concentrated and the residue purified by flash chromatography (Biotage SNAP cartridge silica 25 g, methanol:dichloromethane) and chrystallization from methanol to give 19 mg (15%) of the title compound.

LC-MS: m/z=352.2 [M+H]$^+$.

$^1$H-NMR (400 MHz, DMSO-d6), δ [ppm]=1.73 (2H), 1.85 (2H), 2.00 (2H), 2.48 (3H), 2.83 (2H), 8.55 (1H), 8.57 (1H), 8.70 (1H), 9.44 (1H), 10.00 (1H), 13.78 (1H).

Example 69

8'-methyl-6'-{[6-(methylsulfonyl)-6,7-dihydro-5H-pyrrolo[3,4-d]pyrimidin-4-yl]amino}-2'H-spiro[cyclohexane-1,3'-imidazo[1,5-a]pyridine]-1',5'-dione

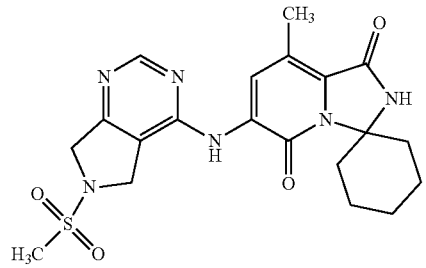 [SMILES: Cc1cc(Nc2ncnc3c2CN(S(C)(=O)=O)C3)c(=O)n2c1C(=O)NC21CCCCC1]

To a solution of 50 mg (136 µmol) 6'-(6,7-dihydro-5H-pyrrolo[3,4-d]pyrimidin-4-ylamino)-8'-methyl-2'H-spiro [cyclohexane-1,3'-imidazo[1,5-a]pyridine]-1',5'-dione (prepared according to example 36) in 1.4 mL pyridine were added 21 µL methanesulfonyl chloride and the mixture was stirred at RT for 2 hours. Methanol was added, the precipitate washed with methanol and dried to give 42 mg (66%) of the title compound.

LC-MS: m/z=445.3 [M+H]$^+$.

¹H-NMR (400 MHz, DMSO-d6), δ [ppm]=1.21 (1H), 1.47 (2H), 1.56-1.79 (5H), 2.48 (3H), 2.98 (2H), 3.04 (3H), 4.62 (2H), 4.81 (2H), 8.33 (1H), 8.52 (1H), 8.77 (1H), 10.19 (1H).

Example 70

8'-methyl-6'-{[6-(phenylsulfonyl)-6,7-dihydro-5H-pyrrolo[3,4-d]pyrimidin-4-yl]amino}-2'H-spiro[cyclohexane-1,3'-imidazo[1,5-a]pyridine]-1',5'-dione

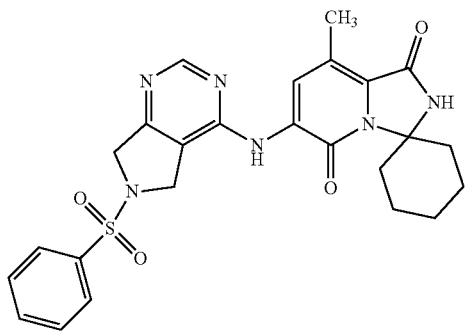 [SMILES: Cc1cc(Nc2ncnc3c2CN(S(=O)(=O)c2ccccc2)C3)c(=O)n2c1C(=O)NC21CCCCC1]

To a solution of 50 mg (136 μmol) 6'-(6,7-dihydro-5H-pyrrolo[3,4-d]pyrimidin-4-ylamino)-8'-methyl-2'H-spiro[cyclohexane-1,3'-imidazo[1,5-a]pyridine]-1',5'-dione (prepared according to example 36) in 1.4 mL pyridine were added 35 μL benzenesulfonyl chloride and the mixture was stirred at RT for 2 hours. Methanol was added, the precipitate washed with methanol and dried to give 48 mg (66%) of the title compound.

LC-MS: m/z=507.3 [M+H]⁺.

¹H-NMR (400 MHz, DMSO-d6), δ [ppm]=1.21 (1H), 1.46 (2H), 1.57-1.80 (5H), 2.44 (3H), 2.98 (2H), 4.52 (2H), 4.77 (2H), 7.62 (2H), 7.70 (1H), 7.94 (2H), 8.40 (1H), 8.45 (1H), 8.66 (1H), 10.18 (1H).

Example 71

6'-({6-[(difluoromethyl)sulfonyl]-6,7-dihydro-5H-pyrrolo[3,4-d]pyrimidin-4-yl}amino)-8'-methyl-2'H-spiro[cyclohexane-1,3'-imidazo[1,5-a]pyridine]-1',5'-dione

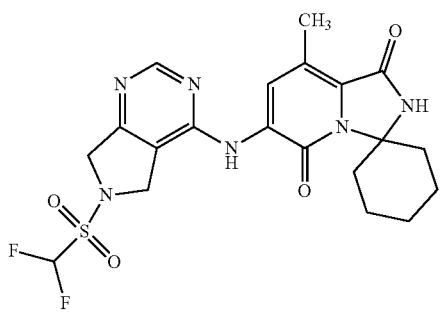 [SMILES: Cc1cc(Nc2ncnc3c2CN(S(=O)(=O)C(F)F)C3)c(=O)n2c1C(=O)NC21CCCCC1]

To a solution of 50 mg (136 μmol) 6'-(6,7-dihydro-5H-pyrrolo[3,4-d]pyrimidin-4-ylamino)-8'-methyl-2'H-spiro[cyclohexane-1,3'-imidazo[1,5-a]pyridine]-1',5'-dione (prepared according to example 36) in 1.4 mL pyridine were added 24 μL difluoromethanesulfonyl chloride and the mixture was stirred at RT for 2 hours. Methanol was added, the precipitate washed with methanol and dried to give 35 mg (51%) of the title compound.

LC-MS: m/z=481.3 [M+H]⁺.

¹H-NMR (400 MHz, DMSO-d6), δ [ppm]=1.21 (1H), 1.47 (2H), 1.56-1.80 (5H), 2.47 (3H), 2.98 (2H), 4.77 (2H), 4.98 (2H), 7.26 (1H), 8.47 (1H), 8.51 (1H), 8.76 (1H), 10.20 (1H).

Example 72

8'-methyl-6'-({6-[(trifluoromethyl)sulfonyl]-6,7-dihydro-5H-pyrrolo[3,4-d]pyrimidin-4-yl}amino)-2'H-spiro[cyclohexane-1,3'-imidazo[1,5-a]pyridine]-1',5'-dione

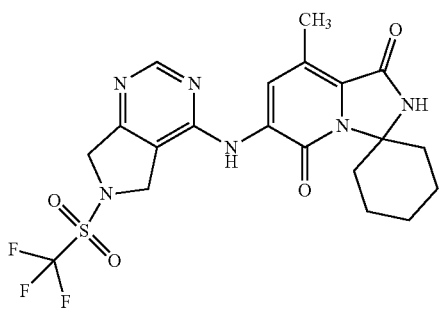 [SMILES: Cc1cc(Nc2ncnc3c2CN(S(=O)(=O)C(F)(F)F)C3)c(=O)n2c1C(=O)NC21CCCCC1]

To a solution of 50 mg (136 μmol) 6'-(6,7-dihydro-5H-pyrrolo[3,4-d]pyrimidin-4-ylamino)-8'-methyl-2'H-spiro[cyclohexane-1,3'-imidazo[1,5-a]pyridine]-1',5'-dione (prepared according to example 36) in 1.4 mL pyridine were added 29 μL trifluoromethanesulfonyl chloride and the mixture was stirred at RT for 2 hours. Methanol was added, the precipitate washed with methanol and dried to give 33 mg (46%) of the title compound.

LC-MS: m/z=499.2 [M+H]⁺.

¹H-NMR (400 MHz, DMSO-d6), δ [ppm]=1.21 (1H), 1.47 (2H), 1.57-1.80 (5H), 2.47 (3H), 2.98 (2H), 4.84 (2H), 5.07 (2H), 8.47 (1H), 8.58 (1H), 8.77 (1H), 10.20 (1H).

Example 73

8'-methyl-6'-({6-[(2,2,2-trifluoroethyl)sulfonyl]-6,7-dihydro-5H-pyrrolo[3,4-d]pyrimidin-4-yl}amino)-2'H-spiro[cyclohexane-1,3'-imidazo[1,5-a]pyridine]-1',5'-dione

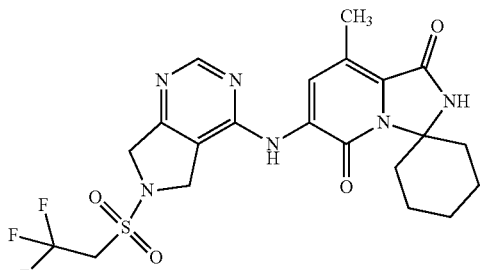

To a solution of 50 mg (136 μmol) 6'-(6,7-dihydro-5H-pyrrolo[3,4-d]pyrimidin-4-ylamino)-8'-methyl-2'H-spiro[cyclohexane-1,3'-imidazo[1,5-a]pyridine]-1',5'-dione (prepared according to example 36) in 1.4 mL pyridine were added 21 μL 2,2,2-trifluoroethanesulfonyl chloride and the mixture was stirred at RT for 2 hours. Methanol was added, the precipitate washed with methanol and dried to give 51 mg (69%) of the title compound.

LC-MS: m/z=513.3 [M+H]⁺.

¹H-NMR (400 MHz, DMSO-d6), δ [ppm]=1.21 (1H), 1.47 (2H), 1.57-1.81 (5H), 2.50 (3H*), 2.98 (2H), 4.66-4.77 (4H), 4.91 (2H), 8.37 (1H), 8.51 (1H), 8.77 (1H), 10.20 (1H);

*: at least partially hidden by solvent peak.

Example 74

6'-({6-[(3-Aminoazetidin-1-yl)carbonyl]thieno[2,3-d]pyrimidin-4-yl}amino)-8'-methyl-2'H-spiro[cyclopentane-1,3'-imidazo[1,5-a]pyridine]-1',5'-dione

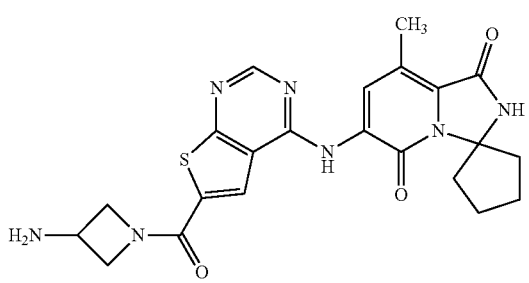 [SMILES: Cc1cc(Nc2ncnc3sc(C(=O)N4CC(N)C4)cc23)c(=O)n2c1C(=O)NC21CCCC1]

A mixture of 70 mg (124 μmol) tert-butyl [1-({4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidin-6-yl}carbonyl)azetidin-3-yl]carbamate (prepared according to example 62) and 191 μL trifluoroacetic acid in 4.8 mL dichloromethane was stirred at RT overnight. The mixture was poured into aqueous ammonia (25%) and extracted with dichloromethane/methanol. The organic layer was washed with water, dried over sodium sulfate. After filtration and concentration the residue was purified by Flash-Prep-HPLC (column: C18 silica gel; mobile phase, ACN/water (0.05% NH₄OH)=5% increasing to ACN/water (0.05% NH₄OH)=20% within 12 min; Detector, UV 254 nm) to give 28.1 mg (46%) of the title compound.

LC-MS: m/z=466.3 [M+H]⁺.

¹H-NMR (400 MHz, DMSO-d6), δ [ppm]=1.73 (2H), 1.85 (2H), 1.99 (2H), 2.17-2.44 (2H), 2.47 (3H), 2.83 (2H), 3.73 (1H), 3.84 (1H), 4.26 (2H), 4.77 (1H), 8.25 (1H), 8.48 (1H), 8.67 (1H), 9.55 (1H), 10.04 (1H).

Example 75

N-Ethyl-4-[(8'-methyl-1',5'-dioxo-1',5'-dihydro-2'H-spiro[cyclohexane-1,3'-imidazo[1,5-a]pyridin]-6'-yl)amino]-5,7-dihydro-6H-pyrrolo[3,4-d]pyrimidine-6-carboxamide

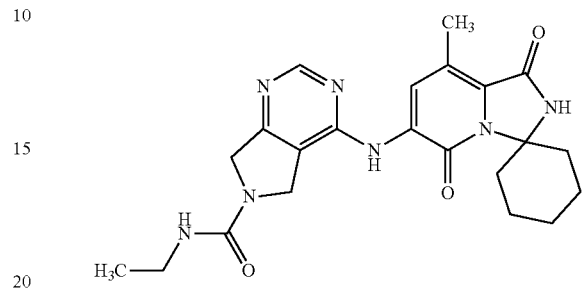

To a solution of 50 mg (136 μmol) 6'-(6,7-dihydro-5H-pyrrolo[3,4-d]pyrimidin-4-ylamino)-8'-methyl-2'H-spiro[cyclohexane-1,3'-imidazo[1,5-a]pyridine]-1',5'-dione (prepared according to example 36) in 1.4 mL pyridine were added 22 μL isocyanatoethane and the mixture was stirred at RT for 2 hours. Methanol was added, the precipitate washed with methanol and dried to give 31 mg (49%) of the title compound.

LC-MS: m/z=438.4 [M+H]⁺.

¹H-NMR (400 MHz, DMSO-d6), δ [ppm]=1.07 (3H), 1.14-1.29 (1H), 1.48 (2H), 1.57-1.80 (5H), 2.48 (3H), 2.97 (2H), 3.12 (2H), 4.52 (2H), 4.65 (2H), 6.50 (1H), 8.16 (1H), 8.54 (1H), 8.76 (1H), 10.18 (1H).

Example 76

Ethyl 4-[(8'-methyl-1',5'-dioxo-1',5'-dihydro-2'H-spiro[cyclohexane-1,3'-imidazo[1,5-a]pyridin]-6'-yl)amino]-5,7-dihydro-6H-pyrrolo[3,4-d]pyrimidine-6-carboxylate

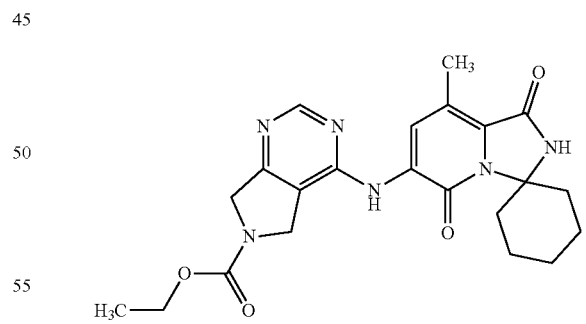

To a solution of 50 mg (136 μmol) 6'-(6,7-dihydro-5H-pyrrolo[3,4-d]pyrimidin-4-ylamino)-8'-methyl-2'H-spiro[cyclohexane-1,3'-imidazo[1,5-a]pyridine]-1',5'-dione (prepared according to example 36) in 1.4 mL pyridine were added 26 μL ethyl carbonochloridate and the mixture was stirred at RT for 1.5 hours. Methanol was added, the precipitate washed with methanol and dried to give 12 mg (19%) of the title compound.

LC-MS: m/z=439.4 [M+H]⁺.

¹H-NMR (400 MHz, DMSO-d6), δ [ppm]=1.16-1.31 (4H), 1.47 (2H), 1.57-1.80 (5H), 2.48 (3H), 2.98 (2H), 4.14 (2H), 4.56+4.59 (2H), 4.72+4.76 (2H), 8.28+8.32 (1H), 8.51 (1H), 8.75 (1H), 10.19 (1H).

Example 77

8'-Methyl-6'-[(6-{[(2S)-5-oxopyrrolidin-2-yl]carbonyl}-6,7-dihydro-5H-pyrrolo[3,4-c]pyrimidin-4-yl)amino]-2'H-spiro[cyclohexane-1,3'-imidazo[1,5-a]pyridine]-1',5'-dione

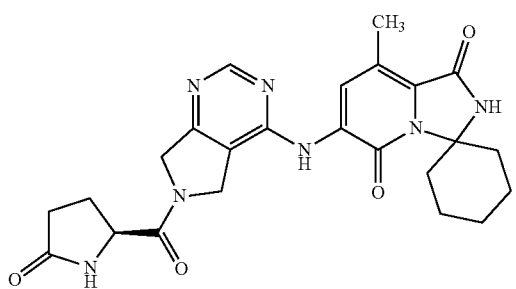 [SMILES: Cc1cc(Nc2ncnc3c2CN(C(=O)[C@@H]2CCC(=O)N2)C3)c(=O)n2c1C(=O)NC21CCCCC1]

A mixture of 45 mg (123 μmol) 6'-(6,7-dihydro-5H-pyrrolo[3,4-d]pyrimidin-4-ylamino)-8'-methyl-2'H-spiro[cyclohexane-1,3'-imidazo[1,5-a]pyridine]-1',5'-dione (prepared according to example 36), 1.9 mL N,N-dimethylacetamide, 171 μL N-ethyl-N-isopropylpropan-2-amine, 63 mg 5-oxo-L-proline and 219 μL 2,4,6-tripropyl-1,3,5,2,4,6-trioxatriphosphinane 2,4,6-trioxide solution (50% in N,N-dimethylformamide) was stirred at RT overnight. The mixture was concentrated, water was added and the precipitate digested with ethanol and diethyl ether to give after drying 28 mg (45%) of the title compound.

LC-MS: m/z=478.4 [M+H]⁺.

¹H-NMR (400 MHz, DMSO-d6), δ [ppm]=1.13-1.31 (1H), 1.48 (2H), 1.57-1.81 (5H), 2.03 (1H), 2.12-2.21 (2H), 2.36-2.45 (1H), 2.48 (3H), 2.99 (2H), 4.50 (1H), 4.58-5.13 (4H), 7.86+7.88 (1H), 8.31+8.39 (1H), 8.53+8.56 (1H), 8.77+8.78 (1H), 10.19 (1H).

Example 78

6'-[(6-Acetyl-6,7-dihydro-5H-pyrrolo[3,4-d]pyrimidin-4-yl)amino]-8'-methyl-2'H-spiro[cyclohexane-1,3'-imidazo[1,5-a]pyridine]-1',5'-dione

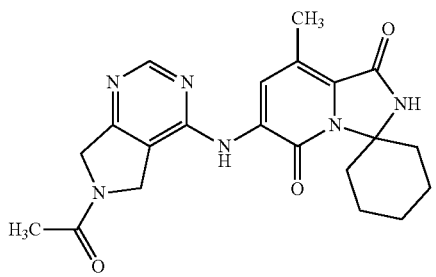 [SMILES: CC(=O)N1Cc2ncnc(Nc3cc(C)c4n(c3=O)C3(CCCCC3)NC4=O)c2C1]

To a solution of 50 mg (136 μmol) 6'-(6,7-dihydro-5H-pyrrolo[3,4-d]pyrimidin-4-ylamino)-8'-methyl-2'H-spiro[cyclohexane-1,3'-imidazo[1,5-a]pyridine]-1',5'-dione (prepared according to example 36) in 1.2 mL THF and 55 μL pyridine were added 19 μL acetyl chloride and the mixture was stirred at RT for 1.5 hours. Methanol was added, the precipitate washed with methanol and dried to give 33 mg (56%) of the title compound.

LC-MS: m/z=409.4 [M+H]⁺.

¹H-NMR (400 MHz, DMSO-d6), δ [ppm]=1.22 (1H), 1.47 (2H), 1.58-1.80 (5H), 2.08+2.10 (3H), 2.48 (3H), 2.98 (2H), 4.54+4.70 (2H), 4.81+4.95 (2H), 8.28+8.33 (1H), 8.52+8.54 (1H), 8.76 (1H), 10.19 (1H).

Example 79

8'-Methyl-6'-{[6-(pyridin-2-ylsulfonyl)-6,7-dihydro-5H-pyrrolo[3,4-d]pyrimidin-4-yl]amino}-2'H-spiro[cyclohexane-1,3'-imidazo[1,5-a]pyridine]-1',5'-dione

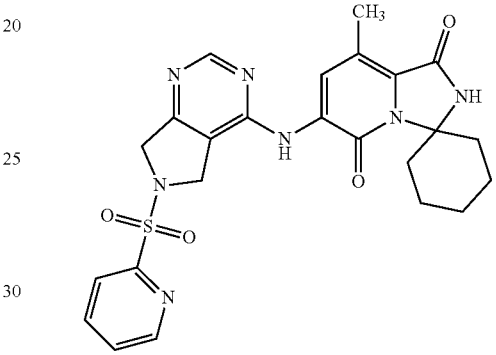

To a solution of 50 mg (136 μmol) 6'-(6,7-dihydro-5H-pyrrolo[3,4-c]pyrimidin-4-ylamino)-8'-methyl-2'H-spiro[cyclohexane-1,3'-imidazo[1,5-a]pyridine]-1',5'-dione (prepared according to example 36) in 1.4 mL pyridine were added 48 mg pyridine-2-sulfonyl chloride and the mixture was stirred at RT for 1.5 hours. Methanol was added, the precipitate washed with methanol and dried to give 48 mg (66%) of the title compound.

LC-MS: m/z=508.3 [M+H]⁺.

¹H-NMR (400 MHz, DMSO-d6), δ [ppm]=1.23 (1H), 1.45 (2H), 1.59-1.78 (5H), 2.45 (3H), 2.96 (2H), 4.76 (2H), 4.87 (2H), 7.67 (1H), 8.03 (1H), 8.12 (1H), 8.40 (1H), 8.43 (1H), 8.66 (1H), 8.69 (1H), 10.18 (1H).

Example 80

4-[(4,4-Difluoro-8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid

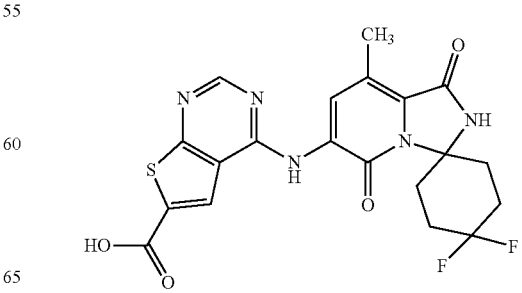

A mixture of 453 mg (953 μmol) methyl 4-[(4,4-difluoro-8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylate (prepared according to example 80a) in 14 mL tetrahydrofuran, 13 mL ethanol and 5.7 mL lithium hydroxide solution (1M in water) was stirred at RT overnight. Water was added and the mixture was acidified with hydrochloric acid. The precipitate was filtered off, washed with water and dried to give 377 mg (86%) of the title compound.

LC-MS: m/z=462.3 [M+H]+.

1H-NMR (400 MHz, DMSO-d6), δ [ppm]=1.68 (2H), 2.12-2.36 (4H), 2.50 (3H*), 3.30 (2H*), 8.48 (1H), 8.54 (1H), 8.71 (1H), 9.42 (1H), 10.43 (1H), 13.79 (1H);

*: at least partially hidden by solvent or water signal

Example 80a

Methyl 4-[(4,4-difluoro-8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylate

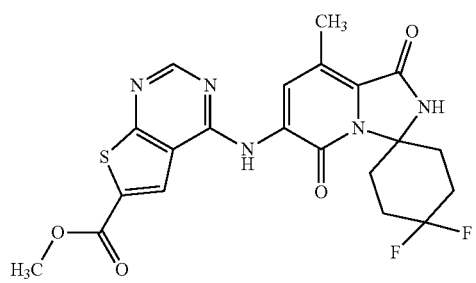 [SMILES: COC(=O)c1cc2c(Nc3cc(C)c4n(c3=O)C3(CCC(F)(F)CC3)NC4=O)ncnc2s1]

To a solution of 500 mg (1.44 mmol) 6'-bromo-4,4-difluoro-8'-methyl-2'H-spiro[cyclohexane-1,3'-imidazo[1,5-a]pyridine]-1',5'-dione (prepared according to PCT Int. Appl. (2015), WO 2015200481) and 331 mg (1.58 mmol) methyl 4-aminothieno[2,3-d]pyrimidine-6-carboxylate (CAS-No: 155087-15-3) in 60 mL 1,4-dioxane was added 1.41 g cesium carbonate and the mixture was degassed and purged with argon several times. 89 mg 4,5-bis(diphenylphosphino)-9,9-dimethylxanthene, 73 mg 2-(dicyclohexyl-phosphino)-2',4',6'-triisopropylbiphenyl, 35 mg palladium(II)acetate and 141 mg tris(dibenzylideneacetone)dipalladium(0) were added and the mixture was stirred at 100° C. for 2 hours. After concentration the mixture was purified by flash chromatography (Biotage SNAP cartridge silica 50 g, methanol:dichloromethane) and crystallization from methanol to give 453 mg (66%) of the title compound.

LC-MS: m/z=476.3 [M+H]+.

Example 81

4-[(4,4-Difluoro-8'-methyl-1',5'-dioxo-1',5'-dihydro-2'H-spiro[cyclohexane-1,3'-imidazo[1,5-a]pyridin]-6'-yl)amino]-N-[2-(dimethylamino)ethyl]thieno[2,3-d]pyrimidine-6-carboxamide

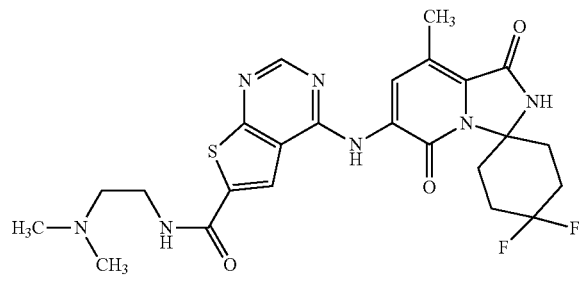 [SMILES: Cc1cc(Nc2ncnc3sc(C(=O)NCCN(C)C)cc23)c(=O)n2c1C(=O)NC21CCC(F)(F)CC1]

A mixture of 50 mg (108 μmol) 4-[(4,4-difluoro-8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 80), 1.7 mL N,N-dimethylacetamide, 151 μL N-ethyl-N-isopropylpropan-2-amine, 47 μL N,N-dimethylethane-1,2-diamine and 194 μL 2,4,6-tripropyl-1,3,5,2,4,6-trioxatriphosphinane 2,4,6-trioxide solution (50% in N,N-dimethylformamide) was stirred at RT overnight. 24 μL N,N-dimethylethane-1,2-diamine and 65 μL 2,4,6-tripropyl-1,3,5,2,4,6-trioxatriphosphinane 2,4,6-trioxide solution (50% in N,N-dimethylformamide) were added and stirring continued at 70° C. for 3 hours. After concentration the mixture was purified by flash chromatography (Biotage SNAP cartridge silica 10 g+NH 11 g, methanol:dichloromethane) to give 28 mg (45%) of the title compound.

LC-MS: m/z=532.3 [M+H]+.

1H-NMR (500 MHz, DMSO-d6), δ [ppm]=1.72 (2H), 2.13-2.35 (10H), 2.47 (2H*), 2.52 (3H), 3.33 (2H), 3.41 (2H), 8.49 (1H), 8.72 (1H), 8.79 (1H), 8.91 (1H), 9.02 (1H), 10.43 (1H);

*: at least partially hidden by solvent or water signal

Example 82

4-[(4,4-Difluoro-8'-methyl-1',5'-dioxo-1',5'-dihydro-2'H-spiro[cyclohexane-1,3'-imidazo[1,5-a]pyridin]-6'-yl)amino]-N-[2-(dimethylamino)ethyl]-N-methylthieno[2,3-d]pyrimidine-6-carboxamide

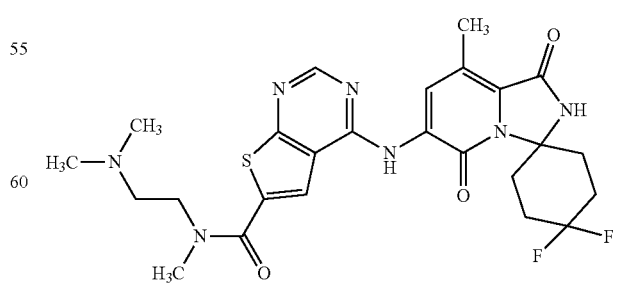

A mixture of 50 mg (108 μmol) 4-[(4,4-difluoro-8'-methyl-1',5'-dioxo-1',5'-dihydro-2'H-spiro[cyclohexane-1, 3'-imidazo[1,5-a]pyridin]-6'-yl)amino]thieno[2,3-d]pyrimidine-6-carboxylic acid (prepared according to example 80), 1.7 mL N,N-dimethylacetamide, 151 μL N-ethyl-N-isopropylpropan-2-amine, 56 μL N,N,N'-trimethylethane-1,2-diamine and 194 μL 2,4,6-tripropyl-1,3,5,2,4,6-trioxatriphosphinane 2,4,6-trioxide solution (50% in N,N-dimethylformamide) was stirred at RT overnight. The mixture was concentrated and purified by flash chromatography (Biotage SNAP cartridge silica 10 g+NH 11 g, methanol:dichloromethane) to give 43 mg (69%) of the title compound.

LC-MS: m/z=546.3 [M+H]$^+$.

$^1$H-NMR (500 MHz, CHLOROFORM-d), δ [ppm]=1.72 (3H), 2.01-2.21 (2H), 2.29 (6H), 2.40 (2H), 2.59 (2H), 2.62 (3H), 3.26 (3H), 3.58 (2H), 3.68 (2H), 8.76 (2H), 8.79 (1H), 8.88 (1H).

Example 83 tert-Butyl [1-({4-[(4,4-difluoro-8'-methyl-1',5'-dioxo-1',5'-dihydro-2'H-spiro[cyclohexane-1,3'-imidazo[1,5-a]pyridin]-6'-yl)amino]thieno[2,3-d]pyrimidin-6-yl}carbonyl)azetidin-3-yl]carbamate

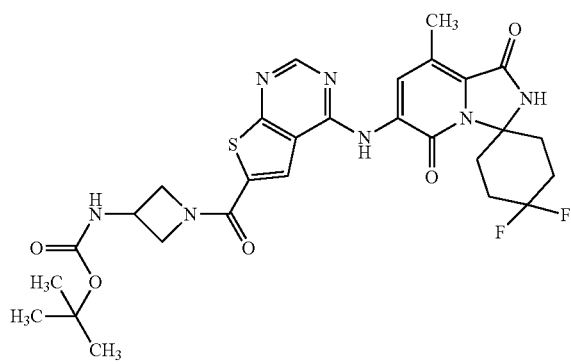 [SMILES: Cc1cc(Nc2ncnc3sc(C(=O)N4CC(NC(=O)OC(C)(C)C)C4)cc23)c(=O)n2c1C(=O)NC21CCC(F)(F)CC1]

A mixture of 100 mg (217 μmol) 4-[(4,4-difluoro-8'-methyl-1',5'-dioxo-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 80), 3.4 mL N,N-dimethylacetamide, 302 μL N-ethyl-N-isopropylpropan-2-amine, 181 mg tert-butyl azetidin-3-ylcarbamate hydrochloride and 387 μL 2,4,6-tripropyl-1,3,5,2,4,6-trioxatriphosphinane 2,4,6-trioxide solution (50% in N,N-dimethylformamide) was stirred at RT overnight. The mixture was concentrated, water was added, the precipitate filtered off, digested with methanol and diethyl ether and dried to give 100 mg (71%) of the title compound.

LC-MS: m/z=616.4 [M+H]$^+$.

$^1$H-NMR (500 MHz, DMSO-d6), δ [ppm]=1.40 (9H), 1.68 (2H), 2.14-2.34 (5H), 2.52 (3H*), 3.37 (1H), 3.99 (1H), 4.32 (1H), 4.44 (2H), 4.87 (1H), 7.71 (1H), 8.26 (1H), 8.52 (1H), 8.68 (1H), 9.56 (1H), 10.43 (1H);

*: at least partially hidden by solvent or water signal

Example 84

6'-({6-[(3-Aminoazetidin-1-yl)carbonyl]thieno[2,3-d]pyrimidin-4-yl}amino)-4,4-difluoro-8'-methyl-2'H-spiro[cyclohexane-1,3'-imidazo[1,5-a]pyridine]-1',5'-dione

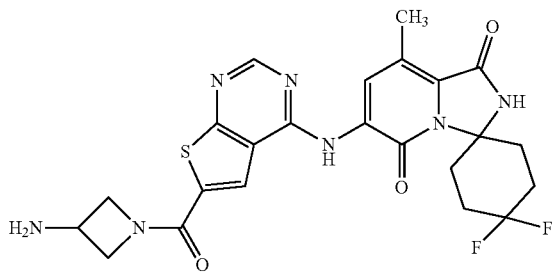 [SMILES: Cc1cc(Nc2ncnc3sc(C(=O)N4CC(N)C4)cc23)c(=O)n2c1C(=O)NC21CCC(F)(F)CC1]

A mixture of 60 mg (97 μmol) tert-butyl [1-({4-[(4,4-difluoro-8'-methyl-1',5'-dioxo-1',5'-dihydro-2'H-spiro[cyclohexane-1,3'-imidazo[1,5-a]pyridin]-6'-yl)amino]thieno[2,3-d]pyrimidin-6-yl}carbonyl)azetidin-3-yl]carbamate (prepared according to example 83) and 150 μL trifluoroacetic acid in 3.8 mL dichloromethane was stirred at RT overnight. The mixture was poured into aqueous ammonia (25%) and extracted with dichloromethane/methanol. The organic layer was washed with water and dried over sodium sulfate. After filtration and concentration the residue was digested with ethanol and diethyl ether and dried to give 8.0 mg (15%) of the title compound.

LC-MS: m/z=516.3 [M+H]$^+$.

$^1$H-NMR (400 MHz, DMSO-d6), δ [ppm]=1.69 (2H), 2.12-2.37 (4H), 2.53 (3H*), 3.28-3.40 (2H*), 3.80 (1H), 3.91 (1H), 4.29 (2H), 4.81 (1H), 8.26 (1H), 8.53 (1H), 8.69 (1H), 9.53 (1H), 10.43 (1H);

*: at least partially hidden by solvent or water signal

Example 85

1-({4-[(4,4-Difluoro-8'-methyl-1',5'-dioxo-1',5'-dihydro-2'H-spiro[cyclohexane-1,3'-imidazo[1,5-a]pyridin]-6'-yl)amino]thieno[2,3-d]pyrimidin-6-yl}carbonyl)azetidine-3-carbonitrile

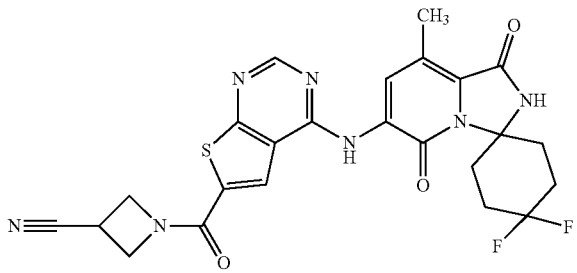 [SMILES: Cc1cc(Nc2ncnc3sc(C(=O)N4CC(C#N)C4)cc23)c(=O)n2c1C(=O)NC21CCC(F)(F)CC1]

A mixture of 50 mg (108 μmol) 4-[(4,4-difluoro-8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 80), 1.7 mL N,N-dimethylacetamide, 151 μL N-ethyl-N-isopropylpropan-2-amine, 51 mg azetidine-3-carbonitrile hydrochloride and 194 μL 2,4,6-tripropyl-1,3,5,2,4,6-trioxatriphosphinane 2,4,6-trioxide solution (50% in N,N-dimethylformamide) was stirred at RT overnight. The mixture was concentrated, water was added, the precipitate filtered off, digested with ethanol and diethyl ether and dried to give 48 mg (57%) of the title compound.

LC-MS: m/z=526.3 [M+H]⁺.

¹H-NMR (400 MHz, DMSO-d6), δ [ppm]=1.69 (2H), 2.10-2.37 (4H), 2.53 (3H*), 3.31 (2H*), 3.96 (1H), 4.27 (1H), 4.41 (1H), 4.90 (2H), 8.32 (1H), 8.55 (1H), 8.70 (1H), 9.48 (1H), 10.43 (1H);

*: at least partially hidden by solvent or water signal

Example 86

6'-[(6-{[(3R)-3-(Dimethylamino)pyrrolidin-1-yl]carbonyl}thieno[2,3-d]pyrimidin-4-yl)amino]-4,4-difluoro-8'-methyl-2'H-spiro[cyclohexane-1,3'-imidazo[1,5-a]pyridine]-1',5'-dione

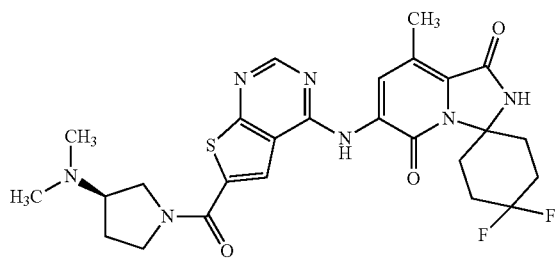 [SMILES: Cc1cc(Nc2ncnc3sc(C(=O)N4CC[C@@H](N(C)C)C4)cc23)c(=O)n2c1C(=O)NC21CCC(F)(F)CC1]

A mixture of 50 mg (108 μmol) 4-[(4,4-difluoro-8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 80), 1.7 mL N,N-dimethylacetamide, 151 μL N-ethyl-N-isopropylpropan-2-amine, 49 mg (3R)—N,N-dimethylpyrrolidin-3-amine and 194 μL 2,4,6-tripropyl-1,3,5,2,4,6-trioxatriphosphinane 2,4,6-trioxide solution (50% in N,N-dimethylformamide) was stirred at RT overnight. The mixture was concentrated and purified by flash chromatography (Biotage SNAP cartridge silica 10 g+NH 11 g, methanol:dichloromethane) to give 53 mg (83%) of the title compound.

LC-MS: m/z=558.3 [M+H]⁺.

¹H-NMR (400 MHz, DMSO-d6), δ [ppm]=1.69 (2H), 1.74-1.95 (1H), 2.03-2.36 (6H), 2.22 (6H), 2.53 (3H*), 2.71-2.88 (1H), 3.25-3.54 (3H), 3.66-3.97 (2H), 4.07 (1H), 8.41+8.43 (1H), 8.53+8.57 (1H), 8.68+8.70 (1H), 9.46+9.47 (1H), 10.43 (1H);

*: at least partially hidden by solvent or water signal

Example 87

6'-[(6-{[4-(Dimethylamino)piperidin-1-yl]carbonyl}thieno[2,3-d]pyrimidin-4-yl)amino]-4,4-difluoro-8'-methyl-2'H-spiro[cyclohexane-1,3'-imidazo[1,5-a]pyridine]-1',5'-dione

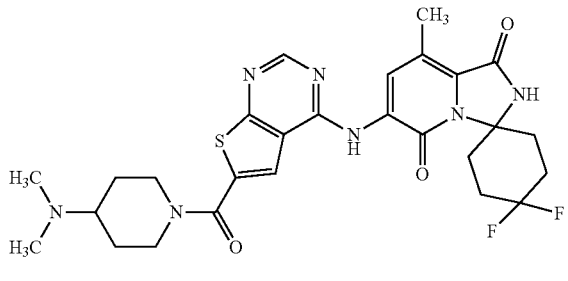 [SMILES: Cc1cc(Nc2ncnc3sc(C(=O)N4CCC(N(C)C)CC4)cc23)c(=O)n2c1C(=O)NC21CCC(F)(F)CC1]

A mixture of 50 mg (108 μmol) 4-[(4,4-difluoro-8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 80), 1.7 mL N,N-dimethylacetamide, 151 μL N-ethyl-N-isopropylpropan-2-amine, 56 mg N,N-dimethylpiperidin-4-amine and 194 μL 2,4,6-tripropyl-1,3,5,2,4,6-trioxatriphosphinane 2,4,6-trioxide solution (50% in N,N-dimethylformamide) was stirred at RT overnight. The mixture was concentrated and purified by flash chromatography (Biotage SNAP cartridge silica 10 g+NH 11 g, methanol:dichloromethane) to give 52 mg (80%) of the title compound.

LC-MS: m/z=572.4 [M+H]⁺.

¹H-NMR (400 MHz, DMSO-d6), δ [ppm]=1.46 (2H), 1.69 (2H), 1.87 (2H), 2.10-2.37 (9H), 2.41-2.61 (5H*), 2.77-3.27 (2H), 3.27-3.39 (2H*), 4.33 (2H), 8.20 (1H), 8.61 (1H), 8.71 (1H), 9.34 (1H), 10.42 (1H);

*: at least partially hidden by solvent or water signal

Example 88

4,4-Difluoro-8'-methyl-6'-({6-[(1R,4R)-2-oxa-5-azabicyclo[2.2.1]hept-5-ylcarbonyl]thieno[2,3-d]pyrimidin-4-yl}amino)-2'H-spiro[cyclohexane-1,3'-imidazo[1,5-a]pyridine]-1',5'-dione

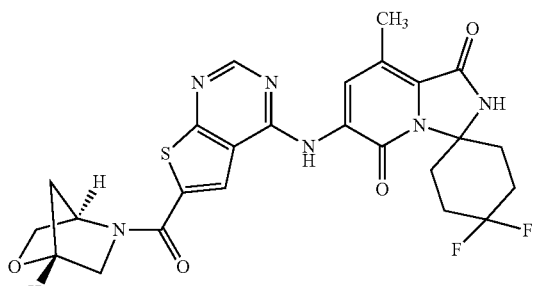

A mixture of 50 mg (108 μmol) 4-[(4,4-difluoro-8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 80), 1.7 mL N,N-dimethylacetamide, 75 μL N-ethyl-N-isopropylpropan-2-amine, 59 mg (1R,4R)-2-oxa-5-azabicyclo

[2.2.1]heptane hydrochloride and 194 µL 2,4,6-tripropyl-1,3,5,2,4,6-trioxatriphosphinane 2,4,6-trioxide solution (50% in N,N-dimethylformamide) was stirred at RT overnight. Water was added, the precipitate digested with ethanol and diethyl ether and dried to give 53 mg (81%) of the title compound.

LC-MS: m/z=543.3 [M+H]+.

1H-NMR (400 MHz, DMSO-d6), δ [ppm]=1.69 (2H), 1.84-2.04 (2H), 2.10-2.38 (4H), 2.53 (3H*), 3.26-3.44 (2H), 3.53-4.02 (4H), 4.70+4.80 (1H), 4.94+5.24 (1H), 8.30+8.42 (1H), 8.57+8.61 (1H), 8.70 (1H), 9.45 (1H), 10.42 (1H);

*: at least partially hidden by solvent or water signal

Example 89

4,4-Difluoro-8'-methyl-6'-(thieno[2,3-d]pyrimidin-4-ylamino)-2'H-spiro[cyclohexane-1,3'-imidazo[1,5-a]pyridine]-1',5'-dione

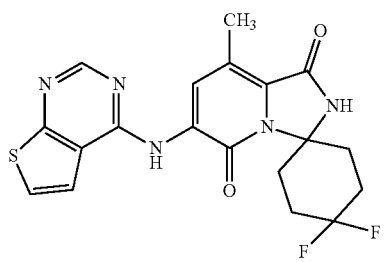 [SMILES: Cc1cc(Nc2ncnc3sccc23)c(=O)n2c1C(=O)NC21CCC(F)(F)CC1]

To a solution of 100 mg (288 µmol) 6'-bromo-4,4-difluoro-8'-methyl-2'H-spiro[cyclohexane-1,3'-imidazo[1,5-a]pyridine]-1',5'-dione (prepared according to PCT Int. Appl. (2015), WO 2015200481) and 48 mg (317 µmol) thieno[2,3-d]pyrimidin-4-amine (CAS-No: 14080-56-9) in 10 mL 1,4-dioxane was added 282 mg cesium carbonate and the mixture was degassed and purged with argon several times. 18 mg 4,5-bis(diphenylphosphino)-9,9-dimethylxanthene, 15 mg 2-(dicyclohexyl-phosphino)-2',4',6'-triisopropylbiphenyl, 7 mg palladium(II)acetate and 28 mg tris(dibenzylideneacetone)dipalladium(0) were added and the mixture was stirred at 100° C. for 2 hours. After concentration the mixture was purified by flash chromatography (Biotage SNAP cartridge silica 25 g, ethanol:dichloromethane) and crystallization from methanol to give 31 mg (24%) of the title compound.

LC-MS: m/z=418.3 [M+H]+.

1H-NMR (400 MHz, DMSO-d6), δ [ppm]=1.68 (2H), 2.12-2.37 (4H), 2.52 (3H*), 3.26-3.39 (2H), 7.82 (1H), 7.87 (1H), 8.65 (1H), 8.70 (1H), 9.05 (1H), 10.40 (1H);

*: at least partially hidden by solvent or water signal

Example 90

4,4-Difluoro-8'-methyl-6'-(7H-pyrrolo[2,3-d]pyrimidin-4-ylamino)-2'H-spiro[cyclohexane-1,3'-imidazo[1,5-a]pyridine]-1',5'-dione

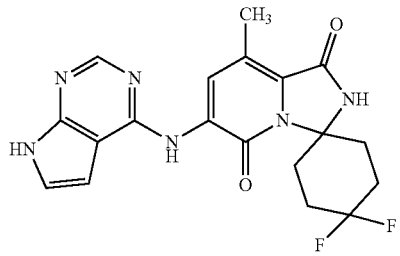 [SMILES: Cc1cc(Nc2ncnc3[nH]ccc23)c(=O)n2c1C(=O)NC21CCC(F)(F)CC1]

To a solution of 135 mg (388 µmol) 6'-bromo-4,4-difluoro-8'-methyl-2'H-spiro[cyclohexane-1,3'-imidazo[1,5-a]pyridine]-1',5'-dione (prepared according to PCT Int. Appl. (2015), WO 2015200481) and 100 mg (427 µmol) tert-butyl 4-amino-7H-pyrrolo[2,3-d]pyrimidine-7-carboxylate (prepared according to example 90a) in 10 mL 1,4-dioxane was added 379 mg cesium carbonate and the mixture was degassed and purged with argon several times. 24 mg 4,5-bis(diphenylphosphino)-9,9-dimethylxanthene, 20 mg 2-(dicyclohexyl-phosphino)-2',4',6'-triisopropylbiphenyl, 9 mg palladium(II)acetate and 38 mg tris(dibenzylideneacetone)dipalladium(0) were added and the mixture was stirred at 100° C. for 2 hours. After concentration the mixture was purified by flash chromatography (Biotage SNAP cartridge silica 25 g, methanol:dichloromethane) and crystallization from methanol to give 77 mg (47%) of the title compound.

LC-MS: m/z=401.3 [M+H]+.

1H-NMR (400 MHz, DMSO-d6), δ [ppm]=1.67 (2H), 2.09-2.36 (4H), 2.53 (3H*), 3.26-3.39 (2H*), 6.82 (1H), 7.37 (1H), 8.46 (1H), 8.63 (1H), 8.75 (1H), 10.32 (1H), 12.02 (1H);

*: at least partially hidden by solvent or water signal

Example 90a tert-Butyl 4-amino-7H-pyrrolo[2,3-d]pyrimidine-7-carboxylate

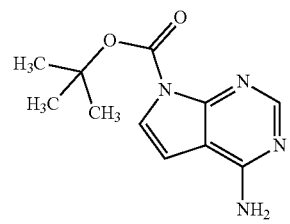 [SMILES: CC(C)(C)OC(=O)n1ccc2c(N)ncnc21]

To a solution of 1.00 g (7.46 mmol) 7H-pyrrolo[2,3-d]pyrimidin-4-amine (CAS-No. 1500-85-2) and 182 mg N,N-dimethylpyridin-4-amine in 20 mL pyridine was added 1.63 g di-tert-butyl carbonate and the mixture was stirred at RT overnight. After concentration the residue was purified by flash chromatography (Biotage SNAP cartridge silica 100 g, methanol:dichloromethane) to give 715 mg (41%) of the title compound.

LC-MS: m/z=235.2 [M+H]+.

Example 91

4,4-Difluoro-8'-methyl-6'-(7H-pyrrolo[2,3-d]pyrimidin-4-ylamino)-2'H-spiro[cyclohexane-1,3'-imidazo[1,5-a]pyridine]-1',5'-dione methanesulfonate

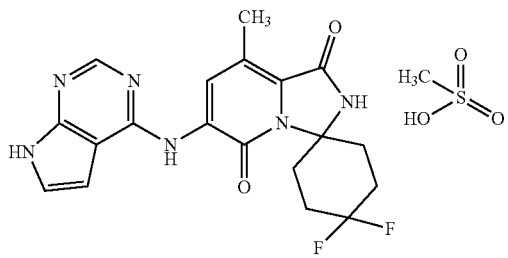

To a solution of 25 mg (62 mmol) 4,4-difluoro-8'-methyl-6'-(7H-pyrrolo[2,3-d]pyrimidin-4-ylamino)-2'H-spiro[cyclohexane-1,3'-imidazo[1,5-a]pyridine]-1',5'-dione (prepared according to example 90) in 1,4-dioxane and methanol was added 6.00 mg methanesulfonic acid and the mixture was stirred at RT for 10 minutes. After concentration and crystallization from methanol 28 mg (86%) of the title compound were isolated.

LC-MS: m/z=401.3 [M+H]$^+$.

$^1$H-NMR (400 MHz, DMSO-d6), δ [ppm]=1.67 (2H), 2.12-2.36 (4H), 2.30 (3H), 2.53 (3H*), 3.31 (2H), 6.87 (1H), 7.43 (1H), 8.46 (1H), 8.54 (1H), 10.41 (1H), 12.25 (1H);

*: at least partially hidden by solvent or water signal

Example 92

4,4-Difluoro-8'-methyl-6'-(7H-pyrrolo[2,3-d]pyrimidin-4-ylamino)-2'H-spiro[cyclohexane-1,3'-imidazo[1,5-a]pyridine]-1',5'-dione hydrochloride

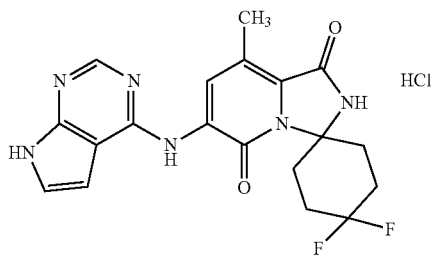 [SMILES: Cc1cc(Nc2ncnc3[nH]ccc23)c(=O)n2c1C(=O)NC21CCC(F)(F)CC1 ; Cl]

To a solution of 34 mg (85 mmol) 4,4-difluoro-8'-methyl-6'-(7H-pyrrolo[2,3-d]pyrimidin-4-ylamino)-2'H-spiro[cyclohexane-1,3'-imidazo[1,5-a]pyridine]-1',5'-dione (prepared according to example 90) in 10 mL 1,4-dioxane was added 127 μL hydrochloric acid (4 M in 1,4-dioxane). The mixture was stirred at RT for 10 minutes. After concentration 37 mg (95%) of the title compound were isolated.

LC-MS: m/z=401.3 [M+H]$^+$.

$^1$H-NMR (400 MHz, DMSO-d6), δ [ppm]=1.67 (2H), 2.10-2.36 (4H), 2.52 (3H*), 3.31 (2H), 6.87 (1H), 7.42 (1H), 8.46 (1H), 8.52 (1H), 10.41 (1H), 12.25 (1H)

*: at least partially hidden by solvent or water signal

Example 93

4-[(4,4-Difluoro-8'-methyl-1',5'-dioxo-1',5'-dihydro-2'H-spiro[cyclohexane-1,3'-imidazo[1,5-a]pyridin]-6'-yl)amino]-5-methylthieno[2,3-d]pyrimidine-6-carboxylic acid

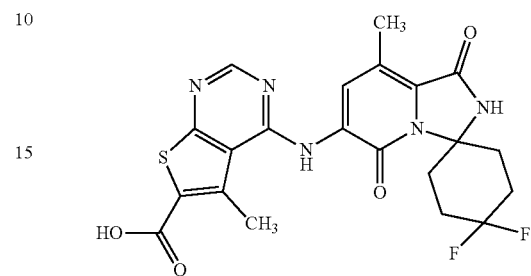

A mixture of 260 mg (516 μmol) ethyl 4-[(4,4-difluoro-8'-methyl-1',5'-dioxo-1',5'-dihydro-2'H-spiro[cyclohexane-1,3'-imidazo[1,5-a]pyridin]-6'-yl)amino]-5-methylthieno[2,3-d]pyrimidine-6-carboxylate (prepared according to example 93a) in 8 mL tetrahydrofuran, 8 mL ethanol and 3.1 mL lithium hydroxide solution (1M in water) was stirred at RT overnight.

Water was added and the mixture was acidified with hydrochloric acid. The precipitate was filtered off, washed with water and dried to give 240 mg (93%) of the title compound.

LC-MS: m/z=476.2 [M+H]$^+$.

$^1$H-NMR (400 MHz, DMSO-d6), δ [ppm]=1.69 (2H), 2.14-2.35 (4H), 2.53 (3H*), 3.12 (3H), 3.29 (2H), 8.77 (1H), 8.80 (1H), 9.34 (1H), 10.44 (1H), 13.83 (1H);

*: at least partially hidden by solvent peak.

Example 93a

Ethyl 4-[(4,4-difluoro-8'-methyl-1',5'-dioxo-1',5'-dihydro-2'H-spiro[cyclohexane-1,3'-imidazo[1,5-a]pyridin]-6'-yl)amino]-5-methylthieno[2,3-c]pyrimidine-6-carboxylate

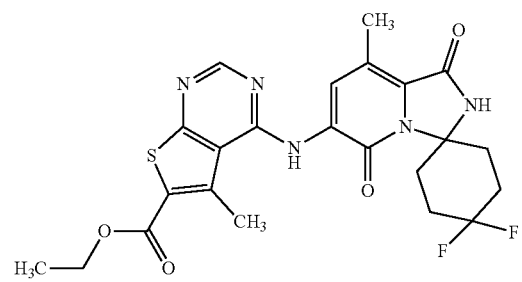 [SMILES: CCOC(=O)c1sc2ncnc(Nc3cc(C)c4n(c3=O)C3(CCC(F)(F)CC3)NC4=O)c2c1C]

To a solution of 200 mg (576 μmol) 6'-bromo-4,4-difluoro-8'-methyl-2'H-spiro[cyclohexane-1,3'-imidazo[1,5-a]pyridine]-1',5'-dione (prepared according to PCT Int. Appl. (2015), WO 2015200481) and 150 mg (634 μmol) ethyl 4-amino-5-methylthieno[2,3-d]pyrimidine-6-carboxylate (CAS-No: 60598-74-5) in 17 mL 1,4-dioxane was added 563 mg cesium carbonate and the mixture was degassed and purged with argon several times. 35.7 mg 4,5-bis(diphenylphosphino)-9,9-dimethylxanthene, 29.4 mg 2-(dicyclohexyl-phosphino)-2',4',6'-triisopropylbiphenyl, 13.8 mg palladium(II)acetate and 56.4 mg tris(dibenzylideneacetone)dipalladium(0) were added and the mixture was stirred at 100° C. for 2 hours. After concentration the mixture was purified by flash chromatography (Biotage SNAP cartridge silica 25 g, ethanol:dichloromethane) and crystallization from ethanol to give 260 mg (90%) of the title compound.

LC-MS: m/z=504.3 [M+H]⁺.

Example 94

6'-[(4-Amino-1,3,5-triazin-2-yl)amino]-4,4-difluoro-8'-methyl-2'H-spiro[cyclohexane-1,3'-imidazo[1,5-a]pyridine]-1',5'-dione

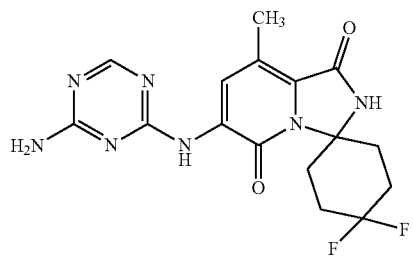 [SMILES: Cc1cc(Nc2ncnc(N)n2)c(=O)n2c1C(=O)NC21CCC(F)(F)CC1]

To a solution of 150 mg (432 µmol) 6'-bromo-4,4-difluoro-8'-methyl-2'H-spiro[cyclohexane-1,3'-imidazo[1,5-a]pyridine]-1',5'-dione (prepared according to PCT Int. Appl. (2015), WO 2015200481) and 85 mg (475 µmol) N-(4-amino-1,3,5-triazin-2-yl)cyclopropanecarboxamide (prepared according to example 1a) in 17 mL 1,4-dioxane was added 422 mg cesium carbonate and the mixture was degassed and purged with argon several times. 26.8 mg 4,5-bis(diphenylphosphino)-9,9-dimethylxanthene, 22 mg 2-(dicyclohexyl-phosphino)-2',4',6'-triisopropylbiphenyl, 10.4 mg palladium(II)acetate and 42.3 mg tris(dibenzylideneacetone)dipalladium(0) were added and the mixture was stirred at 100° C. for 2 hours. After concentration the mixture was purified by flash chromatography (Biotage SNAP cartridge silica 25 g, ethanol:dichloromethane) and crystallization from methanol to give 43 mg (25%) of the title compound.

LC-MS: m/z=378.2 [M+H]⁺.

¹H-NMR (400 MHz, DMSO-d6), δ [ppm]=1.63 (2H), 2.08-2.35 (4H), 2.47 (3H), 3.26 (2H), 7.47 (2H), 8.05 (1H), 8.27 (1H), 8.48 (1H), 10.33 (1H).

Example 95

5-Methyl-4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxylic acid

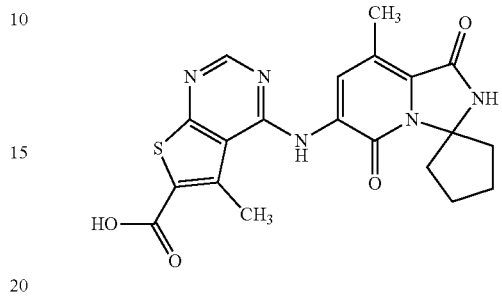

A mixture of 120 mg (265 µmol) ethyl 5-methyl-4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxylate (prepared according to example 95a) in 4 mL tetrahydrofuran, 4 mL ethanol and 1.6 mL lithium hydroxide solution (1M in water) was stirred at RT overnight. Water was added and the mixture was acidified with hydrochloric acid. The precipitate was filtered off, washed with water and dried to give 110 mg (88%) of the title compound.

LC-MS: m/z=426.3 [M+H]⁺.

¹H-NMR (400 MHz, DMSO-d6), δ [ppm]=1.71 (2H), 1.85 (2H), 1.99 (2H), 2.52 (3H*), 2.87 (2H), 3.10 (3H), 8.75 (2H), 9.31 (1H), 10.04 (1H), 13.80 (1H);

*: at least partially hidden by solvent peak.

Example 95a

Ethyl 5-methyl-4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxylate

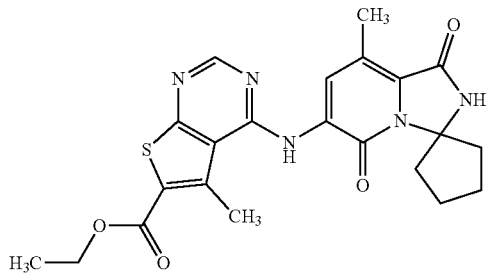 [SMILES: CCOC(=O)c1sc2ncnc(Nc3cc(C)c4n(c3=O)C3(CCCC3)NC4=O)c2c1C]

To a solution of 200 mg (673 µmol) 6'-bromo-8'-methyl-2'H-spiro[cyclopentane-1,3'-imidazo[1,5-a]pyridine]-1',5'-dione (CAS-No: 1849592-55-7; PCT Int. Appl. (2015), WO 2015200481) and 176 mg (740 µmol) ethyl 4-amino-5-methylthieno[2,3-d]pyrimidine-6-carboxylate (CAS-No: 60598-74-5) in 20 mL 1,4-dioxane was added 658 mg cesium carbonate and the mixture was degassed and purged with argon several times. 41.7 mg 4,5-bis(diphenylphosphino)-9,9-dimethylxanthene, 34.3 mg 2-(dicyclohexyl-phosphino)-2',4',6'-triisopropylbiphenyl, 16.2 mg palladium (II)acetate and 65.9 mg tris(dibenzylideneacetone) dipalladium(0) were added and the mixture was stirred at 100° C. for 2 hours. After concentration the mixture was purified by flash chromatography (Biotage SNAP cartridge silica 25 g, ethanol:dichloromethane) and crystallization from ethanol to give 120 mg (39%) of the title compound.

LC-MS: m/z=454.3 [M+H]⁺.

Example 96

8'-Methyl-6'-({6-[(1R,4R)-2-oxa-5-azabicyclo[2.2.1]hept-5-ylcarbonyl]thieno[2,3-d]pyrimidin-4-yl}amino)-2'H-spiro[cyclopentane-1,3'-imidazo[1,5-a]pyridine]-1',5'-dione

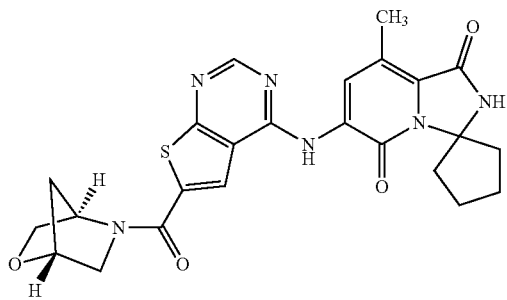 [SMILES: Cc1cc(Nc2ncnc3sc(C(=O)N4C[C@H]5C[C@@H]4CO5)cc23)c(=O)n2c1C(=O)NC21CCCC1]

A mixture of 50 mg (122 µmol) 4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxylic acid (prepared according to example 58), 1.9 mL N,N-dimethylacetamide, 85 µL N-ethyl-N-isopropylpropan-2-amine, 66 mg (1R,4R)-2-oxa-5-azabicyclo[2.2.1]heptane hydrochloride and 217 µL 2,4,6-tripropyl-1,3,5,2,4,6-trioxatriphosphinane 2,4,6-trioxide solution (50% in N,N-dimethylformamide) was stirred at RT overnight. The mixture was concentrated the precipitate filtered off, washed with ethanol and diethyl ether and dried to give 51 mg (81%) of the title compound.

LC-MS: m/z=493.3 [M+H]⁺.

¹H-NMR (400 MHz, DMSO-d6), δ [ppm]=1.73 (2H), 1.79-2.05 (6H), 2.48 (3H), 2.50 (2H*), 2.83 (2H), 3.36-4.04 (4H), 4.71+4.80 (1H), 4.94+5.24 (1H), 8.30+8.43 (1H), 8.54+8.58 (1H), 8.69 (1H), 9.49 (1H), 10.03 (1H);

*: at least partially hidden by solvent or water signal

Example 97

4-[(8'-Methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxamide

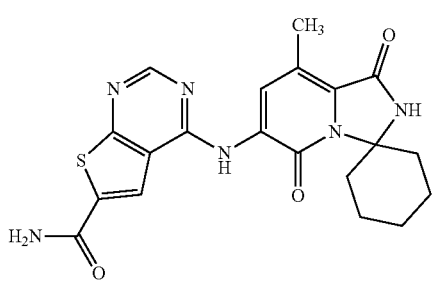 [SMILES: Cc1cc(Nc2ncnc3sc(C(N)=O)cc23)c(=O)n2c1C(=O)NC21CCCCC1]

To a solution of 92 mg (216 µmol) 4-[(8'-methyl-1',5'-dioxo-1',5'-dihydro-2'H-spiro[cyclohexane-1,3'-imidazo[1,5-a]pyridin]-6'-yl)amino]thieno[2,3-d]pyrimidine-6-carboxylic acid (prepared according to example 9), 123 mg N-[(dimethylamino)-1H-1,2,3-triazolo-[4,5-b]pyridin-1-yl-methylene]-N-methylmethanaminium hexafluorophosphate N-oxide and 39.6 mg N,N-dimethylpyridin-4-amine in 6.0 mL N,N-dimethylacetamide were added 2.7 mL ammonia (0.4M in THF) and the mixture was stirred at RT overnight. After concentration the mixture was purified by flash chromatography (Biotage SNAP cartridge silica 10 g, methanol:dichloromethane) and crystalline material digested with methanol to give 60 mg (62%) of the title compound.

LC-MS: m/z=425.3 [M+H]⁺.

¹H-NMR (400 MHz, DMSO-d6), δ [ppm]=1.22 (1H), 1.52 (2H), 1.59-1.81 (5H), 2.52 (3H*), 3.01 (2H), 7.78 (1H), 8.38 (1H), 8.49 (1H), 8.69 (1H), 8.78 (1H), 9.01 (1H), 10.24 (1H);

*: at least partially hidden by solvent or water signal

Example 98

6'-[(6-Chloroquinazolin-4-yl)amino]-8'-methyl-2'H-spiro[cyclopentane-1,3'-imidazo[1,5-a]pyridine]-1',5'-dione

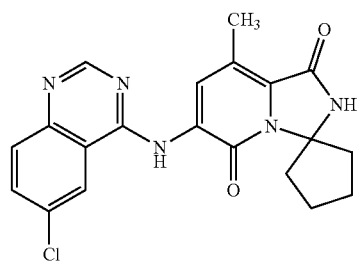 [SMILES: Cc1cc(Nc2ncnc3ccc(Cl)cc23)c(=O)n2c1C(=O)NC21CCCC1]

To a solution of 100 mg (337 µmol) 6'-bromo-8'-methyl-2'H-spiro[cyclopentane-1,3'-imidazo[1,5-a]pyridine]-1',5'-dione (CAS-No: 1849592-55-7; PCT Int. Appl. (2015), WO 2015200481) and 66 mg (370 µmol) 6-chloroquinazolin-4-amine (CAS-No: 19808-35-6) in 12.6 mL 1,4-dioxane was added 329 mg cesium carbonate and the mixture was degassed and purged with argon several times. 21 mg 4,5-bis(diphenylphosphino)-9,9-dimethylxanthene, 17 mg 2-(dicyclohexyl-phosphino)-2',4',6'-triisopropylbiphenyl, 8.1 mg palladium(II)acetate and 33 mg tris(dibenzylideneacetone) dipalladium(0) were added and the mixture was stirred at 100° C. for 2 hours. The mixture was concentrated and the residue purified by flash chromatography (Biotage SNAP cartridge silica 25 g, ethanol:dichloromethane) and chrystallization from ethanol to give 74 mg (56%) of the title compound.

LC-MS: m/z=396.3 [M+H]⁺.

¹H-NMR (400 MHz, DMSO-d6), δ [ppm]=1.73 (2H), 1.85 (2H), 1.99 (2H), 2.52 (3H*), 2.84 (2H), 7.87 (1H), 7.94 (1H), 8.44 (1H), 8.59 (1H), 8.79 (1H), 9.47 (1H), 10.05 (1H);

*: at least partially hidden by solvent or water signal

Example 99

6'-[(6-chloroquinazolin-4-yl)amino]-4,4-difluoro-8'-methyl-2'H-spiro[cyclohexane-1,3'-imidazo[1,5-a]pyridine]-1',5'-dione

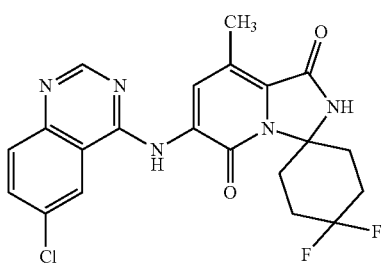 [SMILES: Cc1cc(Nc2ncnc3ccc(Cl)cc23)c(=O)n2c1C(=O)NC21CCC(F)(F)CC1]

To a solution of 100 mg (288 μlDA) 6'-bromo-4,4-difluoro-8'-methyl-2'H-spiro[cyclohexane-1,3'-imidazo[1,5-a]pyridine]-1',5'-dione (prepared according to PCT Int. Appl. (2015), WO 2015200481) and 57 mg (317 μlDA) 6-chloroquinazolin-4-amine (CAS-No: 19808-35-6) in 10.8 mL 1,4-dioxane was added 282 mg cesium carbonate and the mixture was degassed and purged with argon several times. 17.8 mg 4,5-bis(diphenylphosphino)-9,9-dimethylxanthene, 14.7 mg 2-(dicyclohexyl-phosphino)-2',4',6'-triisopropylbiphenyl, 6.9 mg palladium(II)acetate and 28.2 mg tris(dibenzylideneacetone)dipalladium(0) were added and the mixture was stirred at 100° C. for 2 hours. After concentration the mixture was purified by flash chromatography (Biotage SNAP cartridge silica 25 g, ethanol:dichloromethane) and crystallization from ethanol to give 64 mg (50%) of the title compound.

LC-MS: m/z=446.3 [M+H]$^+$.

$^1$H-NMR (400 MHz, DMSO-d6), δ [ppm]=1.70 (2H), 2.12-2.37 (4H), 2.52 (3H*), 3.27-3.38 (2H*), 7.88 (1H), 7.95 (1H), 8.45 (1H), 8.63 (1H), 8.80 (1H), 9.45 (1H), 10.45 (1H);

*: at least partially hidden by solvent or water signal

Example 100

8'-Methyl-6'-([1,3]thiazolo[5,4-d]pyrimidin-7-ylamino)-2'H-spiro[cyclopentane-1,3'-imidazo[1,5-a]pyridine]-1',5'-dione

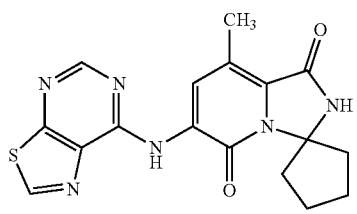 [SMILES: Cc1cc(Nc2ncnc3scnc23)c(=O)n2c1C(=O)NC21CCCC1]

To a solution of 100 mg (337 μmol) 6'-bromo-8'-methyl-2'H-spiro[cyclopentane-1,3'-imidazo[1,5-a]pyridine]-1',5'-dione (CAS-No: 1849592-55-7; PCT Int. Appl. (2015), WO 2015200481) and 56 mg (370 μmol) [1,3]thiazolo[5,4-d]pyrimidin-7-amine (CAS-No: 2846-90-4) in 12.6 mL 1,4-dioxane was added 329 mg cesium carbonate and the mixture was degassed and purged with argon several times. 21 mg 4,5-bis(diphenylphosphino)-9,9-dimethylxanthene, 17 mg 2-(dicyclohexyl-phosphino)-2',4',6'-triisopropylbiphenyl, 8.1 mg palladium(II)acetate and 33 mg tris(dibenzylideneacetone) dipalladium(0) were added and the mixture was stirred at 100° C. for 2 hours. The mixture was concentrated and the residue purified by flash chromatography (Biotage SNAP cartridge silica 25 g, ethanol:dichloromethane) followed by crystallization from ethanol to give 66 mg (51%) of the title compound.

LC-MS: m/z=369.2 [M+H]$^+$.

$^1$H-NMR (400 MHz, DMSO-d6), δ [ppm]=1.72 (2H), 1.84 (2H), 1.99 (2H), 2.51 (3H*), 2.83 (2H), 8.71 (1H), 8.83 (1H), 9.36 (1H), 9.50 (1H), 10.02 (1H);

*: at least partially hidden by solvent or water signal

Example 101

4,4-Difluoro-8'-methyl-6'-([1,3]thiazolo[5,4-d]pyrimidin-7-ylamino)-2'H-spiro[cyclohexane-1,3'-imidazo[1,5-a]pyridine]-1',5'-dione

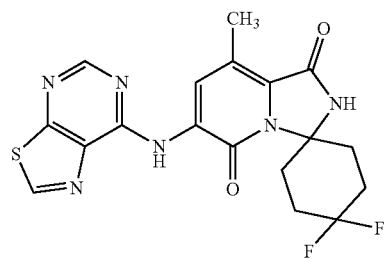 [SMILES: Cc1cc(Nc2ncnc3scnc23)c(=O)n2c1C(=O)NC21CCC(F)(F)CC1]

To a solution of 100 mg (288 μmol) 6'-bromo-4,4-difluoro-8'-methyl-2'H-spiro[cyclohexane-1,3'-imidazo[1,5-a]pyridine]-1',5'-dione (prepared according to PCT Int. Appl. (2015), WO 2015200481) and 48.2 mg (317 μmol) [1,3]thiazolo[5,4-d]pyrimidin-7-amine (CAS-No: 2846-90-4) in 10.8 mL 1,4-dioxane was added 282 mg cesium carbonate and the mixture was degassed and purged with argon several times. 17.8 mg 4,5-bis(diphenylphosphino)-9,9-dimethylxanthene, 14.7 mg 2-(dicyclohexyl-phosphino)-2',4',6'-triisopropylbiphenyl, 6.9 mg palladium(II)acetate and 28.2 mg tris(dibenzylideneacetone)dipalladium(0) were added and the mixture was stirred at 100° C. for 2 hours. After concentration the mixture was purified by flash chromatography (Biotage SNAP cartridge silica 25 g, ethanol:dichloromethane) and crystallization from ethanol to give 73 mg (58%) of the title compound.

LC-MS: m/z=419.3 [M+H]$^+$.

$^1$H-NMR (400 MHz, DMSO-d6), δ [ppm]=1.69 (2H), 2.10-2.36 (4H), 2.53 (3H*), 3.29 (2H), 8.73 (1H), 8.83 (1H), 9.35 (1H), 9.51 (1H), 10.42 (1H);

*: at least partially hidden by solvent or water signal

Example 102

4-[(8'-Methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxamide

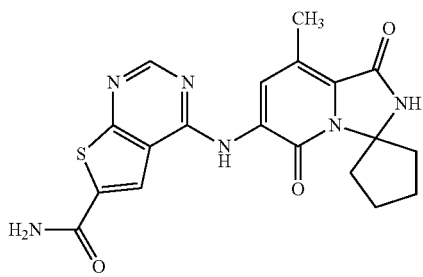 [SMILES: Cc1cc(Nc2ncnc3sc(C(N)=O)cc23)c(=O)n2c1C(=O)NC21CCCC1]

To a solution of 35 mg (85 µmol) 4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxylic acid (prepared according to example 58) in 2.4 mL N,N-dimethylacetamide, were added 48.5 mg 1-[bis(dimethylamino)methylene]-1H-1,2,3-triazolo[4,5-b]pyridinium 3-oxid hexafluorophosphate, 22.3 mg N,N-dimethylpyridin-4-amine, 1.1 mL ammonia (0.4 M in THF) and the mixture was stirred at 100° C. for 10 hours. After concentration, the residue was washed with methanol and dried to give 25 mg (68%) of the title compound.

LC-MS: m/z=411.3 [M+H]$^+$.

$^1$H-NMR (400 MHz, DMSO-d6), δ [ppm]=1.75 (2H), 1.86 (2H), 1.99 (2H), 2.52 (3H*), 2.83 (2H), 7.78 (1H), 8.39 (1H), 8.49 (1H), 8.71 (1H), 8.78 (1H), 8.99 (1H), 10.03 (1H);

*: at least partially hidden by solvent or water signal

Example 103 tert-Butyl 4-[(8'-methyl-1',5'-dioxo-1',5'-dihydro-2'H-spiro[cyclopentane-1,3'-imidazo[1,5-a]pyridin]-6'-yl)amino]-5,7-dihydro-6H-pyrrolo[3,4-d]pyrimidine-6-carboxylate

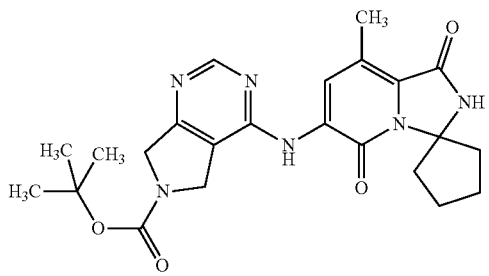 [SMILES: Cc1cc(Nc2ncnc3c2CN(C(=O)OC(C)(C)C)C3)c(=O)n2c1C(=O)NC21CCCC1]

To a solution of 200 mg (673 µmol) 6'-bromo-8'-methyl-2'H-spiro[cyclopentane-1,3'-imidazo[1,5-a]pyridine]-1',5'-dione (CAS-No: 1849592-55-7; PCT Int. Appl. (2015), WO 2015200481) and 175 mg (740 µmol) tert-butyl 4-amino-5,7-dihydro-6H-pyrrolo[3,4-d]pyrimidine-6-carboxylate (CAS-No: 1227461-25-7) in 20 mL 1,4-dioxane was added 658 mg cesium carbonate and the mixture was degassed and purged with argon several times. 42 mg 4,5-bis(diphenylphosphino)-9,9-dimethylxanthene, 34 mg 2-(dicyclohexyl-phosphino)-2',4',6'-triisopropylbiphenyl, 16 mg palladium(II)acetate and 66 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, methanol:dichloromethane) to give 115 mg (36%) of the title compound.

LC-MS: m/z=453.4 [M+H]$^+$.

$^1$H-NMR (400 MHz, DMSO-d6), δ [ppm]=1.47+1.49 (9H), 1.71 (2H), 1.84 (2H), 1.97 (2H), 2.46 (3H), 2.79 (2H), 4.50+4.53 (2H), 4.66+4.70 (2H), 8.28+8.33 (1H), 8.53 (1H), 8.74 (1H), 9.98 (1H).

Example 104 tert-Butyl 4-[(4,4-difluoro-8'-methyl-1',5'-dioxo-1',5'-dihydro-2'H-spiro[cyclohexane-1,3'-imidazo[1,5-a]pyridin]-6'-yl)amino]-5,7-dihydro-6H-pyrrolo[3,4-d]pyrimidine-6-carboxylate

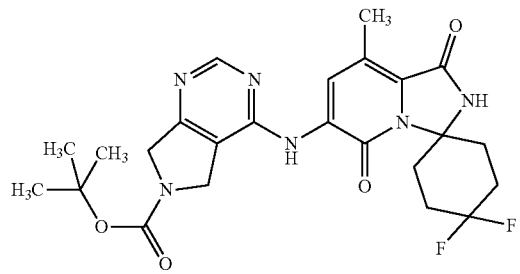 [SMILES: Cc1cc(Nc2ncnc3c2CN(C(=O)OC(C)(C)C)C3)c(=O)n2c1C(=O)NC21CCC(F)(F)CC1]

To a solution of 200 mg (576 µmol) 6'-bromo-4,4-difluoro-8'-methyl-2'H-spiro[cyclohexane-1,3'-imidazo[1,5-a]pyridine]-1',5'-dione (prepared according to PCT Int. Appl. (2015), WO 2015200481) and 150 mg (634 µmol) tert-butyl 4-amino-5,7-dihydro-6H-pyrrolo[3,4-d]pyrimidine-6-carboxylate (CAS-No: 1227461-25-7) in 20 mL 1,4-dioxane was added 563 mg cesium carbonate and the mixture was degassed and purged with argon several times. 35.7 mg 4,5-bis(diphenylphosphino)-9,9-dimethylxanthene, 29.4 mg 2-(dicyclohexyl-phosphino)-2',4',6'-triisopropylbiphenyl, 13.8 mg palladium(II)acetate and 56.4 mg tris(dibenzylideneacetone)dipalladium(0) were added and the mixture was stirred at 100° C. for 2 hours. After concentration the mixture was purified by flash chromatography (Biotage SNAP cartridge silica 25 g, methanol:dichloromethane) and crystallization from methanol to give 200 mg (66%) of the title compound.

LC-MS: m/z=503.4 [M+H]$^+$.

$^1$H-NMR (400 MHz, DMSO-d6), δ [ppm]=1.47+1.49 (9H), 1.66 (2H), 2.09-2.32 (4H), 2.48 (3H*), 3.28 (2H), 4.51+4.53 (2H), 4.67+4.70 (2H), 8.27+8.32 (1H), 8.55 (1H), 8.75 (1H), 10.38 (1H);

*: at least partially hidden by solvent or water signal

Example 105

4,4-Difluoro-8'-methyl-6'-(1H-pyrazolo[3,4-d]pyrimidin-4-ylamino)-2'H-spiro[cyclohexane-1,3'-imidazo[1,5-a]pyridine]-1',5'-dione

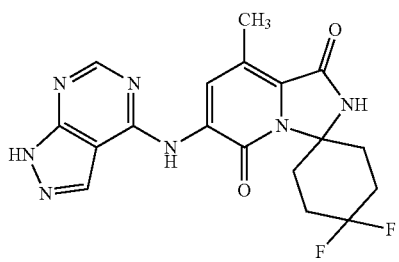 [SMILES: Cc1cc(Nc2ncnc3[nH]ncc23)c(=O)n2c1C(=O)NC21CCC(F)(F)CC1]

To a solution of 250 mg (720 µmol) 6'-bromo-4,4-difluoro-8'-methyl-2'H-spiro[cyclohexane-1,3'-imidazo[1,5-a]pyridine]-1',5'-dione (prepared according to PCT Int. Appl. (2015), WO 2015200481) and 107 mg (792 µmol) 1H-pyrazolo[3,4-d]pyrimidin-4-amine (CAS-No: 2380-63-4) in 16 mL 1,4-dioxane was added 704 mg cesium carbonate and the mixture was degassed and purged with argon several times. 44.6 mg 4,5-bis(diphenylphosphino)-9,9-dimethylxanthene, 36.7 mg 2-(dicyclohexyl-phosphino)-2',4',6'-triisopropylbiphenyl, 17.3 mg palladium(II)acetate and 70.6 mg tris(dibenzylideneacetone)dipalladium(0) were added and the mixture was stirred at 100° C. for 2 hours. After concentration the mixture was purified by flash chromatography (Biotage SNAP cartridge silica 25 g, methanol:dichloromethane) and crystallization from methanol to give 61 mg (20%) of the title compound.

LC-MS: m/z=402.3 [M+H]+.

1H-NMR (400 MHz, DMSO-d6), δ [ppm]=1.68 (2H), 2.13-2.32 (4H), 2.50 (3H*), 3.35 (2H*), 8.56 (1H), 8.59 (1H), 8.72 (1H), 9.42 (1H), 10.39 (1H), 13.79 (1H);

*: at least partially hidden by solvent or water signal

Example 106

4,4-Difluoro-8'-methyl-6'-(9H-purin-6-ylamino)-2'H-spiro[cyclohexane-1,3'-imidazo[1,5-a]pyridine]-1',5'-dione

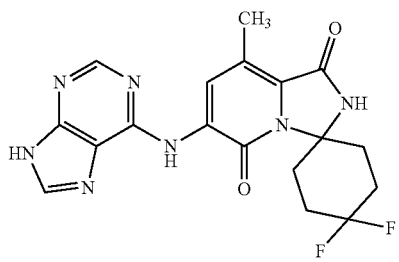 [SMILES: Cc1cc(Nc2ncnc3[nH]cnc23)c(=O)n2c1C(=O)NC21CCC(F)(F)CC1]

To a solution of 250 mg (720 µmol) 6'-bromo-4,4-difluoro-8'-methyl-2'H-spiro[cyclohexane-1,3'-imidazo[1,5-a]pyridine]-1',5'-dione (prepared according to PCT Int. Appl. (2015), WO 2015200481) and 136 mg (792 µmol) 9H-purin-6-amine hydrochloride (CAS-No: 2922-28-3) in 20 mL 1,4-dioxane was added 704 mg cesium carbonate and the mixture was degassed and purged with argon several times. 44.6 mg 4,5-bis(diphenylphosphino)-9,9-dimethylxanthene, 36.7 mg 2-(dicyclohexyl-phosphino)-2',4',6'-triisopropylbiphenyl, 17.3 mg palladium(II)acetate and 70.6 mg tris(dibenzylideneacetone)dipalladium(0) were added and the mixture was stirred at 100° C. for 2 hours. After concentration the mixture was purified by flash chromatography (Biotage SNAP cartridge silica 25 g, methanol:dichloromethane) and crystallization from methanol to give 10 mg (3%) of the title compound.

LC-MS: m/z=402.3 [M+H]+.

1H-NMR (400 MHz, DMSO-d6), δ [ppm]=1.68 (2H), 2.14-2.36 (4H), 2.50 (3H*), 3.31 (2H*), 8.40 (1H), 8.60 (1H), 8.74 (1H), 8.86 (1H), 10.36 (1H), 13.46 (1H);

*: at least partially hidden by solvent or water signal

Example 107

5-Methyl-4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxamide

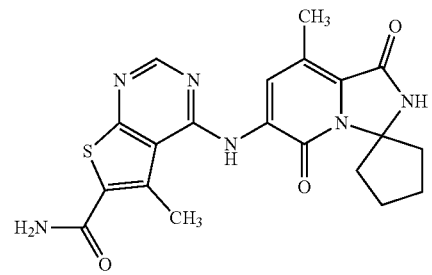 [SMILES: Cc1cc(Nc2ncnc3sc(C(N)=O)c(C)c23)c(=O)n2c1C(=O)NC21CCCC1]

To a solution of 63 mg (148 µmol) 5-methyl-4-[(8'-methyl-1',5'-dioxo-1',5'-dihydro-2'H-spiro[cyclopentane-1,3'-imidazo[1,5-a]pyridin]-6'-yl)amino]thieno[2,3-d]pyrimidine-6-carboxylic acid (prepared according to example 95) in 4.1 mL N,N-dimethylacetamide, were added 84.5 mg 1-[bis(dimethylamino)methylene]-1H-1,2,3-triazolo[4,5-b]pyridinium 3-oxid hexafluorophosphate (HATU), 27.1 mg N,N-dimethylpyridin-4-amine, 2.6 mL ammonia (0.4 M in THF) and the mixture was stirred at Rt for 2.5 days. 2.5 mL ammonia (0.4 M in THF) and 56.3 mg HATU were added and the mixture heated at 100° C. for 16 hours. 2.5 mL ammonia (0.4 M in THF) were added and the mixture heated at 100° C. for 16 hours. Another 2.0 mL ammonia (0.4 M in THF) and 56.3 mg HATU were added and the mixture heated at 100° C. for 10 hours. After concentration, the residue was washed with methanol and dried to give 31 mg (47%) of the title compound.

LC-MS: m/z=425.3 [M+H]+.

1H-NMR (400 MHz, DMSO-d6), δ [ppm]=1.70 (2H), 1.85 (2H), 1.99 (2H), 2.52 (3H*), 2.86 (2H), 2.96 (3H), 7.77-8.01 (2H), 8.74 (1H), 8.78 (1H), 9.29 (1H), 10.02 (1H);

*: at least partially hidden by solvent or water signal

Example 108

6'-[(7-Chloroquinazolin-4-yl)amino]-8'-methyl-2'H-spiro[cyclohexane-1,3'-imidazo[1,5-a]pyridine]-1',5'-dione

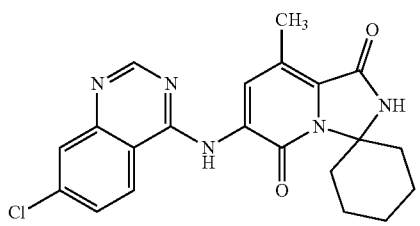 [SMILES: Cc1cc(Nc2ncnc3cc(Cl)ccc23)c(=O)n2c1C(=O)NC21CCCCC1]

To a solution of 100 mg (321 μmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 63.5 mg (353 μmol) 7-chloroquinazolin-4-amine (CAS-No: 19808-36-7) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, ethanol:dichloromethane) and crystallization from ethanol to give 69 mg (50%) of the title compound.

LC-MS: m/z=410.3 [M+H]$^+$.

$^1$H-NMR (400 MHz, DMSO-d6), δ [ppm]=1.24 (1H), 1.51 (2H), 1.59-1.81 (5H), 2.52 (3H*), 3.01 (2H), 7.73 (1H), 7.93 (1H), 8.32 (1H), 8.64 (1H), 8.82 (1H), 9.46 (1H), 10.26 (1H)

*: at least partially hidden by solvent or water signal

Example 109

6'-[(5-Chloroquinazolin-4-yl)amino]-8'-methyl-2'H-spiro[cyclohexane-1,3'-imidazo[1,5-a]pyridine]-1',5'-dione

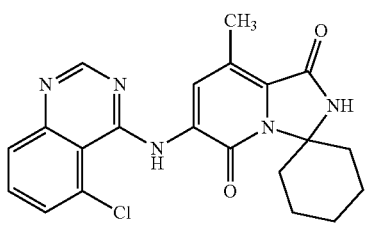 [SMILES: Cc1cc(Nc2ncnc3cccc(Cl)c23)c(=O)n2c1C(=O)NC21CCCCC1]

To a solution of 100 mg (321 μmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 63.5 mg (353 μmol) 5-chloroquinazolin-4-amine (CAS-No: 19808-34-5) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, ethanol:dichloromethane) and crystallization from ethanol to give 74 mg (53%) of the title compound.

LC-MS: m/z=410.3 [M+H]$^+$.

$^1$H-NMR (400 MHz, DMSO-d6), δ [ppm]=1.29 (1H), 1.49 (2H), 1.58-1.81 (5H), 2.52 (3H*), 2.99 (2H), 7.79-7.88 (3H), 8.84 (1H), 8.95 (1H), 10.24 (1H), 10.97 (1H)

*: at least partially hidden by solvent or water signal

Example 110

6'-[(6,8-Dichloroquinazolin-4-yl)amino]-8'-methyl-2'H-spiro[cyclohexane-1,3'-imidazo[1,5-a]pyridine]-1',5'-dione

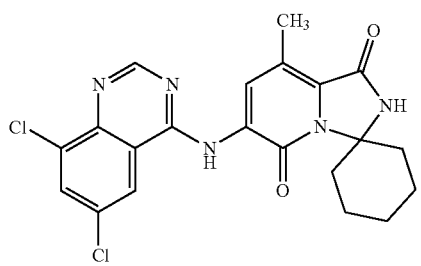 [SMILES: Cc1cc(Nc2ncnc3c(Cl)cc(Cl)cc23)c(=O)n2c1C(=O)NC21CCCCC1]

To a solution of 100 mg (321 μmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 75.7 mg (353 μmol) 6,8-dichloroquinazolin-4-amine (CAS-No: 19808-35-6) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, ethanol:dichloromethane) and crystallization from ethanol to give 40 mg (27%) of the title compound.

LC-MS: m/z=444.3 [M+H]$^+$.

$^1$H-NMR (400 MHz, DMSO-d6), δ [ppm]=1.23 (1H), 1.50 (2H), 1.58-1.82 (5H), 2.52 (3H*), 3.01 (2H), 8.24 (1H), 8.43 (1H), 8.52 (1H), 8.85 (1H), 9.56 (1H), 10.28 (1H)

*: at least partially hidden by solvent or water signal

Example 111

6'-[(8-Fluoroquinazolin-4-yl)amino]-8'-methyl-2'H-spiro[cyclohexane-1,3'-imidazo[1,5-a]pyridine]-1',5'-dione

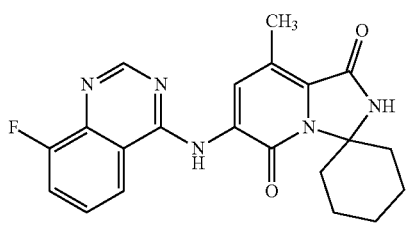 [SMILES: Cc1cc(Nc2ncnc3c(F)cccc23)c(=O)n2c1C(=O)NC21CCCCC1]

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 57.7 mg (353 µmol) 8-fluoroquinazolin-4-amine (CAS-No: 1378808-30-0) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, ethanol:dichloromethane) and crystallization from ethanol to give 68 mg (51%) of the title compound.

LC-MS: m/z=394.3 [M+H]$^+$.

$^1$H-NMR (400 MHz, DMSO-d6), δ [ppm]=1.24 (1H), 1.51 (2H), 1.59-1.81 (5H), 2.51 (3H*), 3.01 (2H), 7.68 (1H), 7.79 (1H), 8.08 (1H), 8.67 (1H), 8.85 (1H), 9.46 (1H), 10.27 (1H)

*: at least partially hidden by solvent or water signal

Example 112

6'-[(7-Fluoroquinazolin-4-yl)amino]-8'-methyl-2'H-spiro[cyclohexane-1,3'-imidazo[1,5-a]pyridine]-1',5'-dione

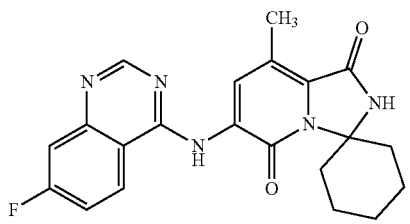 [SMILES: Cc1cc(Nc2ncnc3cc(F)ccc23)c(=O)n2c1C(=O)NC21CCCCC1]

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 57.7 mg (353 µmol) 7-fluoroquinazolin-4-amine (CAS-No: 1009036-29-6) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, ethanol:dichloromethane) and crystallization from ethanol to give 96 mg (72%) of the title compound.

LC-MS: m/z=394.3 [M+H]$^+$.

$^1$H-NMR (400 MHz, DMSO-d6), δ [ppm]=1.24 (1H), 1.51 (2H), 1.59-1.81 (5H), 2.50 (3H*), 3.02 (2H), 7.57-7.66 (2H), 8.40 (1H), 8.65 (1H), 8.80 (1H), 9.44 (1H), 10.25 (1H)

*: at least partially hidden by solvent or water signal

Example 113

6'-[(6-Fluoroquinazolin-4-yl)amino]-8'-methyl-2'H-spiro[cyclohexane-1,3'-imidazo[1,5-a]pyridine]-1',5'-dione

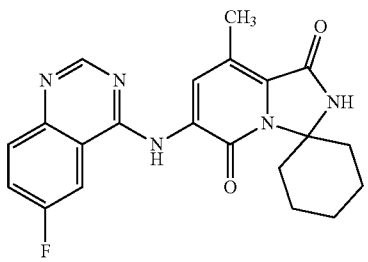 [SMILES: Cc1cc(Nc2ncnc3ccc(F)cc23)c(=O)n2c1C(=O)NC21CCCCC1]

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 57.7 mg (353 µmol) 6-fluoroquinazolin-4-amine (CAS-No: 1190320-08-1) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, ethanol:dichloromethane) and crystallization from ethanol to give 73 mg (55%) of the title compound.

LC-MS: m/z=394.3[M+H]$^+$.

$^1$H-NMR (400 MHz, DMSO-d6), δ [ppm]=1.24 (1H), 1.51 (2H), 1.59-1.81 (5H), 2.52 (3H*), 3.02 (2H), 7.85 (1H), 7.95 (1H), 8.12 (1H), 8.62 (1H), 8.79 (1H), 9.33 (1H), 10.25 (1H)

*: at least partially hidden by solvent or water signal

Example 114

6'-[(5,7-Difluoroquinazolin-4-yl)amino]-8'-methyl-2'H-spiro[cyclohexane-1,3'-imidazo[1,5-a]pyridine]-1',5'-dione

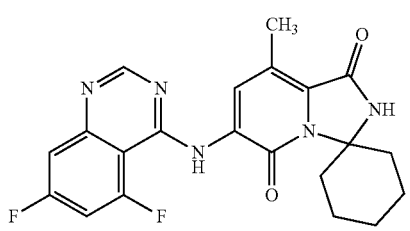 [SMILES: Cc1cc(Nc2ncnc3cc(F)cc(F)c23)c(=O)n2c1C(=O)NC21CCCCC1]

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 64.0 mg (353 µmol) 5,7-difluoroquinazolin-4-amine (CAS-No: 1009034-66-5) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, ethanol:dichloromethane) and crystallization from ethanol to give 116 mg (79%) of the title compound.

LC-MS: m/z=412.3 [M+H]$^+$.

$^1$H-NMR (400 MHz, DMSO-d6), δ [ppm]=1.27 (1H), 1.49 (2H), 1.59-1.81 (5H), 2.52 (3H*), 2.99 (2H), 7.54 (1H), 7.70 (1H), 8.85 (2H), 9.96 (1H), 10.25 (1H)

*: at least partially hidden by solvent or water signal

Example 115

6'-[(7,8-Difluoroquinazolin-4-yl)amino]-8'-methyl-2'H-spiro[cyclohexane-1,3'-imidazo[1,5-a]pyridine]-1',5'-dione

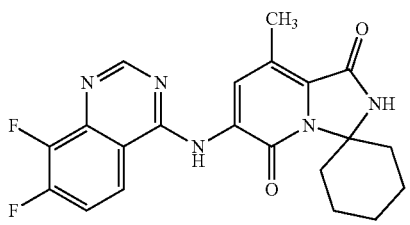 [SMILES: Cc1cc(Nc2ncnc3c(F)c(F)ccc23)c(=O)n2c1C(=O)NC21CCCCC1]

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 64.0 mg (353 µmol) 7,8-difluoroquinazolin-4-amine (can be prepared according to Bioorganic and Medicinal Chemistry Letters, 2012, 22, 2550-2554) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, ethanol:dichloromethane) and crystallization from ethanol to give 82 mg (59%) of the title compound.

LC-MS: m/z=412.3 [M+H]$^+$.

$^1$H-NMR (400 MHz, DMSO-d6), δ [ppm]=1.24 (1H), 1.51 (2H), 1.59-1.81 (5H), 2.52 (3H*), 3.00 (2H), 7.78 (1H), 8.22 (1H), 8.59 (1H), 8.83 (1H), 9.52 (1H), 10.28 (1H)

*: at least partially hidden by solvent or water signal

Example 116

6'-[(7-Methoxyquinazolin-4-yl)amino]-8'-methyl-2'H-spiro[cyclohexane-1,3'-imidazo[1,5-a]pyridine]-1',5'-dione

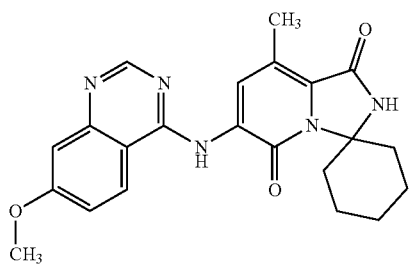 [SMILES: COc1ccc2c(Nc3cc(C)c4n(c3=O)C3(CCCCC3)NC4=O)ncnc2c1]

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 61.9 mg (353 µmol) 7-methoxyquinazolin-4-amine (CAS-No: 21560-97-4) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, ethanol:dichloromethane) and crystallization from ethanol to give 88 mg (64%) of the title compound.

LC-MS: m/z=406.3 [M+H]$^+$.

$^1$H-NMR (400 MHz, DMSO-d6), δ [ppm]=1.24 (1H), 1.50 (2H), 1.59-1.81 (5H), 2.52 (3H*), 3.01 (2H), 3.94 (3H), 7.26 (1H), 7.30 (1H), 8.14 (1H), 8.68 (1H), 8.75 (1H), 9.26 (1H), 10.22 (1H)

*: at least partially hidden by solvent or water signal

Example 117

6'-[(6-Methoxyquinazolin-4-yl)amino]-8'-methyl-2'H-spiro[cyclohexane-1,3'-imidazo[1,5-a]pyridine]-1',5'-dione

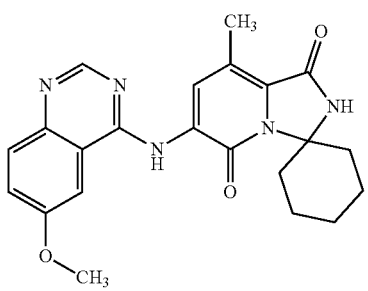 [SMILES: COc1ccc2ncnc(Nc3cc(C)c4n(c3=O)C3(CCCCC3)NC4=O)c2c1]

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 61.9 mg (353 µmol) 6-methoxyquinazolin-4-amine (CAS-No: 885277-51-0) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, ethanol:dichloromethane) and crystallization from ethanol to give 75 mg (55%) of the title compound.

LC-MS: m/z=406.3[M+H]$^+$.

$^1$H-NMR (400 MHz, DMSO-d6), δ [ppm]=1.26 (1H), 1.50 (2H), 1.60-1.81 (5H), 2.52 (3H*), 3.03 (2H), 3.99 (3H), 7.51 (1H), 7.57 (1H), 7.82 (1H), 8.68 (1H), 8.71 (1H), 9.28 (1H), 10.23 (1H)

*: at least partially hidden by solvent or water signal

Example 118

6'-[(5-Methoxyquinazolin-4-yl)amino]-8'-methyl-2'H-spiro[cyclohexane-1,3'-imidazo[1,5-a]pyridine]-1',5'-dione

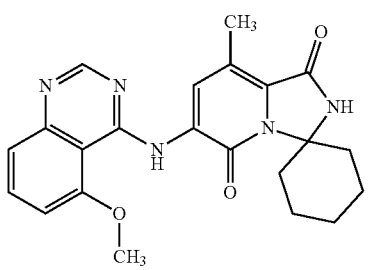 [SMILES: COc1cccc2ncnc(Nc3cc(C)c4n(c3=O)C3(CCCCC3)NC4=O)c12]

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 61.9 mg (353 µmol) 5-methoxyquinazolin-4-amine (CAS-No: 885277-54-3) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, ethanol:dichloromethane) and crystallization from ethanol to give 76 mg (55%) of the title compound.

LC-MS: m/z=406.3 [M+H]$^+$.

$^1$H-NMR (400 MHz, DMSO-d6), δ [ppm]=1.29 (1H), 1.49 (2H), 1.58-1.81 (5H), 2.52 (3H*), 3.02 (2H), 4.15 (3H), 7.22 (1H), 7.42 (1H), 7.81 (1H), 8.74 (1H), 8.92 (1H), 10.19 (1H), 11.40 (1H)

*: at least partially hidden by solvent or water signal

Example 119

6'-[(6,7-Dimethoxyquinazolin-4-yl)amino]-8'-methyl-2'H-spiro[cyclohexane-1,3'-imidazo[1,5-a]pyridine]-1',5'-dione

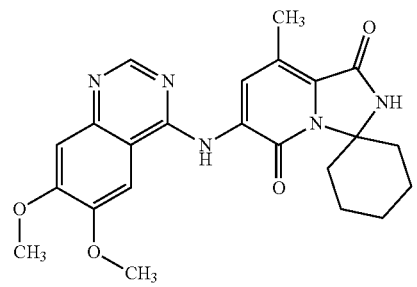 [SMILES: COc1cc2ncnc(Nc3cc(C)c4n(c3=O)C3(CCCCC3)NC4=O)c2cc1OC]

To a solution of 100 mg (321 µmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 72.5 mg (353 µmol) 6,7-dimethoxyquinazolin-4-amine (CAS-No: 21575-13-3) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, ethanol:dichloromethane) and crystallization from ethanol to give 93 mg (63%) of the title compound.

LC-MS: m/z=436.3 [M+H]$^+$.

$^1$H-NMR (400 MHz, DMSO-d6), δ [ppm]=1.26 (1H), 1.50 (2H), 1.60-1.81 (5H), 2.52 (3H*), 3.03 (2H), 3.95 (3H), 4.00 (3H), 7.26 (1H), 7.45 (1H), 8.65 (1H), 8.66 (1H), 9.13 (1H), 10.20 (1H)

*: at least partially hidden by solvent or water signal

Example 120

8'-methyl-6'-[(8-methylquinazolin-4-yl)amino]-2'H-spiro[cyclohexane-1,3'-imidazo[1,5-a]pyridine]-1',5'-dione

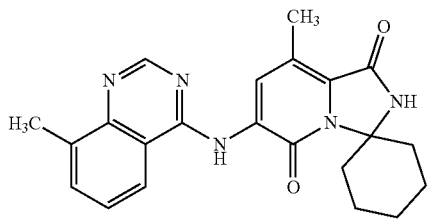 [SMILES: Cc1cc(Nc2ncnc3c(C)cccc23)c(=O)n2c1C(=O)NC21CCCCC1]

To a solution of 100 mg (321 μmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 56.3 mg (353 mol) 8-methylquinazolin-4-amine (commercially available from UkrOrgSynthesis Ltd., article no. BBV-39698539) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, ethanol:dichloromethane) and crystallization from ethanol to give 97 mg (74%) of the title compound.

LC-MS: m/z=390.3 [M+H]$^+$.

$^1$H-NMR (400 MHz, DMSO-d6), δ [ppm]=1.25 (1H), 1.51 (2H), 1.59-1.81 (5H), 2.52 (3H*), 2.65 (3H), 3.02 (2H), 7.60 (1H), 7.80 (1H), 8.04 (1H), 8.75 (1H), 8.88 (1H), 9.38 (1H), 10.24 (1H)

*: at least partially hidden by solvent or water signal

Example 121

8'-Methyl-6'-[(7-methylquinazolin-4-yl)amino]-2'H-spiro[cyclohexane-1,3'-imidazo[1,5-a]pyridine]-1',5'-dione

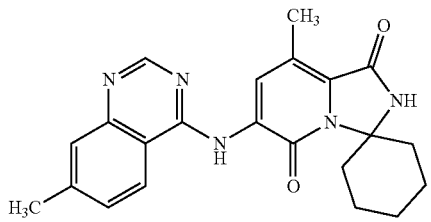 [SMILES: Cc1ccc2c(Nc3cc(C)c4n(c3=O)C3(CCCCC3)NC4=O)ncnc2c1]

To a solution of 100 mg (321 μmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 56.3 mg (353 μmol) 7-methylquinazolin-4-amine (CAS-No: 63963-38-2) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, ethanol:dichloromethane) and crystallization from ethanol to give 93 mg (71%) of the title compound.

LC-MS: m/z=390.3 [M+H]$^+$.

$^1$H-NMR (400 MHz, DMSO-d6), δ [ppm]=1.25 (1H), 1.51 (2H), 1.59-1.82 (5H), 2.48-2.52 (6H*), 3.02 (2H), 7.54 (1H), 7.67 (1H), 8.11 (1H), 8.71 (1H), 8.78 (1H), 9.32 (1H), 10.23 (1H)

*: at least partially hidden by solvent or water signal

Example 122

8'-Methyl-6'-[(6-methylquinazolin-4-yl)amino]-2'H-spiro[cyclohexane-1,3'-imidazo[1,5-a]pyridine]-1',5'-dione

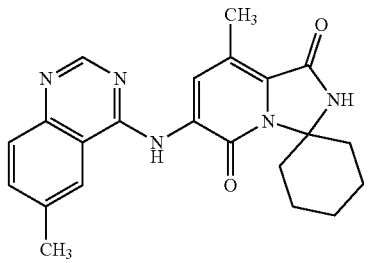 [SMILES: Cc1ccc2ncnc(Nc3cc(C)c4n(c3=O)C3(CCCCC3)NC4=O)c2c1]

To a solution of 100 mg (321 μmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 56.3 mg (353 μmol) 6-methylquinazolin-4-amine (CAS-No: 21419-47-6) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, ethanol:dichloromethane) and crystallization from ethanol to give 68 mg (52%) of the title compound.

LC-MS: m/z=390.3 [M+H]$^+$.

$^1$H-NMR (400 MHz, DMSO-d6), δ [ppm]=1.25 (1H), 1.51 (2H), 1.60-1.82 (5H), 2.52 (3H*), 2.57 (3H), 3.03 (2H), 7.79 (2H), 7.98 (1H), 8.76 (1H), 8.78 (1H), 9.32 (1H), 10.23 (1H)

*: at least partially hidden by solvent or water signal

Example 123

8'-Methyl-6'-[(5-methylquinazolin-4-yl)amino]-2'H-spiro[cyclohexane-1,3'-imidazo[1,5-a]pyridine]-1',5'-dione

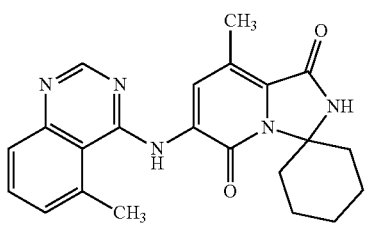

To a solution of 100 mg (321 μmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 56.3 mg (353 μmol) 5-methylquinazolin-4-amine (commercially available from UkrOrgSynthesis Ltd., article no. BBV-39700386) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, methanol:dichloromethane) and crystallization from methanol to give 130 mg (82%) of the title compound.

LC-MS: m/z=390.3 [M+H]$^+$.

$^1$H-NMR (400 MHz, DMSO-d6), δ [ppm]=1.29 (1H), 1.50 (2H), 1.58-1.81 (5H), 2.52 (3H*), 3.01 (2H), 3.11 (3H), 7.48 (1H), 7.68-7.77 (2H), 8.76 (1H), 8.92 (1H), 9.76 (1H), 10.22 (1H)

*: at least partially hidden by solvent or water signal

Example 124

8'-Methyl-6'-{[6-(trifluoromethyl)quinazolin-4-yl]amino}-2'H-spiro[cyclohexane-1,3'-imidazo[1,5-a]pyridine]-1',5'-dione

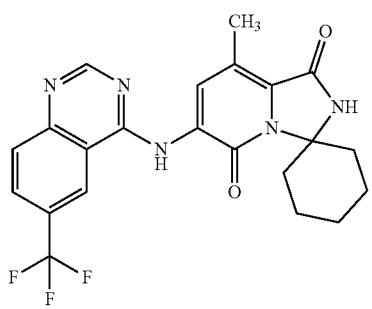 [SMILES: Cc1cc(Nc2ncnc3ccc(C(F)(F)F)cc23)c(=O)n2c1C(=O)NC21CCCCC1]

To a solution of 100 mg (321 μmol) 6'-bromo-8'-methyl-2'H-spiro[cyclohexane-1,3'-imidazo[1,5-a]pyridine]-1',5'-dione (CAS-No: 1849592-70-6; PCT Int. Appl. (2015), WO 2015200481) and 75.4 mg (353 μmol) 6-(trifluoromethyl)quinazolin-4-amine (CAS-No: 1020263-19-7) in 12 mL 1,4-dioxane was added 314 mg cesium carbonate and the mixture was degassed and purged with argon several times. 19.9 mg 4,5-bis(diphenylphosphino)-9,9-dimethylxanthene, 16.4 mg 2-(dicyclohexyl-phosphino)-2',4',6'-triisopropylbiphenyl, 7.7 mg palladium(II)acetate and 31.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, methanol:dichloromethane) to give 84 mg (56%) and crystallization from methanol of the title compound.

LC-MS: m/z=444.3 [M+H]$^+$.

$^1$H-NMR (400 MHz, DMSO-d6), δ [ppm]=1.25 (1H), 1.50 (2H), 1.59-1.81 (5H), 2.52 (3H*), 3.02 (2H), 8.02 (1H), 8.17 (1H), 8.53 (1H), 8.79 (1H), 8.86 (1H), 9.76 (1H), 10.28 (1H)

*: at least partially hidden by solvent or water signal

Example 125

6'-(6,7-Dihydro-5H-pyrrolo[3,4-d]pyrimidin-4-ylamino)-4,4-difluoro-8'-methyl-2'H-spiro[cyclohexane-1,3'-imidazo[1,5-a]pyridine]-1',5'-dione

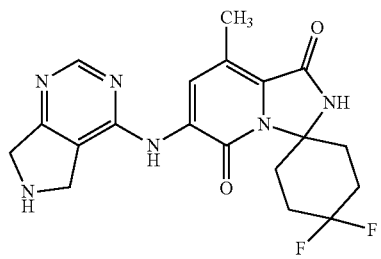 [SMILES: Cc1cc(Nc2ncnc3c2CNC3)c(=O)n2c1C(=O)NC21CCC(F)(F)CC1]

A mixture of 190 mg (378 μmol) tert-butyl 4-[(8-methyl-1',5'-dioxo-1',5'-dihydro-2'H-dihydro-2'H-spiro[cyclohexane-1,3'-imidazo[1,5-d]pyridin]-6'-yl)amino]-5,7-dihydro-6H-pyrrolo[3,4-d]pyrimidine-6-carboxylate (prepared according to example 104) and 583 μL trifluoroacetic acid in 14.8 mL dichloromethane was stirred at RT overnight. The mixture was poured into aqueous ammonia (25%) and extracted with dichloromethane/methanol. The organic layer was washed with water, dried over sodium sulfate. After filtration and concentration the residue was digested with ethanol and dried to give 123 mg (77%) of the title compound.

LC-MS: m/z=403.3 [M+H]$^+$.

$^1$H-NMR (400 MHz, DMSO-d6), δ [ppm]=1.65 (2H), 2.05-2.31 (4H), 2.48 (3H*), 3.14 (1H), 3.26 (2H), 4.02 (2H), 4.17 (2H), 8.05 (1H), 8.57 (1H), 8.69 (1H), 10.35 (1H)

*: at least partially hidden by solvent or water signal

Example 126

6'-(6,7-Dihydro-5H-pyrrolo[3,4-d]pyrimidin-4-ylamino)-8'-methyl-2'H-spiro[cyclopentane-1,3'-imidazo[1,5-a]pyridine]-1',5'-dione

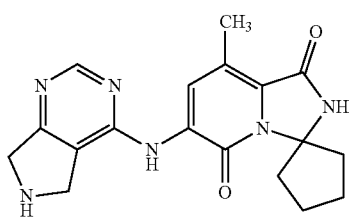 [SMILES: Cc1cc(Nc2ncnc3c2CNC3)c(=O)n2c1C(=O)NC21CCCC1]

A mixture of 105 mg (232 μmol) tert-butyl 4-[(8'-methyl-1',5'-dioxo-1',5'-dihydro-2'H-spiro[cyclopentane-1,3'-imidazo[1,5-a]pyridin]-6'-yl)amino]-5,7-dihydro-6H-pyrrolo[3,4-c]pyrimidine-6-carboxylate (prepared according to example 103) and 358 μL trifluoroacetic acid in 9.0 mL dichloromethane was stirred at RT overnight. The mixture was poured into aqueous ammonia (25%) and extracted with dichloromethane/methanol. The organic layer was washed with water, dried over sodium sulfate. After filtration and concentration the residue was digested with ethanol and dried to give 75 mg (87%) of the title compound.

LC-MS: m/z=353.3 [M+H]$^+$.

$^1$H-NMR (400 MHz, DMSO-d6), δ [ppm]=1.70 (2H), 1.83 (2H), 1.97 (2H), 2.47 (3H), 2.79 (2H), 4.03 (2H), 4.18 (2H), 8.07 (1H), 8.56 (1H), 8.69 (1H), 9.95 (1H)

*: at least partially hidden by solvent or water signal

Example 127

6'-[(4-Amino-1,3,5-triazin-2-yl)amino]-4-hydroxy-8'-methyl-4-(trifluoromethyl)-2'H-spiro[cyclohexane-1,3'-imidazo[1,5-a]pyridine]-1',5'-dione

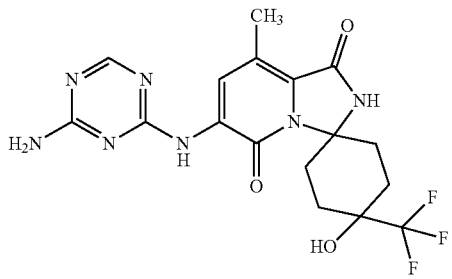

To a solution of 120 mg (304 μmol) 6'-Bromo-4-hydroxy-8'-methyl-4-(trifluoromethyl)-2'H-spiro[cyclohexane-1,3'-imidazo[1,5-a]pyridine]-1',5'-dione (prepared according to example 127a) and 60 mg (334 μmol) N-(4-amino-1,3,5-triazin-2-yl)cyclopropanecarboxamide (prepared according to example 1a) in 11 mL 1,4-dioxane was added 297 mg cesium carbonate and the mixture was degassed and purged with argon several times. 18.8 mg 4,5-bis(diphenylphosphino)-9,9-dimethylxanthene, 15.5 mg 2-(dicyclohexylphosphino)-2',4',6'-triisopropylbiphenyl, 7.3 mg palladium (II)acetate and 29.8 mg tris(dibenzylideneacetone) dipalladium(0) were added and the mixture was stirred at 100° C. for 2 hours. After concentration the residue was purified by repeated flash chromatography (Biotage SNAP cartridge silica 25 g, methanol:dichloromethane). The material was dissolved in 1.3 mL tetrahydrofurane, 1.3 mL water, 2.7 mL ethanol and 53 μL potassium hydroxide (50% in water) were added. The mixture was stirred at RT overnight, extracted with ethyl acetate, the organic layer washed with water and dried over sodium sulfate. After filtration and concentration the residue was purified by preparative TLC (methanol:dichloromethane) to give 14 mg (22%) of the title compound.

LC-MS: m/z=426.3 [M+H]$^+$.

$^1$H-NMR (400 MHz, DMSO-d6), δ [ppm]=1.38 (2H), 1.81 (2H), 1.94 (2H), 2.47 (3H), 3.39 (2H), 6.01 (1H), 7.47 (2H), 8.07 (1H), 8.27 (1H), 8.47 (1H), 10.36 (1H).

Example 127a

6'-Bromo-4-hydroxy-8'-methyl-4-(trifluoromethyl)-2'H-spiro[cyclohexane-1,3'-imidazo[1,5-a]pyridine]-1',5'-dione

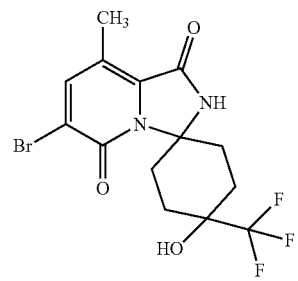 [SMILES: Cc1cc(Br)c(=O)n2c1C(=O)NC21CCC(O)(C(F)(F)F)CC1]

A mixture of 1.18 g (5.12 mmol) 5-bromo-3-methyl-6-oxo-1,6-dihydropyridine-2-carboxamide (prepared according to PCT Int. Appl. (2015), WO 2015200481), 3.73 g (20.5 mmol) 4-hydroxy-4-(trifluoromethyl)cyclohexanone (CAS-No.: 120929-90-0), 135 μL sulfuric acid and 14 mL 1,4-dioxane was heated at 95° C. for 3 hours. After concentration, water was added, the precipitate washed with water and diethyl ether and dried to give 1.78 g (88%) of the title compound as mixture of cis/trans-isomers.

LC-MS: m/z=395.2 [M+H]$^+$.

Another batch of example 127a prepared as above (9.3 g, mixture of cis/trans isomers) was separated by chiral preperative HPLC to give, after additional recrystallization from ethanol, 3.34 g of example 127b (cis isomer) and 2.64 g of example 127c (trans isomer).

Preparation:

Instrument: Labomatic HD5000, Labocord-5000; Gilson GX-241, Labcol Vario 4000, column: Chiralpak IA 5 μm 250×50 mm No. 12; eluent A: MtBE; eluent B: ethanol; isokratic: 90% A+10% B; flow 150.0 mL/min; UV 325 nm.

Example 127b (cis)-6'-bromo-4-hydroxy-8'-methyl-4-(trifluoromethyl)-2'H-spiro[cyclohexane-1,3'-imidazo[1,5-a]pyridine]-1',5'-dione

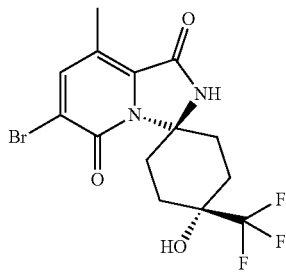

The title compound was isolated in the preparative chiral HPLC of example 127a.

Analytical HPLC-Method:
Instrument: Agilent HPLC 1260; column: Chiralpak IA 3 µm 100×4.6 mm; eluent A: MtBE+0.1 vol-% diethylamine (99%); eluent B: ethanol; isokratic: 90% A+10% B; flow 1.4 mL/min; temperature: 25° C.; DAD 325 nm.
Rt=2.67 min.
$^1$H-NMR (400 MHz, DMSO-d6) δ[ppm]=1.052 (0.48), 1.361 (1.32), 1.392 (1.35), 1.777 (0.89), 1.810 (1.50), 1.872 (0.77), 1.881 (0.87), 1.907 (1.23), 1.915 (1.22), 1.941 (0.55), 1.951 (0.45), 2.332 (0.61), 2.382 (16.00), 2.518 (3.21), 2.522 (2.12), 2.673 (0.60), 3.348 (1.34), 3.359 (1.22), 3.382 (0.73), 3.392 (0.55), 5.989 (4.33), 8.031 (6.40), 10.606 (2.79).

Example 127c (trans)-6'-bromo-4-hydroxy-8'-methyl-4-(trifluoromethyl)-2'H-spiro[cyclohexane-1,3'-imidazo[1,5-a]pyridine]-1',5'-dione

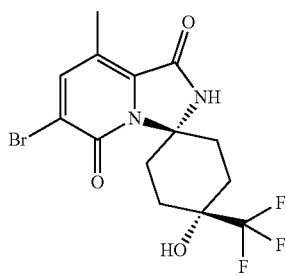 [SMILES: Cc1cc(Br)c(=O)n2c1C(=O)N[C@]21CC[C@](O)(C(F)(F)F)CC1]

The title compound was isolated in the preparative chiral HPLC of example 127a.

Analytical HPLC-method:
Instrument: Agilent HPLC 1260; column: Chiralpak IA 3 µm 100×4.6 mm; eluent A: MtBE+0.1 vol-% diethylamine (99%); eluent B: ethanol; isokratic: 90% A+10% B; flow 1.4 mL/min; temperature: 25° C.; DAD 325 nm.
Rt=7.26 min.
$^1$H-NMR (400 MHz, DMSO-d6) δ [ppm]=1.103 (0.85), 1.513 (1.12), 1.546 (1.15), 1.857 (0.48), 1.884 (1.04), 1.919 (0.65), 2.084 (0.50), 2.179 (1.40), 2.216 (1.14), 2.376 (16.00), 2.518 (1.06), 2.522 (0.65), 2.986 (0.58), 2.997 (0.69), 3.020 (1.19), 3.031 (1.16), 3.055 (0.62), 3.065 (0.52), 3.073 (0.43), 6.041 (5.81), 8.022 (6.23), 10.512 (2.49).

Example 128

4-Hydroxy-8'-methyl-6'-(7H-pyrrolo[2,3-d]pyrimidin-4-ylamino)-4-(trifluoromethyl)-2'H-spiro[cyclohexane-1,3'-imidazo[1,5-a]pyridine]-1',5'-dione

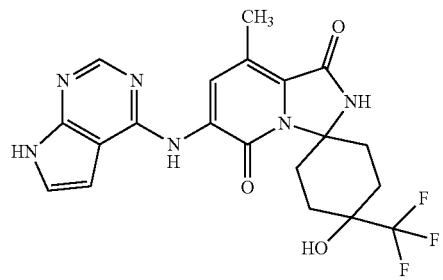

A mixture of 90 mg (164 µmol) tert-butyl 4-{[4-hydroxy-8'-methyl-1',5'-dioxo-4-(trifluoromethyl)-1',5'-dihydro-2'H-spiro[cyclohexane-1,3'-imidazo[1,5-a]pyridin]-6'-yl]amino}-7H-pyrrolo[2,3-d]pyrimidine-7-carboxylate (prepared according to example 128a) and 253 µL trifluoroacetic acid in 2.0 mL dichloromethane was stirred at RT for 2 hours. The mixture was poured into aqueous ammonia (25%) and extracted with dichloromethane/methanol. The organic layer was washed with water, dried over sodium sulfate. After filtration and concentration the residue was digested with ethanol and diethyl ether and dried to give 5.0 mg (6%) of the title compound.
LC-MS: m/z=449.3 [M+H]$^+$.
$^1$H-NMR (400 MHz, DMSO-d6), δ [ppm]=1.42 (2H), 1.83 (2H), 1.96 (2H), 2.50 (3H*), 3.47 (2H), 5.99 (1H), 6.82 (1H), 7.38 (1H), 8.47 (1H), 8.64 (1H), 8.73 (1H), 10.35 (1H), 12.03 (1H);
*: at least partially hidden by solvent or water signal

Example 128a tert-Butyl 4-{[4-hydroxy-8'-methyl-1',5'-dioxo-4-(trifluoromethyl)-1',5'-dihydro-2'H-spiro[cyclohexane-1,3'-imidazo[1,5-a]pyridin]-6'-yl]amino}-7H-pyrrolo[2,3-d]pyrimidine-7-carboxylate

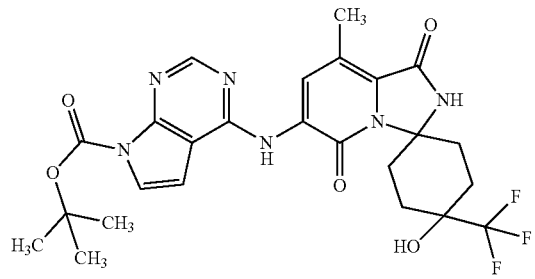

To a solution of 110 mg (278 µmol) 6'-bromo-4-hydroxy-8'-methyl-4-(trifluoromethyl)-2'H-spiro[cyclohexane-1,3'-imidazo[1,5-a]pyridine]-1',5'-dione (prepared according to example 127a) and 71.7 mg (306 µmol) tert-butyl 4-amino- 7H-pyrrolo[2,3-d]pyrimidine-7-carboxylate (prepared according to example 90a) in 7.1 mL 1,4-dioxane was added 272 mg cesium carbonate and the mixture was degassed and purged with argon several times. 17.2 mg 4,5-bis(diphenylphosphino)-9,9-dimethylxanthene, 14.2 mg 2-(dicyclohexyl-phosphino)-2',4',6'-triisopropylbiphenyl, 6.7 mg palladium(II)acetate and 27.3 mg tris(dibenzylideneacetone)dipalladium(0) were added and the mixture was stirred at 100° C. for 2 hours. After concentration the residue was purified by flash chromatography (Biotage SNAP cartridge silica 25 g, methanol:dichloromethane) to give 90 mg (59%) of the title compound.

LC-MS: m/z=549.4 [M+H]$^+$.

Example 129

N-[2-(Dimethylamino)ethyl]-4-{[4-hydroxy-8'-methyl-1',5'-dioxo-4-(trifluoromethyl)-1',5'-dihydro-2'H-spiro[cyclohexane-1,3'-imidazo[1,5-a]pyridin]-6'-yl]amino}thieno[2,3-d]pyrimidine-6-carboxamide

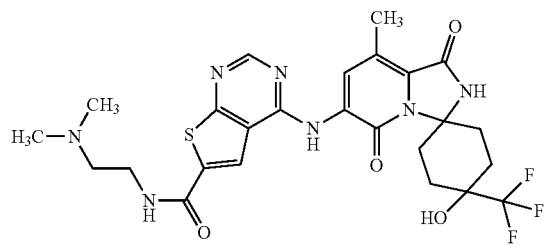

A mixture of 76 mg (149 μmol) 4-{[4-hydroxy-8'-methyl-1',5'-dioxo-4-(trifluoromethyl)-1',5'-dihydro-2'H-spiro[cyclohexane-1,3'-imidazo[1,5-a]pyridin]-6'-yl]amino}thieno[2,3-d]pyrimidine-6-carboxylic acid (prepared according to example 129a), 2.4 mL N,N-dimethylacetamide, 208 μL N-ethyl-N-isopropylpropan-2-amine, 65 μL N,N-dimethylethane-1,2-diamine and 266 μL 2,4,6-tripropyl-1,3,5,2,4,6-trioxatriphosphinane 2,4,6-trioxide solution (50% in N,N-dimethylformamide) was stirred at RT for 2.5 days. The mixture was concentrated and the residue purified by flash chromatography (Biotage SNAP cartridge NH 11 g, methanol:dichloromethane) to give 7.5 mg (8%) of the title compound.

LC-MS: m/z=580.4 [M+H]$^+$.

$^1$H-NMR (400 MHz, DMSO-d6), δ [ppm]=1.45 (2H), 1.84 (2H), 1.97 (2H), 2.20 (6H), 2.43 (2H), 2.50 (3H*), 3.36-3.50 (4H), 5.95 (1H), 8.51 (1H), 8.72 (1H), 8.78 (1H), 8.94 (1H), 9.03 (1H), 10.43 (1H);

*: at least partially hidden by solvent or water signal

Example 129a

4-{[4-Hydroxy-8'-methyl-1',5'-dioxo-4-(trifluoromethyl)-1',5'-dihydro-2'H-spiro[cyclohexane-1,3'-imidazo[1,5-a]pyridin]-6'-yl]amino}thieno[2,3-d]pyrimidine-6-carboxylic acid

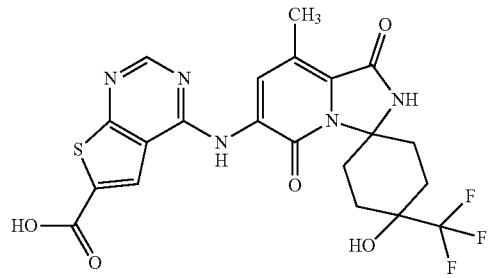

A mixture of 100 mg (191 μmol) methyl 4-{[4-hydroxy-8'-methyl-1',5'-dioxo-4-(trifluoromethyl)-1',5'-dihydro-2'H-spiro[cyclohexane-1,3'-imidazo[1,5-a]pyridin]-6'-yl] amino}thieno[2,3-d]pyrimidine-6-carboxylate (prepared according to example 129b) in 3.0 mL tetrahydrofuran, 3.0 mL ethanol and 3.8 mL lithium hydroxide solution (1M in water) was stirred at RT overnight. Water was added and the mixture was acidified with hydrochloric acid. The precipitate was filtered off, washed with water and dried to give 85 mg (87%) of the title compound.

LC-MS: m/z=510.2 [M+H]$^+$.

Example 129b

Methyl 4-{[4-hydroxy-8'-methyl-1',5'-dioxo-4-(trifluoromethyl)-1',5'-dihydro-2'H-spiro[cyclohexane-1,3'-imidazo[1,5-a]pyridin]-6'-yl]amino}thieno[2,3-d]pyrimidine-6-carboxylate

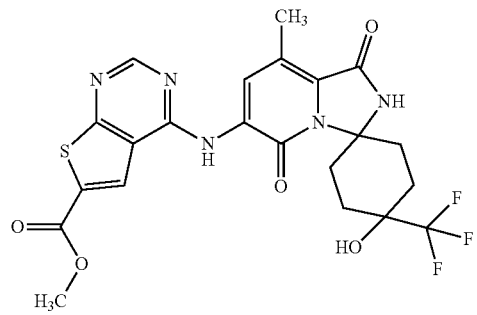

To a solution of 120 mg (304 μmol) 6'-bromo-4-hydroxy-8'-methyl-4-(trifluoromethyl)-2'H-spiro[cyclohexane-1,3'-imidazo[1,5-a]pyridine]-1',5'-dione (prepared according to example 127a) and 69.9 mg (334 μmol) methyl 4-aminothieno[2,3-d]pyrimidine-6-carboxylate (CAS-No.: 155087-15-3) in 12.3 mL N,N-dimethylacetamide was added 297 mg cesium carbonate and the mixture was degassed and purged with argon several times. 18.8 mg 4,5-bis(diphenylphosphino)-9,9-dimethylxanthene, 15.5 mg 2-(dicyclohexylphosphino)-2',4',6'-triisopropylbiphenyl, 7.3 mg palladium(II)acetate and 29.8 mg tris(dibenzylideneacetone)dipalladium(0) were added and the mixture was stirred at 100° C. for 2 hours. After concentration the residue was purified by flash chromatography (Biotage SNAP cartridge silica 25 g, methanol:dichloromethane) to give 100 mg (63%) of the title compound.

LC-MS: m/z=524.1 [M+H]$^+$.

Example 130

4-Hydroxy-8'-methyl-6'-(thieno[2,3-d]pyrimidin-4-ylamino)-4-(trifluoromethyl)-2'H-spiro[cyclohexane-1,3'-imidazo[1,5-a]pyridine]-1',5'-dione

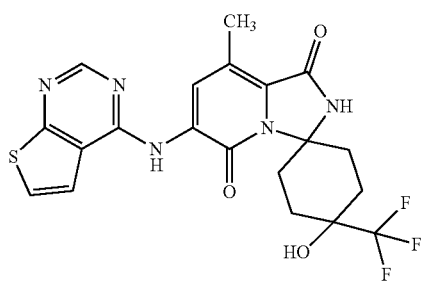

To a solution of 100 mg (253 µmol) 6'-bromo-4-hydroxy-8'-methyl-4-(trifluoromethyl)-2'H-spiro[cyclohexane-1,3'-imidazo[1,5-a]pyridine]-1',5'-dione (prepared according to example 127a) and 42 mg (278 µmol) thieno[2,3-d]pyrimidin-4-amine (CAS-No.: 14080-56-9) in 8.2 mL 1,4-dioxane was added 247 mg cesium carbonate and the mixture was degassed and purged with argon several times. 15.7 mg 4,5-bis(diphenylphosphino)-9,9-dimethylxanthene, 12.9 mg 2-(dicyclohexyl-phosphino)-2',4',6'-triisopropylbiphenyl, 6.1 mg palladium(II)acetate and 24.8 mg tris(dibenzylideneacetone)dipalladium(0) were added and the mixture was stirred at 100° C. for 2 hours. After concentration the residue was purified by flash chromatography (Biotage SNAP cartridge silica 25 g, methanol:dichloromethane) and crystallization from methanol to give 42 mg (32%) of the title compound.

LC-MS: m/z=466.2 [M+H]$^+$.

$^1$H-NMR (400 MHz, DMSO-d6), δ [ppm]=1.43 (2H), 1.83 (2H), 1.96 (2H), 2.52 (3H*), 3.46 (2H), 5.99 (1H), 7.82 (1H), 7.87 (1H), 8.65 (1H), 8.70 (1H), 9.07 (1H), 10.43 (1H);

*: at least partially hidden by solvent or water signal

Example 131

6-[(4-Amino-1,3,5-triazin-2-yl)amino]-3,3,8-trimethyl-2,3-dihydroimidazo[1,5-a]pyridine-1,5-dione

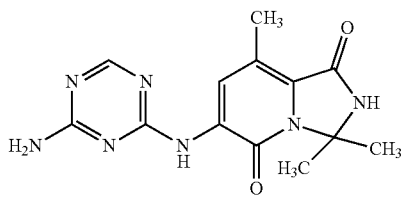

To a solution of 150 mg (553 µmol) 6-bromo-3,3,8-trimethyl-2,3-dihydroimidazo[1,5-a]pyridine-1,5-dione (prepared according to PCT Int. Appl. (2015), WO 2015200481) and 109 mg (609 µmol) N-(4-amino-1,3,5-triazin-2-yl)cyclopropanecarboxamide (prepared according to example 40a) in 21 mL 1,4-dioxane was added 541 mg cesium carbonate and the mixture was degassed and purged with argon several times. 34 mg 4,5-bis(diphenylphosphino)-9,9-dimethylxanthene, 28 mg 2-(dicyclohexyl-phosphino)-2',4',6'-triisopropylbiphenyl, 13 mg palladium(II)acetate and 54 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, methanol:dichloromethane) to give 56 mg (32%) of the title compound.

LC-MS: m/z=302.2 [M+H]$^+$.

$^1$H-NMR (400 MHz, DMSO-d6), δ [ppm]=1.77 (6H), 2.45 (3H), 7.46 (2H), 8.04 (1H), 8.27 (1H), 8.45 (1H), 9.58 (1H)

Example 132

3,3,8-Trimethyl-6-(7H-pyrrolo[2,3-d]pyrimidin-4-ylamino)-2,3-dihydroimidazo[1,5-a]pyridine-1,5-dione

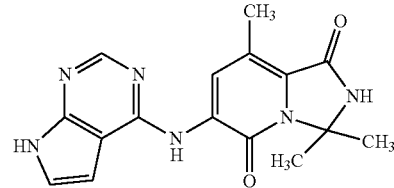

A mixture of 100 mg (max. 236 µmol) tert-butyl 4-[(3,3,8-trimethyl-1,5-dioxo-1,2,3,5-tetrahydroimidazo[1,5-a]pyridin-6-yl)amino]-7H-pyrrolo[2,3-d]pyrimidine-7-carboxylate (prepared according to example 132a) and 363 µL trifluoroacetic acid in 3.0 mL dichloromethane was stirred at RT overnight. The mixture was poured into aqueous ammonia (25%) and extracted with dichloromethane/methanol. The organic layer was washed with water, dried over sodium sulfate. After filtration and concentration the residue was digested with ethanol and dried to give 30 mg (35%) of the title compound.

LC-MS: m/z=325.2 [M+H]$^+$.

$^1$H-NMR (400 MHz, DMSO-d6), δ [ppm]=1.81 (6H), 2.48 (3H*), 6.79 (1H), 7.37 (1H), 8.46 (1H), 8.61 (1H), 8.72 (1H), 9.57 (1H), 12.01 (1H)

*: at least partially hidden by solvent peak.

Example 132a tert-Butyl 4-[(3,3,8-trimethyl-1,5-dioxo-1,2,3,5-tetrahydroimidazo[1,5-a]pyridin-6-yl)amino]-7H-pyrrolo[2,3-d]pyrimidine-7-carboxylate

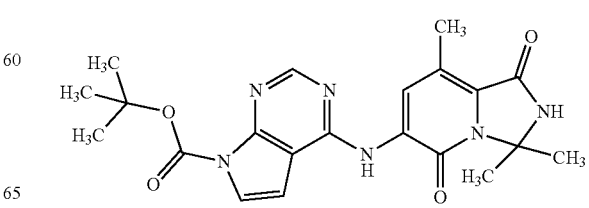

To a solution of 49 mg (182 µmol) 6-bromo-3,3,8-trimethyl-2,3-dihydroimidazo[1,5-a]pyridine-1,5-dione (prepared according to PCT Int. Appl. (2015), WO 2015200481) and 47 mg (201 µmol) tert-butyl 4-amino-7H-pyrrolo[2,3-d]pyrimidine-7-carboxylate (prepared according to example 132b) in 5.9 mL 1,4-dioxane was added 178 mg cesium carbonate and the mixture was degassed and purged with argon several times. 11 mg 4,5-bis(diphenylphosphino)-9,9-dimethylxanthene, 9.3 mg 2-(dicyclohexyl-phosphino)-2',4',6'-triisopropylbiphenyl, 4.4 mg palladium(II)acetate and 17.9 mg tris(dibenzylideneacetone)dipalladium(0) were added and the mixture was stirred at 100° C. for 2 hours. The mixture was concentrated and used without further purification in the next step.

LC-MS: m/z=425.3 [M+H]⁺.

Example 132b tert-Butyl 4-amino-7H-pyrrolo[2,3-d]pyrimidine-7-carboxylate

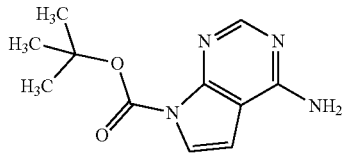 [SMILES: CC(C)(C)OC(=O)n1ccc2c(N)ncnc21]

To a solution of 1.00 g (7.46 mmol) 7H-pyrrolo[2,3-d]pyrimidin-4-amine (CAS-No: 1500-85-2) in 20 mL pyridine were added 182 mg N,N-dimethylpyridin-4-amine, 1.63 g di-tert-butyl dicarbonate and the mixture was stirred at RT overnight. After concentration the residue was purified by flash chromatography (Biotage SNAP cartridge silica 100 g, methanol:dichloromethane) to give 715 mg (41%) of the title compound.

LC-MS: m/z=235.2 [M+H]⁺.

Example 133

3,3,8-Trimethyl-6-(1H-pyrazolo[3,4-d]pyrimidin-4-ylamino)-2,3-dihydroimidazo[1,5-a]pyridine-1,5-dione

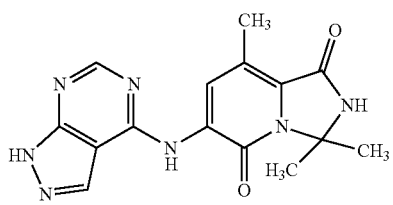

To a solution of 100 mg (369 µmol) 6-bromo-3,3,8-trimethyl-2,3-dihydroimidazo[1,5-a]pyridine-1,5-dione (prepared according to PCT Int. Appl. (2015), WO 2015200481) and 55 mg (406 µmol) 1H-pyrazolo[3,4-d]pyrimidin-4-amine (CAS-No: 2380-63-4) in 13.8 mL 1,4-dioxane was added 361 mg cesium carbonate and the mixture was degassed and purged with argon several times. 22.8 mg 4,5-bis(diphenylphosphino)-9,9-dimethylxanthene, 18.8 mg 2-(dicyclohexyl-phosphino)-2',4',6'-triisopropylbiphenyl, 8.9 mg palladium(II)acetate and 36.1 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, methanol:dichloromethane) to give 24 mg (19%) of the title compound.

LC-MS: m/z=326.2 [M+H]⁺.

¹H-NMR (400 MHz, DMSO-d6), δ [ppm]=1.82 (6H), 2.47 (3H), 8.55 (1H), 8.57 (1H), 8.68 (1H), 9.42 (1H), 9.65 (1H), 13.78 (1H)

Example 134

3,3,8-Trimethyl-6-(9H-purin-6-ylamino)-2,3-dihydroimidazo[1,5-a]pyridine-1,5-dione

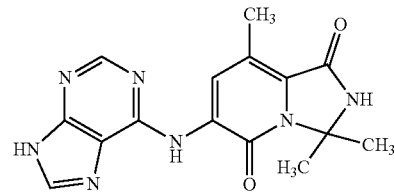 [SMILES: Cc1cc(Nc2ncnc3[nH]cnc23)c(=O)n2c1C(=O)NC2(C)C]

To a solution of 100 mg (369 µmol) 6-bromo-3,3,8-trimethyl-2,3-dihydroimidazo[1,5-a]pyridine-1,5-dione (prepared according to PCT Int. Appl. (2015), WO 2015200481) and 69.6 mg (406 µmol) 9H-purin-6-amine hydrochloride (CAS-No: 2922-28-3) in 13.8 mL 1,4-dioxane was added 361 mg cesium carbonate and the mixture was degassed and purged with argon several times. 22.8 mg 4,5-bis(diphenylphosphino)-9,9-dimethylxanthene, 18.8 mg 2-(dicyclohexyl-phosphino)-2',4',6'-triisopropylbiphenyl, 8.9 mg palladium(II)acetate and 36.1 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, methanol:dichloromethane) to give 4.0 mg (3%) of the title compound.

LC-MS: m/z=326.2 [M+H]⁺.

¹H-NMR (400 MHz, DMSO-d6), δ [ppm]=1.81 (6H), 2.50 (3H*), 8.39 (1H), 8.59 (1H), 8.72 (1H), 8.86 (1H), 9.61 (1H), 13.45 (1H)

*: at least partially hidden by solvent peak.

Example 135

3,3,8-Trimethyl-6-(thieno[2,3-d]pyrimidin-4-ylamino)-2,3-dihydroimidazo[1,5-a]pyridine-1,5-dione

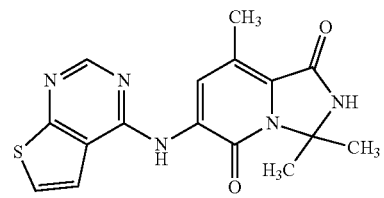 [SMILES: Cc1cc(Nc2ncnc3sccc23)c(=O)n2c1C(=O)NC2(C)C]

To a solution of 100 mg (369 µmol) 6-bromo-3,3,8-trimethyl-2,3-dihydroimidazo[1,5-a]pyridine-1,5-dione (prepared according to PCT Int. Appl. (2015), WO 2015200481) and 61.3 mg (406 µmol) thieno[2,3-d]pyrimidin-4-amine (CAS-No: 14080-56-9) in 13.8 mL 1,4-dioxane was added 361 mg cesium carbonate and the mixture was degassed and purged with argon several times. 22.8 mg 4,5-bis(diphenylphosphino)-9,9-dimethylxanthene, 18.8 mg 2-(dicyclohexyl-phosphino)-2',4',6'-triisopropylbiphenyl, 8.9 mg palladium(II)acetate and 36.1 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, methanol:dichloromethane) to give 53 mg (40%) of the title compound.

LC-MS: m/z=342.2 [M+H]$^+$.

$^1$H-NMR (400 MHz, DMSO-d6), δ [ppm]=1.81 (6H), 2.48 (3H), 7.81 (1H), 7.85 (1H), 8.62 (1H), 8.69 (1H), 9.06 (1H), 9.65 (1H)

Example 136

4-[(3,3,8-Trimethyl-1,5-dioxo-1,2,3,5-tetrahydroimidazo[1,5-a]pyridin-6-yl)amino]thieno[2,3-d]pyrimidine-6-carboxylic acid

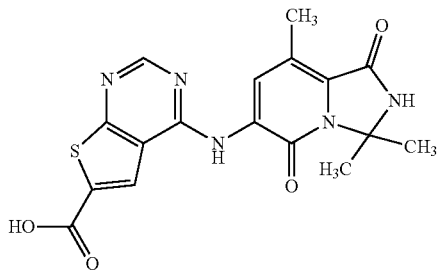 [SMILES: Cc1cc(Nc2ncnc3sc(C(=O)O)cc23)c(=O)n2c1C(=O)NC2(C)C]

A mixture of 580 mg (1.45 mmol) methyl 4-[(3,3,8-trimethyl-1,5-dioxo-1,2,3,5-tetrahydroimidazo[1,5-a]pyridin-6-yl)amino]thieno[2,3-d]pyrimidine-6-carboxylate (prepared according to intermediate example 136a) in 22.5 mL tetrahydrofuran, 22.5 mL ethanol and 29 mL lithium hydroxide solution (1M in water) was stirred at RT overnight. Water was added and the mixture was acidified with hydrochloric acid. The precipitate was filtered off, washed with water and dried to give 520 mg (88%) of the title compound.

LC-MS: m/z=386.2 [M+H]$^+$.

$^1$H-NMR (400 MHz, DMSO-d6), δ [ppm]=1.81 (6H), 2.47 (3H), 8.49 (1H), 8.52 (1H), 8.71 (1H), 9.47 (1H), 9.69 (1H), 13.77 (1H)

Example 136a

Methyl 4-[(3,3,8-trimethyl-1,5-dioxo-1,2,3,5-tetrahydroimidazo[1,5-a]pyridin-6-yl)amino]thieno[2,3-d]pyrimidine-6-carboxylate

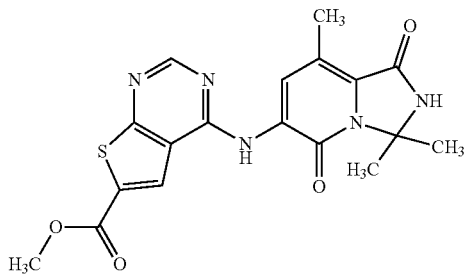

To a solution of 500 mg (1.84 mmol) 6-bromo-3,3,8-trimethyl-2,3-dihydroimidazo[1,5-a]pyridine-1,5-dione (prepared according to PCT Int. Appl. (2015), WO 2015200481) and 424 mg (2.03 mmol) methyl 4-aminothieno[2,3-d]pyrimidine-6-carboxylate (CAS-No: 155087-15-3) in 75 mL N,N-dimethylacetamide was added 1.80 g cesium carbonate and the mixture was degassed and purged with argon several times. 114 mg 4,5-bis(diphenylphosphino)-9,9-dimethylxanthene, 94 mg 2-(dicyclohexyl-phosphino)-2',4',6'-triisopropylbiphenyl, 44 mg palladium(II)acetate and 181 mg tris(dibenzylideneacetone)dipalladium(0) were added and the mixture was stirred at 100° C. for 2 hours. The mixture was concentrated and the residue purified by flash chromatography (Biotage SNAP cartridge silica 50 g, methanol:dichloromethane) to give 580 mg (79%) of the title compound.

LC-MS: m/z=400.2 [M+H]$^+$.

Example 137

N-[2-(Dimethylamino)ethyl]-4-[(3,3,8-trimethyl-1,5-dioxo-1,2,3,5-tetrahydroimidazo[1,5-a]pyridin-6-yl)amino]thieno[2,3-d]pyrimidine-6-carboxamide

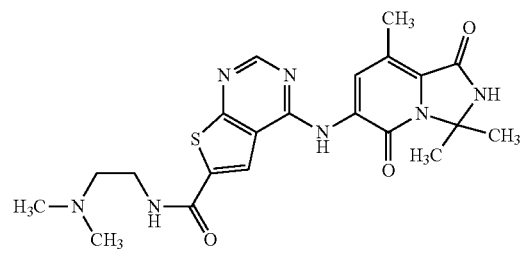

A mixture of 50 mg (130 μmol) 4-[(3,3,8-trimethyl-1,5-dioxo-1,2,3,5-tetrahydroimidazo[1,5-a]pyridin-6-yl)amino]thieno[2,3-d]pyrimidine-6-carboxylic acid (prepared according to example 136), 2.0 mL N,N-dimethylacetamide, 181 μL N-ethyl-N-isopropylpropan-2-amine, μL N,N-dimethylethane-1,2-diamine and 232 μL 2,4,6-tripropyl-1,3,5,2,4,6-trioxatriphosphinane 2,4,6-trioxide solution (50% in N,N-dimethylformamide) was stirred at RT overnight and at 70° C. for 3 hours. 14 μL N,N-dimethylethane-1,2-diamine and 77 μL 2,4,6-tripropyl-1,3,5,2,4,6-trioxatriphosphinane 2,4,6-trioxide solution (50% in N,N-dimethylformamide) were added and stirring continued at RT overnight The mixture was concentrated, and the residue purified by flash chromatography (Biotage SNAP cartridge NH 11 g and silica 10 g, methanol:dichloromethane) to give 38 mg (61%) of the title compound.

LC-MS: m/z=456.3 [M+H]$^+$.

$^1$H-NMR (400 MHz, CHLOROFORM-d), δ [ppm]=1.98 (6H), 2.31 (6H), 2.56 (2H), 2.61 (3H), 3.56 (2H), 6.45 (1H), 6.81 (1H), 7.82 (1H), 8.74 (1H), 8.79 (1H), 8.86 (1H)

Example 138

N-[2-(Dimethylamino)ethyl]-N-methyl-4-[(3,3,8-trimethyl-1,5-dioxo-1,2,3,5-tetrahydroimidazo[1,5-a]pyridin-6-yl)amino]thieno[2,3-d]pyrimidine-6-carboxamide

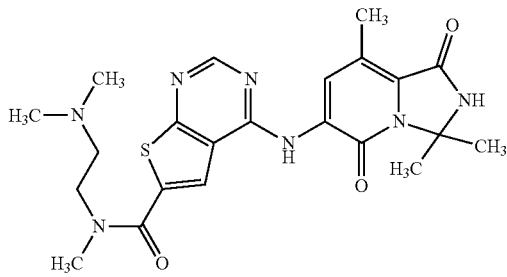

A mixture of 50 mg (130 μmol) 4[(3,3,8-trimethyl-1,5-dioxo-1,2,3,5-tetrahydroimidazo[1,5-a]pyridin-6-yl)amino]thieno[2,3-d]pyrimidine-6-carboxylic acid (prepared according to example 136), 2.1 mL N,N-dimethylacetamide, 181 μL N-ethyl-N-isopropylpropan-2-amine, 67 μL N,N,N-trimethylethylendiamin and 232 μL 2,4,6-tripropyl-1,3,5,2,4,6-trioxatriphosphinane 2,4,6-trioxide solution (50% in N,N-dimethylformamide) was stirred at RT overnight. The mixture was concentrated and the residue purified by flash chromatography (Biotage SNAP cartridge NH 11 g and silica 10 g, ethanol:dichloromethane) to give 55 mg (81%) of the title compound.

LC-MS: m/z=470.3 [M+H]⁺.

¹H-NMR (400 MHz, CHLOROFORM-d), δ [ppm]=1.97 (6H), 2.29 (6H), 2.50-2.75 (5H), 3.28 (3H), 3.70 (2H), 6.27 (1H), 7.75 (1H), 8.73 (1H), 8.78 (1H), 8.85 (1H)

Example 139 tert-Butyl [1-({4-[(3,3,8-trimethyl-1,5-dioxo-1,2,3,5-tetrahydroimidazo[1,5-a]pyridin-6-yl)amino]thieno[2,3-d]pyrimidin-6-yl}carbonyl)azetidin-3-yl]carbamate

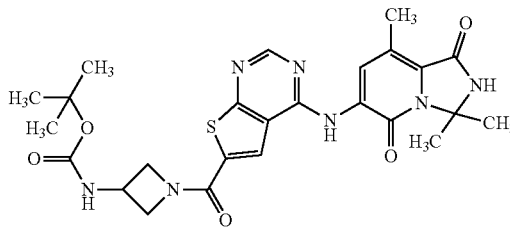

A mixture of 100 mg (259 μmol) 4-[(3,3,8-trimethyl-1,5-dioxo-1,2,3,5-tetrahydroimidazo[1,5-a]pyridin-6-yl)amino]thieno[2,3-d]pyrimidine-6-carboxylic acid (prepared according to example 136), 4.1 mL N,N-dimethylacetamide, 362 μL N-ethyl-N-isopropylpropan-2-amine, 217 mg tert-butyl azetidin-3-ylcarbamate hydrochloride and 463 μL 2,4,6-tripropyl-1,3,5,2,4,6-trioxatriphosphinane 2,4,6-trioxide solution (50% in N,N-dimethylformamide) was stirred at RT overnight. The crude mixture was concentrated, and the residue purified by flash chromatography (Biotage SNAP cartridge NH 11 g and silica 10 g, methanol:dichloromethane) to give 97 mg (66%) of the title compound.

LC-MS: m/z=540.3 [M+H]⁺.

¹H-NMR (400 MHz, DMSO-d6), δ [ppm]=1.40 (9H), 1.81 (6H), 2.46 (3H), 4.00 (1H), 4.34 (1H), 4.43 (2H), 4.87 (1H), 7.72 (1H), 8.26 (1H), 8.48 (1H), 8.67 (1H), 9.56 (1H), 9.69 (1H)

Example 140

6-({6-[(3-Aminoazetidin-1-yl)carbonyl]thieno[2,3-d]pyrimidin-4-yl}amino)-3,3,8-trimethyl-2,3-dihydroimidazo[1,5-a]pyridine-1,5-dione

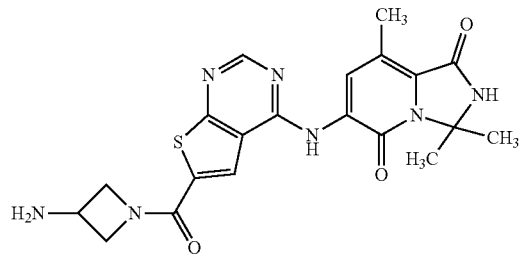 [SMILES: Cc1cc(Nc2ncnc3sc(C(=O)N4CC(N)C4)cc23)c(=O)n2c1C(=O)NC2(C)C]

A mixture of 70 mg (130 μmol) tert-butyl [1-({4-[(3,3,8-trimethyl-1,5-dioxo-1,2,3,5-tetrahydroimidazo[1,5-a]pyridin-6-yl)amino]thieno[2,3-d]pyrimidin-6-yl}carbonyl)azetidin-3-yl]carbamate (prepared according to example 139) and 200 μL trifluoroacetic acid in 5.1 mL dichloromethane was stirred at RT for 3 days. The mixture was poured into aqueous ammonia (25%) and extracted with dichloromethane/methanol. The organic layer was washed with water, dried over sodium sulfate. After filtration and concentration the residue was digested with ethanol and dried to give 28 mg (47%) of the title compound.

LC-MS: m/z=440.2 [M+H]⁺.

¹H-NMR (400 MHz, DMSO-d6), δ [ppm]=1.82 (6H), 2.47 (3H), 3.30 (2H*), 3.74 (1H), 3.84 (1H), 4.26 (2H), 4.77 (1H), 8.26 (1H), 8.47 (1H), 8.67 (1H), 9.53 (1H), 9.69 (1H)

*: at least partially hidden by solvent peak.

Example 141

1-({4-[(3,3,8-Trimethyl-1,5-dioxo-1,2,3,5-tetrahydroimidazo[1,5-a]pyridin-6-yl)amino]thieno[2,3-d]pyrimidin-6-yl}carbonyl)azetidine-3-carbonitrile

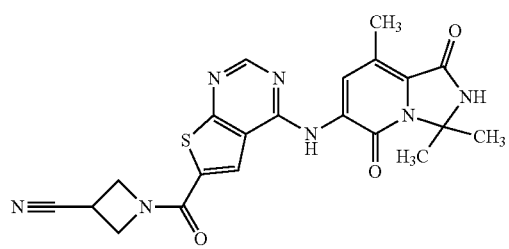 [SMILES: Cc1cc(Nc2ncnc3sc(C(=O)N4CC(C#N)C4)cc23)c(=O)n2c1C(=O)NC2(C)C]

A mixture of 50 mg (130 μmol) 4-[(3,3,8-trimethyl-1,5-dioxo-1,2,3,5-tetrahydroimidazo[1,5-a]pyridin-6-yl)amino]thieno[2,3-d]pyrimidine-6-carboxylic acid (prepared according to example 136), 2.1 mL N,N-dimethylacetamide, 181 μL N-ethyl-N-isopropylpropan-2-amine, 61.5 mg azetidine-3-carbonitrile hydrochloride and 232 μL 2,4,6-tripropyl-1,3,5,2,4,6-trioxatriphosphinane 2,4,6-trioxide solution (50% in N,N-dimethylformamide) was stirred at RT overnight. The mixture was concentrated, and the residue purified by flash chromatography (Biotage SNAP cartridge NH 11 g and silica 10 g, ethanol:dichloromethane) to give 46 mg (75%) of the title compound.

LC-MS: m/z=450.2 [M+H]⁺.

¹H-NMR (400 MHz, DMSO-d6), δ [ppm]=1.82 (6H), 2.47 (3H), 3.97 (1H), 4.27 (1H), 4.41 (1H), 4.90 (2H), 8.33 (1H), 8.50 (1H), 8.69 (1H), 9.49 (1H), 9.69 (1H)

Example 142

6-[(6-{[(3R)-3-(Dimethylamino)pyrrolidin-1-yl]carbonyl}thieno[2,3-d]pyrimidin-4-yl)amino)-3,3,8-trimethyl-2,3-dihydroimidazo[1,5-a]pyridine-1,5-dione

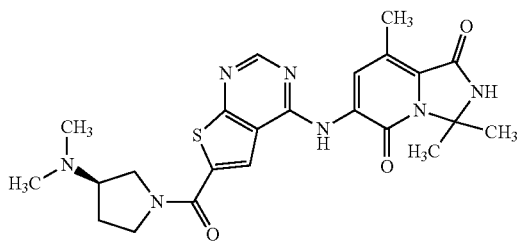

A mixture of 50 mg (130 μmol) 4-[(3,3,8-trimethyl-1,5-dioxo-1,2,3,5-tetrahydroimidazo[1,5-a]pyridin-6-yl)amino]thieno[2,3-d]pyrimidine-6-carboxylic acid (prepared according to example 136), 2.1 mL N,N-dimethylacetamide, 181 μL N-ethyl-N-isopropylpropan-2-amine, 59 mg (3R)—N,N-dimethylpyrrolidin-3-amine and 232 μL 2,4,6-tripropyl-1,3,5,2,4,6-trioxatriphosphinane 2,4,6-trioxide solution (50% in N,N-dimethylformamide) was stirred at RT overnight. The mixture was concentrated, and the residue purified by flash chromatography (Biotage SNAP cartridge NH 11 g and silica 10 g, ethanol:dichloromethane) to give 23 mg (33%) of the title compound.

LC-MS: m/z=482.3 [M+H]⁺.

¹H-NMR (400 MHz, CHLOROFORM-d), δ [ppm]=1.97 (6H), 2.04 (1H), 2.31 (6H), 2.62 (3H), 2.72-3.00 (2H), 3.38-4.12 (4H), 6.13 (1H), 7.82 (1H), 8.75 (1H), 8.79 (1H), 8.86 (1H)

Example 143

6-[(6-{[4-(Dimethylamino)piperidin-1-yl]carbonyl}thieno[2,3-d]pyrimidin-4-yl)amino)-3,3,8-trimethyl-2,3-dihydroimidazo[1,5-a]pyridine-1,5-dione

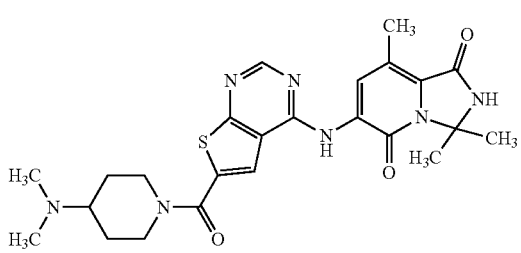

A mixture of 50 mg (130 μmol) 4-[(3,3,8-trimethyl-1,5-dioxo-1,2,3,5-tetrahydroimidazo[1,5-a]pyridin-6-yl)amino]thieno[2,3-d]pyrimidine-6-carboxylic acid (prepared according to example 136), 2.1 mL N,N-dimethylacetamide, 181 μL N-ethyl-N-isopropylpropan-2-amine, 66.5 mg N,N-dimethylpiperidin-4-amine and 232 μL 2,4,6-tripropyl-1,3,5,2,4,6-trioxatriphosphinane 2,4,6-trioxide solution (50% in N,N-dimethylformamide) was stirred at RT overnight. The mixture was concentrated, and the residue purified by flash chromatography (Biotage SNAP cartridge NH 11 g and silica 10 g, ethanol:dichloromethane) to give 35 mg (52%) of the title compound.

LC-MS: m/z=496.3 [M+H]⁺.

¹H-NMR (400 MHz, CHLOROFORM-d), δ [ppm]=1.55 (2H), 1.93 (2H), 1.97 (6H), 2.32 (6H), 2.45 (1H), 2.62 (3H), 3.07 (2H), 4.46 (2H), 6.20 (1H), 7.57 (1H), 8.71 (1H), 8.78 (1H), 8.85 (1H)

Example 144

3,3,8-Trimethyl-6-({6-[(1R,4R)-2-oxa-5-azabicyclo[2.2.1]hept-5-ylcarbonyl]thieno[2,3-d]pyrimidin-4-yl}amino)-2,3-dihydroimidazo[1,5-a]pyridine-1,5-dione

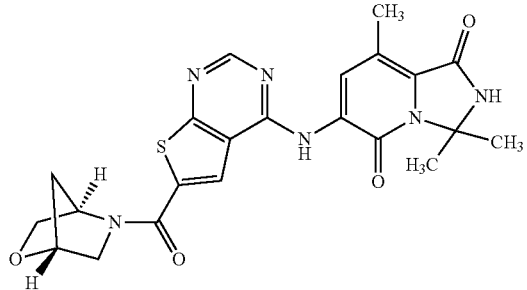 [SMILES: Cc1cc(Nc2ncnc3sc(C(=O)N4C[C@H]5C[C@@H]4CO5)cc23)c(=O)n2c1C(=O)NC2(C)C]

A mixture of 50 mg (130 μmol) 4-[(3,3,8-trimethyl-1,5-dioxo-1,2,3,5-tetrahydroimidazo[1,5-a]pyridin-6-yl)amino]thieno[2,3-d]pyrimidine-6-carboxylic acid (prepared according to example 136), 2.1 mL N,N-dimethylacetamide, 90 μL N-ethyl-N-isopropylpropan-2-amine, 70 mg (1R,4R)-2-oxa-5-azabicyclo[2.2.1]heptane hydrochloride and 232 μL 2,4,6-tripropyl-1,3,5,2,4,6-trioxatriphosphinane 2,4,6-trioxide solution (50% in N,N-dimethylformamide) was stirred at RT overnight. Water was added, the precipitate washed with ethanol and diethyl ether and dried to give 42 mg (66%) of the title compound.

LC-MS: m/z=467.3 [M+H]⁺.

¹H-NMR (400 MHz, DMSO-d6), δ [ppm]=1.82 (6H), 1.85-2.04 (2H), 2.47 (3H), 3.39+3.56 (1H), 3.81 (1H), 3.88 (1H), 3.98 (1H), 4.71+4.79 (1H), 4.95+5.24 (1H), 8.30+8.42 (1H), 8.52+8.56 (1H), 8.69 (1H), 9.47 (1H), 9.68 (1H)

Example 145

5-Methyl-4-[(3,3,8-trimethyl-1,5-dioxo-1,2,3,5-tetrahydroimidazo[1,5-a]pyridin-6-yl)amino]thieno[2,3-d]pyrimidine-6-carboxylic acid

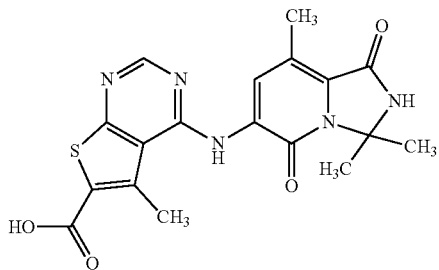 [SMILES: Cc1cc(Nc2ncnc3sc(C(=O)O)c(C)c23)c(=O)n2c1C(=O)NC2(C)C]

A mixture of 105 mg (246 µmol) ethyl 5-methyl-4-[(3,3,8-trimethyl-1,5-dioxo-1,2,3,5-tetrahydroimidazo[1,5-a]pyridin-6-yl)amino]thieno[2,3-d]pyrimidine-6-carboxylate (prepared according to intermediate example 145a) in 3.8 mL tetrahydrofuran, 3.8 mL ethanol and 1.47 mL lithium hydroxide solution (1M in water) was stirred at RT overnight. Water was added and the mixture was acidified with hydrochloric acid. The precipitate was filtered off, washed with water and dried to give 97 mg (94) of the title compound.

LC-MS: m/z=400.3 [M+H]$^+$.

$^1$H-NMR (400 MHz, DMSO-d6), δ [ppm]=1.81 (6H), 2.48 (3H), 3.09 (3H), 8.72 (2H), 9.30 (1H), 9.69 (1H), 13.77 (1H)

Example 145a

Ethyl 5-methyl-4-[(3,3,8-trimethyl-1,5-dioxo-1,2,3,5-tetrahydroimidazo[1,5-a]pyridin-6-yl)amino]thieno[2,3-d]pyrimidine-6-carboxylate

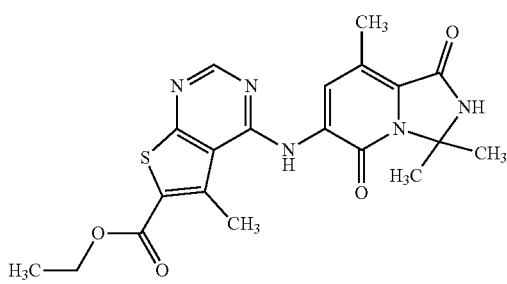 [SMILES: CCOC(=O)c1sc2ncnc(Nc3cc(C)c4n(c3=O)C(C)(C)NC4=O)c2c1C]

To a solution of 200 mg (738 µmol) 6-bromo-3,3,8-trimethyl-2,3-dihydroimidazo[1,5-a]pyridine-1,5-dione (prepared according to PCT Int. Appl. (2015), WO 2015200481) and 193 mg (811 µmol) ethyl 4-amino-5-methyl-5,6-dihydrothieno[2,3-d]pyrimidine-6-carboxylate (purchased from Santai Labs Inc.; can also be prepared according to Indian Journal of Chemistry, Section B: 1976, 14, 357-360) in 20 mL 1,4-dioxane was added 721 mg cesium carbonate and the mixture was degassed and purged with argon several times. 45.7 mg 4,5-bis(diphenylphosphino)-9,9-dimethylxanthene, 37.6 mg 2-(dicyclohexylphosphino)-2',4',6'-triisopropylbiphenyl, 17.7 mg palladium (II)acetate and 72.3 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, ethanol:dichloromethane) to give 105 mg (33%) of the title compound.

LC-MS: m/z=428.3 [M+H]$^+$.

Example 146

N-{4-[(8'-Methyl-1',5'-dioxo-1',5'-dihydro-2'H-spiro[cyclobutane-1,3'-imidazo[1,5-a]pyridin]-6'-yl)amino]-1,3,5-triazin-2-yl}cyclopropanecarboxamide

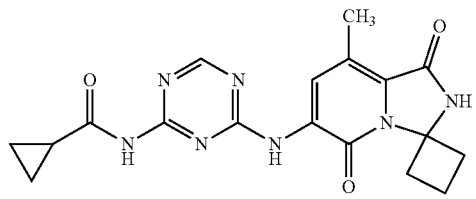 [SMILES: Cc1cc(Nc2ncnc(NC(=O)C3CC3)n2)c(=O)n2c1C(=O)NC21CCC1]

To a solution of 150 mg (530 mmol) 6'-bromo-8'-methyl-2'H-spiro[cyclobutane-1,3'-imidazo[1,5-a]pyridine]-1',5'-dione (prepared according to example 146a) and 104 mg (583 µmol) N-(4-amino-1,3,5-triazin-2-yl)cyclopropanecarboxamide (prepared according to example 40a) in 20 mL 1,4-dioxane was added 518 mg cesium carbonate and the mixture was degassed and purged with argon several times. 32.8 mg 4,5-bis(diphenylphosphino)-9,9-dimethylxanthene, 27 mg 2-(dicyclohexyl-phosphino)-2',4',6'-triisopropylbiphenyl, 12.7 mg palladium(II)acetate and 51.9 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, ethanol:dichloromethane) to give 10 mg (5%) of the title compound.

LC-MS: m/z=382.3 [M+H]$^+$.

$^1$H-NMR (400 MHz, DMSO-d6), δ [ppm]=0.85-0.94 (4H), 1.91 (1H), 2.11 (1H), 2.19 (1H), 2.25-2.36 (2H), 2.42 (3H), 3.41 (2H), 8.58 (1H), 8.66 (1H), 8.91 (1H), 10.14 (1H), 11.24 (1H)

Example 146a

6'-Bromo-8'-methyl-2'H-spiro[cyclobutane-1,3'-imidazo[1,5-a]pyridine]-1',5'-dione

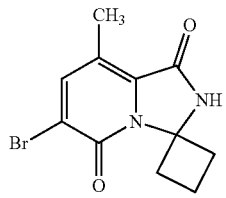 [SMILES: Cc1cc(Br)c(=O)n2c1C(=O)NC21CCC1]

To a solution of 5.00 g (21.6 mmol) 5-bromo-3-methyl-6-oxo-1,6-dihydropyridine-2-carbaldehyde (prepared according to PCT Int. Appl. (2015), WO 2015200481) and 6.07 g (86.6 mmol) cyclobutanone in 60 mL 1,4-dioxane were added 570 µl sulfuric acid and the mixture was stirred at 95° C. for 3 hours. After concentration water was added, the precipitate washed with water and diethyl ether and dried to give 5.42 g (88%) of the title compound.
LC-MS: m/z=283.1 [M+H]$^+$.

Example 147

6'-[(4-Amino-1,3,5-triazin-2-yl)amino]-8'-methyl-2'H-spiro[cyclobutane-1,3'-imidazo[1,5-a]pyridine]-1',5'-dione

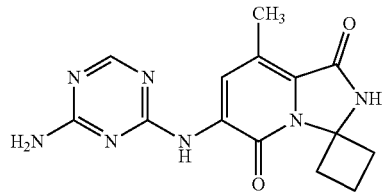 [SMILES: Cc1cc(Nc2ncnc(N)n2)c(=O)n2c1C(=O)NC21CCC1]

To a solution of 150 mg (530 mmol) 6'-bromo-8'-methyl-2'H-spiro[cyclobutane-1,3'-imidazo[1,5-a]pyridine]-1',5'-dione (prepared according to example 146a) and 104 mg (583 µmol) N-(4-amino-1,3,5-triazin-2-yl)cyclopropanecarboxamide (prepared according to example 40a) in 20 mL 1,4-dioxane was added 518 mg cesium carbonate and the mixture was degassed and purged with argon several times. 32.8 mg 4,5-bis(diphenylphosphino)-9,9-dimethylxanthene, 27 mg 2-(dicyclohexyl-phosphino)-2',4',6'-triisopropylbiphenyl, 12.7 mg palladium(II)acetate and 51.9 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, ethanol:dichloromethane) to give 60 mg (34%) of the title compound.
LC-MS: m/z=314.2 [M+H]$^+$.
$^1$H-NMR (400 MHz, DMSO-d6), δ [ppm]=1.91 (1H), 2.10 (1H), 2.29 (2H), 2.43 (3H), 3.41 (2H), 7.47 (2H), 8.09 (1H), 8.27 (1H), 8.46 (1H), 10.10 (1H)

Example 148

8'-Methyl-6'-(7H-pyrrolo[2,3-d]pyrimidin-4-ylamino)-2'H-spiro[cyclobutane-1,3'-imidazo[1,5-a]pyridine]-1',5'-dione

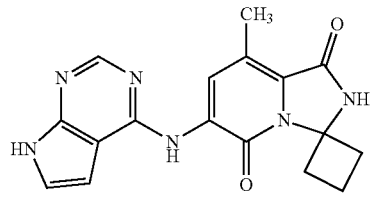 [SMILES: Cc1cc(Nc2ncnc3[nH]ccc23)c(=O)n2c1C(=O)NC21CCC1]

To a solution of 110 mg (338 µmol) 6'-bromo-8'-methyl-2'H-spiro[cyclobutane-1,3'-imidazo[1,5-a]pyridine]-1',5'-dione (prepared according to example 146a) and 100 mg (427 µmol) tert-butyl 4-amino-7H-pyrrolo[2,3-d]pyrimidine-7-carboxylate (prepared according to example 132b) in 10 mL 1,4-dioxane was added 379 mg cesium carbonate and the mixture was degassed and purged with argon several times. 24 mg 4,5-bis(diphenylphosphino)-9,9-dimethylxanthene, 19.8 mg 2-(dicyclohexyl-phosphino)-2',4',6'-triisopropylbiphenyl, 9.3 mg palladium(II)acetate and 38 mg tris(dibenzylideneacetone)dipalladium(0) were added and the mixture was stirred at 100° C. for 2 hours. After concentration the residue was purified by flash chromatography (Biotage SNAP cartridge silica 25 g, methanol:dichloromethane) to give 40 mg (29%) of the title compound.
LC-MS: m/z=337.2 [M+H]$^+$.
$^1$H-NMR (400 MHz, DMSO-d6), δ [ppm]=1.93 (1H), 2.15 (1H), 2.35 (2H), 2.46 (3H), 3.44 (2H), 6.83 (1H), 7.38 (1H), 8.46 (1H), 8.67 (1H), 8.73 (1H), 10.09 (1H), 12.02 (1H)

Example 149

8'-Methyl-6'-(thieno[2,3-d]pyrimidin-4-ylamino)-2'H-spiro[cyclobutane-1,3'-imidazo[1,5-a]pyridine]-1',5'-dione

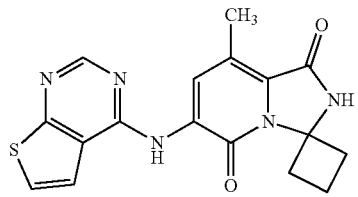 [SMILES: Cc1cc(Nc2ncnc3sccc23)c(=O)n2c1C(=O)NC21CCC1]

To a solution of 100 mg (353 µmol) 6'-bromo-8'-methyl-2'H-spiro[cyclobutane-1,3'-imidazo[1,5-a]pyridine]-1',5'-dione (prepared according to example 146a) and 58.7 mg (389 µmol) thieno[2,3-d]pyrimidin-4-amine (CAS-No: 14080-56-9) in 12 mL 1,4-dioxane was added 345 g cesium carbonate and the mixture was degassed and purged with argon several times. 21.9 mg 4,5-bis(diphenylphosphino)-9,9-dimethylxanthene, 18 mg 2-(dicyclohexyl-phosphino)-2',4',6'-triisopropylbiphenyl, 8.5 mg palladium(II)acetate and 34.6 mg tris(dibenzylideneacetone)dipalladium(0) were added and the mixture was stirred at 100° C. for 2 hours. Dichloromethane and methanol were added, the precipitate filtered off and the filtrate concentrated. After concentration the residue was purified by flash chromatography (Biotage SNAP cartridge silica 25 g, ethanol:dichloromethane) to give 64 mg (49%) of the title compound.
LC-MS: m/z=354.2 [M+H]$^+$.
$^1$H-NMR (400 MHz, DMSO-d6), δ [ppm]=1.93 (1H), 2.15 (1H), 2.36 (2H), 2.46 (3H), 3.43 (2H), 7.82 (1H), 7.88 (1H), 8.62 (1H), 8.69 (1H), 9.12 (1H), 10.16 (1H)

Example 150

4-[(8'-Methyl-1',5'-dioxo-1',5'-dihydro-2'H-spiro[cyclobutane-1,3'-imidazo[1,5-a]pyridin]-6'-yl)amino]thieno[2,3-d]pyrimidine-6-carboxylic acid

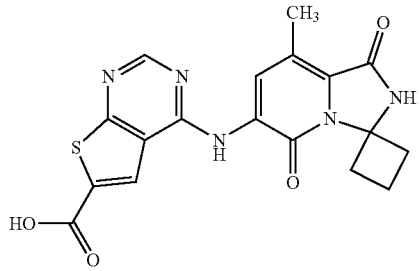 [SMILES: Cc1cc(Nc2ncnc3sc(C(=O)O)cc23)c(=O)n2c1C(=O)NC21CCC1]

A mixture of 442 mg (1.07 mmol) methyl 4-[(8'-methyl-1',5'-dioxo-1',5'-dihydro-2'H-spiro[cyclobutane-1,3'-imidazo pyridin]-6'-yl)amino]thieno[2,3-d]pyrimidine-6-carboxylate (prepared according to intermediate example 150a) in 16 mL tetrahydrofuran, 8 mL ethanol and 6.4 mL lithium hydroxide solution (1M in water) was stirred at RT overnight. Water was added and the mixture was acidified with hydrochloric acid. The precipitate was filtered off, washed with water and dried to give 420 mg (93%) of the title compound.

LC-MS: m/z=398.2 [M+H]$^+$.

$^1$H-NMR (400 MHz, DMSO-d6), δ [ppm]=1.92 (1H), 2.15 (1H), 2.36 (2H), 2.45 (3H), 3.41 (2H), 8.49 (1H), 8.56 (1H), 8.71 (1H), 9.53 (1H), 10.19 (1H), 13.75 (1H)

Example 150a

Methyl 4-[(8'-methyl-1',5'-dioxo-1',5'-dihydro-2'H-spiro[cyclobutane-1,3'-imidazo[1,5-a]pyridin]-6'-yl) amino]thieno[2,3-d]pyrimidine-6-carboxylate

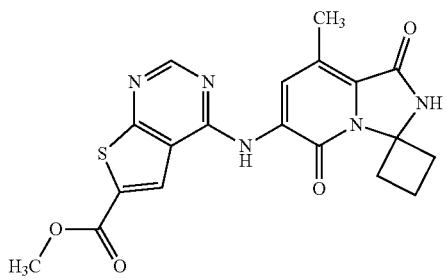 [SMILES: COC(=O)c1cc2c(Nc3cc(C)c4n(c3=O)C3(CCC3)NC4=O)ncnc2s1]

To a solution of 500 mg (1.77 mmol) 6'-bromo-8'-methyl-2'H-spiro[cyclobutane-1,3'-imidazo[1,5-a]pyridine]-1',5'-dione (prepared according to example 146a) and 406 mg (1.94 mmol) methyl 4-aminothieno[2,3-d]pyrimidine-6-carboxylate (CAS-No: 155087-15-3) in 70 mL 1,4-dioxane was added 1.73 g cesium carbonate and the mixture was degassed and purged with argon several times. 109 mg 4,5-bis(diphenylphosphino)-9,9-dimethylxanthene, 90.1 mg 2-(dicyclohexyl-phosphino)-2',4',6'-triisopropylbiphenyl, 42.4 mg palladium(II)acetate and 173 mg tris(dibenzylideneacetone)dipalladium(0) were added and the mixture was stirred at 100° C. for 2 hours. Dichloromethane and methanol were added, the precipitate filtered off and the filtrate concentrated. After concentration the residue was purified by flash chromatography (Biotage SNAP cartridge silica 100 g, ethanol:dichloromethane) to give 444 mg (61%) of the title compound.

LC-MS: m/z=412.3 [M+H]$^+$.

Example 151

N-[2-(Dimethylamino)ethyl]-4-[(8'-methyl-1',5'-dioxo-1',5'-dihydro-2'H-spiro[cyclobutane-1,3'-imidazo[1,5-a]pyridin]-6'-yl)amino]thieno[2,3-d]pyrimidine-6-carboxamide

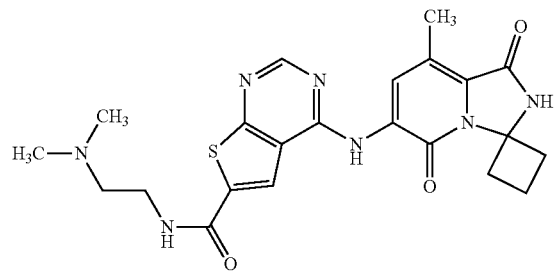 [SMILES: Cc1cc(Nc2ncnc3sc(C(=O)NCCN(C)C)cc23)c(=O)n2c1C(=O)NC21CCC1]

A mixture of 50 mg (126 μmol) 4-[(8'-methyl-1',5'-dioxo-1',5'-dihydro-2'H-spiro[cyclobutane-1,3'-imidazo[1,5-a] pyridin]-6'-yl)amino]thieno[2,3-d]pyrimidine-6-carboxylic acid (prepared according to example 150), 2.0 mL N,N-dimethylacetamide, 175 μL N-ethyl-N-isopropylpropan-2-amine, 61 μL N,N-dimethylethane-1,2-diamine and 225 μL 2,4,6-tripropyl-1,3,5,2,4,6-trioxatriphosphinane 2,4,6-trioxide solution (50% in N,N-dimethylformamide) was stirred at RT overnight. The mixture was concentrated, and the residue purified by flash chromatography (Biotage SNAP cartridge NH 11 g and silica 10 g, methanol:dichloromethane) to give 48 mg (78%) of the title compound.

LC-MS: m/z=468.3 [M+H]$^+$.

$^1$H-NMR (500 MHz, CHLOROFORM-d), δ [ppm]=2.01 (1H), 2.28-2.49 (9H), 2.54 (3H), 2.65 (2H), 3.61 (2H), 3.70 (2H), 6.85 (1H), 7.85 (1H), 8.74 (1H), 8.79 (2H)

Example 152

N-[2-(Dimethylamino)ethyl]-N-methyl-4-[(8'-methyl-1',5'-dioxo-1',5'-dihydro-2'H-spiro[cyclobutane-1,3'-imidazo[1,5-a]pyridin]-6'-yl)amino]thieno[2,3-d]pyrimidine-6-carboxamide

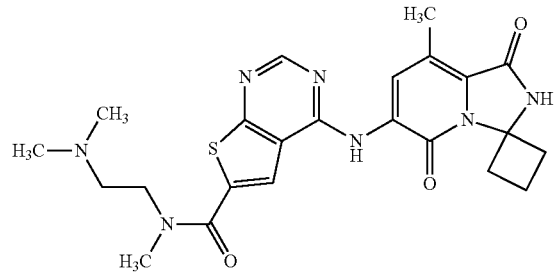 [SMILES: Cc1cc(Nc2ncnc3sc(C(=O)N(C)CCN(C)C)cc23)c(=O)n2c1C(=O)NC21CCC1]

A mixture of 50 mg (126 μmol) 4-[(8'-methyl-1',5'-dioxo-1',5'-dihydro-2'H-spiro[cyclobutane-1,3'-imidazo[1,5-a] pyridin]-6'-yl)amino]thieno[2,3-d]pyrimidine-6-carboxylic acid (prepared according to example 150), 2.0 mL N,N-dimethylacetamide, 175 μL N-ethyl-N-isopropylpropan-2-amine, 65 μL N,N,N-trimethylethylendiamin and 225 μL 2,4,6-tripropyl-1,3,5,2,4,6-trioxatriphosphinane 2,4,6-trioxide solution (50% in N,N-dimethylformamide) was stirred at RT overnight. The mixture was concentrated, and the residue purified by flash chromatography (Biotage SNAP cartridge NH 11 g and silica 10 g, methanol:dichloromethane) to give 50 mg (78%) of the title compound.

LC-MS: m/z=482.3 [M+H]+.

1H-NMR (500 MHz, CHLOROFORM-d), δ [ppm]=2.01 (1H), 2.18-2.48 (9H), 2.60 (5H), 3.26 (3H), 3.62-3.73 (4H), 6.74 (1H), 7.76 (1H), 8.76 (1H), 8.78 (1H), 8.86 (1H)

Example 153 tert-Butyl [1-({4-[(8'-methyl-1',5'-dioxo-1',5'-dihydro-2'H-spiro[cyclobutane-1,3'-imidazo[1,5-a]pyridin]-6'-yl)amino]thieno[2,3-d]pyrimidin-6-yl}carbonyl)azetidin-3-yl]carbamate

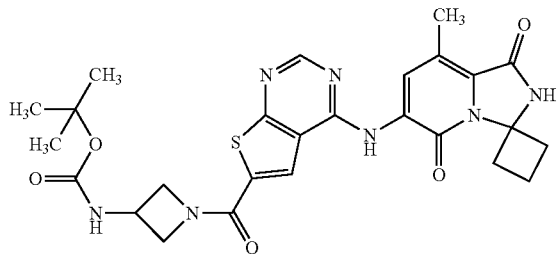 [SMILES: Cc1cc(Nc2ncnc3sc(C(=O)N4CC(NC(=O)OC(C)(C)C)C4)cc23)c(=O)n2c1C(=O)NC21CCC1]

A mixture of 100 mg (252 μmol) 4-[(8'-methyl-1',5'-dioxo-1',5'-dihydro-2'H-spiro[cyclobutane-1,3'-imidazo[1,5-a]pyridin]-6'-yl)amino]thieno[2,3-d]pyrimidine-6-carboxylic acid (prepared according to example 150), 4.0 mL N,N-dimethylacetamide, 351 μL N-ethyl-N-isopropylpropan-2-amine, 210 mg tert-butyl azetidin-3-ylcarbamate hydrochloride and 449 μL 2,4,6-tripropyl-1,3,5,2,4,6-trioxatriphosphinane 2,4,6-trioxide solution (50% in N,N-dimethylformamide) was stirred at RT overnight. Water was added, the precipitate washed with methanol and dried to give 78 mg (53%) of the title compound.

LC-MS: m/z=552.3 [M+H]+.

1H-NMR (400 MHz, DMSO-d6), δ [ppm]=1.41 (9H), 1.92 (1H), 2.16 (1H), 2.36 (2H), 2.45 (3H), 3.43 (2H), 4.00 (1H), 4.33 (1H), 4.44 (2H), 4.89 (1H), 7.72 (1H), 8.29 (1H), 8.49 (1H), 8.68 (1H), 9.63 (1H), 10.19 (1H)

Example 154

6'-({6-[(3-Aminoazetidin-1-yl)carbonyl]thieno[2,3-d]pyrimidin-4-yl}amino)-8'-methyl-2'H-spiro[cyclobutane-1,3'-imidazo[1,5-a]pyridine]-1',5'-dione

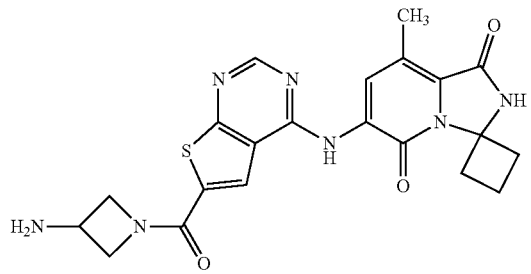 [SMILES: Cc1cc(Nc2ncnc3sc(C(=O)N4CC(N)C4)cc23)c(=O)n2c1C(=O)NC21CCC1]

A mixture of 65 mg (118 μmol) tert-butyl [1-({4-[(8'-methyl-1',5'-dioxo-1',5'-dihydro-2'H-spiro[cyclobutane-1,3'-imidazo[1,5-a]pyridin]-6'-yl)amino]thieno[2,3-d]pyrimidin-6-yl}carbonyl)azetidin-3-yl]carbamate (prepared according to example 153) and 182 μL trifluoroacetic acid in 4.6 mL dichloromethane was stirred at RT overnight. The mixture was poured into aqueous ammonia (25%) and extracted with dichloromethane/methanol. The organic layer was washed with water, dried over sodium sulfate. After filtration and concentration the residue was digested with ethanol and dried to give 37 mg (66%) of the title compound.

LC-MS: m/z=452.3 [M+H]+.

1H-NMR (400 MHz, DMSO-d6), δ [ppm]=1.93 (1H), 2.15 (1H), 2.37 (2H), 2.45 (3H), 3.42 (2H), 3.94 (1H), 4.04 (1H), 4.32 (1H), 4.42 (1H), 4.88 (1H), 6.20 (2H), 8.30 (1H), 8.51 (1H), 8.69 (1H), 9.61 (1H), 10.21 (1H)

Example 155

1-({4-[(8'-Methyl-1',5'-dioxo-1',5'-dihydro-2'H-spiro[cyclobutane-1,3'-imidazo[1,5-a]pyridin]-6'-yl)amino]thieno[2,3-d]pyrimidin-6-yl}carbonyl)azetidine-3-carbonitrile

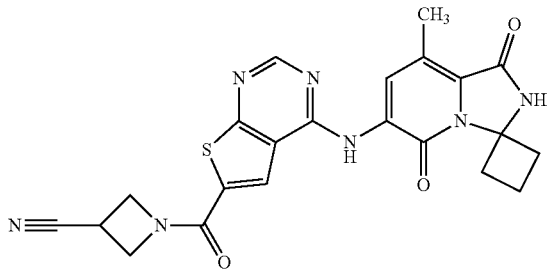 [SMILES: Cc1cc(Nc2ncnc3sc(C(=O)N4CC(C#N)C4)cc23)c(=O)n2c1C(=O)NC21CCC1]

A mixture of 50 mg (126 μmol) 4-[(8'-methyl-1',5'-dioxo-1',5'-dihydro-2'H-spiro[cyclobutane-1,3'-imidazo[1,5-a]pyridin]-6'-yl)amino]thieno[2,3-d]pyrimidine-6-carboxylic acid (prepared according to example 150), 2.0 mL N,N-dimethylacetamide, 175 μL N-ethyl-N-isopropylpropan-2-amine, 61 μL azetidine-3-carbonitrile hydrochloride and 225 μL 2,4,6-tripropyl-1,3,5,2,4,6-trioxatriphosphinane 2,4,6-trioxide solution (50% in N,N-dimethylformamide) was stirred at RT overnight. The mixture was concentrated, water was added and the residue digested with ethanol and diethyl ether to give 49 mg (80%) of the title compound.

LC-MS: m/z=462.3 [M+H]+.

1H-NMR (400 MHz, DMSO-d6), δ [ppm]=1.93 (1H), 2.16 (1H), 2.37 (2H), 2.45 (3H), 3.43 (2H), 3.97 (1H), 4.27 (1H), 4.41 (1H), 4.92 (2H), 8.35 (1H), 8.52 (1H), 8.70 (1H), 9.56 (1H), 10.20 (1H)

Example 156

6'-[(6-{[(3R)-3-(Dimethylamino)pyrrolidin-1-yl]carbonyl}thieno[2,3-d]pyrimidin-4-yl)amino]-8'-methyl-2'H-spiro[cyclobutane-1,3'-imidazo[1,5-a]pyridine]-1',5'-dione

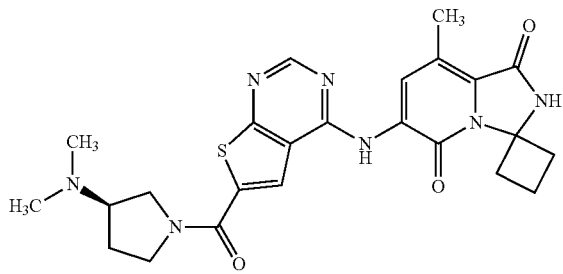 [SMILES: Cc1cc(Nc2ncnc3sc(C(=O)N4CC[C@@H](N(C)C)C4)cc23)c(=O)n2c1C(=O)NC21CCC1]

A mixture of 50 mg (126 μmol) 4-[(8'-methyl-1',5'-dioxo-1',5'-dihydro-2'H-spiro[cyclobutane-1,3'-imidazo[1,5-a]pyridin]-6'-yl)amino]thieno[2,3-d]pyrimidine-6-carboxylic acid (prepared according to example 150), 2.0 mL N,N-dimethylacetamide, 175 μL N-ethyl-N-isopropylpropan-2-amine, 57.5 mg (3R)—N,N-dimethylpyrrolidin-3-amine and 225 μL 2,4,6-tripropyl-1,3,5,2,4,6-trioxatriphosphinane 2,4,6-trioxide solution (50% in N,N-dimethylformamide) was stirred at RT overnight. The mixture was concentrated, and the residue purified by flash chromatography (Biotage SNAP cartridge NH 11 g and silica 10 g, methanol:dichloromethane) to give 49 mg (75%) of the title compound.

LC-MS: m/z=494.3 [M+H]$^+$.

$^1$H-NMR (400 MHz, DMSO-d6), δ [ppm]=1.72-1.99 (2H), 2.05-2.22 (2H), 2.22+2.23 (6H), 2.37 (2H), 2.45 (3H), 2.76+2.84 (1H), 3.22-3.55 (3H), 3.65-4.13 (3H), 8.45 (1H), 8.50+8.53 (1H), 8.68+8.69 (1H), 9.54+9.55 (1H), 10.19 (1H)

Example 157

6'-[(6-{[4-(Dimethylamino)piperidin-1-yl]carbonyl}thieno[2,3-d]pyrimidin-4-yl)amino]-8'-methyl-2'H-spiro[cyclobutane-1,3'-imidazo[1,5-a]pyridine]-1',5'-dione

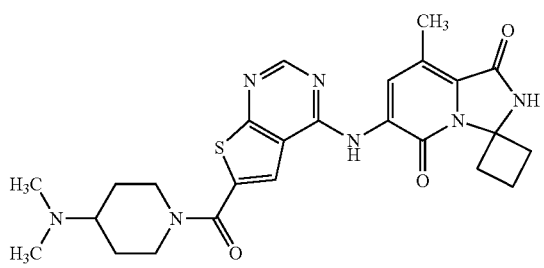 [SMILES: Cc1cc(Nc2ncnc3sc(C(=O)N4CCC(N(C)C)CC4)cc23)c(=O)n2c1C(=O)NC21CCC1]

A mixture of 50 mg (126 μmol) 4-[(8'-methyl-1',5'-dioxo-1',5'-dihydro-2'H-spiro[cyclobutane-1,3'-imidazo[1,5-a]pyridin]-6'-yl)amino]thieno[2,3-d]pyrimidine-6-carboxylic acid (prepared according to example 150), 2.0 mL N,N-dimethylacetamide, 175 μL N-ethyl-N-isopropylpropan-2-amine, 64.5 mg N,N-dimethylpiperidin-4-amine and 225 μL 2,4,6-tripropyl-1,3,5,2,4,6-trioxatriphosphinane 2,4,6-triox-ide solution (50% in N,N-dimethylformamide) was stirred at RT overnight. The mixture was concentrated, and the residue purified by flash chromatography (Biotage SNAP cartridge NH 11 g and silica 10 g, methanol:dichloromethane) to give 50 mg (74%) of the title compound.

LC-MS: m/z=508.3 [M+H]$^+$.

$^1$H-NMR (400 MHz, DMSO-d6), δ [ppm]=1.45 (2H), 1.81-2.03 (3H), 2.16 (1H), 2.23 (6H), 2.37 (2H), 2.45 (3H), 2.53 (1H*), 3.08 (2H), 3.42 (2H), 4.33 (2H), 8.22 (1H), 8.57 (1H), 8.70 (1H), 9.42 (1H), 10.18 (1H)

*: at least partially hidden by solvent peak.

Example 158

8'-Methyl-6'-({6-[(1R,4R)-2-oxa-5-azabicyclo[2.2.1]hept-5-ylcarbonyl]thieno[2,3-d]pyrimidin-4-yl}amino)-2'H-spiro[cyclobutane-1,3'-imidazo[1,5-a]pyridine]-1',5'-dione

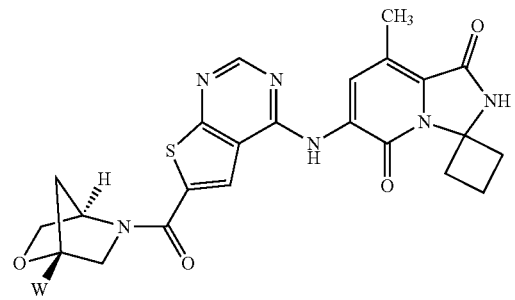

A mixture of 40 mg (101 μmol) 4-[(8'-methyl-1',5'-dioxo-1',5'-dihydro-2'H-spiro[cyclobutane-1,3'-imidazo[1,5-a]pyridin]-6'-yl)amino]thieno[2,3-d]pyrimidine-6-carboxylic acid (prepared according to example 150), 1.6 mL N,N-dimethylacetamide, 70 μL N-ethyl-N-isopropylpropan-2-amine, 54.6 mg (1R,4R)-2-oxa-5-azabicyclo[2.2.1]heptane hydrochloride and 180 μL 2,4,6-tripropyl-1,3,5,2,4,6-trioxatriphosphinane 2,4,6-trioxide solution (50% in N,N-dimethylformamide) was stirred at RT overnight. The mixture was concentrated, water was added and the residue digested with ethanol and diethyl ether to give 29 mg (54%) of the title compound.

LC-MS: m/z=479.3 [M+H]$^+$.

$^1$H-NMR (400 MHz, DMSO-d6), δ [ppm]=1.85-2.03 (3H), 2.16 (1H), 2.37 (2H), 2.45 (3H), 3.41 (2H), 3.52-4.03 (4H), 4.71+4.80 (1H), 4.95+5.25 (1H), 8.33+8.45 (1H), 8.54+8.57 (1H), 8.70 (1H), 9.54 (1H), 10.19 (1H)

Example 159

8'-Methyl-6'-(9H-purin-6-ylamino)-2'H-spiro[cyclobutane-1,3'-imidazo[1,5-a]pyridine]-1',5'-dione

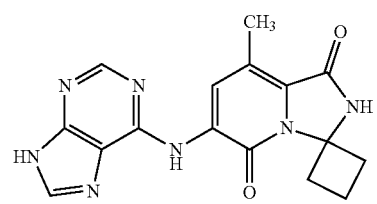 [SMILES: Cc1cc(Nc2ncnc3[nH]cnc23)c(=O)n2c1C(=O)NC21CCC1]

To a solution of 250 mg (883 µmol) 6'-bromo-8'-methyl-2'H-spiro[cyclobutane-1,3'-imidazo[1,5-a]pyridine]-1',5'-dione (prepared according to example 146a) and 167 mg (971 µmol) 9H-purin-6-amine hydrochloride (CAS-No: 2922-28-3) in 20 mL 1,4-dioxane was added 863 mg cesium carbonate and the mixture was degassed and purged with argon several times. 54.7 mg 4,5-bis(diphenylphosphino)-9,9-dimethylxanthene, 45 mg 2-(dicyclohexyl-phosphino)-2',4',6'-triisopropylbiphenyl, 21.2 mg palladium(II)acetate and 86.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, methanol:dichloromethane) to give 19 mg (6%) of the title compound.

LC-MS: m/z=338.3 [M+H]⁺.

¹H-NMR (400 MHz, DMSO-d6), δ [ppm]=1.93 (1H), 2.16 (1H), 2.34 (2H), 2.47 (3H), 3.45 (2H), 8.40 (1H), 8.59 (1H), 8.71 (1H), 8.90 (1H), 10.12 (1H), 13.46 (1H)

Example 160

8'-Methyl-6'-(1H-pyrazolo[3,4-d]pyrimidin-4-ylamino)-2'H-spiro[cyclobutane-1,3'-imidazo[1,5-a]pyridine]-1',5'-dione

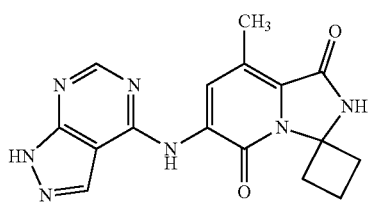 [SMILES: Cc1cc(Nc2ncnc3[nH]ncc23)c(=O)n2c1C(=O)NC21CCC1]

To a solution of 250 mg (883 µmol) 6'-bromo-8'-methyl-2'H-spiro[cyclobutane-1,3'-imidazo[1,5-a]pyridine]-1',5'-dione (prepared according to example 146a) and 131 mg (971 µmol) 1H-pyrazolo[3,4-d]pyrimidin-4-amine (CAS-No: 2380-63-4) in 20 mL 1,4-dioxane was added 863 mg cesium carbonate and the mixture was degassed and purged with argon several times. 54.7 mg 4,5-bis(diphenylphosphino)-9,9-dimethylxanthene, 45 mg 2-(dicyclohexyl-phosphino)-2',4',6'-triisopropylbiphenyl, 21.2 mg palladium(II)acetate and 86.5 mg tris(dibenzylideneacetone)dipalladium(0) were added and the mixture was stirred at 100° C. for 2 hours. The mixture was concentrated and the residue purified by flash chromatography (Biotage SNAP Ultra cartridge silica 25 g, methanol:dichloromethane) to give 70 mg (22%) of the title compound.

LC-MS: m/z=338.3 [M+H]⁺.

¹H-NMR (400 MHz, DMSO-d6), δ [ppm]=1.92 (1H), 2.17 (1H), 2.37 (2H), 2.45 (3H), 3.42 (2H), 8.55 (1H), 8.60 (1H), 8.70 (1H), 9.49 (1H), 10.15 (1H), 13.78 (1H)

Example 161

8'-Methyl-6'-([1,3]thiazolo[5,4-d]pyrimidin-7-ylamino)-2'H-spiro[cyclobutane-1,3'-imidazo[1,5-a]pyridine]-1',5'-dione

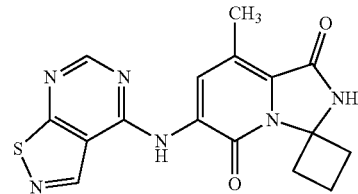 [SMILES: Cc1cc(Nc2ncnc3sncc23)c(=O)n2c1C(=O)NC21CCC1]

To a solution of 100 mg (353 µmol) 6'-bromo-8'-methyl-2'H-spiro[cyclobutane-1,3'-imidazo[1,5-a]pyridine]-1',5'-dione (prepared according to example 146a) and 59.1 mg (389 µmol) [1,3]thiazolo[5,4-d]pyrimidin-7-amine (CAS-No: 2846-90-4) in 13 mL 1,4-dioxane was added 345 mg cesium carbonate and the mixture was degassed and purged with argon several times. 21.9 mg 4,5-bis(diphenylphosphino)-9,9-dimethylxanthene, 18 mg 2-(dicyclohexyl-phosphino)-2',4',6'-triisopropylbiphenyl, 8.5 mg palladium(II)acetate and 34.6 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, ethanol:dichloromethane) to give 70 mg (22%) of the title compound.

LC-MS: m/z=355.2 [M+H]⁺.

¹H-NMR (400 MHz, DMSO-d6), δ [ppm]=1.93 (1H), 2.16 (1H), 2.34 (2H), 2.48 (3H), 3.43 (2H), 8.69 (1H), 8.83 (1H), 9.39 (1H), 9.51 (1H), 10.18 (1H)

Example 162 tert-Butyl 4-[(8'-methyl-1',5'-dioxo-1',5'-dihydro-2'H-spiro[cyclobutane-1,3'-imidazo[1,5-a]pyridin]-6'-yl)amino]-5,7-dihydro-6H-pyrrolo[3,4-d]pyrimidine-6-carboxylate To a solution of 200 mg (706 µmol) 6'-bromo-8'-methyl-2'H-spiro[cyclobutane-1,3'-imidazo[1,5-a]pyridine]-1',5'-dione (prepared according to example 146a) and 184 mg (777 µmol) tert-butyl 4-amino-5,7-dihydro-6H-pyrrolo[3,4-d]pyrimidine-6-carboxylate (CAS-No: 1227461-25-7) in 20 mL 1,4-dioxane was added 690 mg cesium carbonate and the mixture was degassed and purged with argon several times. 43.7 mg 4,5-bis(diphenylphosphino)-9,9-dimethylxanthene, 36 mg 2-(dicyclohexyl-phosphino)-2',4',6'-triisopropylbi-

Example 163 tert-Butyl 4-[(3,3,8-trimethyl-1,5-dioxo-1,2,3,5-tetrahydroimidazo[1,5-a]pyridin-6-yl)amino]-5,7-dihydro-6H-pyrrolo[3,4-d]pyrimidine-6-carboxylate

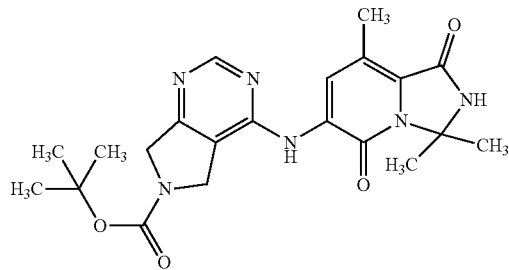 [SMILES: Cc1cc(Nc2ncnc3c2CN(C(=O)OC(C)(C)C)C3)c(=O)n2c1C(=O)NC2(C)C]

To a solution of 200 mg (738 μmol) 6-bromo-3,3,8-trimethyl-2,3-dihydroimidazo[1,5-a]pyridine-1,5-dione (prepared according to PCT Int. Appl. (2015), WO 2015200481) and 191 mg (811 μmol) tert-butyl 4-amino-5,7-dihydro-6H-pyrrolo[3,4-d]pyrimidine-6-carboxylate (CAS-No: 1227461-25-7) in 20 mL 1,4-dioxane was added 721 mg cesium carbonate and the mixture was degassed and purged with argon several times. 45.7 mg 4,5-bis(diphenylphosphino)-9,9-dimethylxanthene, 37.6 mg 2-(dicyclohexyl-phosphino)-2',4',6'-triisopropylbiphenyl, 17.7 mg palladium(II)acetate and 72.3 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, methanol:dichloromethane) to give 194 mg (59%) of the title compound.

LC-MS: m/z=427.4 [M+H]$^+$.

$^1$H-NMR (400 MHz, DMSO-d6), δ [ppm]=1.47+1.49 (9H), 1.79 (6H), 2.46 (3H), 4.50+4.53 (2H), 4.67+4.71 (2H), 8.27+8.30 (1H), 8.52 (1H), 8.74 (1H), 9.63 (1H)

phenyl, 17 mg palladium(II)acetate and 69.2 mg tris(dibenzylideneacetone)dipalladium(0) were added and the mixture was stirred at 100° C. for 2 hours. Dichloromethane and methanol were added, the precipitate filtered off and the filtrate concentrated. The mixture was concentrated and the residue purified by flash chromatography (Biotage SNAP cartridge silica 25 g, methanol:dichloromethane) to give 70 mg (22%) of the title compound.

LC-MS: m/z=439.4 [M+H]$^+$.

$^1$H-NMR (400 MHz, DMSO-d6), δ [ppm]=1.47+1.49 (9H), 1.92 (1H), 2.14 (1H), 2.34 (2H), 2.44 (3H), 3.39 (2H), 4.51+4.54 (2H), 4.69+4.73 (2H), 8.36 (1H), 8.52 (1H), 8.74 (1H), 10.14 (1H)

Example 164

3,3,8-Trimethyl-6-([1,3]thiazolo[5,4-d]pyrimidin-7-ylamino)-2,3-dihydroimidazo[1,5-a]pyridine-1,5-dione

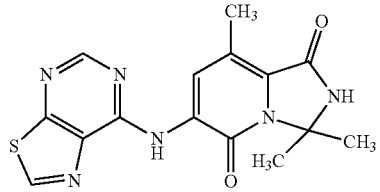 [SMILES: Cc1cc(Nc2ncnc3scnc23)c(=O)n2c1C(=O)NC2(C)C]

To a solution of 100 mg (369 μmol) 6-bromo-3,3,8-trimethyl-2,3-dihydroimidazo[1,5-a]pyridine-1,5-dione (prepared according to PCT Int. Appl. (2015), WO 2015200481) and 61.7 mg (406 μmol) [1,3]thiazolo[5,4-d]pyrimidin-7-amine (CAS-No: 2846-90-4) in 14 mL 1,4-dioxane was added 361 mg cesium carbonate and the mixture was degassed and purged with argon several times. 22.8 mg 4,5-bis(diphenylphosphino)-9,9-dimethylxanthene, 18.8 mg 2-(dicyclohexyl-phosphino)-2',4',6'-triisopropylbiphenyl, 8.9 mg palladium(II)acetate and 36.1 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, ethanol:dichloromethane) to give 47 mg (35%) of the title compound.

LC-MS: m/z=343.2 [M+H]$^+$.

$^1$H-NMR (400 MHz, DMSO-d6), δ [ppm]=1.81 (6H), 2.52 (3H*), 8.71 (1H), 8.83 (1H), 9.36 (1H), 9.50 (1H), 9.68 (1H)

*: at least partially hidden by solvent peak.

Example 165

6-(6,7-Dihydro-5H-pyrrolo[3,4-d]pyrimidin-4-ylamino)-3,3,8-trimethyl-2,3-dihydroimidazo[1,5-a]pyridine-1,5-dione

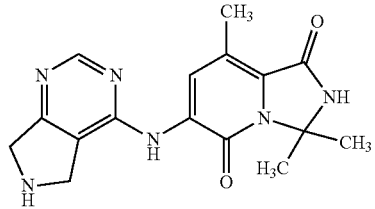 [SMILES: Cc1cc(Nc2ncnc3c2CNC3)c(=O)n2c1C(=O)NC2(C)C]

A mixture of 100 mg (369 μmol) tert-butyl 4-[(3,3,8-trimethyl-1,5-dioxo-1,2,3,5-tetrahydroimidazo[1,5-a]pyridin-6-yl)aminol-5,7-dihydro-6H-pyrrolo[3,4-d]pyrimidine-6-carboxylate (prepared according to example 163) and 650 μL trifluoroacetic acid in 16.5 mL dichloromethane was stirred at RT overnight. The mixture was poured into aqueous ammonia (25%) and extracted with dichloromethane/methanol. The organic layer was washed with water, dried over sodium sulfate. After filtration and concentration the residue was digested with ethanol and dried to give 42 mg (29%) of the title compound.

LC-MS: m/z=327.2 [M+H]$^+$.

¹H-NMR (400 MHz, DMSO-d6), δ [ppm]=1.79 (6H), 2.46 (3H), 4.32 (2H), 4.51 (2H), 8.17 (1H), 8.48 (1H), 8.51 (1H), 8.75 (1H), 9.65 (1H)

Example 166

6-[(6-Chloroquinazolin-4-yl)amino]-3,3,8-trimethyl-2,3-dihydroimidazo[1,5-a]pyridine-1,5-dione

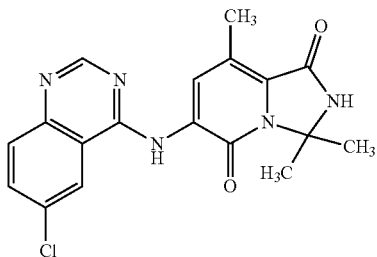 [SMILES: Cc1cc(Nc2ncnc3ccc(Cl)cc23)c(=O)n2c1C(=O)NC2(C)C]

To a solution of 100 mg (369 µmol) 6-bromo-3,3,8-trimethyl-2,3-dihydroimidazo[1,5-a]pyridine-1,5-dione (prepared according to PCT Int. Appl. (2015), WO 2015200481) and 72.9 mg (406 µmol) 6-chloroquinazolin-4-amine (CAS-No: 19808-35-6) in 14 mL 1,4-dioxane was added 361 mg cesium carbonate and the mixture was degassed and purged with argon several times. 22.8 mg 4,5-bis(diphenylphosphino)-9,9-dimethylxanthene, 18.8 mg 2-(dicyclohexyl-phosphino)-2',4',6'-triisopropylbiphenyl, 8.9 mg palladium(II)acetate and 36.1 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, ethanol:dichloromethane) to give 74 mg (52%) of the title compound.

LC-MS: m/z=370.2 [M+H]⁺.

¹H-NMR (400 MHz, DMSO-d6), δ [ppm]=1.82 (6H), 2.52 (3H*), 7.88 (1H), 7.94 (1H), 8.44 (1H), 8.59 (1H), 8.80 (1H), 9.46 (1H), 9.70 (1H)

*: at least partially hidden by solvent peak.

Example 167

6'-[(6-Chloroquinazolin-4-yl)amino]-8'-methyl-2'H-spiro[cyclobutane-1,3'-imidazo[1,5-a]pyridine]-1',5'-dione

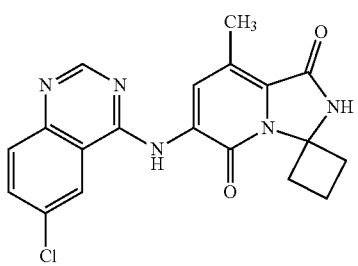 [SMILES: Cc1cc(Nc2ncnc3ccc(Cl)cc23)c(=O)n2c1C(=O)NC21CCC1]

To a solution of 100 mg (353 µmol) 6'-bromo-8'-methyl-2'H-spiro[cyclobutane-1,3'-imidazo[1,5-a]pyridine]-1',5'-dione (prepared according to example 146a) and 69.8 mg (389 µmol) 6-chloroquinazolin-4-amine (CAS-No: 19808-35-6) in 13 mL 1,4-dioxane was added 345 mg cesium carbonate and the mixture was degassed and purged with argon several times. 21.9 mg 4,5-bis(diphenylphosphino)-9,9-dimethylxanthene, 18 mg 2-(dicyclohexyl-phosphino)-2',4',6'-triisopropylbiphenyl, 8.5 mg palladium(II)acetate and 34.6 mg tris(dibenzylideneacetone)dipalladium(0) were added and the mixture was stirred at 100° C. for 2 hours. Dichloromethane and methanol were added, the precipitate filtered off and the filtrate concentrated. The mixture was concentrated and the residue purified by flash chromatography (Biotage SNAP cartridge silica 25 g, ethanol:dichloromethane) to give 67 mg (47%) of the title compound.

LC-MS: m/z=382.2 [M+H]⁺.

¹H-NMR (400 MHz, DMSO-d6), δ [ppm]=1.94 (1H), 2.16 (1H), 2.37 (2H), 2.47 (3H), 3.44 (2H), 7.88 (1H), 7.95 (1H), 8.48 (1H), 8.58 (1H), 8.80 (1H), 9.52 (1H), 10.21 (1H)

Example 168

6'-(6,7-Dihydro-5H-pyrrolo[3,4-d]pyrimidin-4-ylamino)-8'-methyl-2'H-spiro[cyclobutane-1,3'-imidazo[1,5-a]pyridine]-1',5'-dione

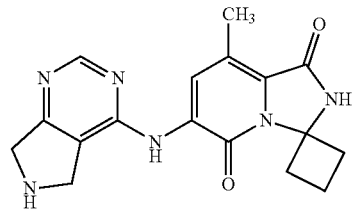 [SMILES: Cc1cc(Nc2ncnc3c2CNC3)c(=O)n2c1C(=O)NC21CCC1]

A mixture of 200 mg (456 µmol) tert-butyl 4-[(8'-methyl-1',5'-dioxo-1',5'-dihydro-2'H-spiro[cyclobutane-1,3'-imidazo[1,5-a]pyridin]-6'-yl)amino]-5,7-dihydro-6H-pyrrolo[3,4-d]pyrimidine-6-carboxylate (prepared according to example 162) and 703 µL trifluoroacetic acid in 18 mL dichloromethane was stirred at RT overnight. The mixture was poured into aqueous ammonia (25%) and extracted with dichloromethane/methanol. The organic layer was washed with water, dried over sodium sulfate. After filtration and concentration the residue was digested with ethanol and dried to give 120 mg (74) of the title compound.

LC-MS: m/z=339.3 [M+H]⁺.

¹H-NMR (400 MHz, DMSO-d6), δ [ppm]=1.91 (1H), 2.14 (1H), 2.34 (2H), 2.44 (3H), 3.17-3.37 (2H), 4.19 (2H), 4.37 (2H), 6.45 (1H), 8.34 (1H), 8.53 (1H), 8.72 (1H), 10.13 (1H)

Example 169

5-Methyl-4-[(8'-methyl-1',5'-dihydro-2'H-spiro[cyclobutane-1,3'-imidazo[1,5-a]pyridin]-6'-yl)amino]thieno[2,3-d]pyrimidine-6-carboxylic acid

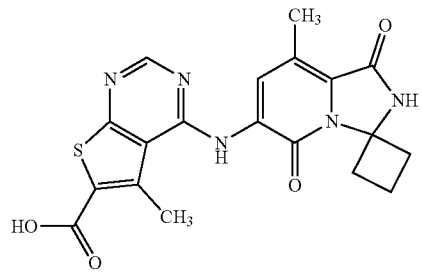 [SMILES: Cc1cc(Nc2ncnc3sc(C(=O)O)c(C)c23)c(=O)n2c1C(=O)NC21CCC1]

A mixture of 190 mg (432 μmol) ethyl 5-methyl-4-[(8'-methyl-1',5'-dioxo-1',5'-dihydro-2'H-spiro[cyclobutane-1,3'-imidazo[1,5-a]pyridin]-6'-yl)amino]thieno[2,3-d]pyrimidine-6-carboxylate (prepared according to intermediate example 169a) in 6.7 mL tetrahydrofuran, 6.7 mL ethanol and 2.6 mL lithium hydroxide solution (1M in water) was stirred at RT overnight. 2.6 mL lithium hydroxide solution (1M in water) were added and stirring continued for 24 hours. Water was added and the mixture was acidified with hydrochloric acid. The precipitate was filtered off, washed with water and dried to give 155 mg (83%) of the title compound.

LC-MS: m/z=412.3 [M+H]$^+$.

$^1$H-NMR (400 MHz, DMSO-d6), δ [ppm]=1.95 (1H), 2.13 (1H), 2.32 (2H), 2.46 (3H), 3.13 (3H), 3.47 (2H), 8.74 (1H), 8.75 (1H), 9.33 (1H), 10.21 (1H), 13.80 (1H)

Example 169a

Ethyl 5-methyl-4-[(8'-methyl-1',5'-dioxo-1',5'-dihydro-2'H-spiro[cyclobutane-1,3'-imidazo[1,5-a]pyridin]-6'-yl)amino]thieno[2,3-d]pyrimidine-6-carboxylate

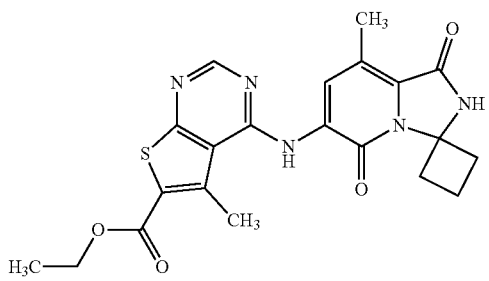 [SMILES: CCOC(=O)c1sc2ncnc(Nc3cc(C)c4n(c3=O)C3(CCC3)NC4=O)c2c1C]

To a solution of 200 mg (706 μmol) 6'-bromo-8'-methyl-2'H-spiro[cyclobutane-1,3'-imidazo[1,5-a]pyridine]-1',5'-dione (prepared according to example 146a) and 184 mg (777 μmol) ethyl 4-amino-5-methylthieno[2,3-d]pyrimidine-6-carboxylate (CAS-No: 60598-74-5) in 19 mL 1,4-dioxane was added 690 mg cesium carbonate and the mixture was degassed and purged with argon several times. 43.7 mg 4,5-bis(diphenylphosphino)-9,9-dimethylxanthene, 36 mg 2-(dicyclohexyl-phosphino)-2',4',6'-triisopropylbiphenyl, 17 mg palladium(II)acetate and 69.2 mg tris(dibenzylideneacetone)dipalladium(0) were added and the mixture was stirred at 100° C. for 2 hours. The mixture was concentrated and the residue purified by flash chromatography (Biotage SNAP cartridge silica 25 g, ethanol:dichloromethane) to give 67 mg (47%) of the title compound.

LC-MS: m/z=440.3 [M+H]$^+$.

Example 170

8'-methyl-6'-[(5-methylquinazolin-4-yl)amino]-2'H-spiro[cyclobutane-1,3'-imidazo[1,5-a]pyridine]-1',5'-dione

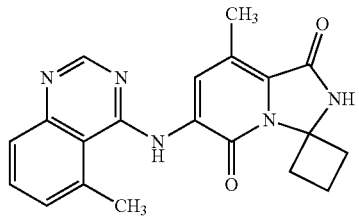

To a solution of 6'-bromo-8'-methyl-2'H-spiro[cyclobutane-1,3'-imidazo[1,5-a]pyridine]-1',5'-dione (prepared according to example 146a, 100 mg, 353 μmol) and 5-methylquinazolin-4-amine (commercial, 61.8 mg, 389 μmol) in 1,4-dioxane (7.0 mL) was added cesium carbonate (345 mg, 1.06 mmol) and the mixture was degassed and purged with argon several times. 4,5-Bis(diphenylphosphino)-9,9-dimethylxanthene (21.9 mg, 37.8 μmol), 2-(dicyclohexyl-phosphino)-2',4',6'-triisopropylbiphenyl (18.0 mg, 37.8 μmol), palladium(II)acetate (8.48 mg, 37.8 μmol) and tris(dibenzylideneacetone)dipalladium(0) (34.6 mg, 37.8 μmol) were added and the mixture was stirred at 100° C. for 2 hours. The mixture was concentrated and the residue purified by flash chromatography (Biotage SNAP cartridge silica 25 g, ethanol:dichloromethane). The isolated product was taken up in methanol and stirred at RT. The solid was filtered off under vacuo and dried to give 45.0 mg (33% yield) of the title compound.

LC-MS: m/z=362.6 [M+H]$^+$.

$^1$H-NMR (400 MHz, DMSO-d6) δ [ppm]=1.941 (0.47), 1.964 (0.53), 2.126 (0.50), 2.139 (0.48), 2.152 (0.47), 2.280 (0.54), 2.291 (0.57), 2.314 (1.16), 2.326 (1.53), 2.332 (1.09), 2.336 (0.86), 2.349 (0.44), 2.482 (16.00), 2.518 (3.27), 2.522 (2.15), 2.665 (0.62), 2.669 (0.85), 2.673 (0.62), 3.136 (6.93), 3.159 (0.51), 3.172 (0.41), 3.442 (0.51), 3.468 (1.07), 3.475 (0.82), 3.495 (0.98), 3.521 (0.45), 7.482 (1.10), 7.499 (1.24), 7.695 (0.82), 7.713 (1.81), 7.738 (1.92), 7.755 (1.59), 7.775 (0.74), 8.768 (4.87), 8.903 (4.46), 9.756 (2.06), 10.193 (2.19).

Example 171

6'-[(6-fluoroquinazolin-4-yl)amino]-8'-methyl-2'H-spiro[cyclobutane-1,3'-imidazo[1,5-a]pyridine]-1',5'-dione

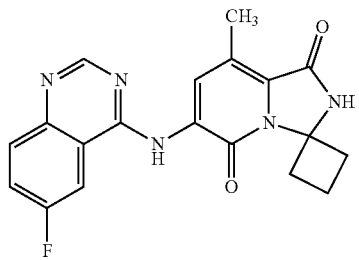

To a solution of 6'-bromo-8'-methyl-2'H-spiro[cyclobutane-1,3'-imidazo[1,5-a]pyridine]-1',5'-dione (prepared according to example 146a, 100 mg, 353 µmol) and 6-fluoroquinazolin-4-amine (CAS 1190320-08-1, 63.4 mg, 389 µmol) in 1,4-dioxane (7.0 mL) was added cesium carbonate (345 mg, 1.06 mmol) and the mixture was degassed and purged with argon several times. 4,5-Bis(diphenylphosphino)-9,9-dimethylxanthene (21.9 mg, 37.8 µmol), 2-(dicyclohexyl-phosphino)-2',4',6'-triisopropylbiphenyl (18.0 mg, 37.8 µmol), palladium(II)acetate (8.48 mg, 37.8 µmol) and tris(dibenzylideneacetone)dipalladium(0) (34.6 mg, 37.8 µmol) were added and the mixture was stirred at 100° C. for 2 hours. The mixture was concentrated and the residue purified by flash chromatography (Biotage SNAP cartridge silica 25 g, ethanol:dichloromethane). The isolated product was taken up in methanol and stirred at RT. The solid was filtered off under vacuo and dried to give 66.0 mg (49% yield) of the title compound.

LC-MS: m/z=366.5 [M+H]$^+$.

$^1$H-NMR (400 MHz, DMSO-d6) δ [ppm]=1.929 (0.53), 1.951 (0.59), 2.146 (0.57), 2.159 (0.57), 2.172 (0.53), 2.327 (1.55), 2.331 (1.49), 2.342 (0.77), 2.364 (1.28), 2.377 (1.06), 2.388 (0.80), 2.401 (0.69), 2.470 (16.00), 2.665 (0.86), 2.669 (1.12), 2.673 (0.84), 3.404 (0.65), 3.429 (1.24), 3.456 (1.12), 3.482 (0.55), 7.825 (0.49), 7.832 (0.57), 7.848 (1.06), 7.855 (1.16), 7.869 (0.77), 7.875 (0.82), 7.935 (1.35), 7.948 (1.39), 7.958 (1.00), 7.972 (0.86), 8.179 (1.08), 8.186 (1.14), 8.203 (1.12), 8.210 (1.06), 8.610 (4.59), 8.789 (4.79), 9.399 (2.65), 10.207 (2.41).

Example 172

8'-methyl-6'-[(quinazolin-4-yl)amino]-2'H-spiro[cyclobutane-1,3'-imidazo[1,5-a]pyridine]-1',5'-dione

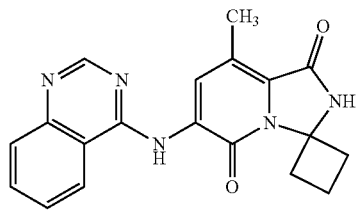 [SMILES: Cc1cc(Nc2ncnc3ccccc23)c(=O)n2c1C(=O)NC21CCC1]

To a solution of 6'-bromo-8'-methyl-2'H-spiro[cyclobutane-1,3'-imidazo[1,5-a]pyridine]-1',5'-dione (prepared according to example 146a, 100 mg, 353 µmol) and quinazolin-4-amine (CAS 15018-66-3, 56.4 mg, 389 µmol) in 1,4-dioxane (7.0 mL) was added cesium carbonate (345 mg, 1.06 mmol) and the mixture was degassed and purged with argon several times. 4,5-Bis(diphenylphosphino)-9,9-dimethylxanthene (21.9 mg, 37.8 µmol), 2-(dicyclohexyl-phosphino)-2',4',6'-triisopropylbiphenyl (18.0 mg, 37.8 µmol), palladium(II)acetate (8.48 mg, 37.8 µmol) and tris(dibenzylideneacetone)dipalladium(0) (34.6 mg, 37.8 µmol) were added and the mixture was stirred at 100° C. for 2 hours. The mixture was concentrated and the residue purified by flash chromatography (Biotage SNAP cartridge silica 25 g, ethanol:dichloromethane). The isolated product was taken up in methanol and stirred at RT. The solid was filtered off under vacuo and dried to give 45.0 mg (35% yield) of the title compound.

LC-MS: m/z=348.5 [M+H]$^+$.

$^1$H-NMR (400 MHz, DMSO-d6) δ [ppm]=1.931 (0.45), 1.955 (0.53), 2.153 (0.52), 2.166 (0.52), 2.179 (0.51), 2.322 (0.63), 2.327 (1.01), 2.332 (1.09), 2.336 (0.68), 2.344 (0.60), 2.355 (0.80), 2.365 (1.05), 2.378 (0.83), 2.389 (0.61), 2.402 (0.47), 2.480 (16.00), 2.518 (2.92), 2.523 (1.93), 2.664 (0.53), 2.669 (0.75), 2.673 (0.55), 3.159 (1.10), 3.171 (1.00), 3.413 (0.56), 3.439 (1.08), 3.447 (0.83), 3.458 (0.83), 3.466 (0.99), 3.472 (0.65), 3.492 (0.49), 5.758 (0.65), 7.699 (0.75), 7.703 (0.79), 7.716 (0.97), 7.720 (1.56), 7.723 (0.93), 7.737 (0.88), 7.740 (0.91), 7.872 (0.88), 7.875 (1.02), 7.893 (2.13), 7.896 (1.94), 7.921 (1.41), 7.924 (1.46), 7.938 (1.24), 7.941 (1.44), 7.945 (0.75), 7.959 (0.61), 7.962 (0.59), 8.279 (1.48), 8.300 (1.38), 8.713 (5.31), 8.829 (6.02), 9.440 (2.56), 10.193 (2.32).

Example 173

8-methyl-6-[([1,3]thiazolo[5,4-d]pyrimidin-7-yl)amino]-2H-spiro[imidazo[1,5-a]pyridine-3,3'-thietane]-1,5-dione

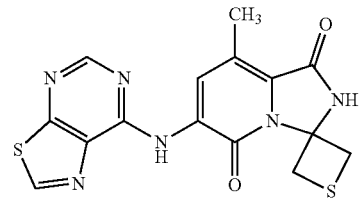 [SMILES: Cc1cc(Nc2ncnc3scnc23)c(=O)n2c1C(=O)NC21CSC1]

To a solution of 6-bromo-8-methyl-2H-spiro[imidazo[1,5-a]pyridine-3,3'-thietane]-1,5-dione (prepared according to example 173a, 100 mg, 332 µmol) and [1,3]thiazolo[5,4-d]pyrimidin-7-amine (CAS 2846-90-4, 55.6 mg, 365 µmol) in 1,4-dioxane (12 mL) was added cesium carbonate (325 mg, 996 µmol) and the mixture was degassed and purged with argon several times. 4,5-Bis(diphenylphosphino)-9,9-dimethylxanthene (20.6 mg, 35.5 µmol), 2-(dicyclohexyl-phosphino)-2',4',6'-triisopropylbiphenyl (16.9 mg, 35.5 µmol), palladium(II)acetate (7.98 mg, 35.5 µmol) and tris(dibenzylideneacetone)dipalladium(0) (32.5 mg, 35.5 µmol) were added and the mixture was stirred at 100° C. for 2 hours. The mixture was concentrated and the residue purified by flash chromatography (Biotage SNAP cartridge silica 25 g, ethanol:dichloromethane). The isolated product was taken up in ethanol and stirred at RT. The solid was filtered off under vacuo and dried to give 10.0 mg (8% yield) of the title compound.

LC-MS: m/z=373.2 [M+H]$^+$.

$^1$H-NMR (400 MHz, DMSO-d6) δ [ppm]=1.052 (0.79), 2.318 (0.55), 2.469 (16.00), 2.518 (6.25), 2.523 (4.15), 2.659 (0.53), 3.273 (3.27), 3.300 (3.42), 3.343 (0.61), 4.696 (3.33), 4.722 (3.27), 5.759 (0.44), 8.694 (5.43), 8.840 (6.28), 9.369 (3.18), 9.533 (8.12), 10.764 (2.57).

Example 173a 6-bromo-8-methyl-2H-spiro[imidazo[1,5-a]pyridine-3,3'-thietane]-1,5-dione

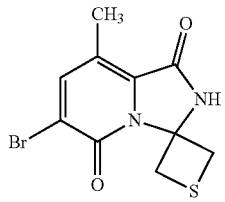

To a solution of 1.50 g (6.49 mmol) 5-bromo-3-methyl-6-oxo-1,6-dihydropyridine-2-carboxamide (prepared according to PCT Int. Appl. (2015), WO 2015200481) and 858 mg (9.74 mmol) thietan-3-one (CAS 22131-92-6) in 1,4-dioxane (18 mL) were added 173 µL (3.2 mmol) concentrated sulfuric acid and the reaction mixture was stirred at 95° C. for 6 hours. The mixture was concentrated under reduced pressure and water was added. The resulting precipitate was filtered off under vacuo, taken up with water and stirred at RT. The solid was filtered off, washed with diethyl ether and dried to give 1.8 g (92% yield) of the title compound.

LC-MS: m/z=301.3/303.3 [M+H]$^+$ (Br isotope pattern).

$^1$H-NMR (400 MHz, DMSO-d6) δ [ppm]=2.333 (16.00), 2.522 (0.99), 3.186 (3.86), 3.212 (4.00), 3.565 (0.78), 4.608 (4.01), 4.635 (3.88), 8.051 (5.43), 10.922 (2.10).

Example 174

8-methyl-6-[(5-methylquinazolin-4-yl)amino]-2H-spiro[imidazo[1,5-a]pyridine-3,3'-thietane]-1,5-dione

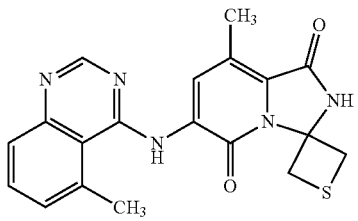 [SMILES: Cc1cc(Nc2ncnc3cccc(C)c23)c(=O)n2c1C(=O)NC21CSC1]

To a solution of 6-bromo-8-methyl-2H-spiro[imidazo[1,5-a]pyridine-3,3'-thietane]-1,5-dione (prepared according to example 173a, 100 mg, 332 µmol) and 5-methylquinazolin-4-amine (commercial, 58.1 mg, 365 µmol) in 1,4-dioxane (6.6 mL) was added cesium carbonate (325 mg, 996 µmol) and the mixture was degassed and purged with argon several times. 4,5-Bis(diphenylphosphino)-9,9-dimethylxanthene (20.6 mg, 35.5 µmol), 2-(dicyclohexyl-phosphino)-2',4',6'-triisopropylbiphenyl (16.9 mg, 35.5 µmol), palladium(II) acetate (7.98 mg, 35.5 µmol) and tris(dibenzylideneacetone)dipalladium(0) (32.5 mg, 35.5 µmol) were added and the mixture was stirred at 100° C. for 2 hours. The mixture was concentrated and the residue purified by flash chromatography (Biotage SNAP cartridge silica 25 g, ethanol:dichloromethane). The isolated product was taken up in ethanol and stirred at RT. The solid was filtered off under vacuo and dried to give 53.0 mg (40% yield) of the title compound.

LC-MS: m/z=380.3 [M+H]$^+$.

$^1$H-NMR (400 MHz, DMSO-d6) δ [ppm]=1.052 (0.42), 1.231 (0.81), 2.468 (16.00), 2.518 (3.75), 2.523 (2.50), 3.155 (7.66), 3.283 (3.42), 3.309 (3.75), 4.690 (3.57), 4.717 (3.52), 7.505 (1.23), 7.522 (1.40), 7.701 (0.86), 7.704 (1.00), 7.721 (2.13), 7.725 (1.86), 7.749 (2.55), 7.766 (2.07), 7.769 (1.31), 7.787 (1.06), 8.781 (6.72), 8.896 (5.70), 9.746 (2.34), 10.749 (2.80).

Example 175

6-[(6-chloroquinazolin-4-yl)amino]-8-methyl-2H-spiro[imidazo[1,5-a]pyridine-3,3'-thietane]-1,5-dione

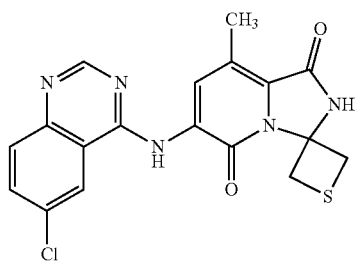 [SMILES: Cc1cc(Nc2ncnc3ccc(Cl)cc23)c(=O)n2c1C(=O)NC21CSC1]

To a solution of 6-bromo-8-methyl-2H-spiro[imidazo[1,5-a]pyridine-3,3'-thietane]-1,5-dione (prepared according to example 173a, 100 mg, 332 µmol) and 6-chloroquinazolin-4-amine (CAS 19808-35-6, 65.6 mg, 365 µmol) in 1,4-dioxane (12 mL) was added cesium carbonate (325 mg, 996 µmol) and the mixture was degassed and purged with argon several times. 4,5-Bis(diphenylphosphino)-9,9-dimethylxanthene (20.6 mg, 35.5 µmol), 2-(dicyclohexyl-phosphino)-2',4',6'-triisopropylbiphenyl (16.9 mg, 35.5 µmol), palladium(II)acetate (7.98 mg, 35.5 µmol) and tris(dibenzylideneacetone)dipalladium(0) (32.5 mg, 35.5 µmol) were added and the mixture was stirred at 100° C. for 2 hours. The mixture was concentrated and the residue purified by flash chromatography (Biotage SNAP cartridge silica 25 g, ethanol:dichloromethane). The isolated product was taken up in ethanol and stirred at RT. The solid was filtered off under vacuo and dried to give 9.00 mg (6% yield) of the title compound.

LC-MS: m/z=400.3 [M+H]$^+$.

$^1$H-NMR (400 MHz, DMSO-d6) δ [ppm]=1.232 (1.17), 2.318 (1.36), 2.454 (16.00), 2.518 (14.70), 2.523 (9.78), 2.659 (1.30), 3.307 (4.02), 4.686 (3.43), 4.713 (3.43), 7.883 (2.01), 7.906 (3.82), 7.947 (2.46), 7.952 (2.40), 7.969 (1.23), 7.974 (1.30), 8.520 (2.59), 8.526 (2.59), 8.583 (4.92), 8.809 (5.70), 9.549 (2.66), 10.785 (2.79).

Example 176

6-[(6-fluoroquinazolin-4-yl)amino]-8-methyl-2H-spiro[imidazo[1,5-a]pyridine-3,3'-thietane]-1,5-dione

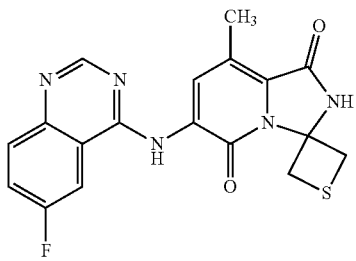 [SMILES: Cc1cc(Nc2ncnc3ccc(F)cc23)c(=O)n2c1C(=O)NC21CSC1]

To a solution of 6-bromo-8-methyl-2H-spiro[imidazo[1,5-a]pyridine-3,3'-thietane]-1,5-dione (prepared according to example 173a, 100 mg, 332 µmol) and 6-fluoroquinazolin-4-amine (CAS 1190320-08-1, 59.6 mg, 365 µmol) in 1,4-dioxane (6.6 mL) was added cesium carbonate (325 mg, 996 µmol) and the mixture was degassed and purged with argon several times. 4,5-Bis(diphenylphosphino)-9,9-dimethylxanthene (20.6 mg, 35.5 µmol), 2-(dicyclohexyl-phosphino)-2',4',6'-triisopropylbiphenyl (16.9 mg, 35.5 µmol), palladium(II)acetate (7.98 mg, 35.5 µmol) and tris(dibenzylideneacetone)dipalladium(0) (32.5 mg, 35.5 µmol) were added and the mixture was stirred at 100° C. for 2 hours. The mixture was concentrated and the residue purified by flash chromatography (Biotage SNAP cartridge silica 25 g, ethanol:dichloromethane). The isolated product was taken up in ethanol and stirred at RT. The solid was filtered off under vacuo and dried to give 50.0 mg (37% yield) of the title compound.

LC-MS: m/z=384.2 [M+H]$^+$.

$^1$H-NMR (400 MHz, DMSO-d6) δ [ppm]=1.035 (0.41), 1.052 (0.83), 1.070 (0.44), 2.323 (0.59), 2.327 (0.82), 2.332 (0.68), 2.454 (16.00), 2.522 (1.84), 2.665 (0.57), 2.669 (0.77), 2.673 (0.58), 3.308 (4.03), 4.688 (4.06), 4.714 (4.09), 5.758 (0.40), 7.832 (0.61), 7.839 (0.72), 7.855 (1.31), 7.861 (1.44), 7.877 (0.95), 7.883 (1.06), 7.941 (1.74), 7.955 (1.77), 7.964 (1.24), 7.977 (1.13), 8.215 (1.30), 8.222 (1.37), 8.239 (1.34), 8.246 (1.31), 8.609 (5.84), 8.796 (6.05), 9.413 (3.39), 10.774 (3.27).

Example 177

8-methyl-6-[(thieno[2,3-d]pyrimidin-4-yl)amino]-2H-spiro[imidazo[1,5-a]pyridine-3,3'-thietane]-1,5-dione

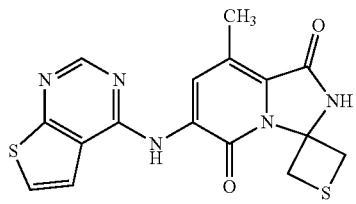 [SMILES: Cc1cc(Nc2ncnc3sccc23)c(=O)n2c1C(=O)NC21CSC1]

To a solution of 6-bromo-8-methyl-2H-spiro[imidazo[1,5-a]pyridine-3,3'-thietane]-1,5-dione (prepared according to example 173a, 100 mg, 332 µmol) and thieno[2,3-d]pyrimidin-4-amine (CAS 14080-56-9, 55.2 mg, 365 µmol) in 1,4-dioxane (11 mL) was added cesium carbonate (20.6 mg, 35.5 µmol) and the mixture was degassed and purged with argon several times. 4,5-Bis(diphenylphosphino)-9,9-dimethylxanthene (16.9 mg, 35.5 µmol), 2-(dicyclohexyl-phosphino)-2',4',6'-triisopropylbiphenyl (7.98 mg, 35.5 µmol), palladium(II)acetate (32.5 mg, 35.5 µmol) and tris(dibenzylideneacetone)dipalladium(0) (325 mg, 996 µmol) were added and the mixture was stirred at 100° C. for 2 hours. The mixture was concentrated and the residue purified by flash chromatography (Biotage SNAP cartridge silica 25 g, ethanol:dichloromethane). The isolated product was taken up in ethanol and stirred at RT. The solid was filtered off under vacuo and dried to give 27.0 mg (21% yield) of the title compound.

LC-MS: m/z=372.2 [M+H]$^+$.

$^1$H-NMR (400 MHz, DMSO-d6) δ [ppm]=1.035 (0.63), 1.052 (1.21), 1.070 (0.63), 2.322 (0.75), 2.327 (1.01), 2.331 (0.79), 2.447 (16.00), 2.522 (3.03), 2.665 (0.75), 2.669 (0.97), 2.673 (0.74), 3.300 (3.97), 4.679 (3.83), 4.705 (3.78), 5.759 (0.60), 7.831 (2.67), 7.846 (3.88), 7.908 (3.86), 7.922 (2.65), 8.625 (5.57), 8.699 (6.02), 9.157 (3.44), 10.731 (3.01).

Example 178

8-methyl-6-[(7H-pyrrolo[2,3-d]pyrimidin-4-yl)amino]-2H-spiro[imidazo[1,5-a]pyridine-3,3'-thietane]-1,5-dione

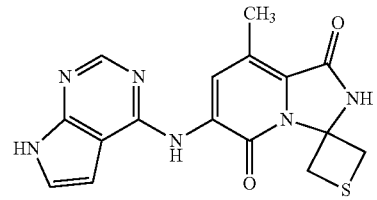 [SMILES: Cc1cc(Nc2ncnc3[nH]ccc23)c(=O)n2c1C(=O)NC21CSC1]

A mixture of crude tert-butyl 4-[(8-methyl-1,5-dioxo-1,5-dihydro-2H-spiro[imidazo[1,5-a]pyridine-3,3'-thietan]-6-yl)amino]-7H-pyrrolo[2,3-d]pyrimidine-7-carboxylate (prepared according to example 178a, 200 mg, 440 µmol) in dichloromethane (5.6 mL) was treated with trifluoroacetic acid (680 µl, 8.8 mmol) and stirred at RT for 72 hours. The mixture was carefully poured onto aqueous ammonia solution (25%) and extracted with a mixture of dichloromethane/methanol. The organic layer was washed with water, dried over sodium sulfate and concentrated. The crude product was taken up in ethanol and stirred at RT. The solid was filtered off under vacuo and dried to give 125 mg (72% yield) of the title compound.

LC-MS: m/z=355.1 [M+H]$^+$.

$^1$H-NMR (400 MHz, DMSO-d6) δ[ppm]=0.892 (0.70), 0.908 (0.71), 1.138 (0.87), 1.155 (0.82), 1.236 (1.22), 1.253 (1.19), 2.446 (16.00), 2.518 (2.90), 2.522 (2.01), 3.294 (3.71), 3.320 (4.44), 4.688 (3.86), 4.715 (3.80), 6.852 (1.88), 6.857 (2.13), 6.860 (2.09), 6.865 (1.79), 6.993 (0.74), 7.381 (2.07), 7.387 (2.32), 7.396 (1.84), 8.467 (6.83), 8.703 (3.85), 8.728 (5.97), 10.652 (2.19), 12.034 (1.32).

Example 178a tert-butyl 4-[(8-methyl-1,5-dioxo-1,5-dihydro-2H-spiro[imidazo[1,5-a]pyridine-3,3'-thietan]-6-yl)amino]-7H-pyrrolo[2,3-d]pyrimidine-7-carboxylate

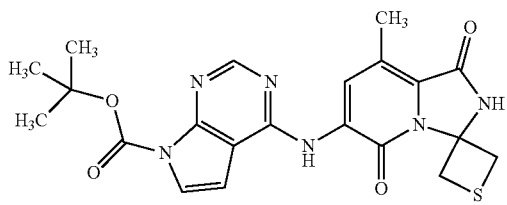 [SMILES: Cc1cc(Nc2ncnc3c2ccn3C(=O)OC(C)(C)C)c(=O)n2c1C(=O)NC21CSC1]

To a solution of 6-bromo-8-methyl-2H-spiro[imidazo[1,5-a]pyridine-3,3'-thietane]-1,5-dione (prepared according to example 173a, 130 mg, 432 µmol) and tert-butyl 4-amino-7H-pyrrolo[2,3-d]pyrimidine-7-carboxylate (prepared according to example 178b, 111 mg, 475 µmol) in 1,4-dioxane (15 mL) was added cesium carbonate (422 mg, 1.29 mmol) and the mixture was degassed and purged with argon several times. 4,5-Bis(diphenylphosphino)-9,9-dimethylxanthene (26.7 mg, 46.2 µmol), 2-(dicyclohexyl-phosphino)-2',4',6'-triisopropylbiphenyl (22.0 mg, 46.2 µmol), palladium(II)acetate (10.4 mg, 46.2 µmol) and tris(dibenzyli-deneacetone)dipalladium(0) (42.3 mg, 46.2 µmol) were added and the mixture was stirred at 100° C. for 2 hours. The mixture was concentrated and the obtained residue used in the next step without further purification.

Example 178b tert-butyl 4-amino-7H-pyrrolo[2,3-d]pyrimidine-7-carboxylate

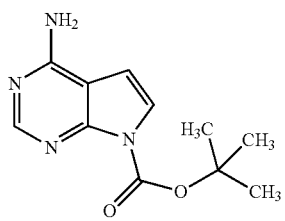 [SMILES: CC(C)(C)OC(=O)n1ccc2c(N)ncnc21]

A mixture of 7H-pyrrolo[2,3-d]pyrimidin-4-amine (CAS 1500-85-2, 1.50 g, 11.2 mmol) in pyridine (30 mL) was treated with N,N-dimethylpyridin-4-amine (273 mg, 2.24 mmol) and stirred at RT for 15 minutes. Di-tert-butyl dicarbonate (CAS 24424-99-5, 2.44 g, 11.2 mmol) was added and it was stirred at RT over night. The mixture was concentrated and the residue purified by flash chromatography (Biotage SNAP cartridge silica 100 g, methanol:dichloromethane) to give 2.30 g (88% yield) of the title compound.

LC-MS: m/z=235.5 [M+H]$^+$.

$^1$H-NMR (400 MHz, DMSO-d6), δ [ppm]=1.58 (9H), 6.74 (1H), 7.22 (2H), 7.44 (1H), 8.17 (1H).

Example 179

8-methyl-6-[(5-methylquinazolin-4-yl)amino]-2H-spiro[imidazo[1,5-a]pyridine-3,3'-thietane]-1,5-dione 1',1'-dioxide

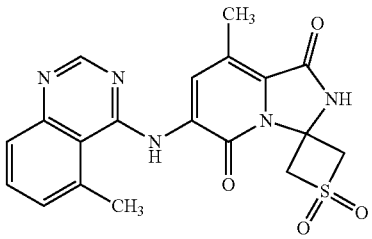 [SMILES: Cc1cc(Nc2ncnc3cccc(C)c23)c(=O)n2c1C(=O)NC21CS(=O)(=O)C1]

To a solution of 6-bromo-8-methyl-2H-spiro[imidazo[1,5-a]pyridine-3,3'-thietane]-1,5-dione 1',1'-dioxide (prepared according to example 179a, 100 mg, 300 µmol) and 5-methylquinazolin-4-amine (commercial, 52.6 mg, 330 µmol) in 1,4-dioxane (12 mL) was added cesium carbonate (293 mg, 900 µmol) and the mixture was degassed and purged with argon several times. 4,5-Bis(diphenylphosphino)-9,9-dimethylxanthene (18.6 mg, 32.1 µmol), 2-(dicyclohexyl-phosphino)-2',4',6'-triisopropylbiphenyl (15.3 mg, 32.1 µmol), palladium(II)acetate (7.21 mg, 32.1 µmol) and tris(dibenzylideneacetone)dipalladium(0) (29.4 mg, 32.1 µmol) were added and the mixture was stirred at 100° C. for 2 hours. The mixture was filtered and concentrated and the residue purified by flash chromatography (Biotage SNAP cartridge silica 25 g, ethanol:dichloromethane). The isolated product was taken up in ethanol and stirred at RT. The solid was filtered off under vacuo, taken up in dichloromethane again and stirred at RT. The solid was filtered off under vacuo and dried to give 32.0 mg (25% yield) of the title compound.

LC-MS: m/z=412.3 [M+H]$^+$.

$^1$H-NMR (400 MHz, DMSO-d6) δ [ppm]=2.322 (1.77), 2.326 (2.41), 2.400 (0.95), 2.522 (6.95), 2.539 (8.32), 2.555 (1.00), 2.664 (1.86), 2.669 (2.45), 2.790 (0.82), 3.141 (16.00), 4.382 (4.86), 4.421 (4.86), 5.620 (5.23), 5.660 (4.95), 7.504 (2.64), 7.521 (2.95), 7.714 (1.91), 7.731 (4.23), 7.757 (4.32), 7.774 (3.64), 7.795 (1.68), 8.796 (11.27), 8.953 (10.32), 9.677 (4.86), 10.650 (6.00).

Example 179a 6-bromo-8-methyl-2H-spiro[imidazo[1,5-a]pyridine-3,3'-thietane]-1,5-dione 1',1'-dioxide

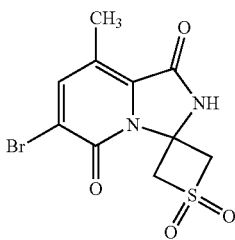 [SMILES: Cc1cc(Br)c(=O)n2c1C(=O)NC21CS(=O)(=O)C1]

To a solution of 1.46 g (6.33 mmol) 5-bromo-3-methyl-6-oxo-1,6-dihydropyridine-2-carboxamide (prepared according to PCT Int. Appl. (2015), WO 2015200481) and 1.90 g (15.8 mmol) thietan-3-one 1,1-dioxide (CAS 1599-23-1) in 1,4-dioxane (18 mL) were added 170 μL (3.1 mmol) concentrated sulfuric acid and the reaction mixture was stirred at 95° C. for 5 hours. The mixture was concentrated under reduced pressure and water was added. The resulting precipitate was filtered off under vacuo, taken up with water and stirred at RT. The solid was filtered off, washed with diethyl ether and dried to give 1.7 g (81% yield) of the title compound.

LC-MS: m/z=333.3/335.3 [M+H]+(Br isotope pattern).

¹H-NMR (400 MHz, DMSO-d6) δ [ppm]=2.365 (16.00), 3.566 (0.56), 4.284 (3.06), 4.290 (1.44), 4.293 (1.20), 4.315 (1.15), 4.318 (1.45), 4.323 (3.24), 5.499 (3.34), 5.504 (1.42), 5.508 (1.24), 5.529 (1.14), 5.533 (1.30), 5.539 (3.13), 8.116 (5.80), 10.822 (2.70).

Example 180

6-[(6-chloroquinazolin-4-yl)amino]-8-methyl-2H-spiro[imidazo[1,5-a]pyridine-3,3'-thietane]-1,5-dione 1',1'-dioxide

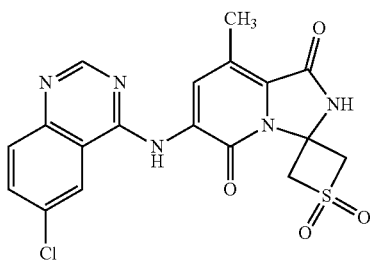 [SMILES: Cc1cc(Nc2ncnc3ccc(Cl)cc23)c(=O)n2c1C(=O)NC21CS(=O)(=O)C1]

To a solution of 6-bromo-8-methyl-2H-spiro[imidazo[1,5-a]pyridine-3,3'-thietane]-1,5-dione 1',1'-dioxide (prepared according to example 179a, 120 mg, 360 μmol) and 6-chloroquinazolin-4-amine (CAS 19808-35-6, 71.2 mg, 396 μmol) in 1,4-dioxane (12 mL) was added cesium carbonate (352 mg, 1.08 mmol) and the mixture was degassed and purged with argon several times. 4,5-Bis(diphenylphosphino)-9,9-dimethylxanthene (22.3 mg, 38.5 μmol), 2-(dicyclohexyl-phosphino)-2',4',6'-triisopropylbiphenyl (18.4 mg, 38.5 μmol), palladium(II)acetate (8.65 mg, 38.5 μmol) and tris(dibenzylideneacetone)dipalladium(0) (35.3 mg, 38.5 μmol) were added and the mixture was stirred at 100° C. for 2 hours. The mixture was filtered and concentrated and the residue purified by flash chromatography (Biotage SNAP cartridge silica 25 g, ethanol:dichloromethane). The isolated product was taken up in ethanol and stirred at RT. The solid was filtered off under vacuo, taken up in dichloromethane again and stirred at RT. The solid was filtered off under vacuo and dried to give 47.0 mg (29% yield) of the title compound.

LC-MS: m/z=432.3 [M+H]+.

¹H-NMR (400 MHz, DMSO-d6) δ [ppm]=1.231 (0.57), 2.318 (0.47), 2.480 (16.00), 2.518 (4.73), 2.522 (3.70), 2.659 (0.41), 3.205 (0.90), 3.565 (0.43), 4.406 (2.33), 4.446 (2.37), 5.574 (2.54), 5.614 (2.37), 7.878 (1.21), 7.901 (2.35), 7.941 (2.11), 7.946 (1.96), 7.963 (1.06), 7.968 (1.02), 8.557 (2.27), 8.562 (2.25), 8.626 (4.32), 8.810 (4.81), 9.585 (2.27), 10.692 (2.50).

Example 181

6-[(7-chloroquinazolin-4-yl)amino]-8-methyl-2H-spiro[imidazo[1,5-a]pyridine-3,3'-thietane]-1,5-dione 1',1'-dioxide

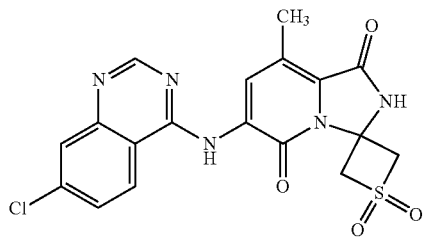 [SMILES: Cc1cc(Nc2ncnc3cc(Cl)ccc23)c(=O)n2c1C(=O)NC21CS(=O)(=O)C1]

To a solution of 6-bromo-8-methyl-2H-spiro[imidazo[1,5-a]pyridine-3,3'-thietane]-1,5-dione 1',1'-dioxide (prepared according to example 179a, 100 mg, 300 μmol) and 7-chloroquinazolin-4-amine (CAS 19808-36-7, 59.3 mg, 330 μmol) in 1,4-dioxane (12 mL) was added cesium carbonate (293 mg, 900 μmol) and the mixture was degassed and purged with argon several times. 4,5-Bis(diphenylphosphino)-9,9-dimethylxanthene (18.6 mg, 32.1 μmol), 2-(dicyclohexyl-phosphino)-2',4',6'-triisopropylbiphenyl (15.3 mg, 32.1 μmol), palladium(II)acetate (7.21 mg, 32.1 μmol) and tris(dibenzylideneacetone)dipalladium(0) (29.4 mg, 32.1 μmol) were added and the mixture was stirred at 100° C. for 2 hours. The mixture was filtered and concentrated and the residue purified by flash chromatography (Biotage SNAP cartridge silica 25 g, ethanol:dichloromethane). The isolated product was taken up in ethanol and stirred at RT. The solid was filtered off under vacuo, taken up in dichloromethane again and stirred at RT. The solid was filtered off under vacuo and dried. The thus obtained material was finally taken up in DMSO, the solid filtered off under vacuo and dried to give 12.0 mg (9% yield) of the title compound.

LC-MS: m/z=432.3 [M+H]+.

¹H-NMR (400 MHz, DMSO-d6) δ [ppm]=1.232 (0.47), 2.486 (16.00), 2.518 (4.05), 2.523 (2.52), 2.534 (0.45), 2.539 (3.25), 4.405 (1.78), 4.445 (1.84), 5.581 (1.92), 5.620 (1.87), 7.720 (1.15), 7.725 (1.16), 7.742 (1.18), 7.748 (1.21), 7.943 (2.29), 7.948 (2.23), 8.417 (1.71), 8.440 (1.66), 8.678 (3.89), 8.831 (4.26), 9.531 (2.08), 10.691 (2.23).

Example 182

8-methyl-6-(quinazolin-4-ylamino)-2H-spiro[imidazo[1,5-a]pyridine-3,3'-thietane]-1,5-dione 1',1'-dioxide

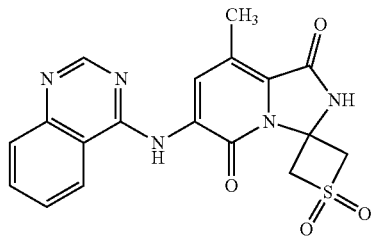 [SMILES: Cc1cc(Nc2ncnc3ccccc23)c(=O)n2c1C(=O)NC21CS(=O)(=O)C1]

To a solution of 6-bromo-8-methyl-2H-spiro[imidazo[1,5-a]pyridine-3,3'-thietane]-1,5-dione 1',1'-dioxide (prepared according to example 179a, 100 mg, 300 µmol) and quinazolin-4-amine (CAS 15018-66-3, 47.9 mg, 330 µmol) in 1,4-dioxane (12 mL) was added cesium carbonate (293 mg, 900 µmol) and the mixture was degassed and purged with argon several times. 4,5-Bis(diphenylphosphino)-9,9-dimethylxanthene (18.6 mg, 32.1 µmol), 2-(dicyclohexyl-phosphino)-2',4',6'-triisopropylbiphenyl (15.3 mg, 32.1 µmol), palladium(II)acetate (7.21 mg, 32.1 µmol) and tris(dibenzylideneacetone)dipalladium(0) (29.4 mg, 32.1 µmol) were added and the mixture was stirred at 100° C. for 2 hours. The mixture was filtered and concentrated and the residue purified by flash chromatography (Biotage SNAP cartridge silica 25 g, ethanol:dichloromethane). The isolated product was taken up in ethanol and stirred at RT. The solid was filtered off under vacuo, taken up in dichloromethane again and stirred at RT. The solid was filtered off under vacuo and dried. The thus obtained material was finally taken up in DMSO and heated, the solid filtered off under vacuo and dried to give 12.0 mg (10% yield) of the title compound.

LC-MS: m/z=398.3 [M+H]$^+$.

$^1$H-NMR (400 MHz, DMSO-d6) δ [ppm]=1.052 (0.75), 1.232 (0.47), 2.322 (2.71), 2.327 (3.59), 2.364 (0.47), 2.400 (0.68), 2.522 (10.44), 2.539 (5.29), 2.665 (2.78), 2.669 (3.66), 4.405 (7.12), 4.445 (7.25), 5.599 (7.73), 5.639 (7.32), 5.759 (2.58), 7.707 (2.17), 7.710 (2.24), 7.727 (4.41), 7.745 (2.58), 7.748 (2.58), 7.886 (3.12), 7.904 (6.58), 7.935 (4.07), 7.952 (4.20), 7.971 (1.69), 8.331 (4.68), 8.351 (4.34), 8.765 (14.58), 8.846 (16.00), 9.434 (8.14), 10.674 (8.68).

Example 183

8'-methyl-6'-[(5-methylquinazolin-4-yl)amino]-2'H-spiro[cyclopentane-1,3'-imidazo[1,5-a]pyridine]-1',5'-dione

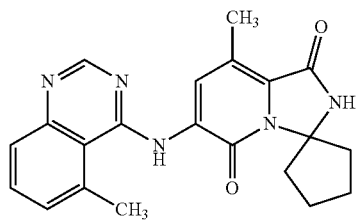 [SMILES: Cc1cc(Nc2ncnc3cccc(C)c23)c(=O)n2c1C(=O)NC21CCCC1]

To a solution of 6'-bromo-8'-methyl-2'H-spiro[cyclopentane-1,3'-imidazo[1,5-a]pyridine]-1',5'-dione (CAS 1849592-55-7; PCT Int. Appl. (2015), WO 2015200481, 100 mg, 337 µmol) and 5-methylquinazolin-4-amine (commercial, 58.9 mg, 370 µmol) in 1,4-dioxane (12 mL) was added cesium carbonate (329 mg, 1.01 mmol) and the mixture was degassed and purged with argon several times. 4,5-Bis(diphenylphosphino)-9,9-dimethylxanthene (20.8 mg, 36.0 µmol), 2-(dicyclohexyl-phosphino)-2',4',6'-triisopropylbiphenyl (17.2 mg, 36.0 µmol), palladium(II)acetate (8.08 mg, 36.0 µmol) and tris(dibenzylideneacetone)dipalladium(0) (33.0 mg, 36.0 µmol) were added and the mixture was stirred at 105° C. for 2 hours. The reaction mixture was diluted with a mixture of dichloromethane/ethanol, anorganic salts were filtered off and the filtrate was concentrated. The residue was purified by preperative TLC (ethanol:dichloromethane) to give 51 mg (38% yield) of the title compound.

LC-MS: m/z=376.2 [M+H]$^+$.

$^1$H-NMR (400 MHz, DMSO-d6) δ [ppm]=1.687 (2.09), 1.701 (2.26), 1.717 (2.09), 1.731 (1.80), 1.840 (2.43), 1.853 (2.43), 1.871 (1.91), 1.988 (2.78), 2.327 (1.91), 2.331 (1.45), 2.336 (0.70), 2.362 (0.52), 2.518 (9.51), 2.522 (5.57), 2.669 (2.14), 2.673 (1.51), 2.678 (0.70), 2.831 (1.33), 2.851 (2.49), 2.867 (2.26), 2.884 (2.38), 2.903 (1.10), 3.103 (16.00), 7.469 (2.61), 7.486 (2.90), 7.689 (1.86), 7.707 (4.23), 7.730 (4.12), 7.748 (3.54), 7.768 (1.57), 8.764 (9.91), 8.915 (8.93), 9.727 (4.17), 10.022 (3.01).

Example 184

8'-methyl-6'-{[6-(trifluoromethyl)quinazolin-4-yl]amino}-2'H-spiro[cyclopentane-1,3'-imidazo[1,5-a]pyridine]-1',5'-dione

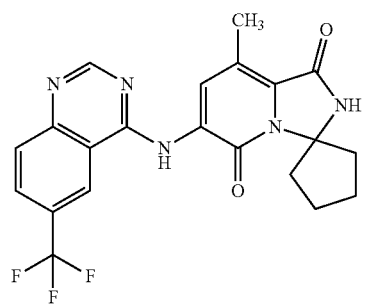 [SMILES: Cc1cc(Nc2ncnc3ccc(C(F)(F)F)cc23)c(=O)n2c1C(=O)NC21CCCC1]

To a solution of 6'-bromo-8'-methyl-2'H-spiro[cyclopentane-1,3'-imidazo[1,5-a]pyridine]-1',5'-dione (CAS 1849592-55-7; PCT Int. Appl. (2015), WO 2015200481, 100 mg, 337 µmol) and 6-(trifluoromethyl)quinazolin-4-amine (CAS 1020263-19-7, 78.9 mg, 370 µmol) in 1,4-dioxane (12 mL) was added cesium carbonate (329 mg, 1.01 mmol) and the mixture was degassed and purged with argon several times. 4,5-Bis(diphenylphosphino)-9,9-dimethylxanthene (20.8 mg, 36.0 µmol), 2-(dicyclohexyl-phosphino)-2',4',6'-triisopropylbiphenyl (17.2 mg, 36.0 µmol), palladium(II)acetate (8.08 mg, 36.0 µmol) and tris(dibenzylideneacetone)dipalladium(0) (33.0 mg, 36.0 µmol) were added and the mixture was stirred at 105° C. for 2 hours. The reaction mixture was diluted with a mixture of dichloromethane/ethanol, anorganic salts were filtered off and the filtrate was concentrated. The residue was taken up in dichloromethane/ethanol and stirred at RT. The solid was isolated by centrifugation and dried to give 47 mg (31% yield) of the title compound.

LC-MS: m/z=430.4 [M+H]$^+$.

$^1$H-NMR (400 MHz, DMSO-d6) δ [ppm]=1.715 (7.03), 1.729 (7.68), 1.746 (6.92), 1.758 (6.05), 1.840 (7.89), 1.851 (8.22), 1.869 (7.89), 1.989 (9.08), 2.323 (4.97), 2.327 (6.16), 2.332 (4.54), 2.665 (4.32), 2.669 (5.62), 2.673 (4.11), 2.805 (4.22), 2.826 (7.68), 2.841 (7.24), 2.857 (7.24), 2.877 (3.46), 5.758 (2.92), 7.988 (6.49), 8.010 (8.22), 8.141 (8.76), 8.162 (6.70), 8.496 (5.08), 8.823 (16.00), 9.805 (2.49), 10.060 (8.22).

Example 185

6'-[(6-fluoroquinazolin-4-yl)amino]-8'-methyl-2'H-spiro[cyclopentane-1,3'-imidazo[1,5-a]pyridine]-1',5'-dione

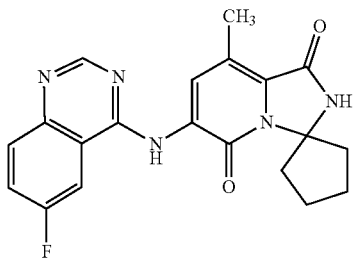 [SMILES: Cc1cc(Nc2ncnc3ccc(F)cc23)c(=O)n2c1C(=O)NC21CCCC1]

To a solution of 6'-bromo-8'-methyl-2'H-spiro[cyclopentane-1,3'-imidazo[1,5-a]pyridine]-1',5'-dione (CAS 1849592-55-7; PCT Int. Appl. (2015), WO 2015200481, 100 mg, 337 µmol) and 6-fluoroquinazolin-4-amine (CAS 1190320-08-1, 60.4 mg, 370 µmol) in 1,4-dioxane (12 mL) was added cesium carbonate (329 mg, 1.01 mmol) and the mixture was degassed and purged with argon several times. 4,5-Bis(diphenylphosphino)-9,9-dimethylxanthene (20.8 mg, 36.0 µmol), 2-(dicyclohexyl-phosphino)-2',4',6'-triisopropylbiphenyl (17.2 mg, 36.0 µmol), palladium(II)acetate (8.08 mg, 36.0 µmol) and tris(dibenzylideneacetone)dipalladium(0) (33.0 mg, 36.0 µmol) were added and the mixture was stirred at 105° C. for 2 hours. The reaction mixture was diluted with a mixture of dichloromethane/ethanol, anorganic salts were filtered off and the filtrate was concentrated. The residue was purified by preperative TLC (ethanol: dichloromethane) and the obtained material was taken up in dichloromethane/methanol and stirred at RT. The solid was isolated by centrifugation and dried to give 42 mg (31% yield) of the title compound.

LC-MS: m/z=380.1 [M+H]$^+$.

$^1$H-NMR (400 MHz, DMSO-d6) δ [ppm]=1.717 (4.64), 1.731 (5.23), 1.748 (4.64), 1.762 (4.15), 1.844 (5.33), 1.855 (5.53), 1.874 (4.44), 1.993 (6.32), 2.331 (3.36), 2.336 (1.38), 2.518 (16.00), 2.523 (10.67), 2.673 (3.06), 2.678 (1.38), 2.805 (2.96), 2.825 (5.53), 2.842 (5.04), 2.857 (5.23), 2.877 (2.47), 3.297 (1.09), 3.368 (1.68), 5.758 (2.57), 7.811 (2.07), 7.818 (2.37), 7.834 (4.44), 7.840 (4.94), 7.855 (3.16), 7.862 (3.36), 7.922 (5.04), 7.935 (5.33), 7.944 (3.85), 7.957 (3.36), 8.141 (4.54), 8.147 (4.74), 8.164 (4.64), 8.170 (4.44), 8.546 (0.59), 8.606 (10.77), 8.776 (12.74), 9.352 (1.88), 10.042 (1.98).

Example 186

6'-[(7-chloroquinazolin-4-yl)amino]-8'-methyl-2'H-spiro[cyclopentane-1,3'-imidazo[1,5-a]pyridine]-1',5'-dione

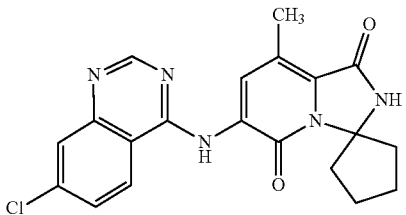 [SMILES: Cc1cc(Nc2ncnc3cc(Cl)ccc23)c(=O)n2c1C(=O)NC21CCCC1]

To a solution of 6'-bromo-8'-methyl-2'H-spiro[cyclopentane-1,3'-imidazo[1,5-a]pyridine]-1',5'-dione (CAS 1849592-55-7; PCT Int. Appl. (2015), WO 2015200481, 100 mg, 337 µmol) and 7-chloroquinazolin-4-amine (CAS 19808-36-7, 66.5 mg, 370 µmol) in 1,4-dioxane (12 mL) was added cesium carbonate (329 mg, 1.01 mmol) and the mixture was degassed and purged with argon several times. 4,5-Bis(diphenylphosphino)-9,9-dimethylxanthene (20.8 mg, 36.0 µmol), 2-(dicyclohexyl-phosphino)-2',4',6'-triisopropylbiphenyl (17.2 mg, 36.0 µmol), palladium(II)acetate (8.08 mg, 36.0 µmol) and tris(dibenzylideneacetone)dipalladium(0) (33.0 mg, 36.0 µmol) were added and the mixture was stirred at 105° C. for 2 hours. The reaction mixture was diluted with a mixture of dichloromethane/ethanol, anorganic salts were filtered off and the filtrate was concentrated. The residue was taken up in dichloromethane/methanol and stirred at RT. The solid was isolated by centrifugation and dried to give 32 mg (23% yield) of the title compound.

LC-MS: m/z=396.3 [M+H]$^+$.

$^1$H-NMR (400 MHz, DMSO-d6) δ [ppm]=1.717 (3.29), 1.732 (3.74), 1.748 (3.29), 1.761 (2.95), 1.841 (3.63), 1.853 (3.86), 1.871 (3.06), 1.991 (4.31), 2.336 (1.13), 2.518 (16.00), 2.523 (9.87), 2.799 (2.04), 2.820 (3.63), 2.836 (3.40), 2.852 (3.52), 2.871 (1.70), 3.297 (2.16), 3.382 (0.57), 3.391 (0.45), 3.565 (1.82), 7.693 (4.20), 7.698 (4.43), 7.715 (4.31), 7.720 (4.54), 7.912 (7.04), 7.917 (6.70), 8.323 (8.17), 8.345 (7.38), 8.617 (4.09), 8.795 (5.33), 9.472 (0.68), 10.036 (0.79).

Example 187

8'-methyl-6'-[(quinazolin-4-yl)amino]-2'H-spiro[cyclopentane-1,3'-imidazo[1,5-a]pyridine]-1',5'-dione

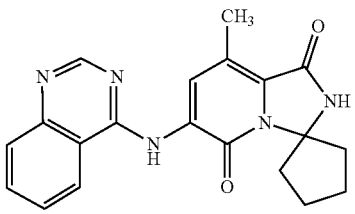 [SMILES: Cc1cc(Nc2ncnc3ccccc23)c(=O)n2c1C(=O)NC21CCCC1]

To a solution of 6'-bromo-8'-methyl-2'H-spiro[cyclopentane-1,3'-imidazo[1,5-a]pyridine]-1',5'-dione (CAS 1849592-55-7; PCT Int. Appl. (2015), WO 2015200481, 100 mg, 337 µmol) and quinazolin-4-amine (CAS 15018-

66-3, 53.7 mg, 370 µmol) in 1,4-dioxane (12 mL) was added cesium carbonate (329 mg, 1.01 mmol) and the mixture was degassed and purged with argon several times. 4,5-Bis(diphenylphosphino)-9,9-dimethylxanthene (20.8 mg, 36.0 µmol), 2-(dicyclohexyl-phosphino)-2',4',6'-triisopropylbiphenyl (17.2 mg, 36.0 µmol), palladium(II)acetate (8.08 mg, 36.0 µmol) and tris(dibenzylideneacetone)dipalladium(0) (33.0 mg, 36.0 µmol) were added and the mixture was stirred at 105° C. for 2 hours. The reaction mixture was diluted with a mixture of dichloromethane/ethanol, anorganic salts were filtered off and the filtrate was concentrated. The residue was purified by preperative TLC (ethanol:dichloromethane) to give 66 mg (52% yield) of the title compound.

LC-MS: m/z=362.1 [M+H]$^+$.

$^1$H-NMR (400 MHz, DMSO-d6) δ [ppm]=1.707 (1.94), 1.721 (3.30), 1.735 (3.68), 1.751 (3.20), 1.765 (2.91), 1.848 (3.78), 1.859 (3.88), 1.877 (3.10), 1.898 (1.07), 1.990 (2.91), 2.000 (4.36), 2.021 (2.23), 2.332 (2.33), 2.336 (1.07), 2.363 (1.36), 2.518 (14.93), 2.523 (9.50), 2.673 (2.33), 2.678 (0.97), 2.813 (2.13), 2.834 (3.78), 2.850 (3.49), 2.866 (3.68), 2.886 (1.75), 3.159 (0.78), 3.171 (0.78), 3.378 (0.58), 5.758 (16.00), 7.686 (2.23), 7.689 (2.42), 7.706 (4.75), 7.724 (2.81), 7.727 (2.81), 7.868 (3.20), 7.886 (6.79), 7.913 (4.36), 7.916 (4.56), 7.933 (4.56), 7.951 (1.84), 8.247 (5.92), 8.267 (5.43), 8.547 (0.48), 8.722 (10.57), 8.824 (13.96), 9.403 (1.16), 10.031 (1.07).

Example 188

(cis)-4-hydroxy-8'-methyl-6'-[(5-methylquinazolin-4-yl)amino]-4-(trifluoromethyl)-2'H-spiro[cyclohexane-1,3'-imidazo[1,5-a]pyridine]-1',5'-dione

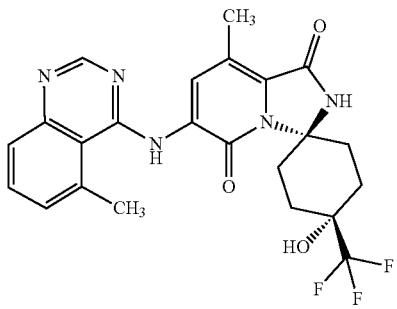 [SMILES: Cc1cc(Nc2ncnc3cccc(C)c23)c(=O)n2c1C(=O)N[C@]21CC[C@@](O)(C(F)(F)F)CC1]

To a solution of (cis)-6'-bromo-4-hydroxy-8'-methyl-4-(trifluoromethyl)-2'H-spiro[cyclohexane-1,3'-imidazo[1,5-a]pyridine]-1',5'-dione (prepared according to example 127b, 100 mg, 253 µmol) and 5-methylquinazolin-4-amine (commercial, 44.3 mg, 278 µmol) in 1,4-dioxane (10 mL) was added cesium carbonate (247 mg, 759 µmol) and the mixture was degassed and purged with argon several times. 4,5-Bis(diphenylphosphino)-9,9-dimethylxanthene (15.7 mg, 27.1 µmol), 2-(dicyclohexyl-phosphino)-2',4',6'-triisopropylbiphenyl (12.9 mg, 27.1 µmol), palladium(II)acetate (6.08 mg, 27.1 µmol) and tris(dibenzylideneacetone)dipalladium(0) (24.8 mg, 27.1 µmol) were added and the mixture was stirred at 100° C. for 2 hours. The mixture was concentrated and the residue purified by flash chromatography (Biotage SNAP cartridge silica 25 g, ethanol:dichloromethane). The isolated product was taken up in ethanol and stirred at RT. The solid was filtered off under vacuo and dried to give 75 mg (56% yield) of the title compound.

LC-MS: m/z=474.5 [M+H]$^+$.

$^1$H-NMR (400 MHz, DMSO-d6) δ [ppm]=1.035 (0.45), 1.052 (0.86), 1.070 (0.82), 1.087 (0.82), 1.105 (0.44), 1.230 (0.51), 1.432 (1.39), 1.463 (1.42), 1.810 (1.13), 1.843 (1.57), 1.939 (0.95), 1.964 (1.33), 1.998 (0.67), 2.326 (0.68), 2.522 (16.00), 2.668 (0.76), 2.812 (0.42), 3.081 (0.74), 3.110 (6.89), 3.370 (0.60), 3.388 (0.53), 3.422 (0.90), 3.434 (0.93), 3.456 (1.33), 3.488 (0.74), 6.056 (3.39), 7.461 (1.33), 7.478 (1.53), 7.689 (0.79), 7.708 (1.76), 7.728 (1.79), 7.745 (1.55), 7.766 (0.70), 8.766 (3.91), 8.916 (4.08), 9.775 (2.15), 10.445 (2.41).

Example 189

(cis)-6'-[(6-fluoroquinazolin-4-yl)amino]-4-hydroxy-8'-methyl-4-(trifluoromethyl)-2'H-spiro[cyclohexane-1,3'-imidazo[1,5-a]pyridine]-1',5'-dione

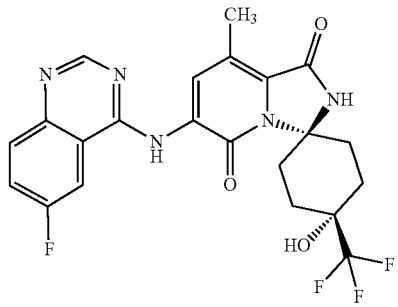 [SMILES: Cc1cc(Nc2ncnc3ccc(F)cc23)c(=O)n2c1C(=O)N[C@]21CC[C@@](O)(C(F)(F)F)CC1]

To a solution of (cis)-6'-bromo-4-hydroxy-8'-methyl-4-(trifluoromethyl)-2'H-spiro[cyclohexane-1,3'-imidazo[1,5-a]pyridine]-1',5'-dione (prepared according to example 127b, 100 mg, 253 µmol) and 6-fluoroquinazolin-4-amine (CAS 1190320-08-1, 45.4 mg, 278 µmop in 1,4-dioxane (10 mL) was added cesium carbonate (247 mg, 759 µmol) and the mixture was degassed and purged with argon several times. 4,5-Bis(diphenylphosphino)-9,9-dimethylxanthene (15.7 mg, 27.1 µmol), 2-(dicyclohexyl-phosphino)-2',4',6'-triisopropylbiphenyl (12.9 mg, 27.1 µmol), palladium(II) acetate (6.08 mg, 27.1 µmol) and tris(dibenzylideneacetone) dipalladium(0) (24.8 mg, 27.1 µmol) were added and the mixture was stirred at 100° C. for 2 hours. The mixture was concentrated and the residue purified by flash chromatography (Biotage SNAP cartridge silica 25 g, ethanol:dichloromethane). The isolated product was taken up in ethanol and stirred at RT. The solid was filtered off under vacuo, taken up in dichloromethane/ethanol again and stirred at RT. The solid was filtered off under vacuo and dried to give 4 mg (3% yield) of the title compound.

LC-MS: m/z=478.5 [M+H]$^+$.

$^1$H-NMR (400 MHz, DMSO-d6) δ [ppm]=1.232 (2.49), 1.360 (1.55), 1.427 (6.02), 1.458 (6.11), 1.818 (5.42), 1.853 (6.88), 1.937 (4.47), 1.964 (6.11), 1.997 (2.92), 2.326 (5.33), 2.381 (8.86), 2.668 (5.33), 3.440 (3.78), 3.466 (5.68), 3.499 (3.18), 5.758 (6.37), 5.991 (3.10), 6.008 (12.99), 7.830 (2.41), 7.852 (4.73), 7.868 (3.18), 7.935 (5.33), 7.949 (5.42), 7.958 (4.22), 7.971 (3.27), 8.030 (2.92), 8.150 (4.47), 8.168 (4.73), 8.615 (1.55), 8.643 (15.66), 8.797 (16.00), 9.351 (10.67), 10.469 (9.81), 10.605 (1.72).

Example 190

(cis)-6'-[(4-amino-1,3,5-triazin-2-yl)amino]-4-hydroxy-8'-methyl-4-(trifluoromethyl)-2'H-spiro[cyclohexane-1,3'-imidazo[1,5-a]pyridine]-1',5'-dione

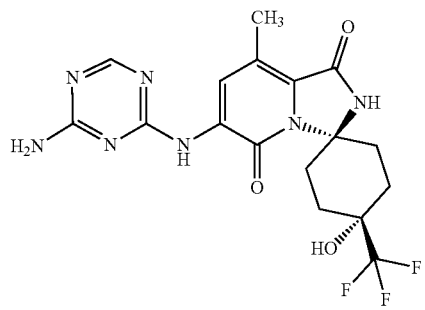 [SMILES: Cc1cc(Nc2ncnc(N)n2)c(=O)n2c1C(=O)N[C@]21CC[C@@](O)(C(F)(F)F)CC1]

In the first step a solution of (cis)-6'-bromo-4-hydroxy-8'-methyl-4-(trifluoromethyl)-2'H-spiro[cyclohexane-1,3'-imidazo[1,5-a]pyridine]-1',5'-dione (prepared according to example 127b, 150 mg, 380 µmol) and N-(4-amino-1,3,5-triazin-2-yl)cyclopropanecarboxamide (prepared according to example 190a, 74.8 mg, 418 µmol) in 1,4-dioxane (15 mL) was treated with cesium carbonate (23.5 mg, 40.6 µmol) and the mixture was degassed and purged with argon several times. 4,5-Bis(diphenylphosphino)-9,9-dimethylxanthene (19.4 mg, 40.6 µmol), 2-(dicyclohexyl-phosphino)-2',4',6'-triisopropylbiphenyl (9.12 mg, 40.6 µmol), palladium(II)-acetate (37.2 mg, 40.6 µmol) and tris(dibenzylideneacetone)dipalladium(0) (371 mg, 1.14 mmol) were added, the mixture was stirred at 100° C. for 2 hours and concentrated. In the second step this crude material was dissolved in a mixture of THF (3.0 mL, 36 mmol), ethanol (4.7 mL, 81 mmol) and water (3.0 mL, 160 mmol), aqueous potassium hydroxide solution (140 µL, 50 wt % in water, 1.9 mmol) was added and the mixture was stirred at RT for 72 hours. The reaction mixture was extracted with ethyl acetate and the organic layer was washed with brine, dried with sodium sulfate and concentrated. The obtained residue was taken up in ethanol and stirred at RT. The solid was filtered off under vacuo and dried to give 42 mg (25% yield) of the title compound.

LC-MS: m/z=426.6 [M+H]+.

$^1$H-NMR (400 MHz, DMSO-d6) δ [ppm]=1.232 (0.75), 1.343 (1.07), 1.370 (1.05), 1.496 (0.57), 1.780 (1.12), 1.813 (1.52), 1.915 (0.87), 1.941 (1.40), 1.954 (1.47), 1.975 (0.65), 2.468 (16.00), 2.518 (5.61), 2.522 (3.76), 2.781 (0.57), 2.941 (0.85), 3.365 (0.97), 3.389 (1.35), 3.399 (1.27), 3.422 (0.77), 7.453 (1.99), 8.066 (3.17), 8.266 (4.56), 8.459 (3.56).

Example 190a

N-(4-amino-1,3,5-triazin-2-yl)cyclopropanecarboxamide

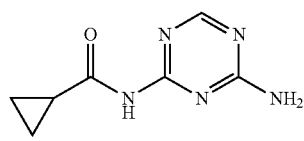 [SMILES: Nc1ncnc(NC(=O)C2CC2)n1]

A mixture of 1,3,5-triazine-2,4-diamine hydrochloride (CAS 504-08-5 for free base, 20.0 g, 136 mmol) in water (500 mL) was treated with cyclopropanecarboxylic anhydride (CAS 33993-24-7, 20 g, 130 mmol) and the resulting solution was stirred for 1 day at room temperature. For complete conversion three more portions of cyclopropanecarboxylic anhydride (20 g, 130 mmol each) were added to the reaction mixture, each time followed by stirring for three days at room temperature. Two batches with the same size of this reaction were combined for work up. The formed solids in the reaction mixture were filtered off and the crude product (1000 mL) was purified by preparative HPLC (column C18 silica gel, mobile phase ACN/water (0.05% NH4OH)=5% increasing to ACN/water (0.05% NH4OH)=20% within 12 min, Detector UV 254 nm) to give 10.5 g (22% yield) of the title compound.

LC-MS: m/z=180 [M+1-1]+.

$^1$H-NMR (300 MHz, DMSO-d6) δ [ppm]=10.47 (s, 1H), 8.29 (s, 1H), 7.39-7.31 (m, 2H), 2.25-2.33 (m, 1H), 0.82-0.80 (m, 4H).

Example 191

(cis)-4-hydroxy-8'-methyl-6'-[(5-methylquinazolin-4-yl)amino]-4-(pentafluoroethyl)-2'H-spiro[cyclohexane-1,3'-imidazo[1,5-a]pyridine]-1',5'-dione

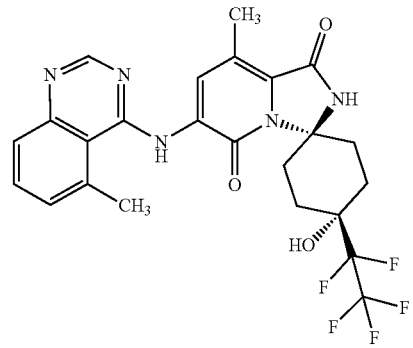 [SMILES: Cc1cc(Nc2ncnc3cccc(C)c23)c(=O)n2c1C(=O)N[C@]21CC[C@@](O)(C(F)(F)C(F)(F)F)CC1]

To a solution of (cis)-6'-bromo-4-hydroxy-8'-methyl-4-(pentafluoroethyl)-2'H-spiro[cyclohexane-1,3'-imidazo[1,5-a]pyridine]-1',5'-dione (prepared according to example 191b, 100 mg, 225 µmol) and 5-methylquinazolin-4-amine (commercial, 39.3 mg, 247 µmol) in 1,4-dioxane (8.9 mL) was added cesium carbonate (220 mg, 674 µmol) and the mixture was degassed and purged with argon several times. 4,5-Bis(diphenylphosphino)-9,9-dimethylxanthene (13.9 mg, 24.0 µmol), 2-(dicyclohexyl-phosphino)-2',4',6'-triisopropylbiphenyl (11.5 mg, 24.0 µmol), palladium(II)acetate (5.40 mg, 24.0 µmol) and tris(dibenzylideneacetone)dipalladium(0) (22.0 mg, 24.0 µmol) were added and the mixture was stirred at 100° C. for 2 hours. The mixture was filtered, concentrated and the residue purified by flash chromatography (Biotage SNAP cartridge silica 25 g, ethanol:dichloromethane). The isolated product was taken up in ethanol and stirred at RT. The solid was filtered off under vacuo and dried to give 38 mg (31% yield) of the title compound.

LC-MS: m/z=524.4 [M+H]+.

$^1$H-NMR (400 MHz, DMSO-d6) δ [ppm]=1.446 (1.55), 1.477 (1.58), 1.894 (1.01), 1.926 (1.76), 1.974 (1.01), 2.003 (1.34), 2.036 (0.57), 2.332 (1.19), 2.382 (0.51), 2.518 (6.87), 2.523 (5.82), 2.529 (16.00), 2.673 (1.19), 3.114 (9.04), 3.457

(0.72), 3.466 (0.81), 3.490 (1.37), 3.499 (1.31), 3.523 (0.78), 5.759 (1.01), 6.174 (4.51), 7.471 (1.49), 7.488 (1.70), 7.698 (1.04), 7.715 (2.48), 7.738 (2.63), 7.755 (2.12), 7.775 (0.99), 8.775 (6.93), 8.930 (6.27), 9.790 (2.90), 10.463 (3.31).

Example 191a

6'-bromo-4-hydroxy-8'-methyl-4-(pentafluoroethyl)-2'H-spiro[cyclohexane-1,3'-imidazo[1,5-a]pyridine]-1',5'-dione

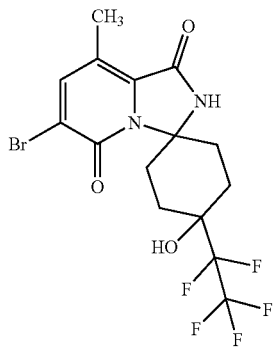 [SMILES: Cc1cc(Br)c(=O)n2c1C(=O)NC21CCC(O)(C(F)(F)C(F)(F)F)CC1]

To a solution of 3.22 g (13.9 mmol) 5-bromo-3-methyl-6-oxo-1,6-dihydropyridine-2-carboxamide (prepared according to PCT Int. Appl. (2015), WO 2015200481) and 4.85 g (20.9 mmol) 4-hydroxy-4-(pentafluoroethyl)-cyclohexan-1-one (prepared according to example 191d) in 1,4-dioxane (18 mL) were added 370 µL (7.0 mmol) concentrated sulfuric acid and the reaction mixture was stirred at 95° C. for 3 hours. The mixture was concentrated under reduced pressure and water was added. The resulting precipitate was filtered off under vacuo, taken up with water and stirred at RT. The solid was filtered off, washed with diethyl ether and dried to give 5.7 g (91% yield) of the title compound as a mixture of cis/trans isomers.

LC-MS: m/z=445.4/447.4 [M+H]$^+$ (Br isotope pattern).

$^1$H-NMR (400 MHz, DMSO-d6) δ [ppm]=1.373 (1.30), 1.404 (1.33), 1.578 (0.58), 1.612 (0.59), 1.859 (0.87), 1.893 (2.10), 1.944 (1.26), 1.978 (0.43), 2.332 (0.72), 2.336 (0.52), 2.351 (0.72), 2.377 (10.24), 2.382 (16.00), 2.518 (3.65), 2.522 (2.45), 2.673 (0.61), 2.964 (0.61), 3.377 (2.20), 3.389 (1.69), 3.411 (0.87), 3.422 (0.64), 3.565 (0.77), 6.101 (2.97), 8.023 (3.33), 8.030 (6.05), 10.497 (1.32), 10.623 (2.72).

The mixture of cis/trans isomers (5.7 g) was seperated by chiral preperative HPLC to give 3.5 g of example 191b (cis isomer) and 1.3 g of example 191c (trans isomer).

Preparation:
Instrument: Labomatic HD5000, Labocord-5000; Gilson GX-241, Labcol Vario 4000, column: Amylose SA 5 µm 250×50 mm; eluent A: hexane+0.1 vol-% diethylamine (99%); eluent B: ethanol; isokratic: 50% A+50% B; flow 80.0 mL/min; UV 325 nm.

Example 191b (cis)-6'-bromo-4-hydroxy-8'-methyl-4-(pentafluoroethyl)-2'H-spiro[cyclohexane-1,3'-imidazo[1,5-a]pyridine]-1',5'-dione

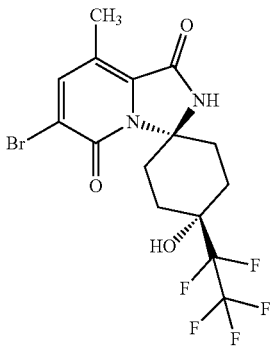 [SMILES: Cc1cc(Br)c(=O)n2c1C(=O)N[C@]21CC[C@@](O)(C(F)(F)C(F)(F)F)CC1]

The title compound was isolated in the preparative chiral HPLC of example 191a.
Analytical HPLC-Method:
Instrument: Agilent HPLC 1260; column: Amylose SA 3 µm 100×4.6 mm; eluent A: hexane+0.1 vol-% diethylamine (99%); eluent B: ethanol; isokratic: 50% A+50% B; flow 1.4 mL/min; temperature: 25° C.; DAD 325 nm.
Rt=1.02 min.
$^1$H-NMR (400 MHz, DMSO-d6) δ[ppm]=1.371 (0.23), 1.402 (0.24), 1.892 (0.28), 1.909 (0.20), 1.918 (0.17), 1.945 (0.20), 1.952 (0.20), 2.083 (0.91), 2.381 (2.76), 2.539 (16.00), 3.378 (0.22), 3.390 (0.20), 6.101 (0.75), 8.027 (1.16), 10.620 (0.17).

Example 191c (trans)-6'-bromo-4-hydroxy-8'-methyl-4-(pentafluoroethyl)-2'H-spiro[cyclohexane-1,3'-imidazo[1,5-a]pyridine]-1',5'-dione

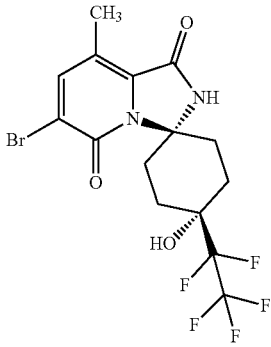 [SMILES: Cc1cc(Br)c(=O)n2c1C(=O)N[C@]21CC[C@](O)(C(F)(F)C(F)(F)F)CC1]

The title compound was isolated in the preparative chiral HPLC of example 191a.
Analytical HPLC-method:
Instrument: Agilent HPLC 1260; column: Amylose SA 3 µm 100×4.6 mm; eluent A: hexane+0.1 vol-% diethylamine (99%); eluent B: ethanol; isokratic: 50% A+50% B; flow 1.4 mL/min; temperature: 25° C.; DAD 325 nm.
Rt=1.77 min.

¹H-NMR (400 MHz, DMSO-d6) δ [ppm]=1.052 (0.50), 1.578 (1.03), 1.613 (1.08), 1.869 (0.50), 1.895 (1.05), 1.929 (0.62), 2.084 (0.66), 2.323 (0.50), 2.327 (0.74), 2.332 (0.66), 2.337 (0.64), 2.351 (1.21), 2.377 (16.00), 2.518 (2.90), 2.523 (1.91), 2.539 (4.37), 2.665 (0.46), 2.669 (0.67), 2.673 (0.47), 2.931 (0.54), 2.940 (0.64), 2.965 (1.10), 2.973 (1.05), 2.998 (0.59), 6.100 (5.85), 8.024 (6.20), 10.497 (2.45).

Example 191d 4-hydroxy-4-(pentafluoroethyl)cyclohexan-1-one

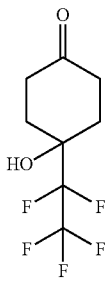

A solution of 8-(pentafluoroethyl)-1,4-dioxaspiro[4.5]decan-8-ol (prepared according to example 191e, 17.8 g, 64.4 mmol) in THF (99 mL) was treated with aqueous hydrochloric acid (49 mL, 1.0 M, 49 mmol) and the mixture was stirred at room temperature for 24 hours. The reaction mixture was concentrated in vacuo and the residue extracted with a mixture of dichloromethane/methanol. The layers were separated and the organic layer was dried, concentrated and the residue purified by flash chromatography (Biotage SNAP cartridge silica 340 g, ethyl acetate:hexane) to give 9.7 g (52% yield) of the title compound.

LC-MS: m/z=233.4 [M+H]⁺.

¹H-NMR (400 MHz, DMSO-d6) δ[ppm]=1.561 (0.88), 1.572 (0.78), 1.589 (1.59), 1.700 (1.02), 1.732 (1.32), 1.748 (2.09), 1.779 (2.51), 1.813 (1.15), 1.973 (1.06), 1.986 (1.75), 2.007 (3.60), 2.018 (4.27), 2.040 (3.38), 2.055 (6.36), 2.073 (4.92), 2.107 (1.56), 2.162 (3.69), 2.194 (4.15), 2.200 (4.36), 2.547 (2.84), 2.563 (3.02), 2.583 (3.42), 2.600 (3.36), 2.617 (2.25), 2.634 (2.01), 3.864 (16.00), 5.935 (3.24), 6.375 (12.92).

Example 191e 8-(pentafluoroethyl)-1,4-dioxaspiro[4.5]decan-8-ol

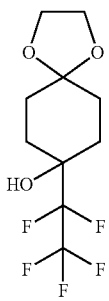

1,1,1,2,2-Pentafluoro-2-iodoethane (CAS 354-64-3, 26 mL, 224 mmol) was cooled to −78° C. and a solution of 1,4-dioxaspiro[4.5]decan-8-one (CAS 4746-97-8, 10.0 g, 64.0 mmol) in dichloromethane (150 mL) was added. Methyllithium (140 mL, 1.5 M in diethyl ether, complexed with lithium bromide, 200 mmol) was slowly added to the reaction mixture and it was stirred at −70° C. for 50 minutes. The mixture was poured onto ice water, stirred and the layers were separated. The aqueous layer was extracted with dichloromethane and ethyl acetate. The combined organic layers were washed, dried and concentrated in vacuo. The residue was purified by flash chromatography (Biotage SNAP cartridge silica 340 g, ethyl acetate:hexane) to give 17.8 g (quant.) of the title compound.

LC-MS: m/z=277.4 [M+H]⁺.

¹H-NMR (400 MHz, DMSO-d6) δ[ppm]=1.172 (0.73), 1.561 (0.69), 1.572 (0.58), 1.589 (1.30), 1.698 (0.82), 1.731 (1.08), 1.746 (1.73), 1.778 (1.99), 1.808 (0.90), 1.987 (1.37), 2.518 (0.96), 2.522 (0.63), 3.329 (16.00), 5.935 (3.13).

Example 192

(cis)-6'-[(6-fluoroquinazolin-4-yl)amino]-4-hydroxy-8'-methyl-4-(pentafluoroethyl)-2'H-spiro[cyclohexane-1,3'-imidazo[1,5-a]pyridine]-1',5'-dione

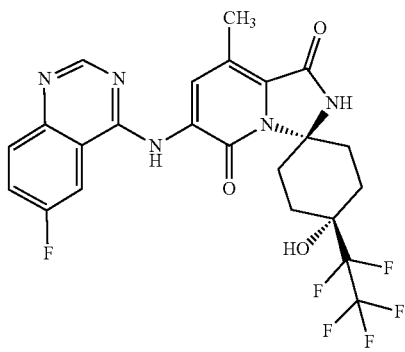 [SMILES: Cc1cc(Nc2ncnc3ccc(F)cc23)c(=O)n2c1C(=O)N[C@]21CC[C@@](O)(C(F)(F)C(F)(F)F)CC1]

To a solution of (cis)-6'-bromo-4-hydroxy-8'-methyl-4-(pentafluoroethyl)-2'H-spiro[cyclohexane-1,3'-imidazo[1,5-a]pyridine]-1',5'-dione (prepared according to example 191b, 100 mg, 225 mmol) and 6-fluoroquinazolin-4-amine (CAS 1190320-08-1, 40.3 mg, 247 µmol) in 1,4-dioxane (9 mL) was added cesium carbonate (220 mg, 674 µmol) and the mixture was degassed and purged with argon several times. 4,5-Bis(diphenylphosphino)-9,9-dimethylxanthene (13.9 mg, 24.0 µmol), 2-(dicyclohexyl-phosphino)-2',4',6'-triisopropylbiphenyl (11.5 mg, 24.0 µmol), palladium(II) acetate (5.40 mg, 24.0 µmol) and tris(dibenzylideneacetone)dipalladium(0) (22.0 mg, 24.0 µmol) were added and the mixture was stirred at 100° C. for 2 hours. The mixture was filtered, concentrated and the residue purified by flash chromatography (Biotage SNAP cartridge silica 25 g, ethanol:dichloromethane). The isolated product was taken up in ethanol and stirred at RT. The solid was filtered off under vacuo and dried to give 68 mg (55% yield) of the title compound.

LC-MS: m/z=528.1 [M+H]⁺.

¹H-NMR (400 MHz, DMSO-d6) δ [ppm]=1.231 (0.92), 1.440 (3.58), 1.471 (3.62), 1.905 (2.66), 1.934 (4.08), 1.973 (2.48), 2.001 (3.07), 2.034 (1.24), 2.332 (1.88), 2.336 (0.83), 2.371 (0.69), 2.518 (12.61), 2.523 (7.43), 2.539 (0.96), 2.673 (1.97), 2.678 (0.87), 3.458 (1.60), 3.468 (1.83), 3.490 (3.16), 3.502 (2.98), 3.523 (1.79), 3.534 (1.38), 6.115

(10.54), 7.823 (1.51), 7.829 (1.79), 7.845 (2.93), 7.852 (3.35), 7.867 (2.29), 7.873 (2.57), 7.934 (4.03), 7.948 (4.08), 7.957 (2.98), 7.971 (2.70), 8.130 (3.07), 8.137 (3.26), 8.154 (3.21), 8.161 (3.12), 8.634 (14.72), 8.795 (16.00), 9.351 (7.79), 10.487 (7.06).

Example 193

(cis)-4-hydroxy-8'-methyl-4-(pentafluoroethyl)-6'-[(thieno[2,3-d]pyrimidin-4-yl)amino]-2'H-spiro[cyclohexane-1,3'-imidazo[1,5-a]pyridine]-1',5'-dione

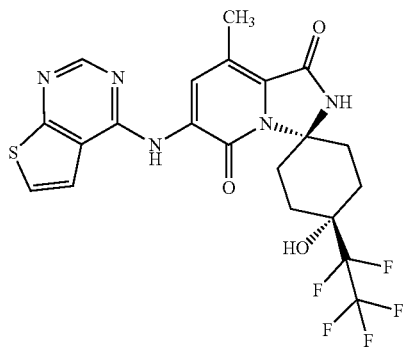 [SMILES: Cc1cc(Nc2ncnc3sccc23)c(=O)n2c1C(=O)N[C@]21CC[C@@](O)(C(F)(F)C(F)(F)F)CC1]

To a solution of (cis)-6'-bromo-4-hydroxy-8'-methyl-4-(pentafluoroethyl)-2'H-spiro[cyclohexane-1,3'-imidazo[1,5-a]pyridine]-1',5'-dione (prepared according to example 191b, 100 mg, 225 μmol) and thieno[2,3-d]pyrimidin-4-amine (CAS 14080-56-9, 37.4 mg, 247 μmol) in 1,4-dioxane (7.3 mL) was added cesium carbonate (220 mg, 674 μmol) and the mixture was degassed and purged with argon several times. 4,5-Bis(diphenylphosphino)-9,9-dimethylxanthene (13.9 mg, 24.0 μmol), 2-(dicyclohexyl-phosphino)-2',4',6'-triisopropylbiphenyl (11.5 mg, 24.0 μmol), palladium(II) acetate (5.40 mg, 24.0 μmol) and tris(dibenzylideneacetone)dipalladium(0) (22.0 mg, 24.0 μmol) were added and the mixture was stirred at 100° C. for 2 hours. The mixture was filtered, concentrated and the residue purified by flash chromatography (Biotage SNAP cartridge silica 25 g, ethanol:dichloromethane). The isolated product was taken up in ethanol and stirred at RT. The solid was filtered off under vacuo and dried to give 58 mg (48% yield) of the title compound.

LC-MS: m/z=516.3 [M+H]$^+$.

$^1$H-NMR (400 MHz, DMSO-d6) δ [ppm]=1.035 (1.25), 1.053 (2.45), 1.070 (1.32), 1.429 (3.01), 1.458 (3.01), 1.894 (1.88), 1.926 (3.45), 1.970 (2.01), 1.996 (2.57), 2.030 (1.13), 2.323 (2.64), 2.327 (3.51), 2.382 (0.82), 2.522 (16.00), 2.539 (3.89), 2.665 (2.57), 2.669 (3.45), 3.159 (7.65), 3.172 (7.40), 3.422 (0.69), 3.435 (0.82), 3.439 (0.88), 3.452 (1.95), 3.463 (1.57), 3.485 (2.70), 3.495 (2.51), 3.518 (1.51), 4.081 (0.69), 4.094 (1.95), 4.107 (1.88), 4.121 (0.56), 4.354 (0.82), 6.099 (8.41), 7.813 (4.45), 7.828 (9.91), 7.849 (10.23), 7.864 (4.58), 8.638 (11.86), 8.697 (13.11), 9.070 (7.34), 10.446 (6.15).

Example 194

(cis)-4-hydroxy-8'-methyl-4-(pentafluoroethyl)-6'-[(7H-pyrrolo[2,3-d]pyrimidin-4-yl)amino]-2'H-spiro[cyclohexane-1,3'-imidazo[1,5-a]pyridine]-1',5'-dione

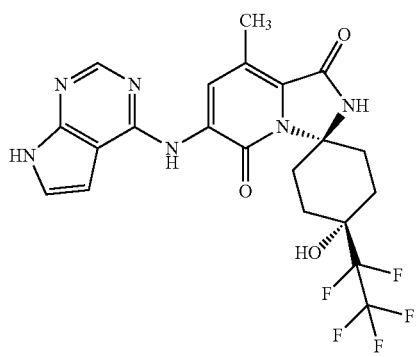 [SMILES: Cc1cc(Nc2ncnc3[nH]ccc23)c(=O)n2c1C(=O)N[C@]21CC[C@@](O)(C(F)(F)C(F)(F)F)CC1]

A mixture of crude tert-butyl 4-{[(cis)-4-hydroxy-8'-methyl-1',5'-dioxo-4-(pentafluoroethyl)-1',5'-dihydro-2'H-spiro[cyclohexane-1,3'-imidazo[1,5-a]pyridin-6'-yl]amino}-7H-pyrrolo[2,3-d]pyrimidine-7-carboxylate (prepared according to example 194a, 170 mg, 284 μmol) in dichloromethane (3.6 mL) was treated with trifluoroacetic acid (219 μL, 2.84 mmol) and stirred at RT over night. The mixture was carefully poured onto aqueous ammonia solution (25%) and extracted with a mixture of dichloromethane/methanol. The organic layer was washed with water, dried over sodium sulfate and concentrated. The crude product was taken up in ethanol and stirred at RT. The solid was filtered off under vacuo and dried to give a first crop of product (7 mg). The aqueous layer was concentrated in vacuo and the obtained residue taken up in DMSO. The inorganic material was filtered off and the filtrate concentrated in vacuo and taken up in ethanol. The solid was filtered off to give a second crop of product (360 mg). Both crops were combined, taken up in ethanol and stirred at RT. The solid was filtered off and the filtrate concentrated in vacuo to give 62 mg (42% yield) of the title compound.

LC-MS: m/z=499.3 [M+H]$^+$.

$^1$H-NMR (400 MHz, DMSO-d6) δ[ppm]=1.43 (2H), 1.89-2.04 (4H), 2.50 (3H*), 3.46-3.53 (2H), 6.09 (1H), 6.81 (1H), 7.38 (1H), 8.46 (1H), 8.64 (1H), 8.73 (1H), 10.36 (1H), 12.02 (1H).

*: hidden by solvent peak.

Example 194a tert-butyl 4-{[(cis)-4-hydroxy-8'-methyl-1',5'-dioxo-4-(pentafluoroethyl)-1',5'-dihydro-2'H-spiro[cyclo-hexane-1,3'-imidazo[1,5-a]pyridin]-6'-yl]amino}-7H-pyrrolo[2,3-d]pyrimidine-7-carboxylate

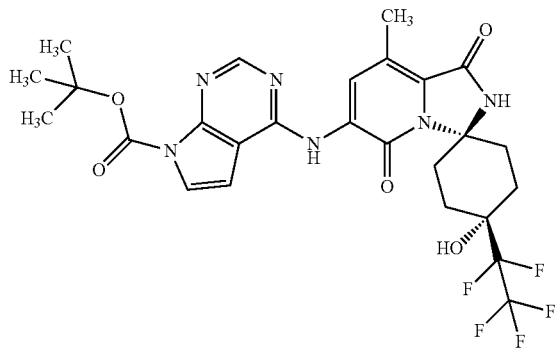 [SMILES: Cc1cc(Nc2ncnc3c2ccn3C(=O)OC(C)(C)C)c(=O)n2c1C(=O)N[C@]21CC[C@@](O)(C(F)(F)C(F)(F)F)CC1]

To a solution of (cis)-6'-bromo-4-hydroxy-8'-methyl-4-(pentafluoroethyl)-2'H-spiro[cyclo-hexane-1,3'-imidazo[1,5-a]pyridine]-1',5'-dione (prepared according to example 191b, 120 mg, 270 µmol) and tert-butyl 4-amino-7H-pyrrolo[2,3-d]pyrimidine-7-carboxylate (prepared according to example 178b, 111 mg, 475 µmol) in 1,4-dioxane (7 mL) was added cesium carbonate (263 mg, 809 µmol) and the mixture was degassed and purged with argon several times. 4,5-Bis(diphenylphosphino)-9,9-dimethylxanthene (17 mg, 29 µmol), 2-(dicyclohexyl-phosphino)-2',4',6'-triisopropyl-biphenyl (14 mg, 29 µmol), palladium(II)acetate (6.5 mg, 29 µmol) and tris(dibenzylideneacetone)dipalladium(0) (26 mg, 29 µmol) were added and the mixture was stirred at 100° C. for 2 hours. The mixture was concentrated and the obtained residue used in the next step without further purification.

Example 195

(cis)-6'-[(6-chloroquinazolin-4-yl)amino]-4-hydroxy-8'-methyl-4-(pentafluoroethyl)-2'H-spiro[cyclo-hexane-1,3'-imidazo[1,5-a]pyridine]-1',5'-dione

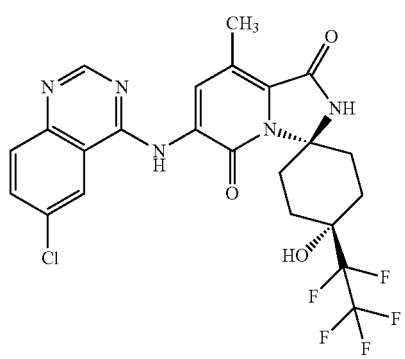 [SMILES: Cc1cc(Nc2ncnc3ccc(Cl)cc23)c(=O)n2c1C(=O)N[C@]21CC[C@@](O)(C(F)(F)C(F)(F)F)CC1]

To a solution of (trans)-6'-bromo-4-hydroxy-8'-methyl-4-(pentafluoroethyl)-2'H-spiro[cyclohexane-1,3'-imidazo[1,5-a]pyridine]-1',5'-dione (prepared according to example 191c, 100 mg, 225 µmol) and 6-chloroquinazolin-4-amine (CAS 19808-35-6, 44.4 mg, 247 µmol) in 1,4-dioxane (8.9 mL) was added cesium carbonate (220 mg, 674 µmol) and the mixture was degassed and purged with argon several times. 4,5-Bis(diphenylphosphino)-9,9-dimethylxanthene (13.9 mg, 24.0 µmol), 2-(dicyclohexyl-phosphino)-2',4',6'-triisopropylbiphenyl (11.5 mg, 24.0 µmol), palladium(II) acetate (5.40 mg, 24.0 µmol) and tris(dibenzylideneacetone) dipalladium(0) (22.0 mg, 24.0 µmol) were added and the mixture was stirred at 100° C. for 2 hours. The mixture was concentrated and the residue purified by flash chromatography (Biotage SNAP cartridge silica 25 g, ethanol:dichloromethane). The isolated product was taken up in ethanol and stirred at RT. The solid was filtered off under vacuo and dried to give 56 mg (41% yield) of the title compound (isomerisation of one chiral center under the reaction conditions).

LC-MS: m/z=544.1 [M+H]$^+$.

$^1$H-NMR (400 MHz, DMSO-d6) δ [ppm]=0.851 (0.48), 1.088 (0.57), 1.144 (0.57), 1.215 (0.76), 1.232 (2.48), 1.439 (3.33), 1.470 (3.52), 1.905 (3.90), 1.934 (4.00), 1.971 (2.57), 2.001 (3.14), 2.031 (1.43), 2.322 (4.00), 2.326 (5.43), 2.331 (4.00), 2.371 (0.48), 2.522 (16.00), 2.539 (2.86), 2.543 (2.67), 2.664 (4.19), 2.669 (5.43), 2.673 (4.00), 3.469 (1.81), 3.492 (3.05), 3.502 (2.86), 3.525 (1.81), 6.117 (8.95), 6.145 (0.57), 7.872 (3.43), 7.894 (6.76), 7.932 (4.48), 7.938 (4.67), 7.954 (2.29), 7.960 (2.48), 8.429 (5.52), 8.434 (5.43), 8.593 (10.19), 8.747 (0.67), 8.790 (0.76), 8.803 (11.33), 8.822 (0.86), 8.838 (0.48), 9.478 (5.81), 10.495 (5.90).

Example 196

8-methyl-6-(7H-pyrrolo[2,3-d]pyrimidin-4-ylamino)-2',3',5',6'-tetrahydro-2H-spiro[imidazo[1,5-a]pyridine-3,4'-thiopyran]-1,5-dione

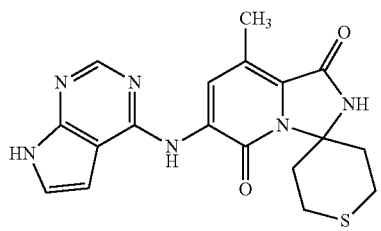 [SMILES: Cc1cc(Nc2ncnc3[nH]ccc23)c(=O)n2c1C(=O)NC21CCSCC1]

To a solution of 100 mg (304 µmol) 6-bromo-8-methyl-2',3',5',6'-tetrahydro-2H-spiro[imidazo[1,5-a]pyridine-3,4'-thiopyran]-1,5-dione (prepared according to example 196a) and 45 mg (334 µmol) 7H-pyrrolo[2,3-d]pyrimidin-4-amine (CAS-No: 1500-85-2) in 10 mL 1,4-dioxane were added 326 mg cesium carbonate and the mixture was degassed and purged with argon several times. 19 mg 4,5-Bis(diphenylphosphino)-9,9-dimethylxanthene, 15 mg 2-(dicyclohexyl-phosphino)-2',4',6'-triisopropylbiphenyl, 7 mg palladium(II)acetate and 30 mg tris(dibenzylideneacetone) dipalladium(0) were added, the mixture was degassed and purged with argon and stirred at 100° C. for 2 hours. The reaction mixture was concentrated and the residue purified by flash chromatography (Biotage SNAP cartridge silica 25 g 15 µM, dichloromethane/methanol). The fractions containing the title compound were pooled and concentrated. The obtained material was taken up with dichloromethane and ethanol, stirred at RT and filtrated. The isolated solid was washed with dichloromethane and dried to give 9.8 mg (8%) of the title compound.

LC-MS: m/z=383.1 [M+H]⁺.

¹H-NMR (400 MHz, DMSO-d6), δ [ppm]=1.81-1.84 (2H), 2.50 (3H*), 2.66-2.70 (2H), 3.03 (2H), 3.28 (2H*), 6.80 (1H), 7.38 (1H), 8.46 (1H), 8.63 (1H), 8.72 (1H), 10.20 (1H), 12.01 (1H).

*: (partially) hidden by solvent/water peak

Example 196a 6-bromo-8-methyl-2',3',5',6'-tetrahydro-2H-spiro[imidazo[1,5-a]pyridine-3,4'-thiopyran]-1,5-dione

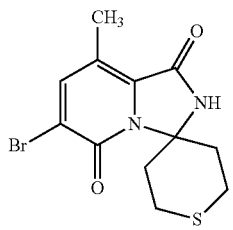 [SMILES: Cc1cc(Br)c(=O)n2c1C(=O)NC21CCSCC1]

To a solution of 555 mg (2.40 mmol) 5-bromo-3-methyl-6-oxo-1,6-dihydropyridine-2-carboxamide (CAS-No: 1849594-90-6; PCT Int. Appl. (2015), WO 2015200481) and 558 mg (4.80 mmol) tetrahydro-4H-thiopyran-4-one (CAS-No: 1072-72-6) in 7 mL 1,4-dioxane were added 64 µL (1.20 mmol) conc. sulfuric acid and the mixture was stirred at 95° C. for 3 hours. The reaction mixture was concentrated and water was added. The precipitate was filtered off, washed with water and diethylether and dried to give 790 mg (99%) of the title compound.

LC-MS: m/z=329.0/331.0 [M+H]⁺ (Br isotope pattern).

¹H-NMR (400 MHz, DMSO-d6), δ [ppm]=1.76-1.79 (2H), 2.38 (3H), 2.64-2.67 (2H), 2.98 (2H), 3.17 (2H), 8.04 (1H), 10.46 (1H).

Example 197

6-[(6-chloroquinazolin-4-yl)amino]-8-methyl-2',3',5',6'-tetrahydro-2H-spiro[imidazo[1,5-a]pyridine-3,4'-thiopyran]-1,5-dione

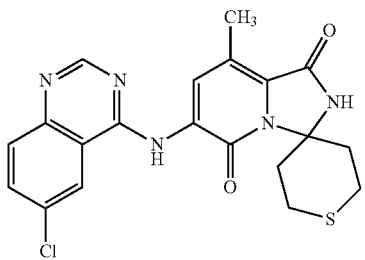 [SMILES: Cc1cc(Nc2ncnc3ccc(Cl)cc23)c(=O)n2c1C(=O)NC21CCSCC1]

To a solution of 101 mg (307 µmol) 6-bromo-8-methyl-2',3',5',6'-tetrahydro-2H-spiro[imidazo[1,5-a]pyridine-3,4'-thiopyran]-1,5-dione (prepared according to example 196a) and 60.6 mg (337 µmol) 6-chloroquinazolin-4-amine (CAS-No: 19$08-35-0) in 10 mL 1,4-dioxane were added 300 mg cesium carbonate and the mixture was degassed and purged with argon several times. 19 mg 4,5-Bis(diphenylphosphino)-9,9-dimethylxanthene, 16 mg 2-(dicyclohexyl-phosphino)-2',4',6'-triisopropylbiphenyl, 7 mg palladium(II)acetate and 30 mg tris(dibenzylideneacetone)dipalladium(0) were added, the mixture was degassed and purged with argon and stirred at 100° C. for 2.5 hours. The reaction mixture was concentrated and the residue purified by flash chromatography (Biotage SNAP cartridge silica 25 g 15 µM, dichloromethane/methanol). The fractions containing the title compound were pooled and concentrated. The obtained material was taken up with dichloromethane, stirred at RT and filtrated. The isolated solid was washed with dichloromethane and dried to give 14.6 mg (10%) of the title compound.

LC-MS: m/z=428.0/430.0 [M+H]⁺ (Cl isotope pattern).

¹H-NMR (400 MHz, DMSO-d6), δ [ppm]=1.83-1.86 (2H), 2.50 (3H*), 2.67-2.71 (2H), 3.03 (2H), 3.24-3.31 (2H*), 7.88 (1H), 7.95 (1H), 8.43 (1H), 8.59 (1H), 8.79 (1H), 9.46 (1H), 10.32 (1H).

*: (partially) hidden by solvent/water peak

Example 198

8-methyl-6-(7H-pyrrolo[2,3-d]pyrimidin-4-ylamino)-2',3',5',6'-tetrahydro-2H-spiro[imidazo[1,5-a]pyridine-3,4'-thiopyran]-1,5-dione 1',1'-dioxide

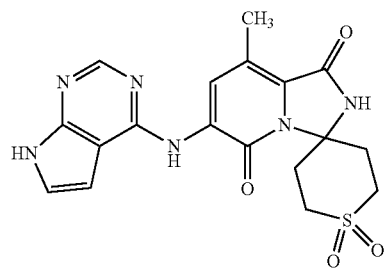 [SMILES: Cc1cc(Nc2ncnc3[nH]ccc23)c(=O)n2c1C(=O)NC21CCS(=O)(=O)CC1]

To a solution of 100 mg (277 µmol) 6-bromo-8-methyl-2',3',5',6'-tetrahydro-2H-spiro[imidazo[1,5-a]pyridine-3,4'-thiopyran]-1,5-dione 1',1'-dioxide (prepared according to example 198a) and 41 mg (305 µmol) 7H-pyrrolo[2,3-d]pyrimidin-4-amine (CAS-No: 1500-85-2) in 10 mL 1,4-dioxane were added 271 mg cesium carbonate and the mixture was degassed and purged with argon several times. 17 mg 4,5-Bis(diphenylphosphino)-9,9-dimethylxanthene, 14 mg 2-(dicyclohexyl-phosphino)-2',4',6'-triisopropylbiphenyl, 7 mg palladium(II)acetate and 27 mg tris(dibenzylideneacetone)dipalladium(0) were added, the mixture was degassed and purged with argon and stirred at 100° C. for 2.5 hours. The reaction mixture was concentrated and the residue purified by flash chromatography (Biotage SNAP cartridge silica 25 g 15 µM, dichloromethane/methanol) to give 40 mg (32%) of the title compound.

LC-MS: m/z=415.1 [M+H]⁺.

¹H-NMR (400 MHz, DMSO-d6), δ [ppm]=2.00-2.03 (2H), 2.50 (3H*), 3.27-3.30 (2H*), 3.49 (2H), 3.77 (2H), 6.85 (1H), 7.38 (1H), 8.47 (1H), 8.65 (1H), 8.75 (1H), 10.38 (1H), 12.03 (1H).

*: (partially) hidden by solvent/water peak

Example 198a 6-bromo-8-methyl-2',3',5',6'-tetrahydro-2H-spiro[imidazo[1,5-a]pyridine-3,4'-thiopyran]-1,5-dione 1',1'-dioxide

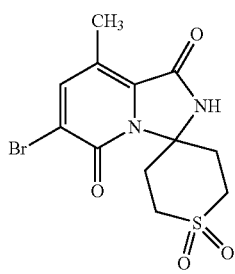

To a solution of 583 mg (2.52 mmol) 5-bromo-3-methyl-6-oxo-1,6-dihydropyridine-2-carboxamide (CAS-No: 1849594-90-6; PCT Int. Appl. (2015), WO 2015200481) and 748 mg (5.05 mmol) tetrahydro-4H-thiopyran-4-one 1,1-dioxide (CAS-No: 17396-35-9) in 7 mL 1,4-dioxane were added 67 µL (1.26 mmol) conc. sulfuric acid and the mixture was stirred at 95° C. for 3 hours. The reaction mixture was concentrated and water was added. The precipitate was filtered off, washed with water and diethylether and dried to give 381 mg (90%) of the title compound.

LC-MS: m/z=360.9/362.9 [M+H]$^+$ (Br isotope pattern).
$^1$H-NMR (400 MHz, DMSO-d6), δ [ppm]=1.97-2.00 (2H), 2.38 (3H), 3.25-3.29 (2H*), 3.43 (2H), 3.63 (2H), 8.07 (1H), 10.63 (1H).
*: partially hidden by water peak

Example 199

6-[(6-chloroquinazolin-4-yl)amino]-8-methyl-2',3',5',6'-tetrahydro-2H-spiro[imidazo[1,5-a]pyridine-3,4'-thiopyran]-1,5-dione 1',1'-dioxide

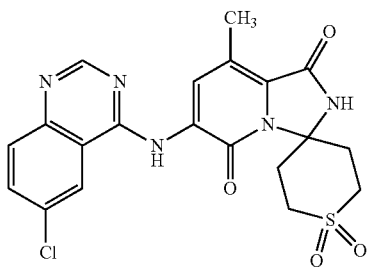 [SMILES: Cc1cc(Nc2ncnc3ccc(Cl)cc23)c(=O)n2c1C(=O)NC21CCS(=O)(=O)CC1]

To a solution of 102 mg (282 µmol) 6-bromo-8-methyl-2',3',5',6'-tetrahydro-2H-spiro[imidazo[1,5-a]pyridine-3,4'-thiopyran]-1,5-dione 1',1'-dioxide (prepared according to example 198a) and 55.8 mg (311 µmol) 6-chloroquinazolin-4-amine (CAS-No: 19808-35-3) in 10 mL 1,4-dioxane were added 276 mg cesium carbonate and the mixture was degassed and purged with argon several times. 17 mg 4,5-Bis(diphenylphosphino)-9,9-dimethylxanthene, 14 mg 2-(dicyclohexyl-phosphino)-2',4',6'-triisopropylbiphenyl, 7 mg palladium(II)acetate and 28 mg tris(dibenzylideneacetone)dipalladium(0) were added, the mixture was degassed and purged with argon and stirred at 100° C. for 2.5 hours. The reaction mixture was concentrated and the residue purified by flash chromatography (Biotage SNAP cartridge silica 25 g 15 µM, dichloromethane/methanol) to give 30 mg (22%) of the title compound.

LC-MS: m/z=460.0/462.0 [M+H]$^+$ (Cl isotope pattern).
$^1$H-NMR (400 MHz, DMSO-d6), δ [ppm]=2.03-2.06 (2H), 2.50 (3H*), 3.28-3.33 (2H*), 3.49 (2H), 3.76 (2H), 7.89 (1H), 7.95 (1H), 8.49 (1H), 8.62 (1H), 8.81 (1H), 9.47 (1H), 10.50 (1H).
*: (partially) hidden by solvent/water peak Pharmaceutical Compositions of the Compounds of the Invention This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc); tablet lubricants (examples include but are not limited to calcium stearate, magnesium stearate, mineral oil, stearic acid and zinc stearate);

tablet/capsule opaquants (examples include but are not limited to titanium dioxide); tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride); viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilised powder for IV administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known chemotherapeutic agents or anti-cancer agents, e.g. anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, topoisomerase inhibitors, proteasome inhibitors, biological response modifiers, anti-hormones or agents used for the treatment of inflammatory diseases or pain disorders.

The terms "chemotherapeutic agent" and anti-cancer agent", include but are not limited to 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, BAY 86-9766 (RDEA 119), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, deforolimus, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, enzastaurin, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, larotaxel, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, novolimus, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, perifosine, picibanil, pirarubicin, plerixafor, plicamycin, poliglusam, polyestradiol phosphate, polysaccharide-K, porfimer sodium, pralatrexate, prednimustine, procarbazine, quinagolide, raloxifene, raltitrexed, ranimustine, rapamycin, razoxane, regorafenib, risedronic acid, rituximab, romidepsin, romiplostim, sagopilone, sargramostim, selumetinib, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trametinib, trastuzumab, treosulfan, tretinoin, triciribine, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin, zotarolimus, ARRY-162, ARRY-300, ARRY-704, AS-703026, AZD-5363, AZD-8055, BEZ-235, BGT-226, BKM-120, BYL-719, CAL-101, CC-223, CH-5132799, E-6201, GDC-0032, GDC-0068, GDC-0623, GDC-0941, GDC-0973, GDC-0980, GSK-2110183, GSK-2126458, GSK-2141795, INK128, MK-2206, OSI-027, PF-04691502, PF-05212384, PX-866, RG-7167, RO-4987655, RO-5126766, TAK-733, UCN-01, WX-554, XL-147, XL-765, ZSTK-474.

The terms "chemotherapeutic agent" and anti-cancer agent", also include protein therapeutics such as an interferon (e.g., interferon.alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, labetuzumab, alpha-particle-emitting radioisotope-llinked lintuzumab, EM-1421, HyperAcute vaccine, tucotuzumab celmoleukin, galiximab, HPV-16-E7, Javelin-prostate cancer, Javelin-melanoma, NY-ESO-1 vaccine, EGF vaccine, CYT-004-MelQbG10, WT1 peptide, oregovomab, ofatumumab, zalutumumab, cintredekin besudotox, WX-G250, Albuferon, aflibercept, denosumab, vaccine, CTP-37, efungumab, or 131I-chTNT-1/B.

The terms "chemotherapeutic agent" and "anti-cancer agent", also include monoclonal antibodies useful as the protein therapeutic such as muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Beyond the "chemotherapeutic agent" and "anti cancer agent" the invention can be combined with further "anti-inflammatory" and "anti-pain agents" which include but are not limited to abatacept, or anti-bacterial agents (e.g. penicillin, vancomycin, ciprofloxacin), anti-viral agents (e.g. aciclovir, oseltamivir), anti-mycotic agents (e.g. naftifine, nystatin), azathioprine, belimumab, corticosteroids (e.g. prednisone, prednisolone, methylprednisolone, hydrocortisone, betamethasone), cyclophosphamide, IgE antibody, immunoglobulin and gammaglobuline, IL-1 inhibitors (e.g. anakinra, canakinumab, rilonacept), "immunomodulatory and immunosuppressive agents" like cyclosporine, mercaptopurine, Methotrexat®; interferon including beta-interferon (IFN beta-1a: Avonex® and IFN beta-1b: Betaferon®), Jak/STAT inhibitors (e.g. tofacitinib, baricitinib, GLPG0634), leflunomide, mycophenolic acid, nonsteroidal anti-inflammatory drugs (NSAIDS) (e.g. ibuprofen, naproxen, etodolac, celecoxib, colchicine), paracetamol, phosphodiesterase-inhibitor (e.g. apremilast, roflumilast), rapamycin, rituximab, sulfasalazine, tacrolimus and TNF-antagonist (e.g. Humira®, etanercept, infliximab).

In addition, combination also includes ACE (angiotensin-converting-enzyme) inhibitors (e.g. benazepril), acetylsalicylic acid, acetylcholinesterase inhibitors (e.g. donepezil, rivastigmine, galantamine, tacrine), anticholinergic agents (e.g. trihexyphenidyle, glycopyrronium bromid), anticonvulsant agents (e.g. gabapentin), anti-diarrhoeal drug (e.g. loperamide or laxatives), antileukotriene agents (e.g. montelukast), beta blocker (e.g. metoprolol), beta2-adrenergic agonists (e.g. salbutamol), calcium channel blockers (e.g. nifedipine), chloroquine, COMT (Catechol-O-Methyltransferase)-inhibitors (e.g. entacapone), diuretics (e.g. hydrochlorothiazide), dopamine agonists (e.g. ropinrole, pramipexole, bromocriptine), efalizumab, fingolimod, glatiramer acetate, glibenclamide, insulin therapy, L-DOPA/Carbidopa (L-3,4-Dihydroxyphenylalanin), MAO-B (monoamine oxidase B) inhibitors (e.g. selegiline), mesalazine, metformin, methylxanthine drugs (e.g. theophylline), mitoxantrone, natalizumab, NMDA (N-Methyl-D-Aspartat) receptor antagonists (e.g. amantadine, memantine), probiotics (e.g. mutaflor, VSL #30, *Lactobacillus* GG, *Lactobacillus plantarum*, *L. acidophilus*, *L. casei*, *Bifidobacterium infantis* 35624, *Enterococcus fecium* SF68, *Bifidobacterium longum*), statin (e.g. simvastatin), sulfonylureas (e.g. tolnutamide, glimepiride), urea and vitamin-D analoga (e.g. calcipotriol, calcitriol, tacalcitol).

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated with one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit MKNK1 and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof, or pancreatitis.

In accordance with another aspect therefore, the present invention covers a compound of general formula (I), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula (I) described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant serin threonin kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Pain-Associated Diseases and Gynaecological Disorders.

The present invention also provides methods for the treatment or prophylaxis of inflammation and pain-associated diseases.

In particular aspect of the invention as reported above a compound of formula (I), (Ia) or (Ib) is for the treatment of pain syndromes including acute, chronic, inflammatory and neuropathic pain, preferably inflammatory pain, surgical pain, visceral pain, dental pain, premenstrual pain, gynaecological disease, preferably dysmenorrhea, dyspareunia or endometriosis, adenomyosis, endometriosis-associated pain, or other endometriosis-associated symptoms, wherein said symptoms are in particular endometriosis-associated dysmenorrhea, dyspareunia, dysuria, or dyschezia, pain associated with fibrotic diseases, central pain, pain due to burning mouth syndrome, pain due to burns, pain due to migraine, cluster headaches, pain due to nerve injury, pain due to neuritis, neuralgias, pain due to poisoning, pain due to ischemic injury, pain due to interstitial cystitis, cancer pain, pain due to viral, parasitic or bacterial infections, pain due to traumatic nerve-injury, pain due to post-traumatic injuries (including fractures and sport injuries), pain due to trigeminal neuralgia, pain associated with small fiber neuropathy, pain associated with diabetic neuropathy, chronic lower back pain, phantom limb pain, pelvic pain syndrome, chronic pelvic pain, neuroma pain, complex regional pain syndrome, pain associated with gastrointestinal distension, chronic arthritic pain and related neuralgias, and pain associated with cancer, pain associated with chemotherapy, HIV and HIV treatment-induced neuropathy; and pain associated with diseases or disorders selected from the group consisting of hyperalgesia, allodynia, irritable bowel syndrome.

In addition, the present invention is for the use of the treatment and prevention of inflammatory diseases including inflammatory bowel disease (ulcerative colitis and Crohn's disease), hyperaemia, sepsis, metabolic disorders, e.g. obesity, insulin resistance, diabetes mellitus type 1 and 2, metabolic endocrine disorder, e.g. Polycystic Ovary Syndrome (PCOS); metabolic syndrome; atherosclerosis, reperfusion injury, inflammatory bone resorption, inflammatory liver diseases, pulmonary fibrosis, acute respiratory distress syndrome, and intestinal polyposis, inflammatory skin diseases like psoriasis, pemphigus vulgaris, inflammatory eye disorders like non-infectious uveitis, primary and secondary autoimmune uveitis, VKH syndrome, anterior uveitis, intermediate uveitis, posterior uveitis, panuveitis, Behcet's disease and neuromyelitis optica, fibrotic diseases like idiopathic pulmonary fibrosis, skin fibrosis, systemic sclerosis, autism disorders, liver diseases like nonalcoholic-, alcoholic- and toxic fatty liver disease, steatohepatitis, hepatic fibrosis; and cirrhosis; lung diseases like chronic obstructive pulmonary disease, asthma, pneumonia; neurodegenerative diseases like Parkinson's disease, Alzheimer's disease; stroke, postischemic brain injury, brain ischemia, post-traumatic brain injury, alopecia, acute coronary syndrome, myocardial infarction, autoimmune diseases like autoimmune encephalomyelitis, multiple sclerosis; arthritis (such as osteoarthritis and rheumatoid arthritis); psoriatic arthritis, ankylosing spondylitis), psoriasis, lupus erythematosus (e.g. systemic lupus erythematosus, cutaneous lupus and neonatal lupus erythematosus); inflammatory, autoimmune and fibrotic kidney diseases (e.g. glomerulonephritis, lupus nephritis, ANCA) interstitial cystitis, hypertrophy of the e.g. kidney, ischemia/reperfusion injury, allergic rhinitis, burn wound, osteoporosis viral and bacterial infections, chemotherapy-induced alopecia, cachexia induced for any reason, e.g. cancer, heart failure, etc., muscular atrophy, pancreatitis, schizophrenia, seizures, epilepsy, Fragile X syndrome, graft-versus-host disease, graft rejection, heart fibrosis, autoimmune myocardial disease, myocarditis, endocarditis, ischemia-reperfusion injury following e.g. myocardial infarction, hypertension, artherosclerosis, acute lung injury, ARDS, hypersensitivity pneumonitis, lung fibrosis, e.g. idiopathic pulmonary fibrosis, lymphocytic bronchiolitis e.g. after lung transplantation, dry eye, subfertility (e.g. associated with inflammatory conditions such as endometriosis, or metabolic endocrine disorders e.g. Polycystic Ovary Syndrome (PCOS)).

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Assays

Examples were tested in selected biological assays one or more times. When tested more than once, data are reported as either average values or as median values, wherein
  the average value, also referred to as the arithmetic mean value, represents the sum of the values obtained divided by the number of times tested, and
  the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

MKNK1 Kinase Assay

MKNK1-inhibitory activity of compounds of the present invention was quantified employing the MKNK1 TR-FRET assay as described in the following paragraphs.

A recombinant fusion protein of Glutathione-S-Transferase (GST, N-terminally) and human full-length MKNK1 (amino acids 1-424 and T344D of accession number BAA 19885.1), expressed in insect cells using baculovirus expression system and purified via glutathione sepharose affinity chromatography, was purchased from Carna Biosciences (product no 02-145) and used as enzyme. As substrate for the kinase reaction the biotinylated peptide biotin-Ahx-IKKRKLTRRKSLKG (SEQ ID NO: 1) (C-terminus in amide form) was used which can be purchased e.g. form the company Biosyntan (Berlin-Buch, Germany)

For the assay 50 nL of a 100 fold concentrated solution of the test compound in DMSO was pipetted into a black low volume 384 well microtiter plate (Greiner Bio-One, Frickenhausen, Germany), 2 µL of a solution of MKNK1 in aqueous assay buffer [50 mM HEPES pH 7.5, 5 mM MgCl$_2$, 1.0 mM dithiothreitol, 0.005% (v/v) Nonidet-P40 (Sigma)] was added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (0.1 µM=>final conc. in the 5 µL assay volume is 0.06 µM) in assay buffer and the resulting mixture was incubated for a reaction time of 45 min at 22° C. The concentration of MKNK1 was adjusted depending of the activity of the enzyme lot and was chosen appropriate to have the assay in the linear range, typical concentrations were in the range of 0.05 µg/ml. The reaction was stopped by the addition of 5 µL of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and IC$_{50}$ values were calculated by a 4 parameter fit using an inhouse software.

MKNK1 Kinase High ATP Assay

MKNK1-inhibitory activity at high ATP of compounds of the present invention after their preincubation with MKNK1 was quantified employing the TR-FRET-based MKNK1 high ATP assay as described in the following paragraphs.

A recombinant fusion protein of Glutathione-S-Transferase (GST, N-terminally) and human full-length MKNK1 (amino acids 1-424 and T344D of accession number BAA 19885.1), expressed in insect cells using baculovirus expression system and purified via glutathione sepharose affinity chromatography, was purchased from Carna Biosciences (product no 02-145) and used as enzyme. As substrate for the kinase reaction the biotinylated peptide biotin-Ahx-IKKRKLTRRKSLKG (SEQ ID NO: 1) (C-terminus in amide form) was used, which can be purchased e.g. from the company Biosyntan (Berlin-Buch, Germany)

For the assay 50 nL of a 100 fold concentrated solution of the test compound in DMSO was pipetted into a black low volume 384 well microtiter plate (Greiner Bio-One, Frickenhausen, Germany), 2 μL of a solution of MKNK1 in aqueous assay buffer [50 mM HEPES pH 7.5, 5 mM $MgCl_2$, 1.0 mM dithiothreitol, 0.005% (v/v) Nonidet-P40 (Sigma)] was added and the mixture was incubated for 15 mM at 22° C. to allow pre-binding of the test compounds to the enzyme before the start of the kinase reaction. Then the kinase reaction was started by the addition of 3 μL of a solution of adenosine-tri-phosphate (ATP, 3.3 mM=>final conc. in the 5 μL assay volume is 2 mM) and substrate (0.1 μM=>final conc. in the 5 μL assay volume is 0.06 μM) in assay buffer and the resulting mixture was incubated for a reaction time of 30 min at 22° C. The concentration of MKNK1 was adjusted depending of the activity of the enzyme lot and was chosen appropriate to have the assay in the linear range, typical concentrations were in the range of 0.003 μg/mL. The reaction was stopped by the addition of 5 μL of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.1 nM (e.g. 20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and $IC_{50}$ values were calculated. Data are presented in Table 1.

TABLE 1

| Example | MKNK1 $IC_{50}$ [nM] |
|---|---|
| 1 | 2.5 |
| 2 | 6.4 |
| 3 | 18.8 |
| 4 | 306.0 |
| 5 | 6.4 |
| 6 | 0.3 |
| 7 | 2.0 |
| 8 | 28.3 |
| 9 | 82.6 |
| 10 | 17.1 |
| 11 | 36.9 |
| 12 | 27.2 |
| 13 | 5.2 |

TABLE 1-continued

| Example | MKNK1 $IC_{50}$ [nM] |
|---|---|
| 14 | 4.1 |
| 15 | 21.3 |
| 16 | 66.7 |
| 17 | 40.3 |
| 18 | 105.0 |
| 19 | 34.2 |
| 20 | 35.2 |
| 21 | 339.0 |
| 22 | 12.3 |
| 23 | 337.0 |
| 24 | 1.5 |
| 25 | 1.9 |
| 26 | 5.0 |
| 27 | 4.0 |
| 28 | 0.6 |
| 29 | 2.9 |
| 30 | 3.2 |
| 31 | 16.8 |
| 32 | 0.3 |
| 33 | 70.7 |
| 34 | 8.1 |
| 35 | 4.1 |
| 36 | 19.1 |
| 37 | 10.3 |
| 38 | 79.9 |
| 39 | 744.0 |
| 40 | 20.7 |
| 41 | 14.0 |
| 42 | 1.9 |
| 43 | 2.9 |
| 44 | 465.0 |
| 45 | 603.0 |
| 46 | 4.1 |
| 47 | 47.2 |
| 48 | 29.4 |
| 49 | 490.0 |
| 50 | 950.0 |
| 51 | 2.9 |
| 52 | 13.0 |
| 53 | 2.4 |
| 54 | 5.7 |
| 55 | 0.3 |
| 56 | 0.1 |
| 57 | 6.2 |
| 58 | 18.8 |
| 59 | 2.7 |
| 60 | 6.3 |
| 61 | 5.9 |
| 62 | 4.0 |
| 63 | 3.8 |
| 64 | 5.5 |
| 65 | 5.9 |
| 66 | 9.0 |
| 67 | 0.7 |
| 68 | 1.8 |
| 69 | 144.0 |
| 70 | 21.7 |
| 71 | 59.2 |
| 72 | 30.4 |
| 73 | 168.0 |
| 74 | 1.5 |
| 75 | 11.9 |
| 76 | 17.7 |
| 77 | 55.9 |
| 78 | 37.9 |
| 79 | 122.0 |
| 80 | 126.0 |
| 81 | 5.0 |
| 82 | 18.3 |
| 83 | 12.2 |
| 84 | 10.8 |
| 85 | 25.2 |
| 86 | 11.9 |
| 87 | 23.1 |
| 88 | 13.5 |
| 89 | 12.8 |
| 90 | 0.7 |

TABLE 1-continued

| Example | MKNK1 IC$_{50}$ [nM] |
|---|---|
| 91 | 1.1 |
| 92 | 1.2 |
| 93 | 42.0 |
| 94 | 27.8 |
| 95 | 5.8 |
| 96 | 3.9 |
| 97 | 5.1 |
| 98 | 7.6 |
| 99 | 18.8 |
| 100 | 70.5 |
| 101 | 187.0 |
| 102 | 5.7 |
| 103 | 4.7 |
| 104 | 30.2 |
| 105 | 8.3 |
| 106 | 3.5 |
| 107 | 111.0 |
| 108 | 16.5 |
| 109 | 10.2 |
| 110 | 5580 |
| 111 | 517.0 |
| 112 | 25.3 |
| 113 | 15.4 |
| 114 | 8.6 |
| 115 | 208.0 |
| 116 | 4.0 |
| 117 | 12.5 |
| 118 | 66.3 |
| 119 | 3.0 |
| 120 | >20000 |
| 121 | 7.1 |
| 122 | 13.2 |
| 123 | 9.7 |
| 124 | 49.9 |
| 125 | 46.5 |
| 126 | 20.3 |
| 127 | 71.2 |
| 128 | 1.0 |
| 129 | 21.0 |
| 130 | 7.9 |
| 131 | 32.2 |
| 132 | 0.7 |
| 133 | 10.1 |
| 134 | 5.8 |
| 135 | 19.8 |
| 136 | 122.0 |
| 137 | 21.1 |
| 138 | 33.6 |
| 139 | 24.1 |
| 140 | 22.3 |
| 141 | 24.2 |
| 142 | 20.0 |
| 143 | 40.3 |
| 144 | 12.9 |
| 145 | 115.0 |
| 146 | 8.2 |
| 147 | 12.7 |
| 148 | 0.4 |
| 149 | 2.3 |
| 150 | 18.5 |
| 151 | 4.0 |
| 152 | 7.4 |
| 153 | 5.3 |
| 154 | 5.0 |
| 155 | 5.3 |
| 156 | 4.3 |
| 157 | 7.9 |
| 158 | 5.0 |
| 159 | 2.1 |
| 160 | 2.9 |
| 161 | 11.6 |
| 162 | 21.7 |
| 163 | 16.8 |
| 164 | 383.0 |
| 165 | 168.0 |
| 166 | 45.9 |
| 167 | 5.7 |
| 168 | 49.5 |
| 169 | 15.7 |
| 170 | 5.3 |
| 171 | 6.0 |
| 172 | 12.1 |
| 173 | 5.8 |
| 174 | 12.8 |
| 175 | 14.4 |
| 176 | 19.0 |
| 177 | 4.3 |
| 178 | 1.1 |
| 179 | 124 |
| 180 | 104 |
| 181 | 104 |
| 182 | 261 |
| 183 | 13.0 |
| 184 | 34.0 |
| 185 | 7.9 |
| 186 | 5.5 |
| 187 | 7.3 |
| 188 | 47.0 |
| 189 | 274 |
| 190 | 31.4 |
| 191 | 67.8 |
| 192 | 281 |
| 193 | 29.8 |
| 194 | 12.2 |
| 195 | 342 |
| 196 | 0.5 |
| 197 | 14.9 |
| 198 | 1.1 |
| 199 | 56.3 |

MKNK 2 Kinase High ATP Assay

MKNK 2-inhibitory activity at high ATP of compounds of the present invention after their preincubation with MKNK 2 was quantified employing the TR-FRET-based MKNK 2 high ATP assay as described in the following paragraphs.

A recombinant fusion protein of Glutathione-S-Transferase (GST, N-terminally) and human full-length MKNK 2 (Genbank accession number NP_060042.2), expressed in insect cells using baculovirus expression system, purified via glutathione sepharose affinity chromatography, and activated in vitro with MAPK12, was purchased from Invitrogen (product no PV5608) and used as enzyme. As substrate for the kinase reaction the biotinylated peptide biotin-Ahx-IKKRKLTRRKSLKG (SEQ ID NO: 1) (C-terminus in amide form) was used which can be purchased e.g. form the company Biosyntan (Berlin-Buch, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of MKNK 2 in aqueous assay buffer [50 mM HEPES pH 7.5, 5 mM MgCl$_2$, 1.0 mM dithiothreitol, 0.005% (v/v) Nonidet-P40 (G-Biosciences, St. Louis, USA)] was added and the mixture was incubated for 15 mM at 22° C. to allow pre-binding of the test compounds to the enzyme before the start of the kinase reaction. Then the kinase reaction was started by the addition of 3 µl of a solution of adenosine-tri-phosphate (ATP, 3.3 mM=>final conc. in the 5 µl assay volume is 2 mM) and substrate (0.1 µM=>final conc. in the 5 µl assay volume is 0.06 µM) in assay buffer and the resulting mixture was incubated for a reaction time of 30 min at 22° C. The concentration of MKNK 2 was adjusted depending of the activity of the enzyme lot and was chosen appropriate to have the assay in the linear range, typical concentrations were in the range of 0.0045 µg/ml. The reaction was stopped by the addition of 5 µl of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL665. Therefore, the fluorescence emissions at 620 nm and 665 nm after excitation at 350 nm were measured in a TR-FRET reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (e.g. 20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and $IC_{50}$ values were calculated.

Descriptions for additional kinase assays are reported in WO 2015/181104 (page 156-163).

AlphaScreen SureFire eIF4E Ser209 Phosphorylation Assay

The AlphaScreen SureFire eIF4E Ser209 phoshorylation assay can be used to measure the phosphorylation of endogenous eIF4E in cellular lysates. The AlphaScreen SureFire technology allows the detection of phosphorylated proteins in cellular lysates. In this assay, sandwich antibody complexes, which are only formed in the presence of the analyte (p-eIF4E Ser209), are captured by AlphaScreen donor and acceptor beads, bringing them into close proximity. The excitation of the donor bead provokes the release of singlet oxygen molecules that triggers a cascade of energy transfer in the Acceptor beads, resulting in the emission of light at 520-620 nm.

Surefire EIF4e Alphascreen in A549 cells with 20% FCS stimulation

For the assay the AlphaScreen SureFire p-eIF4E Ser209 10K Assay Kit and the AlphaScreen ProteinA Kit (for 10K assay points) both from Perkin Elmer are used.

On day one 50,000 A549 cells are plated in a 96-well plate in 100 µL per well in growth medium (DMEM/Hams' F12 with stable Glutamin, 10% FCS) and incubated at 37° C. After attachment of the cells, medium is changed to starving medium (DMEM, 0.1% FCS, without Glucose, with Glutamin, supplemented with 5 g/L Maltose). On day two, test compounds are serially diluted in 50 µL starving medium with a final DMSO concentration of 1% and are added to A549 cells in test plates at a final concentration range from as high 10 µM to as low 10 nM depending on the activities of the tested compounds. Treated cells are incubated at 37° C. for 2 h. 37 ul FCS is added to the wells (=final FCS concentration 20%) for 20 min. Then medium is removed and cells are lysed by adding 50 µL lysis buffer. Plates are then agitated on a plate shaker for 10 min After 10 min lysis time, 40_, of the lysate is transfered to a 384 well plate (Proxiplate from Perkin Elmer) and 50_, Reaction Buffer plus Activation Buffer mix containing AlphaScreen Acceptor beads is added. Plates are sealed with TopSeal-A adhesive film, gently agitated on a plate shaker for 2 hours at room temperature. Afterwards 2 µL Dilution buffer with AlphaScreen Donor beads are added under subdued light and plates are sealed again with TopSeal-A adhesive film and covered with foil. Incubation takes place for further 2 h gently agitation at room temperature. Plates are then measured in an EnVision reader (Perkin Elmer) with the AlphaScreen program. Each data point (compound dilution) is measured as triplicate.

Proliferation Assays

The tumor cell proliferation assay which can be used to test the compounds of the present invention involves a readout called Cell Titer-Glow® Luminescent Cell Viability Assay developed by Promega® (B. A. Cunningham, "A Growing Issue: Cell Proliferation Assays, Modern kits ease quantification of cell growth", *The Scientist* 2001, 15(13), 26; S. P. Crouch et al., "The use of ATP bioluminescence as a measure of cell proliferation and cytotoxicity", *Journal of Immunological Methods* 1993, 160, 81-88), that measures inhibition of cell proliferation. Generation of a luminescent signal corresponds to the amount of ATP present, which is directly proportional to the number of metabolically active (proliferating) cells.

In Vitro Tumor Cell Proliferation Assay:

Cultivated tumour cells (MOLM-13 (human acute myeloid leukemia cells obtained from DSMZ #ACC 554), JJN-3 (human plasma cell leukemia cells obtained from DSMZ #ACC 541), Ramos (RA1) (human Burkitt's lymphoma cells obtained from ATCC #CRL-159)) are plated at a density of 2,500 cells/well (JJN-3), 3,000 cells/well (MOLM-13), 4,000 cells/well (Ramos (RA1)), in a 96-well multititer plate (Costar 3603 black/clear bottom) in 100 µL of their respective growth medium supplemented with 10% fetal calf serum. After 24 hours, the cells of one plate (zero-point plate) are measured for viability. Therefore, 70 µL/well CTG solution (Promega Cell Titer Glo solution (catalog #G755B and G756B)) is added to zero-point plate. The plates are mixed for two minutes on orbital shaker to ensure cell lysis and incubated for ten minutes at room temperature in the dark to stabilize luminescence signal. The samples are read on a VICTOR 3 plate reader. In parallel, serially test compounds are diluted in growth medium, and 50 µL of 3× dilutions/well are pipetted into the test plates (final concentrations: 0 µM, as well as in the range of 0.001-30 µM). The final concentration of the solvent dimethyl sulfoxide is 0.3-0.4%. The cells are incubated for 3 days in the presence of test substances. 105 µL/well CTG solution (Promega Cell Titer Glo solution (catalog #G755B and G756B)) is added to the test wells. The plates are mixed for 2 minutes on an orbital shaker to ensure cell lysis and incubated for 10 min at room temperature in the dark to stabilize luminescence signal. The samples are read on a VICTOR 3 plate reader. The change of cell number, in percent, is calculated by normalization of the measured values to the extinction values of the zero-point plate (=0%) and the extinction of the untreated (0 µm) cells (=100%).

Overview Cell Lines for Proliferation Assays

| Cell line | Origin | Cell number/well | Culture Medium |
|---|---|---|---|
| MOLM-13 (obtained from DSMZ # ACC 554) | human acute myeloid leukemia | 3000 | RPMI 1640 with stable Glutamin with 10% Fetal Bovine Serum |
| JJN-3 (obtained from DSMZ # ACC 541) | human plasma cell leukemia | 2500 | 45% Dulbecco's Modified Eagle Medium with stable Glutamin, 45% Iscove's Modified Dulbecco's Media with stable Glutamin and 10% Fetal Bovine Serum |
| Ramos (RA1) (obtained from ATCC # CRL-159) | human Burkitt's lymphoma | 4000 | RPMI 1640 media with stable Glutamin with 10% Fetal Bovine Serum |

Thus the compounds of the present invention effectively inhibit one or more kinases and are therefore suitable for the treatment or prophylaxis of diseases of uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK, more particularly in which the diseases of uncontrolled cell growth, proliferation and/or survival, inappropriate cellular immune responses, or inappropriate cellular inflammatory responses are haemotological tumours, solid tumours and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In Vitro IL-1β (Interleukin-1 Beta, IL-1β)-Induced Cytokine Secretion of Human PBMCs (Peripheral Blood Mononuclear Cells)

The effect of the chemical compounds on the induced cytokine secretion of human PBMCs has been investigated. Here, the cytokine secretion has been induced by IL-1□ which binding to its receptors leads to the activation of the MKNK signaling pathway.

Human PBMCs have been isolated from anti-coagulated human whole blood donated from healthy volunteers by pre-filling Leucosep tubes with ficoll-paque (15 ml, Biochrom, order ID: L6115) and adding 20 ml whole blood. After centrifugation of the blood at 800 g for 15 min at room temperature (RT) plasma including thrombocytes has been discarded. PBMCs were transferred to a new falcon tube, washed with PBS (phosphate-buffered saline) at 250 g for 10 min at RT and resuspended in complete medium [RPMI 1640, without L-glutamine (PAA, order ID: E15-039), 10% FCS; 50 U/ml Penicillin, 50 µg/ml Streptomycin (PAA, order ID: P11-010) and 1% L-glutamine (Sigma, order ID. G7513)]. The assay was performed in a 96-well plate at a cell density of $2.5 \times 10^5$ cells/well as triplicates. The compounds were serially diluted in DMSO and added to the PBMCs with a final concentration of 0.4% in DMSO, respectively. Treatment of PBMCs with 0.4% DMSO was used as control. After 30 min of incubation, PBMCs were stimulated with 20 ng/ml IL-1□ (R&D, order ID: 201-LB CF) for 24 hours. Cell viability was measured using the CellTiter-Glo Luminescent Assay (Promega, order ID: G7571) following the manufacturers protocol. The amount of secreted IL-2, IL-6, IL-8, IL-10, IL-12p70, GM-CSF, IFN-γ, and TNF-□ (tumor necrosis factor-alpha) in the supernatant was determined using the Human ProInflammatory 9-Plex (MSD, order ID: K15007B) according to manufacturer's instruction. The inhibitory activity was determined as the relation to the control in percent. $IC_{50}$ values were calculated.

In Vitro LPS (Lipopolysaccharide)-Induced Cytokine Secretion of Human PBMCs (Peripheral Blood Mononuclear Cells)

The effect of chemical compounds on the induced cytokine secretion of human PBMCs has been investigated. Here, the cytokine secretion has been induced by IL-18 which binding to its receptor leads to the activation of the MKNK signaling pathway.

Human PBMCs have been isolated from anti-coagulated human whole blood donated from healthy volunteers by pre-filling Leukosep tubes with ficoll-paque (15 ml, Biochrom, order ID: L6115) and adding 20 ml whole blood. After centrifugation of the whole blood at 800 g for 15 min at room temperature (RT) plasma including thrombocytes has been discarded. PBMCs were transferred to a new falcon tube, washed with PBS (phosphate-buffered saline) at 250 g for 10 min at RT and resuspended in complete medium [RPMI 1640, without L-glutamine (PAA, order ID: E15-039), 10% FCS, 50 U/ml Penicillin, 50 µg/ml Streptomycin (PAA, order ID: P11-010) and 1% L-glutamine (Sigma, order ID: G7513)]. The assays were performed in a 96-well plate at a cell density of $2.5 \times 10^5$ cells/well as triplicates. The compounds were serially diluted in DMSO and added to the PBMCs with a final concentration with 0.4% in DMSO, respectively. Treatment of PBMCs with 0.4% DMSO was used as a control. After 30 min of incubation, PBMCs were stimulated with 100 ng/ml LPS (Lipopolysaccharide, Sigma order ID: L4516) for 24 hours. Cell viability was measured using CellTiter-Glo Luminescent Assay (Promega, order ID: G7571) following the manufacturers protocol. The amount of secreted IL-113, IL-2, IL-6, IL-8, IL-10, IL-12p70, IFN-γ, and TNF-α in the supernatant was determined using Human ProInflammatory 9-Plex (MSD, order ID. K15007B) or IL-113, IL-1ra, IL-2, IL-4, IL-5, IL-6, IL-7, IL-8, IL-9, IL-10, IL-12p70, IL-13, IL-15, IL-17, eotaxin, basic FGF, G-CSF, GM-CSF, IFN-γ, IP-10, MCP-1, MIP-1α, MIP-1β, PDGF-BB, RANTES, TNF-α, and VEGF using Bio-Plex Human Group I Assay (Bio-Rad, order ID: M500KCAFOY) according to manufacturer's instruction. The inhibitory activity was determined as the relation to the control in percent. $IC_{50}$ values were calculated.

In Vitro PHA (Phytohaemagglutinin)-Induced Cytokine Secretion of Human PBMCs (Peripheral Blood Mononuclear Cells)

The effect of chemical compounds on the induced cytokine secretion of human PBMCs has been investigated. Here, the cytokine secretion has been induced by IL-18 which binding to its receptor leads to the activation of the MKNK signaling pathway.

Human PBMCs have been isolated from anti-coagulated human whole blood donated from healthy volunteers by pre-filling Leukosep tubes with ficoll-paque (15 ml, Biochrom, order ID: L6115) and adding 20 ml whole blood. After centrifugation of the whole blood at 800 g for 15 min at room temperature (RT) plasma including thrombocytes has been discarded. PBMCs were transferred to a new falcon tube, washed with PBS (phosphate-buffered saline) at 250 g for 10 min at RT and resuspended in complete medium [RPMI 1640, without L-glutamine (PAA, order ID: E15-039), 10% FCS, 50 U/ml Penicillin, 50 µg/ml Streptomycin (PAA, order ID: P11-010) and 1% L-glutamine (Sigma, order ID: G7513)]. The assays were performed in a 96-well plate at a cell density of $2.5 \times 10^5$ cells/well as triplicates. The compounds were serially diluted in DMSO and added to the PBMCs with a final concentration with 0.4% in DMSO, respectively. Treatment of PBMCs with 0.4% DMSO was used as a control. After 30 min of incubation, PBMCs were stimulated with 10 mg/ml PHA (Phytohaemagglutinine, Sigma, order ID: L4144) for 24 hours. Cell viability was measured using CellTiter-Glo Luminescent Assay (Promega, order ID: G7571) following the manufacturers protocol. The amount of secreted pro-inflammatory cytokines (e.g. IL-18, IL-4, IL-6, IL-10, IL-17A, IL-17F, IL-21, IL-22, IL-23, IL-25, IL-31, IL-33, CD40L, TNF-α, IFN-γ) in the supernatant was determined using Bio-Plex Human Assay (Bio-Rad, order ID: 171AA001M) according to manufacturer's instruction. The inhibitory activity was determined as the relation to the control in percent. $IC_{50}$ values were calculated.

In Vitro-3T3-L1 Differentiation into Adipocyte-Like Cells

The effect of chemical compounds on the differentiation of pre-adipocytes into adipocytes has been investigated. Here, 3T3-L1 fibroblasts were differentiated into adipocyte-like cells. Preadipocytes (3T3-L1) were grown to 2 days post-confluence in DMEM supplemented with 10% BCS (day 0) and the medium was changed to DMEM supplemented with 10% FBS, insulin (167 nM), dexamethasone (0.5 µM), isobutylmethylxanthine (IBMX) (0.5 mM) and rosiglitazone (2 µM) and test compounds. After 48 h, the medium replaced by DMEM supplemented with 10% (v/v) FBS and 167 nM insulin and different concentrations of test compound. This maintenance medium was changed every 48 h always containing different concentrations of the test compound. Cells underwent the differentiation program up to 9 days. Gene expression of MNK1, MNK2 as well as of adipocyte differentiation marker such as PPARγ, C/EBPα, SREBP1c, GLUT4, CD36, FAS, cytosolic phospholipase A2a was performed. The relative mRNA expression of each gene in compound treated cells was compared to the relative mRNA expression in differentiated but untreated control cells. Oil Red O staining was used to qualify and quantify intracellular triglyceride levels. For quantification, cells were washed extensively with water to remove unbound dye, and 1 ml isopropanol was added to the stained cells. Photometric evaluation was applied. Lipid incorporation was also measured by triglyceride assay and lipolysis assay.

Lipolysis describes the hydrolysis of triglycerides into glycerol and free fatty acids. Lipolysis is induced by the synthetic catecholamine, Isoproterenol and glycerol serves as a measure for the incorporated fat during differentiation into adipocytes. For the lipolysis assay, 3T3-L1 cells were differentiated, as described above, for 9 days. The lipolysis assay was performed according to the manufacturer's instructions (e.g. Abcam Lipolysis assay kit, ab185433). The amount of glycerol released was measured using colorimetric intensity.

In Vivo CFA (Complete Freund's Adjuvant)-Induced Inflammatory Pain in Rats

The complete Freund's adjuvant (CFA)-induced inflammatory pain model can be used to evaluate the effect of the chemical compounds on pain.

On day 0, rats (Sprague-Dawley, 10 animals/group) receive either vehicle or the chemical compound before injection of CFA followed by daily treatment until day 7. To inject 100 µl of 100% CFA (Sigma, order ID: F5881) subcutaneously into the plantar surface of the left hind paw rats are anesthetized with 2.5-5% isoflurane in oxygen. Mechanical allodynia is assessed using von Frey filaments according to the "up-down" method described by Chaplan et al (1994) on day 7. Here, calibrated monofilaments (von Frey filaments) are applied to the plantar surface of the rat hind paw for a period of 4-6 seconds, or until a nocifensive paw withdrawal occurres.

In Vivo Imiquimod-Induced Psoriasis Model in Mice

Chemical compounds were tested for their effects in an Imiquimod (IMQ)-induced psoriasis model in mice.

Induction of psoriasis was performed on animals by daily administration of Imiquimod after shaving and depilation of the animals at Day −1. 3.5 mg of IMQ (equivalent to 70 mg of Aldara® créme, Meda AB) was topically administered from Day 1 to Day 7 (seven days) in the morning for groups to be induced. Sham group was applied with paraffin oil. The surface of application was about 4 $cm^2$ on the back of the animals which corresponds to a rectangle of about 1.5 cm to 2.5 cm on the back of the animal. The cream was smoothly massaged on the back for 5 seconds. After this time, the internal face of the right ear was massaged with remaining cream from finger glove. Then, the back was massaged again for 5 seconds and afterwards the internal face of the left ear was massaged with the remaining cream from finger gloves. Animals were weighed every second days (Day 1 prior induction, Day 3, Day 5 and Day 7). Due to body weight loss observed with this model, 0.4 ml of sterile saline was injected intraperitoneally (ip) at Day 3 and Day 4. Oral (po) administration of test compounds started at Day 1 not more than 1 hour after IMQ treatment. The test compounds was administered once daily from Day 1 to Day 7. In each treatment group n=10 animals were included with a Sham (no IMQ) group, a negative control group (IMQ plus vehicle), two groups treated with IMQ and different dosages of the test compound, and one group with IMQ treated animals receiving the reference (betamethasone) compound. Development of the disease was determined using a clinical scoring system. Every day, the following clinical scores were recorded from back skin

| Score | Erythema | Scaling | Skin thickness |
|---|---|---|---|
| 0 | Normal | No | Normal |
| 1 | Slight | Slight | Slight |
| 2 | Moderate | Moderate | Moderate |
| 3 | Important | Important | Important |
| 4 | Very important | Very important | Very important |

Both ears and back skin thickness was measured daily using digital sliding caliper (Horex Digital Caliper, Helios Preisser, Germany). At Day 4, 4 hours after morning treatment, blood was collected from the mandibular vein under isofluran anesthesia into heparin sodium tubes (0.5 ml Eppendorf tubes). After blood collection, 0.4 ml of sterile saline was injected ip to the animals. At Day 7 about 500 µl blood were collected after intercardiac puncture from isofluran-anesthetized in to heparin sodium tubes. Blood was centrifuged (3500 g for ~10 min at 5° C. Plasma was separated and stored at −80° C. for further analyses (determination of cytokine levels). At Day 7 animals were euthanized, and back skin calibrated digital punctures were taken. Skin samples from the back and both ears were kept in formalin and placed in 70% ethanol 48 hours after collection. Histopathological evaluation of back and ear skin was done after hematoxylin and eosin (HE) staining by an experienced pathologist.

In Vivo $MOG_{33-35}$-Induced, Chronic EAE (Experimental Autoimmune Encephalomyelitis)-Model in Mice The effects of chemical compounds were evaluated in an experimental autoimmune encephalomyelitis (EAE) model in C57Bl/6 mice.

On Day 0 all mice, except the animals from healthy control group were given a subcutaneous (sc) injection of 0.1 ml on two sites on the back of 200 µg $MOG_{35-55}$ (myelin oligodendrocyte glycoprotein) emulsified in Complete Freund's Adjuvant supplemented with *Mycobacterium tuberculosis*. At this same time point, mice were injected with 200 ng of Pertussis Toxin (PT) dissolved in 0.1 ml PBS (phosphate buffered saline); the PT injection was repeated on Day 2. A group of ten animals served as nave, vehicle-dosed control group. The other groups underwent induction of EAE and received test compound treatment. Mice were weighed daily. Symptoms of EAE were assessed daily, starting on Day 4 and continuing through study end. All remaining mice were sacrificed at the completion of the study (Day 30). Blood was collected for preparation of serum. Animals were then perfused with formalin, and the spinal cord was collected and stored in 10% formalin for subsequent histopathology analysis. Slides were evaluated by a broad certified veterinary pathologist and were assessed for inflammation and demyelination on a 0-5 scoring scale. Terminal serum samples were analyzed via multiplex analyses for levels of TNF-$\alpha$, IL-6, IL-12, IL-23, IL-1l3, IL-17, and IFN$\gamma$.

In Vivo Adjuvant-Induced Arthritis in Rats

The effects of chemical compounds on the adjuvant-induced arthritis in rats were investigated.

At day 0 male Lewis rats (100 to 125 g body weight, Charles River Laboratories, Germany) were treated at the tail subcutaneously (sc) with 100 µl of complete Freund's Adjuvant (CFA) solution [*M. tuberculosis* H37Ra (Difco Lab, cat. No. 231141)] diluted in Incomplete Freund's Adjuvant (Difco Lab, cat. no: 263910). Animals were randomized with n=8 animals per treatment group. As controls a healthy and a disease group treated with vehicle only were included in the studies. Treatment with test compounds was done orally (po) with either one or more dosages using an appropriate vehicle which allowed sufficient exposure of the animals with the test compound. In a preventive treatment setting, treatment start was at day 0 and continued to day 20, the end of the study. Observation of the disease induction as well as the treatment effects of test compound was determined by the RA disease activity score, starting at day 0 and then three times per week. The Score defines the extent of joint inflammation from 0 to 4 including erythema with swelling of the joint (0=no; 1=slight; 2=moderate, 3=important, 4=very important). The disease score was determined for both hind paws and added to one value. As an additional parameter for joint swelling the paw volume was determined using a plethysometer (IITC Life Science Inc., USA). A second parameter determined during the study was the grip strength using an automated grip strength test meter (IITC Life Science Inc., USA) as a measure for hyperalgesia. At the end of the study (day 20) synovial fluid from joints, biopsies of kneejoint and blood serum were obtained and used for determination of proinflammatory cytokines [Meso Scale Discovery (MSD), ProInflammatory Panel 1; cat no: K15059D), and the c-reactive protein (CRP) (BD Biosciences, cat no: 55825).

Synovial fluid is isolated by rinsing the inflamed joints with 150 µl sterile sodium acetate solution. Biopsies of kneejoints were homogenized with a cryo mill (Retsch GmbH, Germany) at −196° C. 200 mg of the powder were used for analysis of cytokines suspended in 0.5 ml RPMI1640 medium. Statistical analyses of obtained results were done with one way Anova (ANOVA; Analysis of variance) and the comparison to the control group via multiple reference analysis (Dunnett-test).

In Vivo—Fertility Model in Mice

Chemical compound were tested for their effects on fertility in a DBA/2J-CBA/J mouse model. Female CBA/J mice bred with mal DBA/2J display a higher abortion rate. Male DBA/2J mice were bred with female CBA/J mice and the vaginal plugs in individual mated female mice were examined daily to determine potential pregnancy. At Day 1 of pregnancy one or two groups of successfully mated female CBA/J mice were treated orally (po) with one or two different dosages of the test compound once daily, whereas the control group was given the vehicle only. In each treatment group n=12 animals were included. At Day 10 to Day 14 of pregnancy the animals were sacrificed, the uteri removed and the implantation sites were documented. The abortion sites were identified by their small size and necrotic, hemorrhagic appearance, compared with normal embryos and placentas. The percentage of abortions was calculated as the ratio of resorption sites to total implantation sites. Uteri were shock frozen and after homogenization cytokine levels were determined using mouse Bio-Plex Assays (M0009RDPD, M6000007NY, LJ00000163).

In Vivo CCL4-Induced Liver Fibrosis in Mice

The effect of chemical compounds was tested in a tetrachlormethan (CCL4)-induced mouse model of liver fibrosis.

Eight week old 90 male C57Bl/6 mice (Charles River) were randomly divided into three groups (Group 1=untreated control, Group 2=vehicle treated control, Group 3=treatment with test compound) with n=30 in each group. For induction of liver fibrosis animals were treated three times per week (Monday, Wednesday, Friday) with 50 µl of CCL4/olive oil suspension (CCL4+olive oil, 1+9 v/v) intraperitoneally (ip) over the whole study time. CCL4 is the most commonly used inducer of a toxically-induced liver fibrosis in animal models (Starkel et al., Animal models for the study of hepatic fibrosis. Best Practice & Research Clinical Gastroenterology 25 (2011) 319-333). Once daily per os (po) treatment of group 2 with the vehicle and of group 3 with test compound suspension started with the first day and was done over the complete study duration. Two weeks after study start fifty percent of animals (of each group) were euthanized and after two additional weeks, the remaining animals were euthanized. After finalization of the study, the liver of each animal as collected and fixed in 4% formaldehyde and paraffin embedded for further histopathological analyses. For determination of severity of liver fibrosis liver slices were stained with pikro-sirius red (Waldeck, Germany) to visualize the collagen content in the tissue. A Carl Zeiss microscope (Axio) connected to a PC was used to scan the pikro-sirius red stained liver sections to make images of these. The sections were scanned at a magnification of 20× and a light intensity of 4.8V. The images were then formatted into jpg and the red-stained area quantified by using the ImageJ Software (National Institue of Health, USA). The results are expressed as % sirius-red per liver area.

Chemical compounds of the invention are tested for their effects in following in vivo models In Vivo—Letrozole-Induced Polycystic Ovary Syndrome in Rats Chemical compounds are tested for their effects in a Polycystic Ovary Syndrome (PCOS) model in rats.

Han Wistar rats are randomly divided into 3 groups with n=8 animals per group. Rats in the control group receive vehicle only once daily per os (po), whereas rats of the other two groups are all administered letrozole at a concentration of 1 mg/kg body weight dissolved in 0.5% carboxymethyl-cellulose (CMC) once daily for consecutive 28 days. Animals of the third group additionally receive the test compound once daily po in 20% HPBCD (HP beta cyclodextrin) for consecutive 28 days. Vaginal smears are performed, and the rat weights are recorded daily. At day 27 animals are fasted and an oral glucose tolerance test will be performed. Rats are euthanized, ovaries are removed and weighed. One ovary of each rat is fixed in formaldehyde for histological examination, whereas the other ovary is stored at −80° C. for mRNA and protein analyses. Fat tissue and liver are also removed and from each tissue one aliquot is fixed in formaldehyde and the other aliquot is shock frozen for further mRNA analyses.

Vaginal Smears: the stage of the estrous cycle is determined by microscopic analysis of the predominant cell type in the daily vaginal smears.

Ovarian morphology: sections from the ovarian tissue are taken from the part of the ovary with largest diameter, stained with hematoxylin and eosin.

In Vivo Diet Induced Obesity in Mice

Effects of chemical compound on diet-induced obesity are tested in C57Bl/6 mice receiving a high fat diet.

Male C57Bl/6 (n=45) mice at an age of 16 weeks are randomly divided into 5 groups. Animals fo groups 1 to 4 are fed with 60% high fat diet for 10 weeks. Animals of group 5 (n=10) are fed with chow diet for the same time. Mice of group 1 are additionally treated orally (BID) with vehicle only. Animals of group 2 (n=15) receive test compound (BID) orally. Mice of group 3 (n=10) receive pioglitazone via oral administration (QD). Compound and vehicle treatment is performed over the complete study duration. Animals of groups 4 (n=10) and 5 (n=10) do not receive any treatment. Body weight is measured daily during the 8 weeks treatment period. At days 26 and 48 of treatment overnight fasted mice undergo an oral glucose tolerance test (OGTT). Mice are weighed and blood (15 μl/EDTA) is collected from the tail tip two hours after compound treatment; 30 min prior glucose load to measure HBA1c, blood glucose, and plasma insulin and HOMAR-IR will then be calculated.

HOMAR-IR index=[(mM glucose×μU/ml insulin)/22.51]

For OGTT blood glucose is measured from tail tip at −30, 0, 15, 30, 60, 90, and 120 min after oral glucose load (1.5 g/kg body weight). Blood (20 μl/EDTA) is also collected at 15 and 30 min after glucose load to measure plasma insulin. Blood glucose levels are used to calculate glucose area under the curve. Mice recover from the OGTT over 2 days.

At days 28 of treatment blood (15 μl/EDTA) is collected 2 hours after compound treatment from the tail tip to measure HBA1c, blood glucose and plasma insulin in fed conditions and HOMAR-IR will then be calculated.

At day 51 of treatment 4 h fasted mice then undergo an Insulin Tolerance Test (ITT) with insulin (0.5 U/kg body weight) injected intraperitoneally. Blood glucose is then measured at time 0, 15, 30, 60, 90, and 120 minutes after insulin injection.

At day 53 of treatment the incorporated body fat is determined by Echo-MRI. At day 56 of treatment (end of the study) blood is taken for determination of blood glucose, leptin, triglycerides, total cholesterol, and free fatty acids.

In Vivo Pharmacokinetics in Rats

For in vivo pharmacokinetic experiments test compounds were administered to male Wistar rats intravenously at doses of 0.3 to 1 mg/kg and intragastral at doses of 0.5 to 10 mg/kg formulated as solutions using solubilizers such as PEG400 in well-tolerated amounts. For pharmacokinetics after intravenous administration test compounds were given as i.v. bolus and blood samples were taken at 2 min, 8 min, 15 min, 30 min, 45 min, 1 h, 2 h, 4 h, 6 h, 8 h and 24 h after dosing. Depending on the expected half-life additional samples were taken at later time points (e.g. 48 h, 72 h). For pharmacokinetics after intragastral administration test compounds were given intragastral to fasted rats and blood samples were taken at 5 min, 15 min, 30 min, 45 min, 1 h, 2 h, 4 h, 6 h, 8 h and 24 h after dosing. Depending on the expected half-life additional samples were taken at later time points (e.g. 48 h, 72 h). Blood was collected into Lithium-Heparintubes (Monovetten®, Sarstedt) and centrifuged for 15 min at 3000 rpm. An aliquot of 100 μL from the supernatant (plasma) was taken and precipitated by addition of 400 μL cold acetonitril and frozen at −20° C. over night. Samples were subsequently thawed and centrifuged at 3000 rpm, 4° C. for 20 minutes. Aliquots of the supernatants were taken for analytical testing using an Agilent 1200 HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. PK parameters calculated from concentration time profiles after i.g.: Cmax: Maximal plasma concentration (in mg/L); Cmaxnorm: Cmax divided by the administered dose (in kg/L); Tmax: Time point at which Cmax was observed (in h). Parameters calculated from both, i.v. and i.g. concentration-time profiles: AUCnorm: Area under the concentration-time curve from t=0 h to infinity (extrapolated) divided by the administered dose (in kg*h/L); AUC(0-tlast)norm: Area under the concentration-time curve from t=0 h to the last time point for which plasma concentrations could be measured divided by the administered dose (in kg*h/L); t½: terminal half-life (in h); F: oral bioavailability: AUCnorm after intragastral administration divided by AUCnorm after intravenous administration (in %).

The invention claimed is:
1. A compound of formula (B):

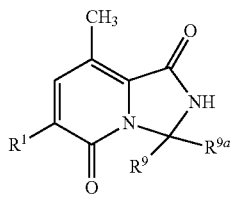

(B)

wherein
$R^1$ is

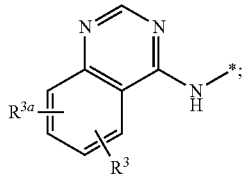

$R^3$ and $R^{3a}$ are independently selected from the group consisting of a hydrogen atom, a halogen atom, cyano, hydroxy, —$C_1$-$C_6$-alkoxy, halo-$C_1$-$C_3$-alkyl, and $C_1$-$C_3$-alkyl-; and
$R^9$ and $R^{9a}$ are the same or different and independently from each other selected from the group consisting of a hydrogen atom and methyl, or
are taken together to form —($CH_2$—$CH_2$—$CH_2$)—, —($CH_2$—$CH_2$—$CH_2$—$CH_2$)—, —($CH_2$—$CH_2$—S—$CH_2$—$CH_2$)—, —($CH_2$—$CH_2$—$SO_2$—$CH_2$—$CH_2$)—, —($CH_2$—$CH_2$—$CH_2$—$CH_2$—$CH_2$)—, —($CH_2$—$CH_2$—$CF_2$—$CH_2$—$CH_2$)—, or —($CH_2$—$CH_2$—C(OH)$CF_3$—$CH_2$—$CH_2$)—,
or a tautomer, an N oxide, a hydrate, a solvate, a salt thereof, or a mixture of any of the foregoing.

2. The compound according to claim 1, which is selected from the group consisting of
8'-methyl-6'-(quinazolin-4-ylamino)-2'H-spiro[cyclohexane-1,3'-imidazo[1,5-a]pyridine]-1',5'-dione
6'-[(5-fluoroquinazolin-4-yl)amino]-8'-methyl-2'H-spiro [cyclohexane-1,3'-imidazo[1,5-a]pyridine]-1',5'-dione,
6'-[(6-chloroquinazolin-4-yl)amino]-8'-methyl-2'H-spiro [cyclohexane-1,3'-imidazo[1,5-a]pyridine]-1',5'-dione,
6'-[(6-chloroquinazolin-4-yl)amino]-8'-methyl-2'H-spiro [cyclopentane-1,3'-imidazo[1,5-a]pyridine]-1',5'-dione,
6'-[(6-chloroquinazolin-4-yl)amino]-4,4-difluoro-8'-methyl-2'H-spiro[cyclohexane-1,3'-imidazo[1,5-a]pyridine]-1',5'-dione,
6'-[(7-chloroquinazolin-4-yl)amino]-8'-methyl-2'H-spiro [cyclohexane-1,3'-imidazo[1,5-a]pyridine]-1',5'-dione,
6'-[(5-chloroquinazolin-4-yl)amino]-8'-methyl-2'H-spiro [cyclohexane-1,3'-imidazo[1,5-a]pyridine]-1',5'-dione,
6'-[(6,8-dichloroquinazolin-4-yl)amino]-8'-methyl-2'H-spiro[cyclohexane-1,3'-imidazo[1,5-a]pyridine]-1',5'-dione,
6'-[(8-fluoroquinazolin-4-yl)amino]-8'-methyl-2'H-spiro [cyclohexane-1,3'-imidazo[1,5-a]pyridine]-1',5'-dione,
6'-[(7-fluoroquinazolin-4-yl)amino]-8'-methyl-2'H-spiro [cyclohexane-1,3'-imidazo[1,5-a]pyridine]-1',5'-dione,
6'-[(6-fluoroquinazolin-4-yl)amino]-8'-methyl-2'H-spiro [cyclohexane-1,3'-imidazo[1,5-a]pyridine]-1',5'-dione,
6'-[(5,7-difluoroquinazolin-4-yl)amino]-8'-methyl-2'H-spiro[cyclohexane-1,3'-imidazo[1,5-a]pyridine]-1',5'-dione,
6'-[(7,8-difluoroquinazolin-4-yl)amino]-8'-methyl-2'H-spiro[cyclohexane-1,3'-imidazo[1,5-a]pyridine]-1',5'-dione,
6'-[(7-methoxyquinazolin-4-yl)amino]-8'-methyl-2'H-spiro[cyclohexane-1,3'-imidazo[1,5-a]pyridine]-1',5'-dione,
6'-[(6-methoxyquinazolin-4-yl)amino]-8'-methyl-2'H-spiro[cyclohexane-1,3'-imidazo[1,5-a]pyridine]-1',5'-dione,
6'-[(5-methoxyquinazolin-4-yl)amino]-8'-methyl-2'H-spiro[cyclohexane-1,3'-imidazo[1,5-a]pyridine]-1',5'-dione,
6'-[(6,7-dimethoxyquinazolin-4-yl)amino]-8'-methyl-2'H-spiro[cyclohexane-1,3'-imidazo[1,5-a]pyridine]-1',5'-dione,
8'-methyl-6'-[(8-methylquinazolin-4-yl)amino]-2'H-spiro [cyclohexane-1,3'-imidazo[1,5-a]pyridine]-1',5'-dione,
8'-methyl-6'-[(7-methylquinazolin-4-yl)amino]-2'H-spiro [cyclohexane-1,3'-imidazo[1,5-a]pyridine]-1',5'-dione,
8'-methyl-6'-[(6-methylquinazolin-4-yl)amino]-2'H-spiro [cyclohexane-1,3'-imidazo[1,5-a]pyridine]-1',5'-dione,
8'-methyl-6'-[(5-methylquinazolin-4-yl)amino]-2'H-spiro [cyclohexane-1,3'-imidazo[1,5-a]pyridine]-1',5'-dione,
6-[(6-chloroquinazolin-4-yl)amino]-3,3,8-trimethyl-2,3-dihydroimidazo[1,5-a]pyridine-1,5-dione,
6'-[(6-chloroquinazolin-4-yl)amino]-8'-methyl-2'H-spiro [cyclobutane-1,3'-imidazo[1,5-a]pyridine]-1',5'-dione,
8'-methyl-6'-[(5-methylquinazolin-4-yl)amino]-2'H-spiro [cyclobutane-1,3'-imidazo[1,5-a]pyridine]-1',5'-dione,
6'-[(6-fluoroquinazolin-4-yl)amino]-8'-methyl-2'H-spiro [cyclobutane-1,3'-imidazo[1,5-a]pyridine]-1',5'-dione, 8'-methyl-6'-[(quinazolin-4-yl)amino]-2'H-spiro[cyclobutane-1,3'-imidazo[1,5-a]pyridine]-1',5'-dione, 8'-methyl-6'-[(5-methylquinazolin-4-yl)amino]-2'H-spiro[cyclopentane-1,3'-imidazo[1,5-a]pyridine]-1',5'-dione, 8'-methyl-6'-{[6-(trifluoromethyl)quinazolin-4-yl]amino}-2'H-spiro[cyclopentane-1,3'-imidazo[1,5-a]pyridine]-1',5'-dione, 6'-[(6-fluoroquinazolin-4-yl)amino]-8'-methyl-2'H-spiro[cyclopentane-1,3'-imidazo[1,5-a]pyridine]-1',5'-dione, 6'-[(7-chloroquinazolin-4-yl)amino]-8'-methyl-2'H-spiro[cyclopentane-1,3'-imidazo[1,5-a]pyridine]-1',5'-dione, 8'-methyl-6'-[(quinazolin-4-yl)amino]-2'H-spiro[cyclopentane-1,3'-imidazo[1,5-a]pyridine]-1',5'-dione (cis)-4-hydroxy-8'-methyl-6'-[(5-methylquinazolin-4-yl)amino]-4-(trifluoromethyl)-2'H-spiro[cyclohexane-1,3'-imidazo[1,5-a]pyridine]-1',5'-dione;

(cis)-6'-[(6-fluoroquinazolin-4-yl)amino]-4-hydroxy-8'-methyl-4-(trifluoromethyl)-2'H-spiro[cyclohexane-1,3'-imidazo[1,5-a]pyridine]-1',5'-dione, 6-[(6-chloroquinazolin-4-yl)amino]-8-methyl-2',3',5',6'-tetrahydro-2H-spiro[imidazo[1,5-a]pyridine-3,4'-thiopyran]-1,5-dione, 6-[(6-chloroquinazolin-4-yl)amino]-8-methyl-2',3',5',6'-tetrahydro-2H-spiro[imidazo[1,5-a]pyridine-3,4'-thiopyran]-1,5-dione 1',1'-dioxide;

or a tautomer, an N-oxide, a hydrate, a solvate, or a salt thereof, or a mixture of any of the foregoing.

3. A pharmaceutical composition comprising the compound of claim 1, or a stereoisomer, a tautomer, an N-oxide, a hydrate, a solvate, or a salt thereof, or a mixture of any of the foregoing and a pharmaceutically acceptable diluent or carrier.

4. A pharmaceutical combination comprising:
one or more first active ingredients comprising the compound of claim 1, or a stereoisomer, a tautomer, an N-oxide, a hydrate, a solvate, or a salt thereof, or a mixture of any of the foregoing; and
one or more second active ingredients selected from chemotherapeutic anti-cancer agents.

5. A method for treatment of acute myeloid leukemia, comprising administering to a patient in need thereof a pharmaceutically effective amount of the compound of claim 1, or a stereoisomer, a tautomer, an N-oxide, a hydrate, a solvate, or a salt thereof, or a mixture of any of the foregoing.

6. The compound of claim 1, wherein compound is of formula (B):

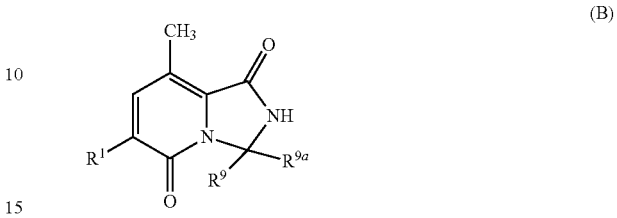

(B)

wherein
$R^1$ is

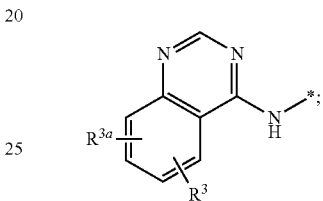

$R^3$ and $R^{3a}$ are independently selected from the group consisting of a hydrogen atom, a halogen atom, cyano, hydroxy, —$C_1$-$C_6$-alkoxy, halo-$C_1$-$C_3$-alkyl, and $C_1$-$C_3$-alkyl-; and $R^9$ and $R^{9a}$ are the same or different and independently from each other selected from the group consisting of a hydrogen atom and methyl, or
are taken together to form —(CH$_2$—CH$_2$—CH$_2$)—, —(CH$_2$—CH$_2$—CH$_2$—CH$_2$)—, —(CH$_2$—CH$_2$—S—CH$_2$—CH$_2$)—, —(CH$_2$—CH$_2$—SO$_2$—CH$_2$—CH$_2$)—, —(CH$_2$—CH$_2$—CH$_2$—CH$_2$—CH$_2$)—, —(CH$_2$—CH$_2$—CF$_2$—CH$_2$—CH$_2$)—, or —(CH$_2$—CH$_2$—C(OH)CF$_3$—CH$_2$—CH$_2$)—, or a pharmaceutically acceptable salt thereof.

7. A compound: 8'-methyl-6'-(quinazolin-4-ylamino)-2'H-spiro[cyclohexane-1,3'-imidazo[1,5-a]pyridine]-1',5'-dione hydrochloride.

* * * * *